(12) United States Patent
Skog et al.

(10) Patent No.: US 10,793,914 B2
(45) Date of Patent: Oct. 6, 2020

(54) CANCER-RELATED BIOLOGICAL MATERIALS IN MICROVESICLES

(71) Applicant: THE GENERAL HOSPITAL CORPORATION, Boston, MA (US)

(72) Inventors: Johan Karl Olov Skog, New York, NY (US); Leonora Balaj, Charlestown, MA (US); Mikkel Noerholm, Gauting (DE); Xandra O. Breakefield, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 186 days.

(21) Appl. No.: 15/012,111

(22) Filed: Feb. 1, 2016

(65) Prior Publication Data

US 2016/0153053 A1    Jun. 2, 2016

Related U.S. Application Data

(63) Continuation of application No. 13/819,539, filed as application No. PCT/US2011/050041 on Aug. 31, 2011.

(60) Provisional application No. 61/493,261, filed on Jun. 3, 2011, provisional application No. 61/438,199, filed on Jan. 31, 2011, provisional application No. 61/437,547, filed on Jan. 28, 2011, provisional application No. 61/421,421, filed on Dec. 9, 2010, provisional application No. 61/378,860, filed on Aug. 31, 2010.

(51) Int. Cl.
*C12Q 1/6886* (2018.01)
*C12Q 1/6806* (2018.01)
*G01N 33/50* (2006.01)

(52) U.S. Cl.
CPC ......... *C12Q 1/6886* (2013.01); *C12Q 1/6806* (2013.01); *C12Q 2600/106* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01); *C12Q 2600/178* (2013.01)

(58) Field of Classification Search
CPC ............ C12Q 1/6806; C12Q 2563/161; C12Q 1/6886; C12Q 2600/106; C12Q 2600/112; C12Q 2600/118; C12Q 2600/154; C12Q 2600/156; C12Q 2600/158; C12Q 2600/178
See application file for complete search history.

(56) References Cited

U.S. PATENT DOCUMENTS

| | | |
|---|---|---|
| 5,219,727 A | 6/1993 | Wang |
| 5,538,871 A | 7/1996 | Nuovo et al. |
| 5,547,859 A | 8/1996 | Goodman et al. |
| 5,556,773 A | 9/1996 | Yourno |
| 5,582,981 A | 12/1996 | Toole et al. |
| 5,639,611 A | 6/1997 | Wallace et al. |
| 5,639,606 A | 7/1997 | Willey |
| 5,811,250 A | 9/1998 | Solum |
| 5,840,867 A | 11/1998 | Toole et al. |
| 6,004,755 A | 12/1999 | Wang |
| 6,329,179 B1 | 12/2001 | Kopreski |
| 6,525,154 B1 | 2/2003 | Shea et al. |
| 6,607,898 B1 | 8/2003 | Kopreski et al. |
| 6,759,217 B2 | 7/2004 | Kopreski |
| 6,794,135 B1 | 9/2004 | Kopreski et al. |
| 6,812,023 B1 | 11/2004 | Lamparski |
| 6,893,837 B2 | 5/2005 | Slamon et al. |
| 6,899,863 B1 | 5/2005 | Dhellin et al. |
| 6,913,879 B1 | 7/2005 | Schena |
| 6,916,634 B2 | 7/2005 | Kopreski |
| 6,939,671 B2 | 9/2005 | Kopreski |
| 6,994,960 B1 | 2/2006 | Foote et al. |
| 7,074,563 B2 | 7/2006 | Koster |
| 7,186,512 B2 | 3/2007 | Martienssen et al. |
| 7,198,893 B1 | 4/2007 | Koster et al. |
| 7,198,923 B1 | 4/2007 | Abrignani et al. |
| 7,332,533 B2 | 2/2008 | Kim et al. |
| 7,332,552 B2 | 2/2008 | Benicewicz et al. |
| 7,332,553 B2 | 2/2008 | Sellergren et al. |

(Continued)

FOREIGN PATENT DOCUMENTS

| | | |
|---|---|---|
| CA | 2453198 A1 | 7/2005 |
| CA | 2676113 A1 | 1/2009 |

(Continued)

OTHER PUBLICATIONS

Ruprecht, K. et al., Human Endogenous Retrovirus Family HERV-K(HML-2) RNA Transcripts Are Selectively Packaged into Retroviral Particles Produced by the Human Germ Cell Tumor Line Tera-1 and Originate Mainly from a Provirus on Chromosome 22q11.21, J. Virol., vol. 82, pp. 10008-10016 (Year: 2008).*

Abravaya et al., "Detection of point mutations with a modified ligase chain reaction (Gap-LCR)", Nucleic Acids Research, 23(4):675-682 (1995).

Allawi et al., "Quantitation of microRNAs using a modified Invader assay", RNA, 10:1153-1161 (2004).

Al-Nedawi et al., "Intercellular transfer of the oncogenic receptor EGFRvIII by microvesicles derived from tumour cells", Nature Cell Biology, 10(5):619-624 (2008).

Ason et al., "Differences in vertebrate microRNA expression", PNAS, 103(39):14385-14389 (2006).

(Continued)

*Primary Examiner* — Teresa E Strzelecka

(74) *Attorney, Agent, or Firm* — Nixon Peabody LLP; David S. Resnick; Shayne Y. Huff

(57) ABSTRACT

Disclosed herein are methods for assaying a biological sample from a subject by analyzing components of microvesicle fractions in aid of risk, diagnosis, prognosis or monitoring of, or directing treatment of the subject for, a disease or other medical condition in the subject. Also disclosed are methods of treatment and identifying biomarkers using a microvesicle fraction of a subject. Kits, pharmaceutical compositions, and profiles related to the methods are also disclosed.

6 Claims, 44 Drawing Sheets

Specification includes a Sequence Listing.

(56) References Cited

U.S. PATENT DOCUMENTS

| | | | |
|---|---|---|---|
| 7,364,848 B2 | 4/2008 | Van Beuningen et al. | |
| 7,378,245 B2 | 5/2008 | Liu | |
| 7,384,589 B2 | 6/2008 | Hart et al. | |
| 7,671,010 B2 | 3/2010 | Arap et al. | |
| 7,691,383 B2 | 4/2010 | Chakrabarty et al. | |
| 7,776,523 B2 | 8/2010 | Garcia et al. | |
| 7,807,183 B2 | 10/2010 | Hong et al. | |
| 7,897,356 B2 | 3/2011 | Klass | |
| 10,174,361 B2 | 1/2019 | Skog et al. | |
| 2002/0106684 A1 | 8/2002 | Kopreski | |
| 2003/0077808 A1 | 4/2003 | Rosen et al. | |
| 2005/0003426 A1 | 1/2005 | Ranum et al. | |
| 2005/0250100 A1 | 11/2005 | Hayashizaki | |
| 2006/0081516 A1 | 4/2006 | Hendrickson et al. | |
| 2006/0116321 A1 | 6/2006 | Robbins et al. | |
| 2006/0160087 A1* | 7/2006 | McGrath | C12Q 1/6883 435/6.16 |
| 2006/0223072 A1 | 10/2006 | Boyes et al. | |
| 2007/0104738 A1 | 5/2007 | Tatischeff et al. | |
| 2007/0105105 A1 | 5/2007 | Clelland | |
| 2007/0254351 A1 | 11/2007 | Abrignani et al. | |
| 2007/0298118 A1 | 12/2007 | Lotvall et al. | |
| 2008/0268429 A1 | 10/2008 | Pietrzkowski et al. | |
| 2008/0287669 A1 | 11/2008 | Braman et al. | |
| 2009/0169636 A1 | 7/2009 | O'Hagan et al. | |
| 2009/0220944 A1 | 9/2009 | Fais et al. | |
| 2009/0227533 A1 | 9/2009 | Bader et al. | |
| 2010/0008978 A1 | 1/2010 | Drummond et al. | |
| 2010/0075315 A1 | 3/2010 | Pietrzkowski | |
| 2010/0184046 A1 | 7/2010 | Klass et al. | |
| 2010/0196426 A1 | 8/2010 | Skog et al. | |
| 2010/0209355 A1 | 8/2010 | Chakrabarty et al. | |
| 2010/0255514 A1 | 10/2010 | Rak et al. | |
| 2011/0081651 A1 | 4/2011 | Hillan | |
| 2012/0142001 A1 | 6/2012 | Skog et al. | |
| 2012/0238467 A1 | 9/2012 | Taylor | |
| 2013/0040833 A1 | 2/2013 | Noerholm et al. | |

FOREIGN PATENT DOCUMENTS

| | | |
|---|---|---|
| CA | 2699646 A1 | 3/2009 |
| CN | 101085349 A | 12/2007 |
| JP | HO8-509806 | 10/1996 |
| JP | 2002521071 A | 7/2002 |
| JP | 2002535665 A | 10/2002 |
| JP | 2003514523 A | 4/2003 |
| JP | 2003531864 A | 10/2003 |
| JP | 2008501336 A | 1/2008 |
| JP | 2008035779 A | 2/2008 |
| JP | 2008509806 A | 4/2008 |
| JP | 2008541699 A | 5/2008 |
| JP | 2010534480 A | 11/2010 |
| JP | 2011510663 A | 4/2011 |
| WO | 1994011018 A1 | 5/1994 |
| WO | 1994/022018 | 9/1994 |
| WO | 00/04194 | 1/2000 |
| WO | 2001/036601 | 5/2001 |
| WO | 2001/082958 A2 | 11/2001 |
| WO | 2002/099064 | 12/2002 |
| WO | 03/023065 A1 | 3/2003 |
| WO | 2003/050290 | 6/2003 |
| WO | 2003/076603 | 9/2003 |
| WO | 2005/00098 | 1/2005 |
| WO | 2005000098 A3 | 1/2005 |
| WO | 2005/081867 | 9/2005 |
| WO | 2005/121359 | 12/2005 |
| WO | 2005/121369 | 12/2005 |
| WO | 2006/020707 | 2/2006 |
| WO | 2006/048291 | 5/2006 |
| WO | 2006048291 A3 | 5/2006 |
| WO | 2006/113590 | 10/2006 |
| WO | 2007/015174 | 2/2007 |
| WO | 2007/103572 | 9/2007 |
| WO | 2007103572 A2 | 9/2007 |
| WO | 2007/0126386 | 11/2007 |
| WO | 2007127848 A2 | 11/2007 |
| WO | 2008084331 | 7/2008 |
| WO | 2008/104543 | 9/2008 |
| WO | 2009/015357 A1 | 1/2009 |
| WO | 2009/021322 | 2/2009 |
| WO | 2009/036236 | 3/2009 |
| WO | 2009030029 A1 | 3/2009 |
| WO | 2009/092386 | 7/2009 |
| WO | 2009/100029 | 8/2009 |
| WO | 2009/100029 A1 | 8/2009 |
| WO | 2009/155505 | 12/2009 |
| WO | 2010/028099 | 3/2010 |
| WO | 2010/056337 | 5/2010 |
| WO | 2010/065968 | 6/2010 |
| WO | 2010/099184 | 9/2010 |
| WO | 2010/141955 | 12/2010 |
| WO | 2011/009104 | 1/2011 |
| WO | 2011/031877 | 3/2011 |
| WO | 2011/031892 | 3/2011 |
| WO | 2011031877 A1 | 3/2011 |
| WO | 2011/088226 | 7/2011 |
| WO | 2011/127219 | 10/2011 |
| WO | 2012/031008 | 3/2012 |

OTHER PUBLICATIONS

Balzar et al., "The biology of the 17-1A antigen (Ep-CAM)", J Mol Med, 77:699-712 (1999).

Benner et al., "Evolution, language and analogy in functional genomics", Trends in Genetics, 17:414-418 (2001).

Booth et al., "Exosomes and HIV GAG BUD From Endosome-Like Domains of the T Cell Plasma Membrane", J Cell Biol., 172(6):923-935 (2006).

Bossi et al., "Molecularly Imprinted Polymers for the Recognition of Proteins: The State of the Art", Biosensors Bioelectronics, 22:1131-1137 (2007).

Carr et al., "Circulating membrane vesicles in leukemic blood", Cancer Res., 45:5944-5951 (1985).

Cermelli et al., "Circulating microRNAs in patients with chronic hepatitis C and non-alcoholic fatty liver disease", PLoS ONE, 6(8):e23937 (2011).

Chaput et al., "The Potential of Exosomes in Immunotherapy", Expert Opin Biol Ther., 5(6):737-747 (2005).

Chen et al., "Characterization of microRNAs in serum: a novel class of biomarkers for diagnosis of cancer and other diseases", Cell Research, 18:997-1006 (2008).

Chen et al., "Microfluidic isolation and transcriptome analysis of serum microvesicles", Lab Chip, 10:505-511 (2010).

Chen et al., "Real-time quantification of microRNAs by stem-loop RT-PCR", Nucleic Acid Research, 33(20):e179 (2005).

Cheruvanky et al., "Rapid isolation of urinary exosomal biomarkers using a nanomembrane ultrafiltration concentrator", Am J Physiol Renal Physiol, 292:F1657-F1661 (2007).

Cheung et al., "Natural variation in human gene expression assessed in lymphoblastoid cells", Nature Genetics, 33:422-425 (2003).

Ciafre et al., "Extensive modulation of a set of microRNAs in primary glioblastoma", Biochemical and Biophysical Research Communications, 334:1351-1358 (2005).

Clayton et al., "Human Tumor-Derived Exosomes Selectively Impair Lymphocyte Responses to Interleukin-2", Cancer Res., 67(15):7458-7466 (2007).

Cocucci et al., "Shedding microvesicles: artefacts no more", Trends Cell Biol, 19:43-51 (2009).

Corsten et al., "Circulating microRNA-208b and microRNA-499 reflect myocardial damage in cardiovascular disease", Circulation Cardiovascular Genetics, 2:499-506 (2010).

Cotton et al., "Reactivity of cytosine and thymine in single-base-pair mismatches with hydroxylamine and osmium tetroxide and its application to the study of mutations", Proc. Natl. Acad. Sci. USA, 85:4397-4401 (1988).

Diehl et al., "BEAMing: single-molecule PCR on microparticles in water-in-oil emulsions", Nature Methods, 3 (7):551-559 with supplemental material (2006).

(56) References Cited

OTHER PUBLICATIONS

Dressman et al., "Transforming single DNA molecules into fluorescent magnetic particles for detection and enumeration of genetic variations", PNAS 100(15):8817-8822 (2003).
El-Hefnawy Talal et al., "Characterization of amplifiable, circulating RNA in plasma and its potential as a tool for cancer diagnostics", Clinical Chemistry, 50(3):564-573 (2004).
Fabbri et al., "MicroRNA-29 family reverts aberrant methylation in lung cancer by targeting DNA methyltransferases 3A and 3B", PNAS, 104(40)15805-15810 (2007).
Florentino et al., "The minisequencing method: an alternative strategy for preimplantation genetic diagnosis of single gene disorders", Molecular Human Reproduction, 9(7):399-410 (2003).
Fischer et al., "Length-Independent Separation of DNA Restriction Fragments in Two-Dimensional Gel lectrophoresis", Cell, 16:191-200 (1979).
Affymetrix, Apr. 20, 2001, Apr. 20, 2001, retrieved from the Internet on May 21, 2003. "Gene chip human genome U133 set." URL: http://www.affymetrix.com/products/arrays/specitic/hgu133.asp.
Duijvesz et al., European Urology, 59(5):823-831 (2011). "Exosomes as biomarker treasure chests for prostate cancer."
Geneannot: Weizmann Institute of Science, Apr. 20, 2001, retrieved from the Internet on Apr. 20, 2012. "Probes for MYC available on affymetrix arrays HG-U95, HG-U133, and HG-U133 Plus 2.0)." URL: http://genecards.weizmann.ac.il/cgi-bin/geneannot/GA_search.pl.
Voisset et al., Microbiol. Mol. Biol. Rev., 72(1):157-196 (2008). "Human RNA 'Rumor' Viruses: the Search for Novel Human Retroviruses in Chronic Disease."
Wang-Johanning et al., Cancer Res, 68(14):5869-5877 (2008). "Human Endogenous Retrovirus K Triggers an Antigen-Specific Immune Response in Breast Cancer Patients."
Wieckowski et al., Immunologic Research, 36/1-3:247-254 (2006). "Human Tumor-Derived vs Dendritic Cell-Derived Exosomes Have Distinct Biologic Roles and Molecular Profiles."
Yuan et al., PLoS One, 4(3):e4772 (2009). "Transfer of MicroRNAs by Embryonic Stem Cell Microvesicles."
Alessi et al., Sci. Signal., 2(67):pe27 (2009). "New Insights into mTOR Signaling: mTORC2 and Beyond."
Baj-Krzyworzeka et al., Cancer Immunol Immunother, 55:808-818 (2006). "Tumour-derived microvesicles carry several surface determinants and mRNA of tumour cells and transfer some of these determinants to monocytes."
Bamford et al., British Journal of Cancer, 9(12):355-358 (2004). "The COSMIC (Catalogue of Somatic Mutations in Cancer) database and website."
Bergsmedh et al., PNAS, 98(11):6407-6411 (2001). "Horizontal transfer of oncogenes by uptake of apoptotic bodies".
Bratthauer et al., Cancer, 73(9):2333-2336 (1994). "Expression of LINE-1 Retrotransposons in Human Breast Cancer."
Burghoff et al., Cardiovascular Research, 77:534-543 (2008). "Horizontal gene transfer from human endothelial cells to rat cardiomyocytes after intracoronary transplantation."
Cadieux et al., Cancer Res, 66:8469-8476 (2006). "Genome-wide Hypomethylation in Human Glioblastomas Associated with Specific Copy Number Alteration Methylenetetrahydrofolate Reductase Allele Status, and Increased Proliferation."
The Cancer Genome Atlas Research Network, Nature, 455:1061-1068 with Corrigendum (2008). "Comprehensive genomic characterization defines human glioblastoma genes and core pathways."
Cheng et al., Current Cancer Drug Targets, 8:2-6 (2008). "Advances of AKT Pathway in Human Oncogenesis and as a Target for Anti-Cancer Drug Discovery."
Cho et al., J Pathol, 211:269-277 (2007). "Hypermethylation fo CpG island loci and hypomethylation of LINE-I and Alu repeats in prostate adenocarcinoma and their relationship to clinicopathological features."
Contreras-Galindo et al., Journal of Virology, 82(19):9329-9336 (2008). "Human Endogenous Retrovirus K (HML-2) Elements in the Plasma of People with Lymphoma and Breast Cancer."
Cortez et al., Expert Opin. Biol. Ther., 9(6):703-711 (2009). "MicroRNA identification in plasma and serum: a new tool to diagnose and monitor diseases."
Cowell et al., Microarray Analysis of the Physical Genome: Methods and Protocols, 556:47-65 (2009). "Application of Oligonucleotides Arrays for Coincident Comparative Genomic Hybridization, Ploidy Status and Loss of Heterozygosity Studies in Human Cancers."
Daskalos et al., Int. J. Cancer, 124:81-87 (2009). "Hypomethylation of retrotransposable elements correlates with genomic instability in non-small cell lung cancer."
Day et al., Cancer Letters, 301:1-6 (2011). "PCA3: From basic molecular science to the clinical lab."
Deregibus et al., Blood, 110(7):2440-2448 (2007). "Endothelial progenitor cell-derived microvesicles activate an angiogenic program in endothelial cells by a horizontal transfer of mRNA."
Diehl et al., Nature Medicine, 14(9):985-990 (2008). "Circulating mutant DNA to assess tumor dynamics."
Dowling et al., Science, 328:1172-1176 (2010). "mTORC1-Mediated Cell Proliferation, But Not Cell Growth, Controlled by the 4E-BPs."
Estecio et al, PLoS One, 5:e399 (2007). "LINE-1 Hypomethylation in Cancer is Highly Variable and Inversely Correlated with Microsatellite Instability."
Forbes et al., Current Protocols in Human Genetics, Supplement 57:10.11.1-10.11.26 (2008). "The Catalogue of Somatic Mutations in Cancer (COSMIC)."
Forbes et al., Nucleic Acids Research, 38(Database issue):D652-657 (2010). "COSMIC (the Catalogue of Somatic Mutations in Cancer): a resource to investigate acquired mutations in human cancer."
Forbes et al., Nucleic Acids Research, 39(Database Issue):D945-D950 (2011). "COSMIC: mining complete cancer genomes in the Catalogue of Somatic Mutations in Cancer."
Golan et al., Neoplasia, 10(6):521-533 (2008). "Human Endogenous Retrovirus (HERV-K) Reverse Transcriptase as a Breast Cancer Prognostic Marker."
Goodier et al., Cell, 135:23-35 (2008). "Retrotransposons Revisited: The Restraint and Rehabilitation of Parasites."
Guescini et al., J Neural Transm, 117:1-4 (2010). "Astrocytes and Glioblastoma cells release exosomes carrying mtDNA."
Hanahan et al., Cell, 100:57-70 (2000). "The Hallmarks of Cancer."
Hildebrandt et al., Journal of Clinical Oncology, 27(6):857-871 (2009). "Genetic Variations in the P13K/PTEN/AKT/mTOR Pathway Are Associated With Clinical Outcomes in Esophageal Cancer Patients Treated with Chemoradiotherapy."
Iero et al., Cell Death and Differentiation, 15:80-88 (2008). "Tumour-released exosomes and their implications in cancer immunity."
Itadani et al., Current Genomics, 9:349-360 (2008). "Can Systems Biology Understand Pathway Activation? Gene Expression Signatures as Surrogate Markers for Understanding the Complexity of Pathway Activation."
Ji et al., Oncogene, 22:8031-8041 (2003). "MALAT-1, a novel noncoding RNA, and thymosin β4 predict metastasis and survival in early-stage non-small cell lung cancer."
Kleiman et al., Int J Cancer, 110:459-461 (2004). "HERV-K(HML-2) GAG/ENV Antibodies as Indicator for Therapy Effect in Patients with Germ Cell Tumors."
Klemke et al., The Journal of Cell Biology, 137(2):481-492 (1997). "Regulation of Cell Motility by Mitogen-activated Protein Kinase."
Kristensen et al., Clinical Chemistry, 55(8):1471-1483 (2009). "PCR-Based Methods for Detecting Single-Locus DNA Methylation Biomarkers in Cancer Diagnostics, Prognostics, and Response to Treatment."
Lower et al., Proc. Natl. Acad. Sci., 93:5177-5184 (1996). "The viruses in all of us: Characteristics and biological significance of human endogenous retrovirus sequences."
Novakova et al., Biochemical and Biophysical Research Communications, 386:1-5 (2009). "Biochemical and Biophysical Research Communications."
Ostrowski et al., Nature Cell Biology, 12(1):19-30 with Supplemental Information (2010). "Rab27a and Rab27b control different steps of the exosome secretion pathway."

(56) References Cited

OTHER PUBLICATIONS

Parsons et al., Science, 321:1807-1812 (2008). "An Integrated Genomic Analysis of Human Glioblastoma Multiforme."
Pelloski et al., Journal of Clinical Oncology, 25(16):2288-2294 (2007). "Epidermal Growth Factor Receptor Variant III Status Defines Clinically Distinct Subtypes of Glioblastoma."
Pleasance et al., Nature, 463:191-197 (2010). "A comprehensive catalogue of somatic mutations from a human cancer genome."
Ratajczak et al., Leukemia, 20:1487-1495 (2006). "Membrane-derived microvesicles: important and underappreciated mediators of cell-to-cell communication."
Roman-Gomez et al., Leukemia Research, 32:487-490 (2008). "Repetitive DNA hypomethylation in the advanced phase of chronic myeloid leukemia."
Ruprecht et al., Cell. Mol. Life Sci., 65:3366-3382 (2008). "Endogenous retroviruses and cancer."
Sarbassov et al., Molecular Cell, 22:159-168 (2006). "Prolonged Rapamycin Treatment Inhibits mTORC2 Assembly and Akt/PKB."
Myers et al., "Detection of Single Base Substitutions by Ribonuclease Cleavage at Mismatches in RNA: DNA Duplexes", Science, 230:1242-6 (1985).
Nagrath et al., "Isolation of Rare Circulating Tumour Cells in Cancer Patients by Microchip Technology", Nature, 450(20/27):1235-1239 (2007).
Nakanishi et al., "PCA3 Molecular Urine Assay Correlates with Prostate Cancer Tumor Volume: Implication in Selecting Candidates for Active Surveillance", The Journal of Urology, 179:1804-1810 (2008).
Nakazawa et al., "UV and skin cancer: Specific p53 gene mutation in normal skin as biologically relevant exposure measurement", Proc. Natl. Acad. Sci. USA 91:360-364 (1994).
Ng et al., "MRNA of Placental Origin Is Readily Detectable in Maternal Plasma", Proc Natl Acad Sci U S A., 100(8):4748-4753 (2003).
Ng et al., "The Concentration of Circulating Corticotropin-Releasing Hormone MRNA in Maternal Plasma Is Increased in Preeclampsia", Clin Chem. 49(5):727-731 (2003).
Nilsson et al., "Prostate cancer-derived urine exosomes: a novel approach to biomarkers for prostate cancer.", British Journal of Cancer 100(10):1603-1607 (2009).
Noerholm et al., "RNA Expression patterns in serum microvesicles from patients with glioblastoma multiforme and controls", BMC Cancer, Biomed Central, 12(1): 22 (2012).
Oliveira et al., "Distinct patterns of KRAS mutations in colorectal carcinomas according to germline mismatch repair lefects and hMLH1 methylation status", Human Molecular Genetics, 13(19): 2303-2311 (2004).
Orita et al., "Detection of polymorphisms of human DNA by gel electrophoresis as single-strand conformation polymorphisms", Proc. Natl. Acad. Sci. USA, 86:2766-2770 (1989).
Pisitkun et al., "Discovery of Urinary Biomarkers", Molecular & Cellular Proteomics, 5:1760-1771 (2006).
Rak et al., "Genetic determinants of cancer coagulopathy, angiogenesis and disease progression", Vnitr Lek. 52(Suppl 1):135-8 (2006).
Raposo et al., "B Lymphocytes Secrete Antigen-presenting Vesicles", J. Exp. Med, 183:1161-1172 (1996).
Ryan et al., "A prospective study of circulating mutant KRAS2 in the serum of patients with colorectal neoplasia: strong prognostic indicator in postoperative follow up", Gut, 52:101-108 (2003).
Saal et al., "MicroRNAS and the kidney: coming of age", Current Opinion in Nephrology and Hypertension 18:317-323 (2009).
Schetter et al., "Microrna Expression Profiles Associated With Prognosis and Therapeutic Outcome in Colon Adenocarcinoma", JAMA, 299(4):425-436 (2008).
Shinojima et al., "Prognostic value of epidermal growth factor receptor in patients with glioblastoma multiforme", Cancer Research 63(20) 6962-70 (2003).
Steemers et al., "Whole-genome genotyping with the single-base extension assay", Nature Methods, 3(1):31-3 (2006).

Stoorvogel et al., "The Biogenesis and Functions of Exosomes", Traffic, 3:321-330 (2002).
Tam, "The Emergent Role of MicroRNAs in Molecular Diagnostics of Cancer", Journal of Molecular Diagnostics, 10 (5):411-414 (2008).
Taylor et al., "Tumour-derived exosomes and their role in cancer-associated T-cell signaling defects", British Journal of Cancer, 92:305-311 (2005).
Taylor et al., "MicroRNA signatures of tumor-derived exosomes as diagnostic biomarkers of ovarian cancer", Gynecologic Oncology, 110:13-21 (2008).
Tewes et al., "Molecular profiling and predictive value of circulating tumor cells in patients with metastatic breast aancer: an option for monitoring response to breast cancer related therapies", Breast Cancer Res Treat, 115:581-590 (2009).
Thery, C., et al., "Isolation and Characterization of Exosomes From Cell Culture Supernatants and Biological Fluids", Curr Protoc Cell Biol. Chapter 3:Unit 3 22.1-32229, (2006).
Van Dijk et al., "Human cell growth requires a functional cytoplasmic exosome, which is involved in various mRNA decay pathways", RNA, 13:1027-1035 (2007).
Velculescu et al., "Serial Analysis of Gene Expression", Science, 270:484-7 (1995).
Went et al., "Frequent EPCAM Protein Expression in Human Carcinomas", Hum Pathol., 35:122-128 (2004).
Wong et al., "Circulating Placental RNA in Maternal Plasma Is Associated with a Preponderance of 5' mRNA Fragments: Implications for Noninvasive Prenatal Diagnosis and Monitoring", Clin Chem, 51(10): 1786-1795 (2005).
Wood et al., "The Genomic Landscapes of Human Breast and Colorectal Cancers", Science, 318:1108-1113 (2007).
Wright et al., "Newer potential biomarkers in prostate cancer", Reviews in Urology, 9(4): 207-13 (2007).
Yan et al., "IDH1 and IDH2 mutations in gliomas.", N. Engl. J. Med., 360(8):765-773 (2009).
Yu et al., "Oncogenic events regulating tissue factor expression", Haematological Reports, 1(9):18-20 (2005).
Simons et al., Current Opinion in Cell Biology, 21:575-581 (2009). "Exosomes—vesicular carriers for intercellular communication."
Skog et al., Nature Cell Biology, 10(12):1470-1476 with Supplemental Information, (2008). "Glioblastoma microvesicles transport RNA and proteins that promote tumour growth and provide diagnostic biomarkers."
Sliva et al., Virology Journal, 7:248 (2010). Selective gene silencing by viral delivery of short hairpin RNA.
Srikantan et al., PNAS, 97(22):12216-12221 (2000). "PCGEM1, a prostate-specific gene, is overexpressed in prostate cancer."
Thery et al., Nature Reviews Immunology, 2:569-579 (2002). "Exosomes: Composition, Biogenesis and Function."
Ting et al., Science, 331:593-596 (2011). "Aberrant Overexpression of Satellite Repeats in Pancreatic and Other Epithelial Cancers."
Valadi et al., Nature Cell Biology, 9(6):654-659 with Supplemental Information (2007). "Exosome-mediated transfer of mRNAs and microRNAs is a novel mechanism of genetic exchange between cells."
Revenfeld et al., "Diagnostic and prognostic potential of extracellular vesicles in peripheral blood", Clin. Ther., 36 (6): 830-846 (2014).
Katoh et al., Frontiers in Oncology, 3, Article 234: 1-8 (2013).
Bess et al., "Microvesicles are a source of contaminating cellular proteins found in purified HIV-1 preparations." Virology 230(1):134-144 (1997).
Biernat et al., "Predominant expression of mutant EGFR (EGFRvIII) is rare in primary glioblastomas", Brain Pathol 14(2) 131-136 (2004).
Chabert et al., "Cell culture of tumors alters endogenous poly(ADPR)polymerase expression and activity", Int J Cancer 53(5) 837-842 (1993).
Cho et al., "Hypermethylation of CpG island loci and hypomethylation of LINE-1 and Alu repeats in prostate adenocarcinoma and their relationship to clinicopathological features", J Pathol 211(3) 269-277 (2007).

(56) References Cited

OTHER PUBLICATIONS

Choi et al., "Proteomic analysis of microvesicles derived from human colorectal cancer ascites.", Proteomic 11(13) 2745-2751 (2011).
Cooperberg et al., "The changing face of low-risk prostate cancer: trends in clinical presentation and primary management", J Clin Oncol 22(11) 2141-9 (2004).
Dermer "Another anniversary for the war on cancer." Nature Biotechnology 12(3):320 (1994).
Diehl et al., "Detection and quantification of mutations in the plasma of pateitns with colorectal tumors." PNAS 102 (45) 16268-16373 (2005).
Eastham et al., "Relationship between clonogenic cell survival, DNA damage and chromosomal radiosensitivity in nine human cervix carcinoma cell lines" Int. Journal Radiat. Biol 77(3) 295-302 (2001).
GenBank (Accession NM_005896) submitted Jan. 31, 2003.
Grant et al., "The proteins of normal urine." Journal of Clinical Pathology 10(4):360-367 (1957).
Keller et al., "Exosomes: from biogenesis and secretion to biological function", Immunol Lett 107(2) 102-8 (2006).
May "How Many Species Are there on Earth?", Science 241(1) 1441-1449 (1998).
Mellinghoff et al., "Molecular determinants of the response of glioblastomas to EGFR kinase inhibitors", N Engl J Med 353(19) 2012-2024 (2005).
Mitchell et al., "Can urinary exosomes act as treatment response markers in prostate cancer?", J Transl Med 7:4 (2009).
Moderk et al., "Genome-wide detection of alternatives splicing in expressed sequences of human genes", Nucleic Acids Research 29(13) 2850-2859 (2001).
Moscatello et al., "Frequent expression of a mutant epidermal growth factor receptor in multiple human tumors", Cancer Res 55(23) 5536-5539 (1995).
Nishikawa et al., Immunohistochemical analysis of the mutant epidermal growth factor, deltaEGFR, in glioblastoma, Brain Tumor Pathol 21(2) 53-56 (2004).
Saito-Hisaminto et al., "Genome-Wide Profiling of Gene Expression in 29 Normal Human Tissues with cDNA Microarray", DNA Research 9 35-45 (2002).
Schmidt et al., "Quantitative multi-gene expression profiling of primary prostate cancer", Prostate 66(14) 1521-34 (2006).
Singh et al., "Gene Expression correlates of clinical prostate cancer behavior", Cancer Cell 1(2) 203-209 (2002).
The International SNP Map Working Group., "A map of human genome sequence variation containing 1.42 million single nucleotide polymorphisms" NATURE 409 928-933 (2001).
Thery et al. "Isolation and Characterization of Exosomes from Cell Culture Supernatants and Biological Fluids" Curr Protoc Cell Biol Chapter 3 Unit 3.22 1-29 (2006).
Tomlins et al., "Recurrent fusion of TMPRSS2 and ETS transcription factor genes in prostate cancer", Science 310 (5748) 644-648 (2005).
Tullis et al., "Calcium protects DNase I from proteinase K: a new method for the removal of contaminating RNase from DNase I." Analytical Biochemistry 107(1):260-264 (1980).
Yoshimoto et al., "Development of a real-time RT-PCR assay for detecting EGFRvIII in glioblastoma samples", Clin Cancer Res 14(2) 488-493 (2008).
Yu et al., "Shedding of tissue factor (TF)-containing microparticles rather than alternatively spliced TF is the main source of TF activity released from human cancer cells", J Throm Haemost 2(11) 2065-2067 (2004).
Huang et al. "Optimization of DNase I Removal of Contaminating DNA from RNA for Use in Quantitative RNA-PCR." Biotechniques 20(6): 1012-1020 (1996).
Johnstone. "Exosomes biological significance: A concise review." Blood Cells, Molecules, and Diseases 36(2): 315-321 (2006).
Lotvall at al. "Cell to Cell Signalling via Exosomes Through esRNA." Cell Adhesion & Migration 1(3): 156-158 (2007).

Perkel. "Finding Points to Possible Blood Test for Brain Tumors." HealthDay News [retrieved Apr. 18, 2019] https://www.medicinenet.com/script/main/art.asp?articlekey=94287 1-3 (2008).
Halatsch et al. "Epidermal growth factor receptor inhibition for the treatment of the glioblastoma multiforme and other malignant brain tumors." Cancer Treatment Reviews, 32: 74-89, (2006).
Schalken "Validation of molecular targets in prostate cancer." BJU International, 96: 23-29 (2005).
Fischer et al., Methods in Enzymology, 68:183-91 (1979). "Two-Dimensional Electrophoretic Separation of Restriction Enzyme Fragments of DNA."
Furnari et al., "Malignant Astrocytic Glioma: Genetics, Biology, and Paths to Treatment", Genes Dev., 21:2683-2710 (2007).
Gambim et al., Critical Care, 11(5):R107 (p. 1-12) (2007). "Platelet-derived exosomes induce endothelial cell apoptosis through peroxynitrite generation: experimental evidence for a novel mechanism of septic vascular dysfunction."
Geiss et al., Nature Biotechnology 26(3):317-325 (2008). "Direct multiplexed measurement of gene expression with color-coded probe pairs."
Ginestra et al., "The Amount and Proteolytic Content of Vesicles Shed by Human Cancer Cell Lines Correlates With Their in Vitro Invasiveness", Anticancer Research, 18:3433-3438 (1998).
Gonzales et al., Nephrol Dial Transplant 23:1799-1801 (2008). "Urinary exosomes: is there a future?"
Gormally, E., et al., "Circulating Free DNA in Plasma or Serum As Biomarker of Carcinogenesis: Practical Aspects and Biological Significance", Mutat Res., 635:105-117 (2007).
Greco, V., et al., "Argosomes: A Potential Vehicle for the Spread of Morphogens Through Epithelia", Cell., 106:633-645 (2001).
Green et al., Blood, 116(15):2779-2782 with supplemental material (2010). "The prognostic significance of IDH1 mutations in younger adult patients with acute myeloid leukemia is dependent on FLT3/ITD status."
Groskopf, J., et al., "Aptima PCA3 Molecular Urine Test: Development of a Method to Aid in the Diagnosis of Prostate Cancer", Clin Chem., 52(6):1089-1095 (2006).
Guatelli et al, Proc. Natl. Acad. Sci. USA, 87:1874-1878 (1990). "Isothermal, in vitro amplification of nucleic acids by a multienzyme reaction modeled after retroviral replication."
Hahn, Bioessays, 15(7):477-484 (1993). "Molecular Biology of Double-Minute Chromosomes."
Hartmann et al., Acta Neuropathol, 120:707-718 (2010). "Patients with IDHI wild type anaplastic astrocytomas exhibit worse prognosis than IDH1-mutated glioblastomas, and IDH1 mutation status accounts for the unfavorable prognostic effect of higher age: implications for classification of gliomas."
Heimberger et al., J Transl Med. Oct. 19, 2005;3:38. "The natural history of EGFR and EGFRvIII in glioblastoma patients."
Hessels et al., "DD3 PCA3-based Molecular Urine Analysis for the Diagnosis of Prostate Cancer", European Urology, 44:8-16 (2003).
Hessels et al., "Detection of TMPRSS2-ERG Fusion Transcripts and Prostate Cancer Antigen 3 in Urinary Sediments May Improve Diagnosis of Prostate Cancer", Clin Cancer Research, 13:5103-5108 (2007).
Holdhoff (Journal of the National Cancer Institute Sep. 16, 2009 vol. 101 Issue 18).
Hunter et al., PLoS ONE, 3(11) e3694 (2008). "Detection of microRNA Expression in Human Peripheral Blood Microvesicles."
Iorio et al., Cancer Research, 67(18):8699-8707 (2007). "microRNA signatures in human ovarian cancer."
Janowska-Wieczorek, A., et al., "Microvesicles Derived From Activated Platelets Induce Metastasis and Angiogenesis in Lung Cancer", Int J Cancer., 113:752-760 (2005).
Johnson, S., et al., "Surface-Immobilized Peptide Aptamers As Probe Molecules for Protein Detection", Anal Chem., 80:978-983 (2008).
Jones, S., et al., "Core Signaling Pathways in Human Pancreatic Cancers Revealed by Global Genomic Analyses", Science, 321(5897)1801-1806 (2008).
Kan et al, Proc. Natl. Acad. Sci. USA, 75(11):5631-5635 (1978). "Polymorphism of DNA sequence adjacent to human β-globin structural gene: Relationship to sickle mutation."

(56) References Cited

OTHER PUBLICATIONS

Kan et al., The Lancet, 2:910-2 (1978). "Antenatal Diagnosis of Sickle-Cell Anaemia by D.N.A. Analysis of Amniotic-Fluid Cells."
Kang et al., "Mutational analysis of IDH1 codon 132 in glioblastomas and other common cancers", Int. J. Cancer, 125, pp. 353-355, 2009.
Kato et al., "A monoclonal antibody Imab-1 specifically recognizes IDH1R132H, the most common glioma-derived mutation", Biocheinical and Biophysical Research Communications, 390, pp. 547-557, 2009.
Keller et al., Kidney International, 72:1095-1102 (2007). "CD24 is a marker of exosomes secreted into urine and amniotic fluid."
Kislauskis, E.H., et al., "Sequences Responsible for Intracellular Localization of Beta-Actin Messenger RNA Also Affect Cell Phenotype", J Cell Biol., 127:441-451 (1994).
Klein et al., Nature Biotechnology, 20:387-392 (2002). "Combined transcriptome and genome analysis of single microstatic cells."
Koga et al., Anticancer Research, 25:3703-3707 (2005). "Purification, Characterization and Biological Significance of Tumor-derived Exosomes."
Kosaka et al., "Circulating microRNA in body fluid: a new potential biomarker for cancer diagnosis and prognosis.", Cancer Sci., 10(101):2087-2092 (2010).
Krupp, G. "Stringent RNA quality control using the Agilent 2100 bioanalyzer" Application note, Agilent Technologies, Feb. 1, 2005.
Kwoh et al., Proc. Natl. Acad. Sci. USA 86:1173-1177 (1989). "Transcription-based amplification system and detection of amplified human immunodeficiency virus type1 with a bead-based sandwich hybridization format."
Landegren et al., Science, 241:1077-1080 (1988). "A Ligase-Mediated Gene Detection Technique."
Laxman et al., Cancer Research, 68:645-649 (2008). "A first-generation multiplex biomarker analysis of urine for the early detection of prostate cancer."
Lee et al., PLoS One, 6(6):e21300 (2011). "microRNA expression and clinical outcome of small cell lung cancer."
Li et al., Nature Medicine, 14(5) 579-584 (2008). "Replacing PCR with COLD-PCR enriches variant DNA sequences and redefines the sensitivity of genetic testing."
Liu et al., Cell, 127:1223-1237 (2006). "Reconstitution, Activities and Structure of the Eukaryotic RNA Exosome."
Liu, C., et al., "Murine Mammary Carcinoma Exosomes Promote Tumor Growth by Suppression of NK Cell Function", J Immunol., 176:1375-1385 (2006).
Lo et al., Cytometry Part A, 73A:321-322 (2008). "Automated Gating of Flow Cytometry Data via Robust Model-Based Clustering."
Lo et al., Nature Reviews Genetics, 8:71-77 (2007). "Prenatal Diagnosis: progress through plasma nucleic acids."
Lo, Y.M., et al., "Plasma Placental RNA Allelic Ratio Permits Noninvasive Prenatal Chromosomal Aneuploidy Detection", Nat Med., 13(2):218-223 (2007).
Mack et al., "Transfer of the Chemokine Receptor CCR5 Between Cells by Membrane-Derived Microparticles: A Mechanism for Cellular Human Immunodeficiency Virus 1 Infection", Nature Medicine, 6(7):769-775 (2000).
Maheswaran et al., The New England Journal of Medicine, 359(4)366-377 (2008). "Detection of Mutations in EGFR in Circulating Lung-Cancer Cells."
Mallardo, M., et al., "Isolation and Characterization of Staufen-Containing Ribonucleoprotein Particles From Rat Brain", Proc Natl Acad Sci U S A, 100(4):2100-2105 (2003).
Maron, J.L., et al., "Gene Expression Analysis in Pregnant Women and Their Infants Identifies Unique Fetal Biomarkers That Circulate in Maternal Blood", J Clin Invest., 117:3007-3019 (2007).
McLendon, R., et al., "Comprehensive Genomic Characterization Defines Human Glioblastoma Genes and Core Pathways", Nature, 455(23):1061-1068 (2008).
Miele et al., J. Mol. Biol. 171:281-295 (1983). "Autocatalytic Replication of Recombinant RNA."
Millimaggi, D., et al., "Tumor Vesicle-Associated CD147 Modulates the Angiogenic Capability of Endothelial Cells", Neoplasia, 9(4):349-357 (2007).
Miranda et al., Kidney International, 78:191-199 (2010). "Nucleic acids within urinary exosomes/microvesides are potential biomarkers for renal disease."

\* cited by examiner

CANCER-RELATED BIOLOGICAL MATERIALS IN MICROVESICLES

CROSS REFERENCE TO RELATED APPLICATIONS

This application is a Continuation Application of U.S. application Ser. No. 13/819,539 filed Oct. 17, 2013 which is a 35 U.S.C. § 371 National Phase Entry Application of International Application No. PCT/US2011/050041 filed Aug. 31, 2011, which designates the U.S., and which claims the benefit of 35 U.S.C. § 119(e) to U.S. Provisional Application Ser. No. 61/378,860 filed Aug. 31, 2010; 61/421,421 filed Dec. 9, 2010; 61/437,547 filed Jan. 28, 2011; 61/438,199 filed Jan. 31, 2011; and 61/493,261 filed Jun. 3, 2011, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 29, 2016, is named Sequence_Listing_030258-069537-C and is 5,407 bytes in size.

GOVERNMENT SUPPORT

This invention was made with Government support under grants CA86355, CA69246, CA141226, and CA141150 awarded by National Cancer Institute. The Government has certain rights in the invention.

FIELD OF INVENTION

The present invention relates to the fields of biomarker analysis, diagnosis, prognosis, patient monitoring, therapy selection, risk assessment, and novel therapeutic agents for human or other animal subjects, particularly the profiling of biological materials from a microvesicle fraction of a biological sample, and novel therapies related to microvesicles.

BACKGROUND OF THE INVENTION

Increasing knowledge of the genetic and epigenetic changes occurring in cancer cells provides an opportunity to detect, characterize, and monitor tumors by analysing tumor-related nucleic acid sequences and profiles. Cancer-related changes include specific mutations in gene sequences (Cortez and Calin, 2009; Diehl et al., 2008; Network, 2008; Parsons et al., 2008), up- and down-regulation of mRNA and miRNA expression (Cortez and Calin, 2009; Itadani et al., 2008; Novakova et al., 2009), mRNA splicing variations, changes in DNA methylation patterns (Cadieux et al., 2006; Kristensen and Hansen, 2009), amplification and deletion of genomic regions (Cowell and Lo, 2009), and aberrant expression of repeated DNA sequences (Ting et al., 2011). Various molecular diagnostic tests such as mutational analysis, methylation status of genomic DNA, and gene expression analysis may detect these changes.

Research uncovering the molecular mechanisms underlying cancer improves our understanding of how to select and design optimal treatment regimes for a patient's disease based on the molecular makeup of his or her particular cancer. Over the past few years, this has led to a significant increase in the development of therapies specifically targeting gene mutations involved in disease progression. In parallel, the use of molecular diagnostic testing for cancer diagnosis, prognosis and treatment selection has expanded, driven by the need for more cost efficient applications of expensive therapies. Current molecular diagnostics has so far almost exclusively relied on assaying cancer cells from tissue biopsy by needle aspiration or surgical resection.

However, the ability to perform these tests using a blood sample is sometimes more desirable than using a tissue sample from a cancer patient because, frequently, fresh tissue samples are difficult or impossible to obtain, and archival tissue samples are often less relevant to the current status of the patient's disease. A less invasive approach using a more easily accessible biological sample, e.g., a blood sample, has wide ranging implications in terms of patient welfare, the ability to conduct longitudinal disease monitoring, and the ability to obtain expression profiles even when tissue cells are not easily accessible, e.g., in ovarian or brain cancer patients.

Currently, gene expression profiling of blood samples involves the analysis of RNA extracted from peripheral blood mononuclear cells (PBMC) (Hakonarson et al., 2005) or circulating tumor cells (CTC) (Cristofanilli and Mendelsohn, 2006).

Many types of cancer cells release an abundance of small membrane-bound vesicles, which have been observed on their surface in culture (Skog et al., 2008). These microvesicles are generated and released through several processes and vary in size (from about 30 nm to about 1 μm in diameter) and content (Simons and Raposo, 2009). Microvesicles can bud/bleb off the plasma membrane of cells, much like retrovirus particles (Booth et al., 2006), be released by fusion of endosomal-derived multivesicular bodies with the plasma membrane (Lakkaraju and Rodriguez-Boulan, 2008), or be formed as apoptotic bodies during programmed cell death (Halicka et al., 2000). In addition, defective (i.e., non-infectious without helper-virus) retrovirus particles derived from human endogenous retroviral (HERV) elements may be found within microvesicle populations (Voisset et al., 2008).

Microvesicles from various cell sources have been studied with respect to protein and lipid content (Iero et al., 2008; Thery et al., 2002; Wieckowski and Whiteside, 2006). They have also been observed to contain cellular RNAs and mitochondria DNA (Baj-Krzyworzeka et al., 2006; Guescini et al.; Skog et al., 2008; Valadi et al., 2007) and may facilitate the transfer of genetic information between cells and/or act as a "release hatch" for DNA, RNA, and/or proteins that the cell is trying to eliminate. Both mRNA and miRNA in microvesicles are observed to be functional following uptake by recipient cells (Burghoff et al., 2008; Deregibus et al., 2007; Ratajczak et al., 2006; Skog et al., 2008; Valadi et al., 2007; Yuan et al., 2009) and it has also been shown that apoptotic bodies can mediate horizontal gene transfer between cells (Bergsmedh et al., 2001).

Knowing the expression profile, mutational profile, or both expression and mutational profiles of individual cancer is helpful for personalized medicine as many drugs target specific pathways affected by the genetic status of the tumors. Detection of genetic biomarkers in blood samples from tumor patients is challenging due to the need for high sensitivity against a background of normal cellular nucleic acids found circulating in blood. Microvesicles released by tumor cells into the circulation can provide a window into the genetic status of individual tumors (Skog et al., 2008).

The present invention is directed to microvesicular nucleic acid profiles of microvesicle fractions obtained from a biological sample from a subject, methods for aiding in diagnosis, prognosis, patient monitoring, treatment selection, and risk assessment based on detecting the presence or absence of a genetic aberration in a nucleic acid profile, or changes in a polypeptide profile of a microvesicle fraction obtained from a biological sample from a patient, and therapeutic agents and methods of cancer treatment or prevention.

SUMMARY OF THE INVENTION

The present invention is based on the discovery of various types of cancer-related biological materials within microvesicles. The biological materials within microvesicles from a biological sample may be characterized and measured, and the results this analysis may be used to aid in biomarker discovery, as well as in diagnosis, prognosis, monitoring, treatment selection, or risk assessment for a disease or other medical condition.

In one aspect, the biological materials are nucleic acids and the invention is a method for assaying a biological sample comprising the steps of: a) obtaining or using a microvesicle fraction from a biological sample from a subject; b) extracting nucleic acid from the fraction; and c) detecting the presence or absence of a biomarker in the extracted nucleic acid. In a method for aiding in the diagnosis, prognosis or monitoring of a subject, the biomarker is a genetic aberration that is associated with the diagnosis, prognosis, or determination of the status or stage of a disease or other medical condition in the subject. In a method for aiding in treatment selection for a subject in need of or potentially in need of therapeutic treatment, the biomarker is a genetic aberration that is associated with a disease or other medical condition or with responsiveness to a specific therapy for the disease or other medical condition in the subject. In a method for aiding in a determination of a subject's risk of developing a disease or other medical condition, the biomarker is a genetic aberration that is associated with the subject's risk of developing a disease or other medical condition.

In some embodiments of the above methods, the genetic aberration is in or corresponds to a c-myc gene, a transposable element, a retrotransposon element, a satellite correlated gene, a repeated DNA element, a non-coding RNA other than miRNA, or a fragment of any of the foregoing.

In other embodiments of the above methods, the genetic aberration is in or corresponds to a transposable element listed in Table 4 or Table 5, or a fragment thereof. For one example, the genetic aberration is in or corresponds to retrotransposon elements including LINE, SINE or HERV, or a fragment thereof. For another example, the genetic aberration is in or corresponds to a retrotransposon element that is Line1 (L1), ALU, HERV-H, HERV-K, HERV-K6, HERV-W or HERV-C, or a fragment thereof.

In further embodiments of the above methods, the genetic aberration is in or corresponds to a satellite-correlated gene listed in Table 6, or a fragment thereof; a repeated DNA element listed in Table 8, or a fragment thereof; or a non-coding RNA listed in Table 9 (other than miRNA) or a fragment thereof. The non-coding RNA, for example, can be 7SL RNA.

In yet further embodiments of the above methods, the genetic aberration is in or corresponds to a cancer gene listed in Table 2 or 3, or a fragment thereof.

In another aspect, the biological material is protein or polypeptide and the invention is a method for assaying a biological sample from a subject comprising the steps of: a) obtaining or using a microvesicle fraction from a biological sample from a subject b) measuring a protein or polypeptide activity in the fraction; and c) determining whether the protein or polypeptide activity is higher or lower than a normal or average activity for the same protein or polypeptide. In a method for aiding in the diagnosis, prognosis or monitoring of a subject, an elevated or lowered activity is associated with a diagnosis, prognosis, status or stage of a disease or other medical condition in the subject. In a method for aiding in directing treatment of a subject, an elevated or lowered activity is associated with a disease or other medical condition or with the subject's responsiveness to a specific therapy for the disease or other medical condition. In a method in aid of a determination of a subject's risk of developing a disease or other medical condition, an elevated or lowered activity is associated with the subject's risk of developing a disease or other medical condition. In some embodiments of the foregoing methods, the polypeptide is an enzyme. For example, the polypeptide can be a reverse transcriptase and the method is to determine whether the reverse transcriptase activity is higher than a normal or average activity for reverse transcriptase.

In the present invention, the methods may further comprise a step of enriching the microvesicle fraction for microvesicles originating from a specific cell type. The enrichment may be achieved, for example, by affinity purification with antibody-coated magnetic beads.

In the present invention, the biological sample from a subject can be a bodily fluid, e.g., blood, serum, plasma, or urine. The subject can be a human subject. When the subject is a human, the disease or other medical condition may be brain cancer such as medulloblastoma and glioblastoma, or melanoma.

In the present invention, the presence or absence of a biomarker in the extracted nucleic acid can be determined by various techniques, e.g., microarray analysis, PCR, quantitative PCR, Digital Gene Expression, or direct sequencing.

In yet another aspect, the present invention is a kit for genetic analysis of a microvesicle fraction obtained from a body fluid sample from a subject, comprising, in a suitable container, one or more reagents capable of hybridizing to or amplifying a nucleic acid corresponding to one or more of the genetic aberrations referenced above.

In yet another aspect, the present invention is an oligonucleotide microarray for genetic analysis of a microvesicle preparation from a body fluid sample from a subject, wherein the oligonucleotides on the array are designed to hybridize to one or more nucleic acids corresponding to one or more of the genetic aberrations referenced above.

In yet another aspect, the present invention is a profile of microvesicular nucleic acid derived from a bodily fluid sample from a subject. The profile may be a genetic aberration in or corresponding to: a) cancer gene listed in Table 2 or 3, or a fragment thereof; b) a transposable element from the subject's genome, preferably an element listed in Table 4 or 5, or a fragment of any of the foregoing; c) a retrotransposon element from the subject's genome, preferably LINE, SINE or HERV, more preferably LINE1 (L1), ALU, HERV-H, HERV-K, HERV-K6, HERV-W or HERV-C, or a fragment of any of the foregoing; d) a satellite correlated gene from the subject's genome, preferably a satellite correlated gene listed in Table 6, or a fragment of any of the foregoing; e) an element of repeated DNA from the subject's genome, preferably an element listed in Table 8, or a fragment of any of the foregoing; or f) a non-coding RNA other than miRNA, preferably a species listed in Table 9, or a fragment of any of the foregoing. In one embodiment, the profile is a genetic aberration in the cancer gene c-myc. In another embodiment, the profile is a genetic aberration in the non-coding 7SL RNA.

In all of the foregoing nucleic acid-related embodiments of the invention, the genetic aberration can be a species of nucleic acid, the level of expression of a nucleic acid, a nucleic acid variant; or a combination of any of the foregoing. For example, the genetic aberration may be an RNA expression profile. For another example, the genetic aberration may be a fragment of a nucleic acid, and in some instances, the fragment contains more than 10 nucleotides.

In yet another aspect, the present invention is a method of identifying a potential new nucleic acid biomarker associated with a disease or other medical condition, status or stage of disease or other medical condition, a subject's risk of developing a disease or other medical condition, or a subject's responsiveness to a specific therapy for a disease or other medical condition. The method comprises the steps of: a) obtaining or using a microvesicle fraction from a biological sample from a subject; b) extracting nucleic acid from the fraction; c) preparing a profile according to any of the above-described profiles; and d) comparing the profile of step c) to a control or reference profile and selecting one or more potential new biomarkers based on one or more differences between the profile of step c) and the control or reference profile.

In yet anther aspect, the present invention is a method of treating a subject having a form of cancer in which cancer cells secrete microvesicles. The method comprises administering to the subject a therapeutically effective amount of a composition including an inhibitor of microvesicle secretion; an inhibitor of a reverse transcriptase; a microvesicle neutralizer that neutralizes the pro-tumor progression activity of tumor microvesicles; or any combination of the forgoing. In some embodiments, the inhibitor of microvesicle secretion is an inhibitor of RAB GTPase which may be Rab 27a, Rab 27b or Rab 35. In other embodiments, the inhibitor of a reverse transcriptase is a nucleoside analog selected from the group comprising 3'-azido2',3'-dideoxythymidine (AZT); 2',3'-dideoxyinosine (ddT), 2',3'-didehyro-3'-deoxythymidine (d4T); nevirapine and efavirenz. In further embodiments, the inhibitor of a reverse transcriptase is RNAi targeting the reverse transcriptase gene. In still further embodiments, the microvesicle neutralizer is a biological agent that binds microvesicles and destroys the integrity of the microvesicles.

In yet another aspect, the present invention is a pharmaceutical composition comprising, in a suitable pharmaceutical carrier: a) an inhibitor of microvesicle secretion, particularly an inhibitor of RAB GTPase, and more particularly Rab 27a, Rab 27b or Rab 35); b) an inhibitor of reverse transcriptase, particularly a nucleoside analog, more particularly 3'-azido2',3'-dideoxythymidine (AZT); 2',3'-dideoxyinosine (ddI), 2',3'-didehydro-3'-deoxythymidine (d4T); nevirapine, or efavirenz, or an RNAi targeting the reverse transcriptase gene; c) a microvesicle neutralizer that neutralizes the pro-tumor progression activity of tumor microvesicles, particularly a biological agent that binds microvesicles and destroys the integrity of the microvesicles; or d) a combination of any of the foregoing.

BRIEF DESCRIPTION OF THE DRAWINGS

FIG. 25A depicts the profile of exoRNA from GBM 11/5 cells. Both 18S and 28S rRNA peaks are detectable (arrowheads). FIG. 25B depicts the profile of exoDNA GBM 11/5 cells. Sizes ranged from 25 to 1000 nucleotides with a peak at 200 nt. FIG. 25C depicts the profile of ExoRNA from human fibroblasts HF19, which was extracted and analyzed as in FIG. 25A. The RNA yield was too low to yield distinct 18S and 28S rRNA peaks. After concentration, these peaks were visible (data not shown). FIG. 25D depicts the profile of ExoDNA from human fibroblasts HF19, which was not readily detectable on the Bioanalyzer even after it was concentrated 30 times. Bioanalyzer profiles were generated using the RNA Pico Chip (Agilent).

FIG. 26A depicts the profile of exoDNA purified from externally DNase-treated microvesicles using the Agilent DNA 7500 bioanalyzer chip (Agilent Technologies Inc., Santa Clara, Calif. Cat. Number 5067-1506) that detects dsDNA. FIG. 26B depicts the profile of exoDNA after a second-strand synthesis treatment. Here the same sample as in (A) was subjected to second strand synthesis with Superscript Double-Stranded cDNA synthesis kit (Invitrogen) according to manufacturer's recommendation.

FIG. 29A depicts the results for c-Myc gene. FIG. 29B depicts the results for POU5F1B, which gene sequence (AF268618) is found 319 kb upstream of the c-Myc gene in the genome, but still within the commonly amplified region in tumor cells. The cell lines are medulloblastoma cell lines D458 and D384, glioblastomas (11/5), and fibroblasts HF19.

DETAILED DESCRIPTION OF THE INVENTION

Figure 1:
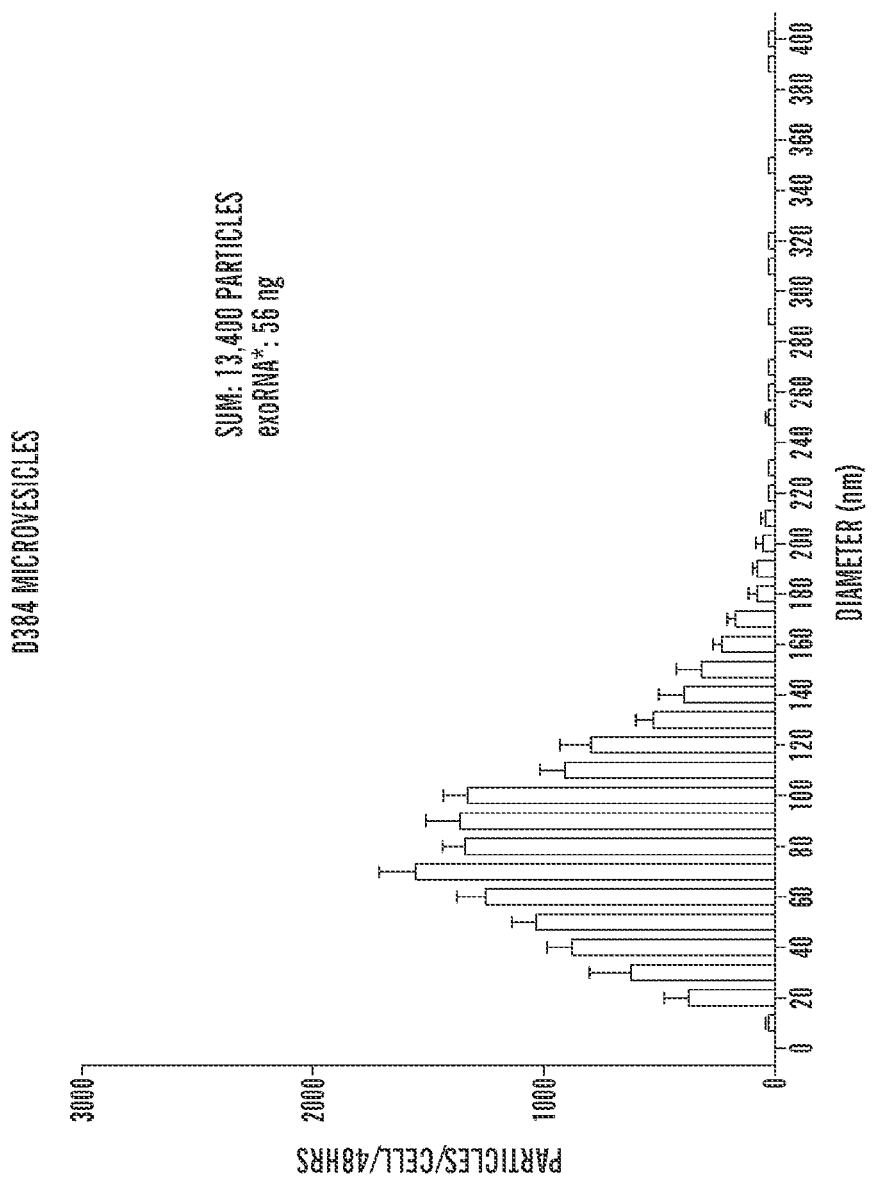
FIG. 1 shows a graph depicting the quantification, size distribution and RNA yield of microvesicles purified from the medulloblastoma cell line D384. Each bar represents the number of particles of a certain size that are present in the media and are released by one cell over 48 hours (hrs). The sum refers to the total number of particles released by one cell over 48 hrs. ExoRNA refers to the total RNA yield in microvesicles from $1 \times 10^6$ cells over 48 hrs. The result is presented as the mean±SEM (n=3).

As described above, cell-derived vesicles are heterogeneous in size with diameters ranging from about 10 nm to about 1 μm. For example, "exosomes" have diameters of approximately 30 to 100 nm, with shedding microvesicles and apoptotic bodies often described as larger (Orozco and Lewis, 2010). Exosomes, shedding microvesicles, microparticles, nanovesicles, apoptotic bodies, nanoparticles and membrane vesicles co-isolate using various techniques and will, therefore, collectively be referred to throughout this specification as "microvesicles" unless otherwise expressly denoted.

The present invention is based on the discovery that cancer-related biological materials such as transposable elements, oncogenes, and reverse transcriptase (RT) can be detected in microvesicles.

The biological materials in microvesicles can be genetic materials, protein materials, lipid materials, or any combination of genetic, protein and lipid materials.

Genetic materials include nucleic acids, which can be DNA and its variations, e.g., double-stranded DNA ("dsDNA"), single-stranded DNA ("ssDNA"), genomic DNA, cDNA; RNA and its variations, e.g., mRNA, rRNA, tRNA, microRNA, siRNA, piwi-RNA, coding RNA, non-coding RNA, transposons, satellite repeats, minisatellite repeats, microsatellite repeats, Interspersed repeats such as short interspersed nuclear elements (SINES), e.g. but not limited to Alus, and long interspersed nuclear elements (LINES), e.g. but not limited to LINE-1, human endogenous retroviruses (HERVs), e.g. but not limited to HERV-K; or any combination of any of the above DNA and RNA species.

Protein materials can be any polypeptides and polypeptide variants recognized in the art. For convenience, "polypeptide" as disclosed in this application refers to both a polypeptide without modifications and a polypeptide variant with modifications. Polypeptides are composed of a chain of amino acids encoded by genetic materials as is well known in the art. For example, a reverse transcriptase is a polypeptide that can function as an enzyme to transcribe RNA into DNA. Polypeptide variants can include, e.g. polypeptides modified by acylation, ubiquitination, SUMOYlation, alkylation, amidation, glycosylation, hydroxylation, carboxylation, phosphorylations, oxidation, sulfation, selenoylation, nitrosylation, or glutathionylation.

Lipid materials include fats, waxes, sterols, fat-soluble vitamins (such as vitamins A, D, E and K), monoglycerides, diglycerides, phospholipids, fatty acids, glycerolipids, glycerophospholipids, sphingolipids, sterol lipids, prenol lipids, saccharolipids, and polyketides.

Microvesicles may be isolated from tissue, cells or other biological samples from a subject. For example, the biological sample may be a bodily fluid from the subject, preferably collected from a peripheral location. Bodily fluids include but are not limited to blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the preferred bodily fluid for use as the biological sample is urine. In other embodiments, the preferred bodily fluid is serum.

The term "subject" is intended to include all animals shown to or expected to harbor nucleic acid-containing microvesicles. In particular embodiments, the subject is a mammal, e.g., a human or nonhuman primate, a dog, cat, horse, cow, other farm animal, or rodent (e.g. a mouse, rat, guinea pig, etc.). In one embodiment, the subject is an avian, amphibian or fish. The terms "subject," "individual" and "patient" are used interchangeably herein.

Methods for isolating microvesicles from a biological sample and extracting biological materials from the isolated microvesicles are described in this application as well as in scientific publications and patent applications, e.g. (Chen et al., 2010; Miranda et al., 2010; Skog et al., 2008). See also WO 2009/100029, WO 2011/009104, WO 2011/031892 and WO 2011/031877. These publications are incorporated herein by reference for their disclosure pertaining to isolation and extraction methods and techniques.

A profile, as used herein, refers to a set of data or a collection of characteristics or features, which can be determined through the quantitative or qualitative analysis of one or more biological materials, particularly biological materials contained in microvesicles isolated from a subject. The biological materials, extraction of the biological materials, and various types of analysis of the biological materials are described herein. A control or reference profile is a profile obtained from the literature, from an independent subject or subjects, or from the same subject at a different time point.

In one aspect, the present invention includes a profile of one or more nucleic acids extracted from microvesicles. The nucleic acids include both RNA and DNA. A nucleic acid profile may be an RNA profile, a DNA profile, or may include profiles of both RNA and DNA. In other aspects, the present invention includes a profile of one or more protein or polypeptide species extracted from microvesicles, particularly, a level of protein activity.

In all of the various aspects of the invention described herein in relation to RNA, the RNA can be coding RNA, e.g., messenger RNA. The RNA can also be non-coding RNA (ncRNA), e.g., ribosomal RNA (rRNA), transfer RNA (tRNA), microRNA, and other non-coding transcripts that may originate from genomic DNA. See Table 9 for more examples of non-coding RNA. Non-coding RNA transcripts may include transcripts from satellite repeats or from transposons, which may be Class I retrotransposons or Class II DNA transposons.

In all of the various aspects of the invention described herein in relation to DNA, the DNA can be single-stranded DNA, e.g., cDNA, which is reverse transcribed from RNA. Reverse transcription is usually mediated by reverse transcriptase encoded by a reverse transcriptase gene in a cell. The DNA can also be single stranded DNA generated during DNA replication. Genomic DNA replicates in the nucleus while the cell is dividing. Some of the replicated DNA may come off its template, be exported out of the nucleus, and packaged into microvesicles. The DNA can further be fragments of double-stranded DNA.

In addition, the DNA can be non-coding DNA (ncDNA). The human genome contains only about 20,000 protein-coding genes, representing less than 2% of the genome. The ratio of non-coding to protein-coding DNA sequences increases as a function of developmental complexity (Mattick, 2004). Prokaryotes have less than 25% ncDNA, simple eukaryotes have between 25-50%, more complex multicellular organisms like plants and animals have more than 50% ncDNA, with humans having about 98.5% ncDNA (Mattick, 2004)

Some of the ncDNA from the genome is transcribed into ncRNA. NcRNAs have been implicated in many important processes in the cell, e.g., enzymes (ribozymes), binding specifically to proteins (aptamers), and regulating gene activity at both the transcriptional and post-transcriptional levels. Examples of ncRNA classes and examples of their functions are shown in Table 9.

Many of the ncRNA species have multiple functions. For example, Ribonuclease P (RNase P) is a ribozyme which is involved in maturation of tRNA by cleaving the precursor tRNA, and nuclear RNaseP can also act as a transcription factor (Jarrous and Reiner, 2007). In addition, bifunctional RNAs have also been described that function both as mRNA and as regulatory ncRNAs (Dinger et al., 2008) or have two different ncRNA functions (Ender et al., 2008).

One example of the many long ncRNAs is the X-inactive specific transcript (Xist) expressed by the inactive X-chromosome, which is used to silence the extra X-chromosome in females (Ng et al., 2007). This RNA transcript binds to and inactivates the same X chromosome from which it is produced.

Another example is the HOX antisense intergenic RNA (HOTAIR) (Rinn et al., 2007). This RNA is expressed from chromosome 12, but controls gene expression on chromosome 2, affecting the skin phenotype on different parts of the body surface (Rinn et al., 2007) and also being involved in cancer metastasis (Gupta et al., 2010).

Yet another example of ncRNA is PCA3, a biomarker for prostate cancer (Day et al., 2011). PCA3 can be readily measured in the RNA from urine microvesicles which can be extracted using a rapid filtration concentrator method (Miranda et al., 2010; Nilsson et al., 2009). Another biomarker for prostate cancer is PCGEM1, which is an ncRNA transcript over-expressed in prostate cancer (Srikantan et al., 2000).

Yet another example of ncRNA is NEAT2/MALAT1, which has been found to be upregulated during metastasis of non-small cell lung cancer, and was correlated with poor patient survival (Ji et al., 2003).

Microvesicles contain a substantial array of the cellular gene expression profile from the cells from which they originate (their parent cells) at any given time. That is, substantially all the RNAs expressed in the parent cell are present within the microvesicle, although the quantitative levels of these RNAs may differ in the microvesicle compared to the parent cell. Substantially all the genes from the parent cell can, therefore, be tracked in the microvesicle fraction. In addition, microvesicles contain DNA from the parent cell, which corresponds to diagnostically relevant aspects of the subject's genome. Therefore, a nucleic acid profile from microvesicles may be associated with a disease or other medical condition.

In one embodiment, the disease is a neurological disease or other medical condition, e.g., Alzheimer's disease. The nucleic acid profile for Alzheimer's disease may be a profile of early-onset familial Alzheimer's disease, associated genes including, but not limited to, amyloid beta (A4) precursor protein gene, presenilin 1 and presenilin 2.

In another embodiment, the disease is a cancer. The microvesicular nucleic acid profile for cancer may, e.g., include nucleic acids of one or more cancer-related genes (e.g., known or suspected oncogenes or tumor suppressor genes; or genes whose expression levels correlate with the expression levels of nearby satellites). The determination of a cancer nucleic acid profile, including such cancer related genes, can aid in understanding the status of the cancer cells. In one embodiment, the oncogenes or tumor suppressor genes are one or more of those listed in Tables 2 and 3. In another embodiment, the cancer-related genes are one or more of those genes whose expression levels correlate with the expression levels of nearby satellites, such as but not limited to the satellite correlated genes listed in Table 6.

In some instances, the cancer-related gene is c-myc. The copy number of c-myc oncogene is usually increased in tumor cells, e.g., medullablastoma cells. The detection of increased c-myc gene copy number in microvesicles indicates an increased c-myc copy number in tumor cells that secret the microvesicles.

Figure 34:
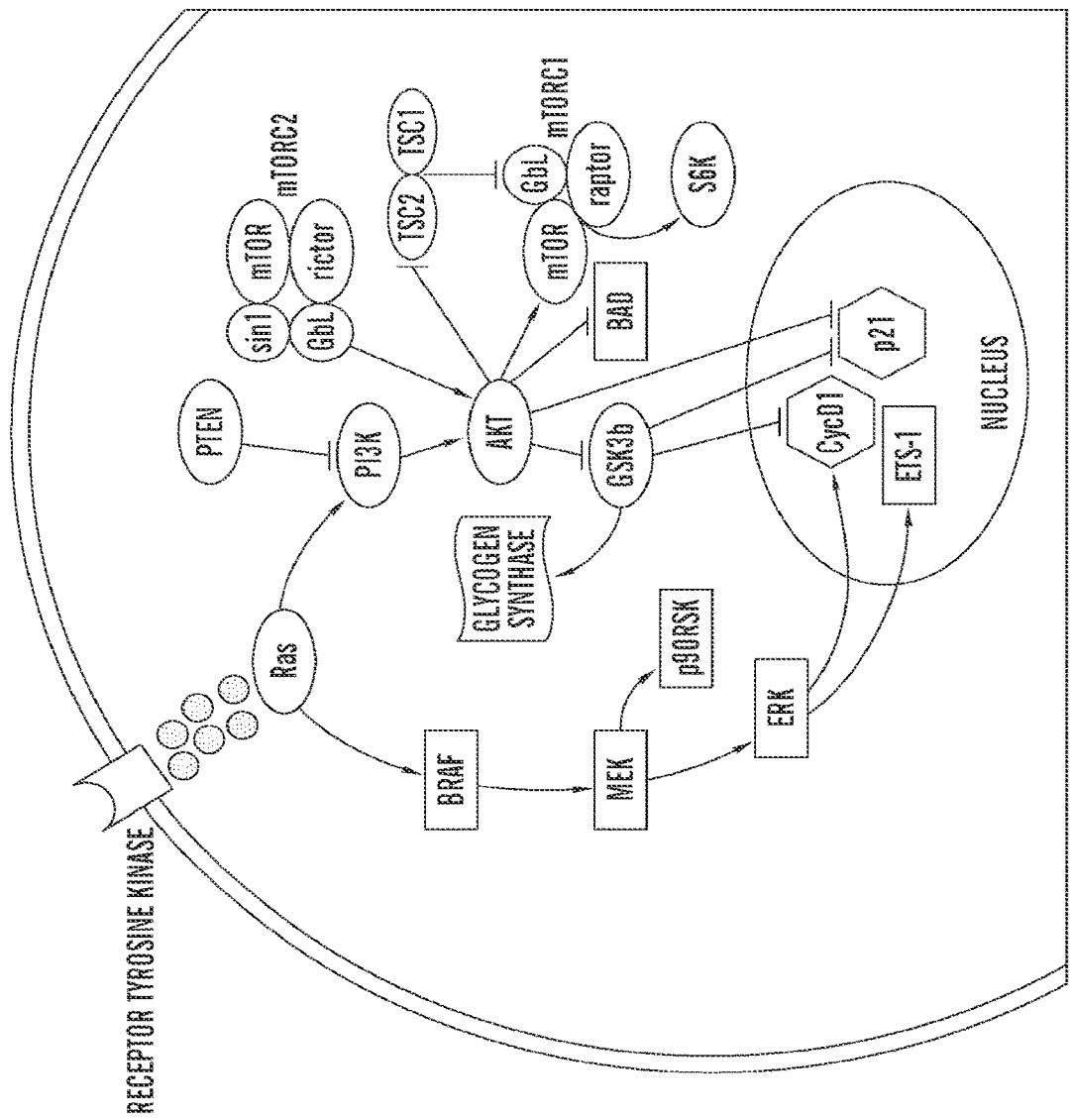
FIG. 34 depicts a series of signaling pathways related to cell proliferation, growth and/or survival.

In other instances, the cancer-related gene is one or more members in the signaling pathways depicted in FIG. 34. These signaling pathways control the growth, proliferation and/or survival of cells (Alessi et al., 2009; Dowling et al.; Hanahan and Weinberg, 2000; Sarbassov et al., 2006). These pathways are sometimes cross-linked to each other, and thus enable extracellular signals to elicit multiple biological effects. For example, the growth promoting Ras protein interacts with the survival promoting PI3K and thus growth signals can concurrently evoke survival signals in the cell (Hanahan and Weinberg, 2000).

For one example, the member is from the RAS/RAF/MEK/MAPK pathway related to melanoma, brain and lung cancers. The MAP kinase is a convergence point for diverse receptor-initiated signaling events at the plasma membrane. The RAS/RAF/MEK/MAPK pathway regulates cell proliferation, differentiation, migration and invasion (Hanahan and Weinberg, 2000). In addition, extracellular signal-regulated kinases (ERKs) become activated upon integrin ligation and, thereby, regulate cell migration (Klemke et al., 1997).

For another sample, the member is from the PI3K/PTEN/AKT pathway related to prostate, bladder and kidney cancers. The PI3K/PTEN/AKT pathway is responsible for regulating cell survival (Cheng et al., 2008). Genetic variations in AKT1, AKY2, PIK3CA, PTEN, and FRAP1 are associated with clinical outcomes in patients who receive chemoradiotherapy (Hildebrandt et al., 2009). Therefore, the determination of genetic variations in members of the pathway may help evaluating cancer treatment efficacy.

The microvesicular nucleic acid profile of the present invention may also reflect the nucleic acid profile of DNA repeats and/or transposable elements in cells from which the microvesicles originate.

DNA repeats include one or more repeated DNA elements that are composed of arrays of tandemly repeated DNA with the repeat unit being a simple or moderately complex sequence. The array of tandemly repeated DNA can be of varying size, thereby giving rise to categories of megasatellite, satellite, minisatellite and microsatellite repeats. See Table 7. Repeated DNA of this type is not transcribed and accounts for the bulk of the heterochromatic regions of the genome, being notably found in the vicinity of the centromeres (i.e., pericentromeric heterochromatin). The base composition, and therefore density, of such DNA regions is dictated by the base composition of constituent short repeat units and may diverge from the overall base composition of other cellular DNA. The nucleic acid profiles of the present invention comprising satellite repeats may include profiles of satellite repeat DNA and/or profiles of transcripts that are transcribed from satellite repeats.

DNA repeats may serve as biomarkers of cancer cells. For example, some satellite repeats like HSATII are over-expressed in many types of cancers including pancreatic, lung, kidney, ovarian and prostate cancers (Ting et al., 2011). The RNA expression level of such satellite repeats correlates with cancer disease status. DNA repeats encompassed within the scope of the present invention can be one or more of those recited in Table 8. In some embodiments, the DNA repeats may be HSATII, ALR, (CATTC)$_n$, or a combination of the HSATII, ALR, and (CATTC)$_n$.

Transposable elements encompassed within the scope of the present invention may be one or more DNA transposons and/or retrotransposons. The retrotransposon can be one or more of those recited in Tables 3 and 4. In other embodiments, the retrotransposon can be one or more LINEs, Alus, HERVs or a combination of the LINES, Alus and HERVs.

Transposable elements can serve as biomarkers of cancer cells. These repetitive elements constitute almost 50% of the human genome and include: half a million LINE-1 (L1) elements, of which about 100 are transcriptionally active and encode proteins involved in retrotransposition, including reverse transcriptase (RT) and integrase; a million Alu elements, which depend on L1 functions for integration; and thousands of provirus HERV sequences, some of which contain near-to-full length coding sequences (Goodier and Kazazian, 2008; Vois set et al., 2008). Without being bound by theory, increased expression of retrotransposon elements in cancer appears to result in part from overall hypomethylation of the genome, which is also associated with genomic instability (Daskalos et al., 2009; Estecio et al., 2007) and tumor progression (Cho et al., 2007; Roman-Gomez et al., 2008).

Increased transcription of retrotransposon elements in the human genome has been noted in a number of cancer cell types. For example, increased expression of L1 and HERV, as well as formation of retrovirus-like particles, has been reported in tumor tissue from breast cancer, melanoma, germ cell carcinoma and prostate cancer. See U.S. Pat. No. 7,776,523 and Bratthauer et al., 1994; Golan et al., 2008; Ruprecht et al., 2008. Retrotransposon RNA and proteins, as well as antibodies against HERV proteins and virus-like particles, have also been found in blood of some cancer patients (Contreras-Galindo et al., 2008; Kleiman et al., 2004; Ruprecht et al., 2008; Wang-Johanning et al., 2008).

High level expression of retrotransposon genes and/or endogenous reverse transcriptase are sometimes associated with cancer. For example, human LINE-1 p40 protein is often expressed at a higher level in breast cancer than in normal mammary gland (Asch et al., 1996). Thus, the microvesicular nucleic acid profiles of retrotransposable elements are suitable for use in aiding the diagnosis, prognosis, and/or monitoring of medical conditions such as cancer, as well as for use in aiding in treatment selection for therapies whose efficacy is affected by the subject's genetic make-up.

In one embodiment of the present invention, the microvesicular profile(s) of retrotransposable element(s) are determined by analyzing the content of microvesicles originating from brain cancer, e.g., medullablastoma, glioblastoma, lymphoma, and breast cancer cells. In one instance, the profile comprises one or more RNA expression levels of L1, Alu and HERV elements. In another instance, the profile comprises one or more DNA levels of L1 and HERV elements.

In one embodiment, the profile comprises a profile of the HERV-K element. For example, the profile may comprise the expression of the HERV-K element in microvesicles isolated from plasma from a subject. The expression of the HERV-K element may be assessed by determining the expression of any gene that the HERV-K element may encode, e.g., the group-specific antigen gene (gag), the protease gene (prt), the polymerase gene (pol), and the envelope gene (env) (Lower et al., 1996).

In one instance, the present invention may comprise a profile of the expression of the gag gene in microvesicles. The gag gene is from the HERV-K element and the profile of gag expression reflects the profile of HERV-K expression. The expression of the gag gene can be measured by methods known in the art, e.g., quantitative reverse transcription PCR analysis.

In another instance, the present invention may comprise a profile of the expression of the env gene in microvesicles. The env gene is from the HERV-K element and the profile of env expression reflects the profile of HERV-K expression. The expression of env gene can be measured by methods known in the art, e.g., quantitative reverse transcription PCR analysis.

In addition to the mRNA expression levels of one or more nucleic acids, the nucleic acid profiles of the present invention may also comprise the copy number of one or more nucleic acids, the fusion of several nucleic acids, the mutations of one or more nucleic acids, the alternative splicing of one or more nucleic acids, the methylation of one or more nucleic acids, and the single nucleotide polymorphism of one or more nucleic acids. The nucleic acids may correspond to genes, repeats, transposable elements, or other non-coding parts of the genomes of various organisms, including human beings.

The present invention encompasses all forms of cancer and pre-cancerous conditions. For example, without limitation, the present invention encompasses cancer and pre-cancer cells in brain, esophagus, lung, liver, stomach, ovary, testicle, kidney, skin, colon, blood, prostate, breast, uterus, and spleen.

The profile of nucleic acids can be obtained through analyzing nucleic acids obtained from isolated microvesicles according to standard protocols in the art.

In one embodiment, the nucleic acid is DNA. The analysis of the DNA may be performed by one or more various methods known in the art, including microarray analysis for determining the nucleic acid species in the extract, Quantitative PCR for measuring the expression levels of genes, DNA sequencing for detecting mutations in genes, and bisulfite methylation assays for detecting methylation patterns of genes.

In some embodiments of the present invention, data analysis may be performed by any of a variety of methods know in the art, e.g., Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination thereof.

In another embodiment, the nucleic acid extracted and analyzed from the microvesicles is RNA. In some instance, the RNA may be subject to Digital Gene Expression (DGE) analysis (Lipson et al., 2009). In this method, the RNA may be digested and converted into single stranded cDNA which may then be subject to sequencing analysis on a DNA sequencing machine, e.g., the HeliScope™ Single Molecule Sequencer from Helicos BioSciences as described in a publication by Ting et al. (Ting et al., 2011).

In other instances, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first step of reverse transcription to convert RNA into cDNA and a second step of quantifying the amount of cDNA using quantitative PCR.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extracted nucleic acids are analyzed directly, e.g., through next-generation sequencing.

The analysis of nucleic acids present in the isolated microvesicles can be quantitative, qualitative, or both quantitative and qualitative. For quantitative analysis, the amounts (expression levels), either relative or absolute, of specific nucleic acids of interest within the isolated microvesicles are measured with methods known in the art (some of which are described below). For qualitative analysis, the species of specific nucleic acids of interest within the isolated particles, whether wild type or variants, are identified with methods known in the art.

The present invention further encompasses methods of creating and using the microvesicular nucleic acid profiles described herein. In one embodiment of a method for creating a microvesicular profile, the method comprises the steps of isolating microvesicles from a biological sample (e.g., from a body fluid) obtained from a subject or obtaining a microvesicle fraction isolated from a biological sample obtained from a subject, extracting nucleic acids from the isolated microvesicles or microvesicle fraction (or obtaining such as extraction), and determining the profile of the nucleic acids in the extract.

The microvesicular profiles of the present invention may be used in methods of aiding diagnosis, prognosis, monitoring, therapy selection, or risk assessment of a disease or other medical condition for a subject as described herein and in the claims.

In some embodiments of the present invention, the one or more nucleic acid(s) may be one or more genes listed in Table 2 (cancer genes), Table 3 (cancer-related somatic mutations) and Table 6 (satellite-correlated genes). In one embodiment, the one or more nucleic acid(s) may be a fragment of a c-myc gene, for example, a fragment of c-myc gene containing more than 10 nucleotides. The fragment may contain incrementally longer sequences of 15, 20, 25, 30, 35, 40, 45, 50, 55, 60 nucleotides, up to the full length of the gene.

In other embodiments, the one or more nucleic acids may be one or more sequences listed in Table 4 (GBM transposable elements), Table 5 (human transposable elements) and Table 8 (repeated DNA). In one embodiment, the one or more nucleic acids may be L1, Alu, HERV, fragments thereof, or any combination of any of the foregoing. The fragment may contain incrementally longer sequences of 10, 15, 20, 25, 30, 35, 40, 45, 50, 55, 60 nucleotides up to the full length of each gene sequence.

In one embodiment, the invention comprises microvesicular profiles and methods based on microvesicular polypeptide species, polypeptide activities, or both the species and activities of polypeptides. The polypeptide may be any polypeptide in microvesicles. In some embodiments, the polypeptide is a reverse transcriptase. The activity of the reverse transcriptase (RT) can be measured by standard protocols known in the art. For example, the RT activity can be measured by the EnzChek RT Assay Kit (Invitrogen).

The human endogenous retrovirus K (HERV-K) reverse transcriptase may serve as a breast cancer prognostic marker (Golan et al., 2008). As such, one particular embodiment of the present invention encompasses profiles and related methods based on detecting the activity of HERV-K reverse transcriptase in microvesicles.

The present invention also includes a kit for genetic analysis of a microvesicle preparation from a biological sample (e.g., a bodily fluid sample) from a subject. The kit in a suitable container may include one or more reagents capable of hybridizing to or amplifying one or more nucleic acids extracted from microvesicles. In some embodiments, the nucleic acids correspond to one or more of those genes listed in Tables 2, 3, 4, 5, 6 and/or 8. In some further embodiments, the nucleic acids correspond to one or more RNA transcripts of one or more genes listed in Tables 2, 3, 4, 5, 6 and/or 8. In other further embodiments, the nucleic acid is DNA corresponding to one or more of the genes listed in Tables 2, 3, 4, 5, 6 and/or 8.

The present invention further includes an oligonucleotide microarray for genetic analysis of a microvesicle preparation from a body fluid sample from a subject, wherein the various oligonucleotides on the array are designed to hybridize exclusively to nucleic acids corresponding to one or more genes listed in Tables 2, 3, 4, 5, 6 and/or 8. The arrays can be made by standard methods known in the art. For example, SurePrint Technology (Agilent Technologies Corp.) may be used to make as many as 8 arrays on a single slide.

The present invention also includes a method of aiding the discovery of one or more biomarkers for a disease or other medical condition. The method may comprise, e.g., the steps of isolating microvesicles from subjects having a disease or other medical condition of interest and also from subjects who do not have the disease or other medical condition of interest; measuring the level of one or more target biological materials extracted from the isolated microvesicles from each of the subjects; comparing the measured levels of the one or more target biological materials from each of the subjects; and determining whether there is a statistically significant difference in the measured levels. The step of determination of a statistically significant difference in the measured levels identifies the one or more target biological materials as potential biomarkers for the disease or other medical condition. As an alternative to isolating microvesicles, the method may be carried out with pre-isolated microvesicle fractions.

The one or more biomarkers and nucleic acids in each of the various embodiments of the invention described herein can be one or a collection of genetic aberrations. The term "genetic aberration" is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs) (e.g., polymorphisms in Alu elements), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

Genetic aberrations can be found in many types of nucleic acids. The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006).

Nucleic acid modifications can be assayed by methods described in, e.g., U.S. Pat. No. 7,186,512 and patent publication WO/2003/023065. Particularly, methylation profiles may be determined by Illumina DNA Methylation OMA003 Cancer Panel.

SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590), nucleic acid sequencing, and combinations/modifications thereof.

Nucleic acid sequencing is to determine the base pair sequences of nucleic acids. Two traditional techniques for sequencing DNA are the Sanger dideoxy termination method (Sanger et al., 1977) and the Maxam-Gilbert chemical degradation method (Maxam and Gilbert, 1977). Both methods deliver four samples with each sample containing a family of DNA strands in which all strands terminate in the same nucleotide. Gel electrophoresis, or more recently capillary array electrophoresis is used to resolve the different length strands and to determine the nucleotide sequence, either by differentially tagging the strands of each sample before electrophoresis to indicate the terminal nucleotide, or by running the samples in different lanes of the gel or in different capillaries. Related methods using dyes or fluorescent labels associated with the terminal nucleotide have been developed, where sequence determination is also made by gel electrophoresis and automated fluorescent detectors. For example, the Sanger-extension method has recently been modified for use in an automated micro-sequencing system which requires only sub-microliter volumes of reagents and dye-labelled dideoxyribonucleotide triphosphates. U.S. Pat. No. 5,846,727.

More recently, high throughput DNA sequencing methods of various types have been developed and used to delineate nuclei acis sequences. These new methods are applied in sequencing machines including the 454 GenomeSequencer FLX instrument (Roche Applied Science), the lumina (Solexa) Genome Analyzer, the Applied Biosystems ABI SOLiD system, the Helicos single-molecule sequencing device (HeliScope), and the Ion semiconductor sequencing by Ion Torrent Systems Inc. See also US patent application publications No. 20110111401 and No. 20110098193. It is understood that as the sequencing technology evolves, the analysis of nucleic acids obtained in the invention may be performed using any new sequencing method as one skilled in the art sees appropriate.

Gene expression levels may be determined by the serial analysis of gene expression (SAGE) technique (Velculescu et al., 1995), quantitative PCR, quantitative reverse transcription PCR, microarray analysis, and next generation DNA sequencing as known in the art.

In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of such biomarkers in nucleic acids extracted from isolated microvesicles, according to the methods disclosed herein, may aid diagnosis of the disease or other medical condition in the subject.

For example, as described in WO 2009/100029, detection of the presence or absence of the EGFRvIII mutation in nucleic acids extracted from microvesicles isolated from a patient serum sample aided in the diagnosis and/or monitoring of glioblastoma in the patient. This is so because the expression of the EGFRvIII mutation is specific to some tumors and defines a clinically distinct subtype of glioma (Pelloski et al., 2007).

For another example, as described in WO 2009/100029, detection of the presence or absence of the TMPRSS2-ERG fusion gene, PCA-3, or both TMPRSS2-ERG and PCA-3 in nucleic acids extracted from microvesicles isolated from a patient's urine sample may aid in the diagnosis of prostate cancer in the patient.

Further, many biomarkers may be associated with disease or medical status monitoring in a subject. Therefore, the detection of the presence or absence of such biomarkers in a nucleic acid extraction from isolated microvesicles, according to the methods disclosed herein, may aid in monitoring the progress or reoccurrence of a disease or other medical condition in a subject.

For example, as described in WO 2009/100029, the determination of matrix metalloproteinase (MMP) levels in nucleic acids extracted from microvesicles isolated from an organ transplantation patient may be used to monitor the post-transplantation condition, as a significant increase in the expression level of MMP-2 after kidney transplantation may indicate the onset and/or deterioration of post-transplantation complications. Similarly, a significantly elevated level of MMP-9 after lung transplantation, suggests the onset and/or deterioration of bronchiolitis obliterans syndrome.

Many biomarkers have also been found to influence the effectiveness of treatment in a particular patient. Therefore, the detection of the presence or absence of such biomarkers in a nucleic acid extraction from isolated microvesicles, according to the methods disclosed herein, may aid in evaluating the efficacy of a given treatment in a given patient. For example, as disclosed in Table 1 in the publication by Furnari et al. (Furnari et al., 2007), biomarkers, e.g., mutations in a variety of genes, affect the effectiveness of specific medicines used in chemotherapy for treating brain tumors. The identification of these and other biomarkers in nucleic acids extracted from isolated particles from a biological sample from a patient can guide the skilled practitioner in the selection of treatment for the patient.

Without limitation, all of the methods mentioned above may further comprise the step of enriching the isolated microvesicles for microvesicles originating from a specific cell type. For example, the cell can be a cancer or pre-cancer cell.

Another aspect of the present invention is a method of treating a subject suffering from a form of cancer in which the cancer cells secret microvesicles. The method comprises administering to the subject a therapeutically effective amount of a composition comprising: an inhibitor of microvesicle secretion; an inhibitor of a reverse transcriptase; another microvesicle neutralizer that neutralizes the pro-tumor progression activity of tumor microvesicles; or any combination of the inhibitors/neutralizers.

In one embodiment, the inhibitor of microvesicle secretion is an inhibitor of the Rab GTPase pathway (Ostrowski et al.).

In some instances, the Rab GTPases are Rab 27a and Rab 27b. The inhibition of the Rab 27a and Rab 27b can be effectuated by silencing the Slp4 gene (also known as SYTL4, synaptotagmin-like 4) and the Slac2b gene (also known as EXPH5, exophilin5), respectively. Gene silencing techniques are well known in the art. One example of such a gene silencing technique is an RNA interference technique that selectively silences genes by delivering shRNA with viral vectors (Sliva and Schnierle).

In other instances, the Rab GTPase is Rab35. The inactivation of Rab35 decreases microvesicle secretion. Therefore, silencing Rab35 may decrease the secretion of microvesicles by cells. Inactivation of Rab35 may be achieved by administering TBC1D10B (TBC1 domain family, member 10B) polypeptide (Sliva and Schnierle).

In another embodiment, instead of, or in addition to, inhibiting microvesicle secretion, the reverse transcriptase activity is inhibited by administration of an RT inhibitor. RT inhibitors may be any one of 3'-azido2',3'-dideoxythymidine (AZT), 2',3'-dideoxyinosine (ddI), 2',3'-didehyro-3'-deoxythymidine (d4T), nevirapine and efavirenz.

Further, a microvesicle neutralizer may be used to block the effects of microvesicles. For example, such neutralizer may bind to microvesicles and destroy the integrity of microvesicles so that the biological materials in microvesicles are not transferred to other intact cells.

It should be understood that this invention is not limited to the particular methodologies, protocols and reagents, described herein, which may vary. The terminology used herein is for the purpose of describing particular embodiments only, and is not intended to limit the scope of the present invention, which is defined solely by the claims.

The contents of earlier filed provisional applications U.S. Ser. No. 61/378,860, filed Aug. 31, 2010, U.S. Ser. No. 61/421,421, filed Dec. 9, 2010, U.S. Ser. No. 61/437,547, filed Jan. 28, 2011, U.S. Ser. No. 61/438,199, filed Jan. 31, 2011, and 61/493,261 filed Jun. 3, 2011 are herein incorporated by reference in their entirety.

All patents, patent applications, and publications cited herein are expressly incorporated herein by reference for the purpose of describing and disclosing, for example, the methodologies and techniques described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method for assaying a biological sample from a subject in aid of diagnosis, prognosis or monitoring of a disease or other medical condition in the subject, comprising the steps of:
   a. obtaining or using a microvesicle fraction from a biological sample from a subject;
   b. extracting nucleic acid from the fraction; and
   c. detecting the presence or absence of a biomarker in the extracted nucleic acid; wherein the biomarker is a genetic aberration associated with diagnosis, prognosis, status or stage of a disease or other medical condition, and wherein the genetic aberration is in or corresponds to:
      i. a c-myc gene;
      ii. a transposable element;
      iii. a retrotransposon element;
      iv. a satellite correlated gene;
      v. a repeated DNA element;
      vi. non-coding RNA other than miRNA; or
      vii. a fragment of any of the foregoing.
2. The method of paragraph 1, wherein the genetic aberration is in or corresponds to a transposable element listed in Table 4 or Table 5, or a fragment thereof.
3. The method of paragraph 1, wherein the genetic aberration is in or corresponds to a retrotransposon element that is LINE, SINE or HERV, or a fragment thereof.
4. The method of paragraph 3, wherein the genetic aberration is in or corresponds to a retrotransposon element that is Line1 (L1), ALU, HERV-H, HERV-K, HERV-K6, HERV-W or HERV-C, or a fragment thereof.
5. The method of paragraph 1, wherein the genetic aberration is in or corresponds to a satellite correlated gene listed in Table 6, or a fragment thereof.
6. The method of paragraph 1, wherein the genetic aberration is in or corresponds to a repeated DNA element listed in Table 8, or a fragment thereof.
7. The method of paragraph 1, wherein the genetic aberration is in or corresponds to a non-coding RNA listed in Table 9 (or a fragment thereof), other than miRNA.
8. The method of paragraph 7, wherein the non-coding RNA is 7SL.
9. A method for assaying a biological sample from a subject in aid of directing treatment of the subject for a disease or other medical condition, comprising the steps of:
   a. obtaining or using a microvesicle fraction from a biological sample from a subject;
   b. extracting nucleic acid from the fraction; and
   c. detecting the presence or absence of a biomarker in the extracted nucleic acid; wherein the biomarker is a genetic aberration associated with a disease or other medical condition or with responsiveness to a specific therapy for the disease or other medical condition, and wherein the genetic aberration is in or corresponds to:
      i. a c-myc gene;
      ii. a transposable element;
      iii. a retrotransposon element;
      iv. a satellite correlated gene;
      v. a repeated DNA element;
      vi. non-coding RNA other than miRNA; or
      vii. a fragment of any of the foregoing.
10. The method of paragraph 9, wherein the genetic aberration is in or corresponds to a transposable element listed in Table 4 or Table 5, or a fragment thereof.
11. The method of paragraph 9, wherein the genetic aberration is in or corresponds to a retrotransposon element that is LINE, SINE or HERV, or a fragment thereof.
12. The method of paragraph 11, wherein the genetic aberration is in or corresponds to a retrotransposon element that is Line1 (L1), ALU, HERV-H, HERV-K, HERV-K6, HERV-W or HERV-C, or a fragment thereof.
13. The method of paragraph 9, wherein the genetic aberration is in or corresponds to a satellite correlated gene listed in Table 6, or a fragment thereof.
14. The method of paragraph 9, wherein the genetic aberration is in or corresponds to a repeated DNA element listed in Table 8, or a fragment thereof.
15. The method of paragraph 9, wherein the genetic aberration is in or corresponds to a non-coding RNA listed in Table 9 (or a fragment thereof), other than miRNA.
16. The method of paragraph 15, wherein the non-coding RNA is 7SL.
17. A method for assaying a biological sample from a subject in aid of a determination of the subject's risk of developing a disease or other medical condition, comprising the steps of:
    a. obtaining or using a microvesicle fraction from a biological sample from a subject;
    b. extracting nucleic acid from the fraction; and
    c. detecting the presence or absence of a biomarker in the extracted nucleic acid, wherein the biomarker is a genetic aberration associated with a determination of the subject's risk of developing a disease or other medical condition, and wherein the genetic aberration is in or corresponds to:
       i. a c-myc gene;
       ii. a transposable element;
       iii. a retrotransposon element;
       iv. a satellite correlated gene;
       v. a repeated DNA element;
       vi. non-coding RNA other than miRNA; or
       vii. a fragment of any of the foregoing.
18. The method of paragraph 17, wherein the genetic aberration is in or corresponds to a transposable element listed in Table 4 or Table 5, or a fragment thereof.
19. The method of paragraph 17, wherein the genetic aberration is in or corresponds to a retrotransposon element that is LINE, SINE or HERV, or a fragment thereof.
20. The method of paragraph 19, wherein the genetic aberration is in or corresponds to a retrotransposon element that is Line1 (L1), ALU, HERV-H, HERV-K, HERV-K6, HERV-W or HERV-C, or a fragment thereof.
21. The method of paragraph 17, wherein the genetic aberration is in or corresponds to a satellite correlated gene listed in Table 6, or a fragment thereof.
22. The method of paragraph 17, wherein the genetic aberration is in or corresponds to a repeated DNA element listed in Table 8, or a fragment thereof.
23. The method of paragraph 17, wherein the genetic aberration is in or corresponds to a non-coding RNA listed in Table 9 (or a fragment thereof), other than miRNA.
24. The method of paragraph 23, wherein the non-coding RNA is 7SL.
25. A method for assaying a biological sample from a subject in aid of diagnosis, prognosis or monitoring of a disease or other medical condition in the subject, comprising the steps of:

a. obtaining or using a microvesicle fraction from a biological sample from a subject;
b. extracting nucleic acid from the fraction; and
c. detecting the presence or absence of a biomarker in the extracted nucleic acid; wherein the biomarker is a genetic aberration associated with diagnosis, prognosis, status or stage of a disease or other medical condition, and wherein the genetic aberration is in or corresponds to a cancer gene listed in Table 2 or 3, or a fragment thereof.

26. A method for assaying a biological sample from a subject in aid of directing treatment of the subject for a disease or other medical condition, comprising the steps of:
a. obtaining or using a microvesicle fraction from a biological sample from a subject;
b. extracting nucleic acid from the fraction; and
c. detecting the presence or absence of a biomarker in the extracted nucleic acid; wherein the biomarker is a genetic aberration associated with a disease or other medical condition or with responsiveness to a specific therapy for the disease or other medical condition, and wherein the genetic aberration is in or corresponds to a cancer gene listed in Table 2 or 3, or a fragment thereof 27. A method for assaying a biological sample from a subject in aid of a determination of the subject's risk of developing a disease or other medical condition, comprising the steps of:
a. obtaining or using a microvesicle fraction from a biological sample from a subject;
b. extracting nucleic acid from the fraction; and
c. detecting the presence or absence of a biomarker in the extracted nucleic acid; wherein the biomarker is a genetic aberration associated with a determination of the subject's risk of developing a disease or other medical condition, and wherein the genetic aberration is in or corresponds to a cancer gene listed in Table 2 or 3, or a fragment thereof.

28. A method for assaying a biological sample from a subject in aid of diagnosis, prognosis or monitoring of a disease or other medical condition in the subject, comprising the steps of:
a. obtaining or using a microvesicle fraction from a biological sample from a subject;
b. measuring a polypeptide activity in the fraction; and
c. determining whether the polypeptide activity is higher or lower than a normal or average activity for the polypeptide;
wherein an elevated or lowered activity is associated with diagnosis, prognosis, status or stage of a disease or other medical condition.

29. The method of paragraph 28, wherein the polypeptide is an enzyme.

30. The method of paragraph 29, wherein the enzyme is reverse transcriptase.

31. The method of paragraph 30, wherein step (c) involves determining whether the reverse transcriptase activity is higher than a normal or average activity for reverse transcriptase.

32. A method for assaying a biological sample from a subject in aid of directing treatment of the subject for a disease or other medical condition, comprising the steps of:
a. obtaining or using a microvesicle fraction from a biological sample from a subject;
b. measuring a polypeptide activity in the fraction; and
c. determining whether the polypeptide activity is higher or lower than a normal or average activity for the same polypeptide;
wherein an elevated or lowered activity is associated with a disease or other medical condition or with responsiveness to a specific therapy for the disease or other medical condition.

33. The method of paragraph 32, wherein the polypeptide is an enzyme.

34. The method of paragraph 33, wherein the enzyme is reverse transcriptase.

35. The method of paragraph 34, wherein step (c) involves determining whether the reverse transcriptase activity is higher than a normal or average activity for reverse transcriptase.

36. A method for assaying a biological sample from a subject in aid of a determination of the subject's risk of developing a disease or other medical condition, comprising the steps of:
a. obtaining or using a microvesicle fraction from a biological sample from a subject;
b. measuring a polypeptide activity in the fraction; and
c. determining whether the polypeptide activity is higher or lower than a normal or average activity for the same polypeptide;
wherein an elevated or lowered activity is associated with a subject's risk of developing a disease or other medical condition.

37. The method of paragraph 36, wherein the polypeptide is an enzyme.

38. The method of paragraph 37, wherein the enzyme is reverse transcriptase.

39. The method of paragraph 38, wherein step (c) involves determining whether the reverse transcriptase activity is higher than a normal or average activity for reverse transcriptase.

40. The method of any of paragraphs 1-27, wherein the genetic aberration is:
a. a species of nucleic acid;
b. the level of expression of a nucleic acid;
c. a nucleic acid variant; or
d. a combination of any of the foregoing.

41. The method of any of paragraphs 1-27, wherein the nucleic acid is RNA and the genetic aberration is an expression profile.

42. The method of any of paragraphs 1-27, wherein the fragment contains more than 10 nucleotides.

43. The method of any of paragraphs 1-39, wherein the biological sample is a bodily fluid.

44. The method of paragraph 43, wherein the bodily fluid is blood, serum, plasma, or urine.

45. The method of any of paragraphs 1-39, wherein the subject is a human subject.

46. The method of paragraph 45, wherein the disease or other medical condition is brain cancer.

47. The method of paragraph 46, wherein the brain cancer is medulloblastoma or glioblastoma.

48. The method of paragraph 45, wherein the disease or other medical condition is melanoma.

49. The method of any of paragraphs 1-27, wherein the step of detecting the presence or absence of a biomarker in the extracted nucleic acid comprises microarray analysis, PCR, quantitative PCR, Digital Gene Expression, or direct sequencing.

50. The method of any of paragraphs 1-39, further comprising the step of enriching the microvesicle fraction for microvesicles originating from a specific cell type.

51. A kit for genetic analysis of a microvesicle fraction obtained from a body fluid sample from a subject, comprising, in a suitable container, one or more reagents capable of hybridizing to or amplifying a nucleic acid corresponding to one or more of the genetic aberrations referenced in any of paragraphs 1-27.
52. An oligonucleotide microarray for genetic analysis of a microvesicle preparation from a body fluid sample from a subject, wherein the oligonucleotides on the array are designed to hybridize to one or more nucleic acids corresponding to one or more of the genetic aberrations referenced in any of paragraphs 1-27.
53. A profile of microvesicular nucleic acid derived from a bodily fluid sample from a subject, wherein the profile comprises a genetic aberration in or corresponding to a cancer gene listed in Table 2 or 3, or a fragment thereof.
54. The profile of paragraph 53, wherein the cancer gene is a c-myc gene.
55. A profile of microvesicular nucleic acid derived from a bodily fluid sample from a subject, wherein the profile comprises a genetic aberration in or corresponding to transposable element from the subject's genome, preferably an element listed in Table 4 or 5, or a fragment of any of the foregoing.
56. A profile of microvesicular nucleic acid derived from a bodily fluid sample from a subject, wherein the profile comprises a genetic aberration in or corresponding to a retrotransposon element from the subject's genome, preferably LINE, SINE or HERV, more preferably LINE1 (L1), ALU, HERV-H, HERV-K, HERV-K6, HERV-W or HERV-C, or a fragment of any of the foregoing.
57. A profile of microvesicular nucleic acid derived from a bodily fluid sample from a subject, wherein the profile comprises a genetic aberration in or corresponding to a satellite correlated gene from the subject's genome, preferably a satellite correlated gene listed in Table 6, or a fragment of any of the foregoing.
58. A profile of microvesicular nucleic acid derived from a bodily fluid sample from a subject, wherein the profile comprises a genetic aberration in or corresponding to an element of repeated DNA from the subject's genome, preferably an element listed in Table 8, or a fragment of any of the foregoing.
59. A profile of microvesicular nucleic acid derived from a bodily fluid sample from a subject, wherein the profile comprises a genetic aberration in or corresponding to non-coding RNA other than miRNA, preferably a species listed in Table 9, or a fragment of any of the foregoing.
60. The profile of paragraph 59, wherein the non-coding RNA is 7SL.
61. The profile of any of paragraphs 53-60, wherein the genetic aberration is:
    a. a species of nucleic acid;
    b. the level of expression of a nucleic acid;
    c. a nucleic acid variant; or
    d. a combination of any of the foregoing.
62. A method of identifying a potential new nucleic acid biomarker associated with a disease or other medical condition, status or stage of disease or other medical condition, a subject's risk of developing a disease or other medical condition, or a subject's responsiveness to a specific therapy for a disease or other medical condition, comprising the steps of:
    (a) obtaining or using a microvesicle fraction from a biological sample from a subject;
    (b) extracting nucleic acid from the fraction;
    (c) preparing a profile according to any of paragraphs 53-60; and
    (d) comparing the profile of step (c) to a control or reference profile and selecting one or more potential new biomarkers based on one or more differences between the profile of step (c) and the control or reference profile.
63. A method of treating a subject having a form of cancer in which cancer cells secrete microvesicles, the method comprising administering to the subject a therapeutically effective amount of a composition comprising:
    a. an inhibitor of microvesicle secretion;
    b. an inhibitor of a reverse transcriptase;
    c. a microvesicle neutralizer that neutralizes the pro-tumor progression activity of tumor microvesicles; or
    d. any combination of the forgoing.
64. The method of paragraph 63, wherein the inhibitor of microvesicle secretion is an inhibitor of RAB GTPase.
65. The method of paragraph 64, where in the Rab GTPase is Rab 27a, Rab 27b or Rab 35.
66. The method of paragraph 63, wherein the inhibitor of a reverse transcriptase is a nucleoside analog selected from the group comprising 3'-azido2',3'-dideoxythymidine (AZT), 2',3'-dideoxyinosine (ddI), 2',3'-didehyro-3'-deoxythymidine (d4T), nevirapine and efavirenz.
67. The method of paragraph 63, wherein the inhibitor of a reverse transcriptase is RNAi targeting the reverse transcriptase gene.
68. The method of paragraph 63, wherein the microvesicle neutralizer is a biological agent that binds microvesicles and destroys the integrity of the microvesicles.
69. A pharmaceutical composition comprising, in a suitable pharmaceutical carrier: (a) an inhibitor of micro vesicle secretion, particularly an inhibitor of RAB GTPase, and more particularly Rab 27a, Rab 27b or Rab 35); (b) an inhibitor of reverse transcriptase, particularly a nucleoside analog, more particularly 3'-azido2',3'-dideoxythymidine (AZT), 2',3'-dideoxyinosine (ddI), 2',3'-didehyro-3'-deoxythymidine (d4T), nevirapine, or efavirenz, or an RNAi targeting the reverse transcriptase gene; (c) a microvesicle neutralizer that neutralizes the pro-tumor progression activity of tumor microvesicles, particularly a biological agent that binds microvesicles and destroys the integrity of the microvesicles; or (d) a combination of any of the foregoing.
1.

The invention is further illustrated by the following examples, which should not be construed as further limiting. Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

EXAMPLES

Example 1 Cultured Cells Release an Abundance of Microvesicles

We found that cultured tumor cells as well as normal cells release microvesicles. Here, we analyzed microvesicles produced by tumor cells from glioblastoma (GBM), a common and malignant brain tumor in adults; medulloblastoma, a common and malignant tumor in children with frequent amplification of c-Myc (Bigner et al., 1990); atypical teratoid rhabdoid tumor (AT/RT), a high-grade malignant tumor in children (Tez et al., 2008); and malignant melanoma, a peripheral tumor which can metastasize to the brain (Jemal et al., 2008). We analyzed microvesicles produced by epidermoid carcinoma cells as a control for the study. Increased expression of EGFR, but not c-Myc gene, was found in epidermoid carcinoma cells (Giard et al., 1973).

We cultured glioblastoma, medulloblastoma, melanoma and normal human fibroblast cells and monitored the release of microvesicles from each cell type. Specifically, primary GBM cell lines 20/3 and 11/5 were generated in our laboratory from tumor specimens kindly provided by Dr. Bob Carter (Massachusetts General Hospital), and diagnosed as GBM by a neuropathologist at Massachusetts General Hospital (Skog et al., 2008). Glioblastoma cells were cultured in Dulbecco modified essential medium (DMEM; Invitrogen, Carlsbad, Calif.) containing 10% fetal bovine serum (FBS; JRH Biosciences, Carlsbad, Calif.), and penicillin and streptomycin (10 IU/ml and 10 respectively; Cellgro, Herndon, Va.).

Primary medulloblastoma cell lines D458, D384 and D425, as well as rhabdoid AT/RT tumor cell line, NS224, were provided by Drs. Y.-J. Cho and S. L. Pomeroy (Children's Hospital, Boston, Mass.). All medulloblastoma cell lines were cultured in suspension in DMEM containing 10% FBS, 1× GlutaMAX (Invitrogen) and penicillin/streptomycin. Rhabdoid tumor cell line NS224 was cultured in suspension in DMEM/F12 containing B27 supplement, 20 ng/ml EGF, 20 ng/ml FGF and penicillin/streptomycin.

Melanoma cell line, Yumel 0106, was kindly provided by Dr. R. Halaban (Yale New Haven Hospital, New Haven, Conn.) and cultured in OptiMEM (Invitrogen) containing 10% FBS and penicillin/streptomycin. Epidermoid carcinoma cell line, A431 (ATCC) was kindly provided by Huilin Shao (Massachusetts General Hospital) and cultured in DMEM containing 10% FBS and penicillin/streptomycin.

Normal human fibroblast lines, HF19 and HF27 were derived from human skin biopsies in the Breakefield laboratory; L2131 was derived in Dr. Christine Klein's laboratory (Univ. Lübeck, Lübeck, Germany) and cultured in DMEM supplemented with 10% FBS, 10 mM HEPES (Invitrogen) and penicillin/streptomycin. All cells were grown in media with 5% exosome-depleted fetal bovine serum (dFBS) (Skog et al., 2008). All cell lines were used over a few passages, as microvesicle yield tended to change over extended passages.

To characterize the size distribution and amount of microvesicles released from tumor cells and normal fibroblasts in culture using Nanosight LM10 nanoparticle tracking analysis (NTA), we isolated microvesicles from the culture media of three medulloblastoma cell lines (D384, D425 and D458), one melanoma (Yumel 0106), two GBMs (20/3 and 11/5) and two normal fibroblasts (HF19 and HF27). The media was first spun at 500×g for 10 min. The supernatant was removed and spun again at 16,500×g, filtered through a 0.22 µm filter and used for Nanosight analysis. The nanosight LM10 nanoparticle characterization system (NanoSight Ltd, UK) equipped with a blue laser (405 nm) illumination was used for real-time characterization of the vesicles. The result is presented as the average±SEM of three independent experiments.

Figure 2:
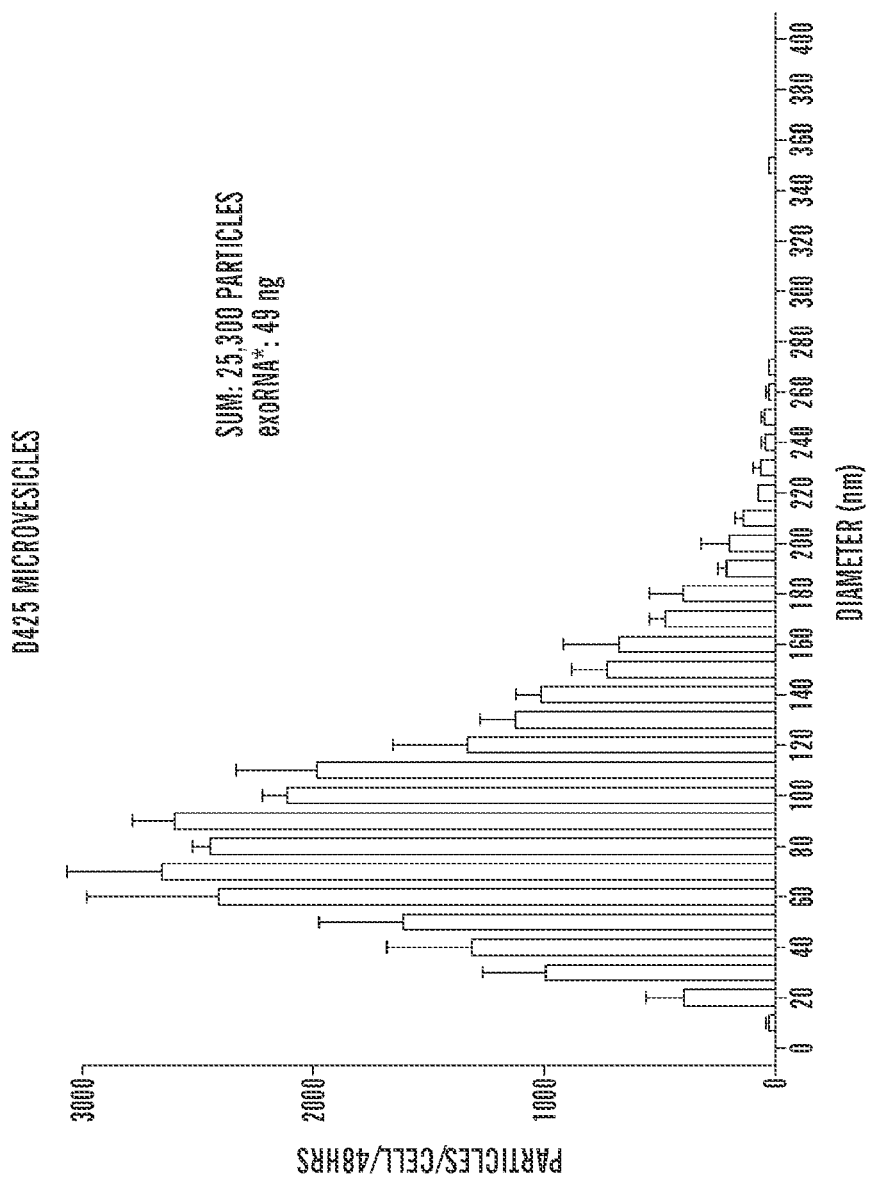
FIG. 2 shows a graph depicting the quantification, size distribution and RNA yield of microvesicles purified from the medulloblastoma cell line D425 in the same manner as in FIG. 1.
Figure 3:
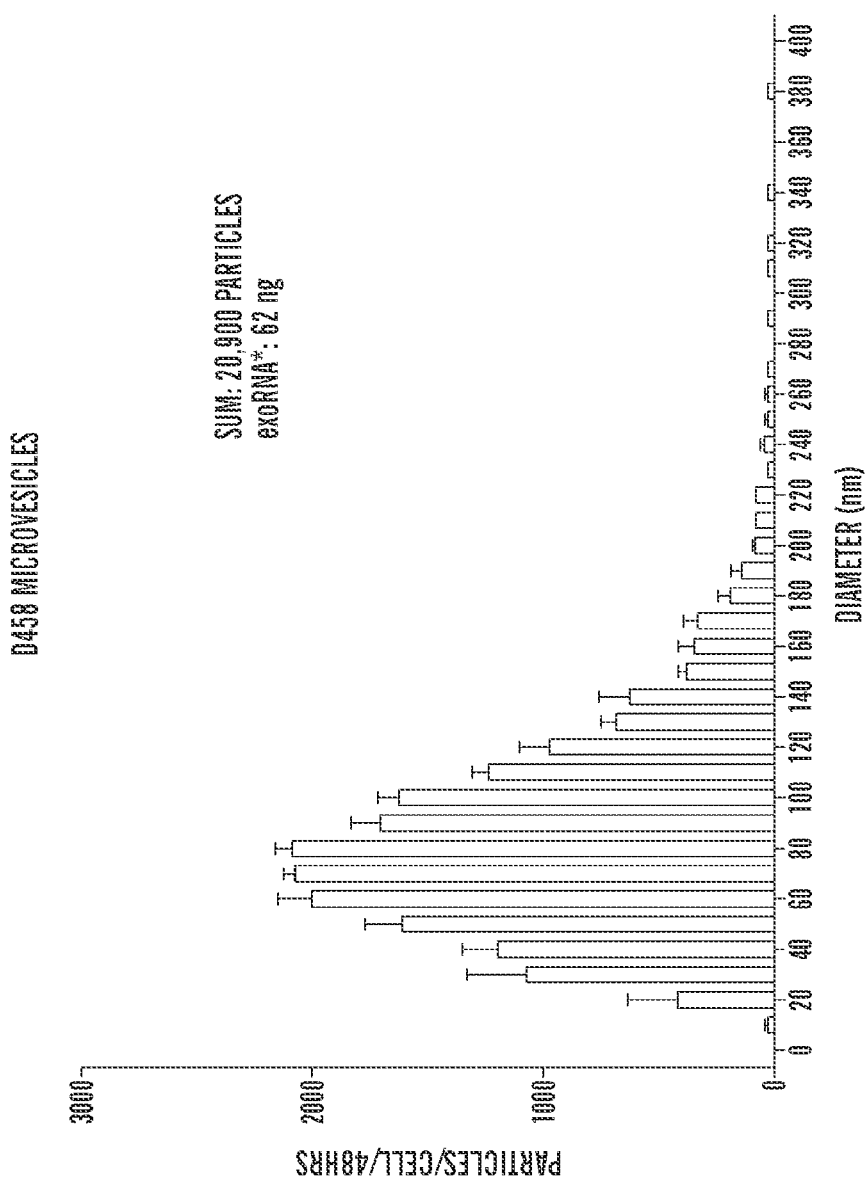
FIG. 3 shows a graph depicting the quantification, size distribution and RNA yield of microvesicles purified from the medulloblastoma cell line D458 in the same manner as in FIG. 1.
Figure 5:
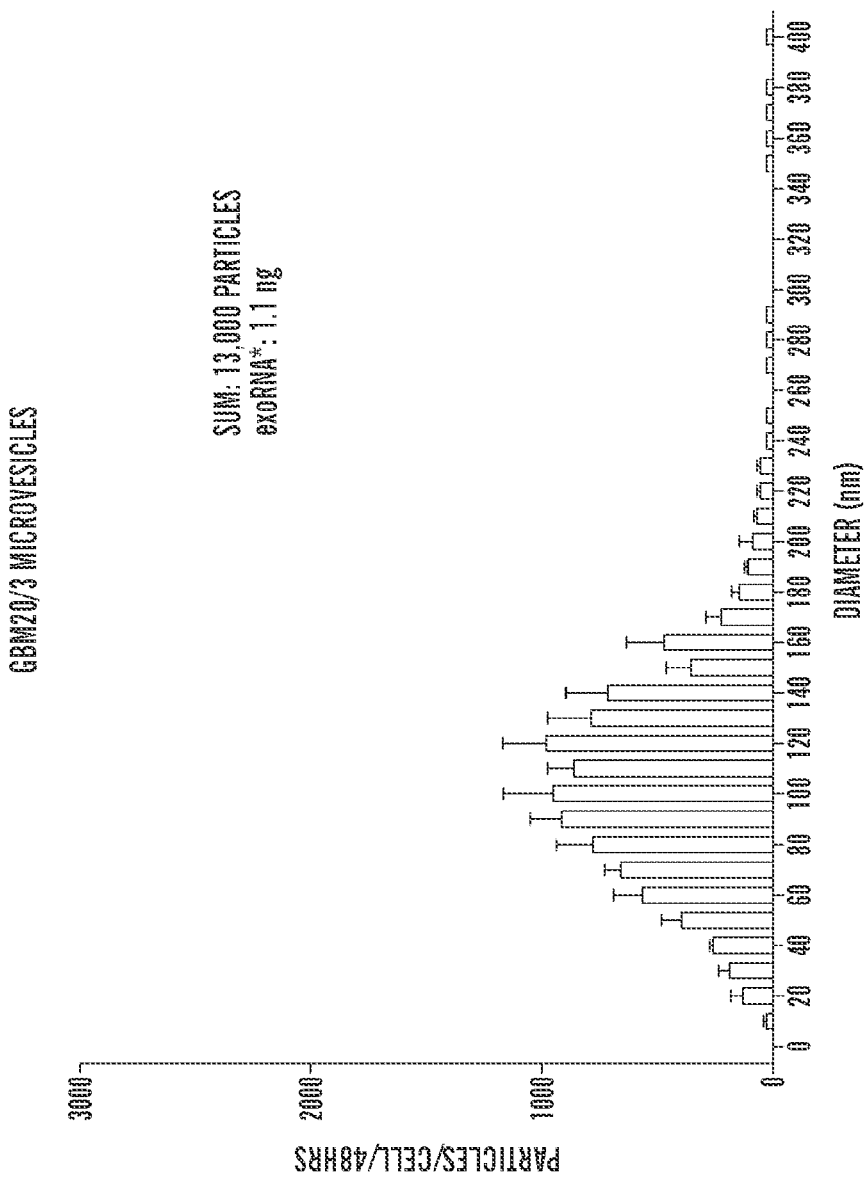
FIG. 5 shows a graph depicting the quantification, size distribution and RNA yield of microvesicles purified from the glioblastoma cell line 20/3 in the same manner as in FIG. 1.
Figure 6:
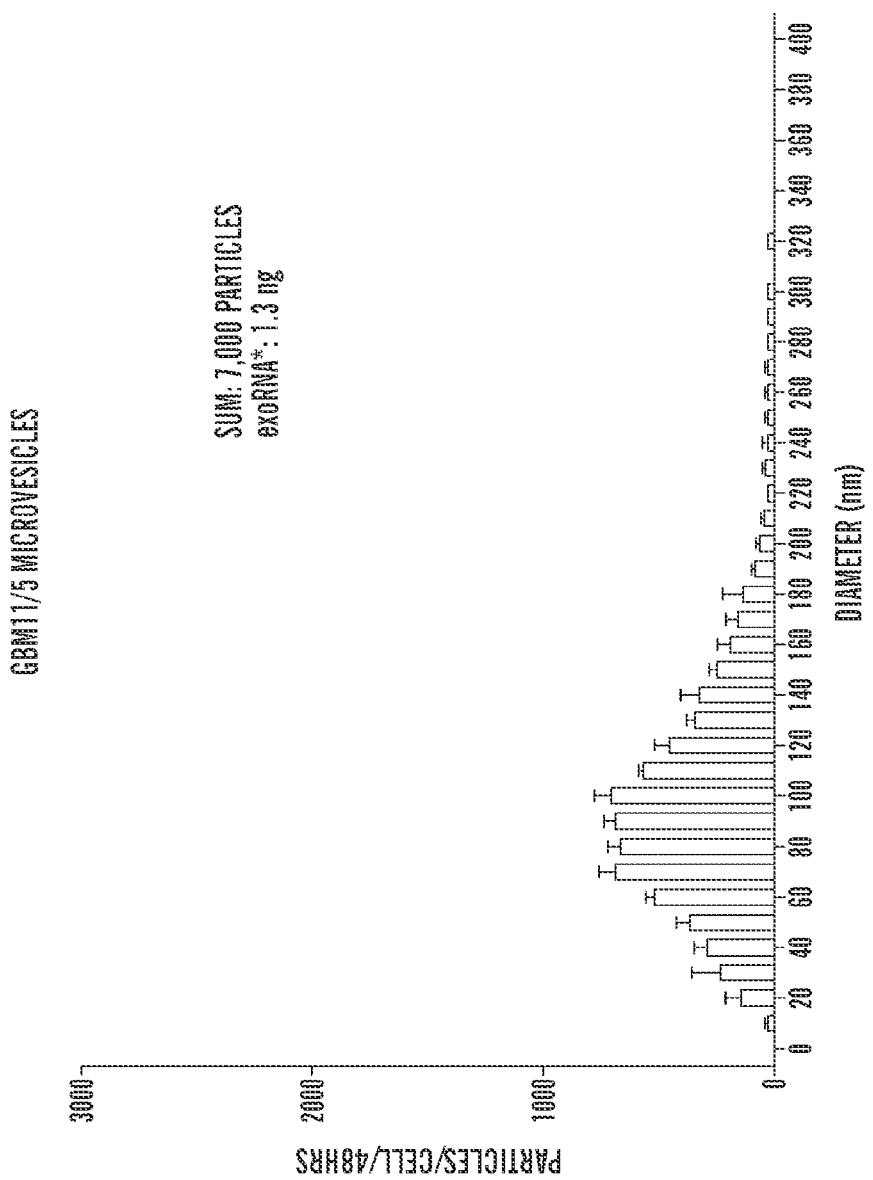
FIG. 6 shows a graph depicting the quantification, size distribution and RNA yield of microvesicles purified from the glioblastoma cell line 11/5 in the same manner as in FIG. 1.
Figure 7:
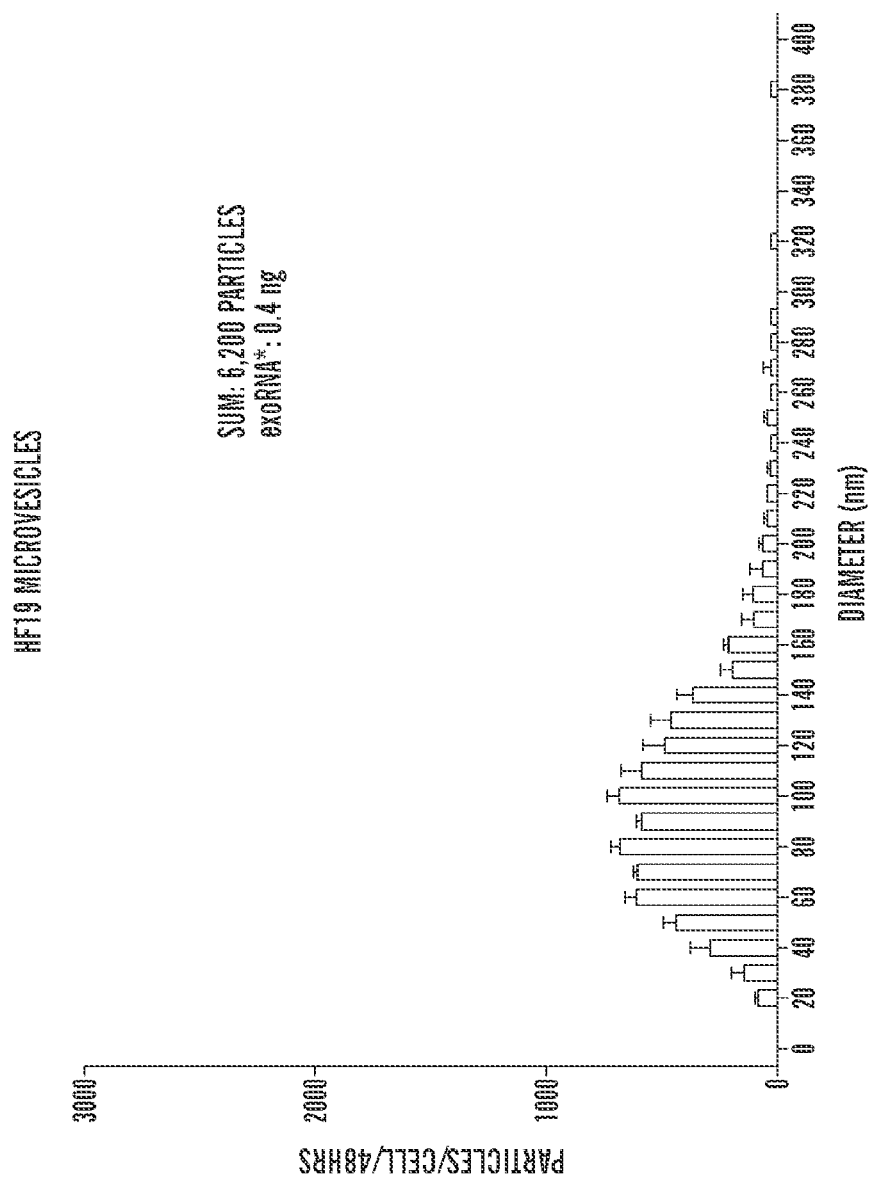
FIG. 7 shows a graph depicting the quantification, size distribution and RNA yield of microvesicles purified from the normal fibroblast cell line HF19 in the same manner as in FIG. 1.
Figure 8:
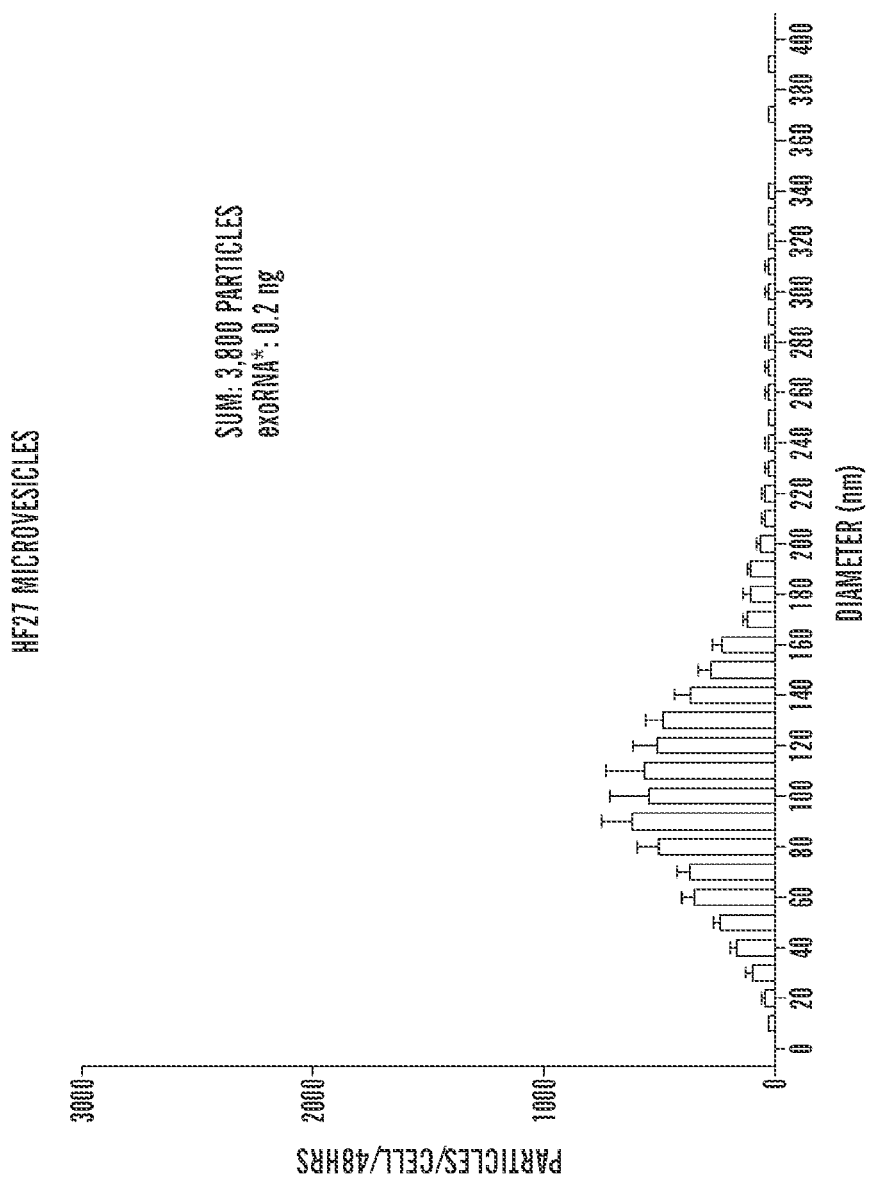
FIG. 8 shows a graph depicting the quantification, size distribution and RNA yield of microvesicles purified from the normal fibroblast cell line HF27 in the same manner as in FIG. 1.

We found that medulloblastoma cells released more microvesicles/cell than the other cells types analyzed. The amount of microvesicles released by each cell type was: 13,400-25,300/cell/48 hrs for medulloblastomas (FIGS. 1-3), 12,600/cell/48 hrs for the melanoma (FIG. 4), 7,000-13,000/cell/48 hrs for the GBM cells (FIGS. 5-6), and 3,800-6,200/cell/48 hrs for the normal human fibroblasts (FIG. 7-8). Normal human fibroblasts were of low passage and grew with similar rates as the tumor lines in culture, but were of larger size and hence greater surface area per cell.

To measure the amount of RNA in the microvesicles released in the culture media from these cells, we collected each conditioned medium after culturing for 48 hr and isolated microvesicles by differential centrifugation and filtration through a 0.22 µm filter followed by ultracentrifugation at 110,000×g as detailed in WO 2009/100029.

For purposes of RNA extraction from microvesicles, microvesicle pellets generated from 39 ml conditioned medium produced from $0.5 \times 10^6$-$3.5 \times 10^6$ cells over 48 hours were resuspended in 50 µL PBS and incubated at 37° C. for 30 min with DNAse I (DNA-Free™ kit, Ambion) and Exonuclease III (Fermentas, Glen Burnie, Md.), according to the manufacturer's instructions. After treatment, the enzymes were inactivated (using the kit's inactivation reagent and heat inactivation, respectively) and samples processed for RNA extraction.

Microvesicles were lysed in 300 µl MirVana lysis buffer (Ambion, Austin, Tex.) followed by extraction with an equal amount of acid-phenol:chloroform. After centrifugation at 10,000×g for 5 min, the upper aqueous phase was removed and further processed to extract RNA using the mirVana RNA isolation kit (Ambion), according to the manufacturer's instructions. RNA extracts were then treated with DNAse (DNA-free kit, Ambion) to exclude DNA carryover. RNA was quantified using a Nanodrop ND-1000 (Thermo Fisher Scientific, Waltham, Mass.) and the quantity and size ranges were evaluated using a 2100 Bioanalyzer (Agilent, Santa Clara, Calif.).

ExoRNA in microvesicles was measured using a 2100 Bioanalyzer (Agilent) with RNA 6000 Pico Chip for RNA. The Bioanalyzer RNA 6000 Pico Chip kit detects mainly single strand nucleic acids, but can also detect double strand DNA when present in large amounts. As shown in FIGS. 1-8, the amount of RNA in microvesicles (exoRNA) from medulloblastoma cells was 120- to 310-fold higher than the amount of exoRNA from normal fibroblasts; the amount of exoRNA from glioblastoma cells was 2.8- to 6.5-fold higher than from normal fibroblasts; and the amount from exoRNA from melanoma cells was similar to that from normal fibroblasts even though melanoma cells shed more than twice as many microvesicles. Thus, medulloblastoma tumor cells, in particular, release abundant microvesicles with a high content of exoRNA.

Example 2 Characterization of RNA and DNA in Microvesicles

To characterize the RNA and DNA in microvesicles, we isolated microvesicles from culture media of medulloblastoma cell line D384, glioblastoma cell line 11/5 and fibroblast cell line H19 as detailed in Example 1. Isolated microvesicles were treated extensively with DNase prior to nucleic acid extraction to reduce the chance of external DNA contamination. Isolated microvesicles may also be treated with RNase prior to nucleic acid extraction although such treatment did not affect the RNA yield from microvesicles probably due to the absence of any significant amounts of external RNA.

ExoRNA was extracted from isolated microvesicles as detailed in Example 1.

For exoDNA extraction, microvesicle pellets generated from 39 ml conditioned medium produced from $0.5 \times 10^6$-$3.5 \times 10^6$ cells over 48 hr were resuspended in 50 µL PBS and incubated at 37° C. for 30 min with DNAse I (DNA-Free™ kit, Ambion) and Exonuclease TIT (Fermentas, Glen Burnie, Md.), according to manufacturer's instructions. After treatment, the enzymes were inactivated (using the kit's inactivation reagent and heat inactivation, respectively) and samples processed for DNA extraction.

Microvesicles were lysed in 300 µl MirVana lysis buffer (Ambion, Austin, Tex.) followed by extraction with an equal amount of acid-phenol:chloroform. After centrifugation at 10,000×g for 5 min, the upper aqueous phase was removed and further processed to extract DNA using the Qiagen PCR purification kit according to manufacturer's instructions. DNA extracts were then treated with RNase (e.g., RNase A, Fermentas, Glen Burnie, Md.) to exclude RNA carryover. DNA were quantified using a Nanodrop ND-1000 (Thermo Fisher Scientific, Waltham, Mass.) and the quantity and size ranges were evaluated using a 2100 Bioanalyzer (Agilent, Santa Clara, Calif.). ExoDNA in microvesicles was measured using a 2100 Bioanalyzer (Agilent) with RNA 6000 Pico Chip and/or DNA 7500 LabChip kits. The Bioanalyzer RNA 6000 Pico Chip kit detects mainly single stranded ("ss") nucleic acids, but can also detect double-stranded DNA (dsDNA) when present in large amounts, while the DNA 7500 LabChip kit only detects dsDNA. S1 nuclease (200 U/ml; Fermentas) was also used to digest single stranded nucleic acid at 37° C. for 30 min. Genomic cell DNA was isolated from cells with the Flexigene DNA kit (Qiagen, Valencia, Calif.), according to manufacturers' recommendation.

Figure 25A:
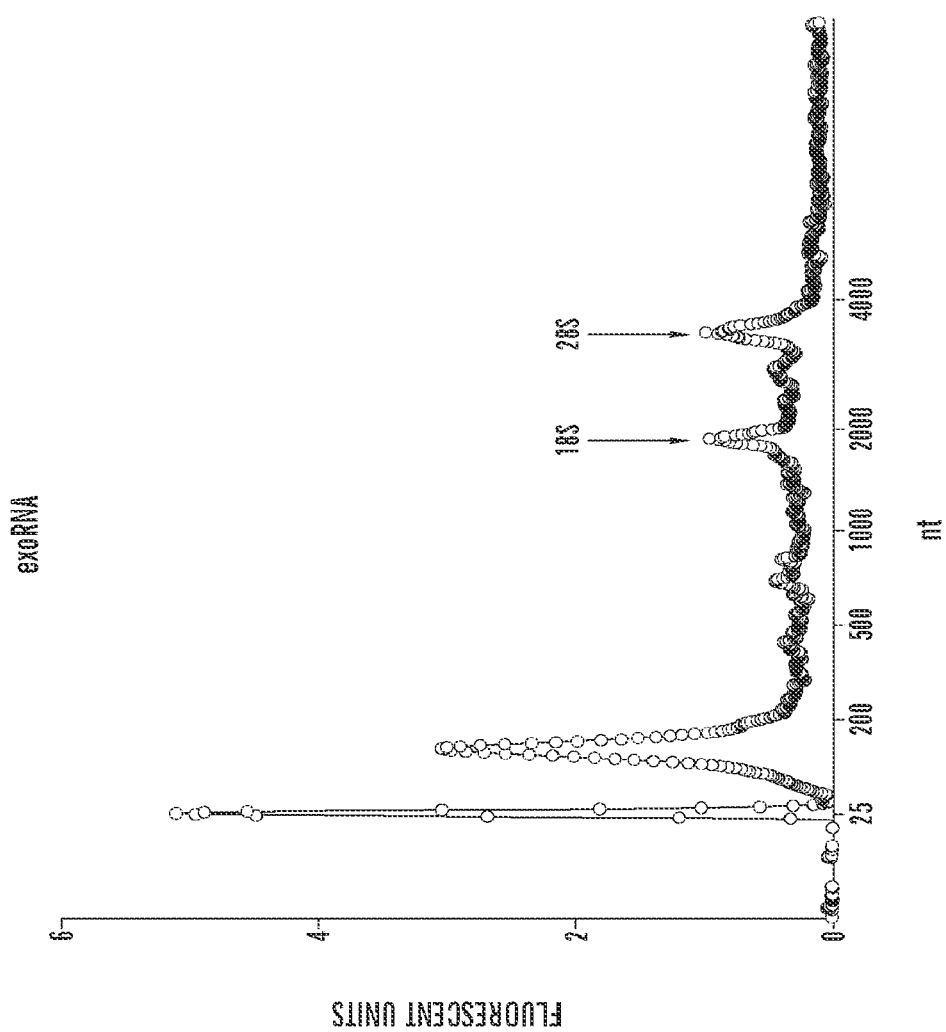
FIGS. 25A, 25B, 25C and 25D show charts depicting Bioanalyzer profiles of exoRNA and exoDNA from tumor or normal cell.
Figure 25B:
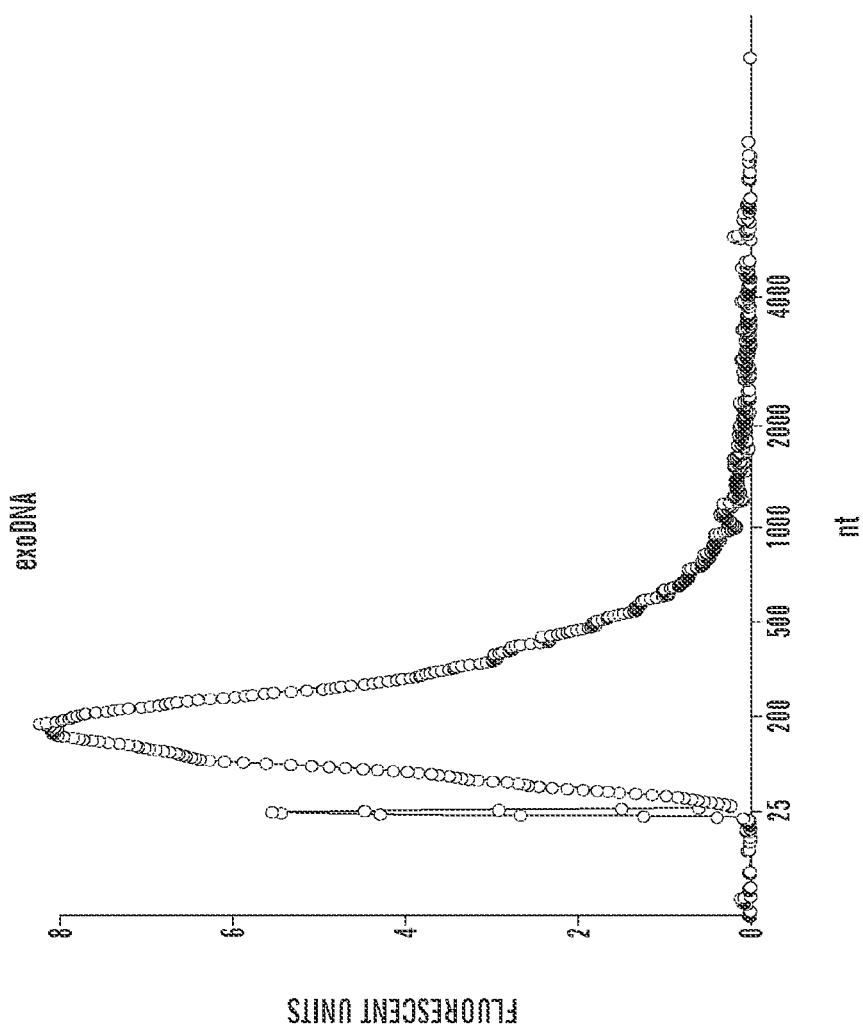
Figure 25C:
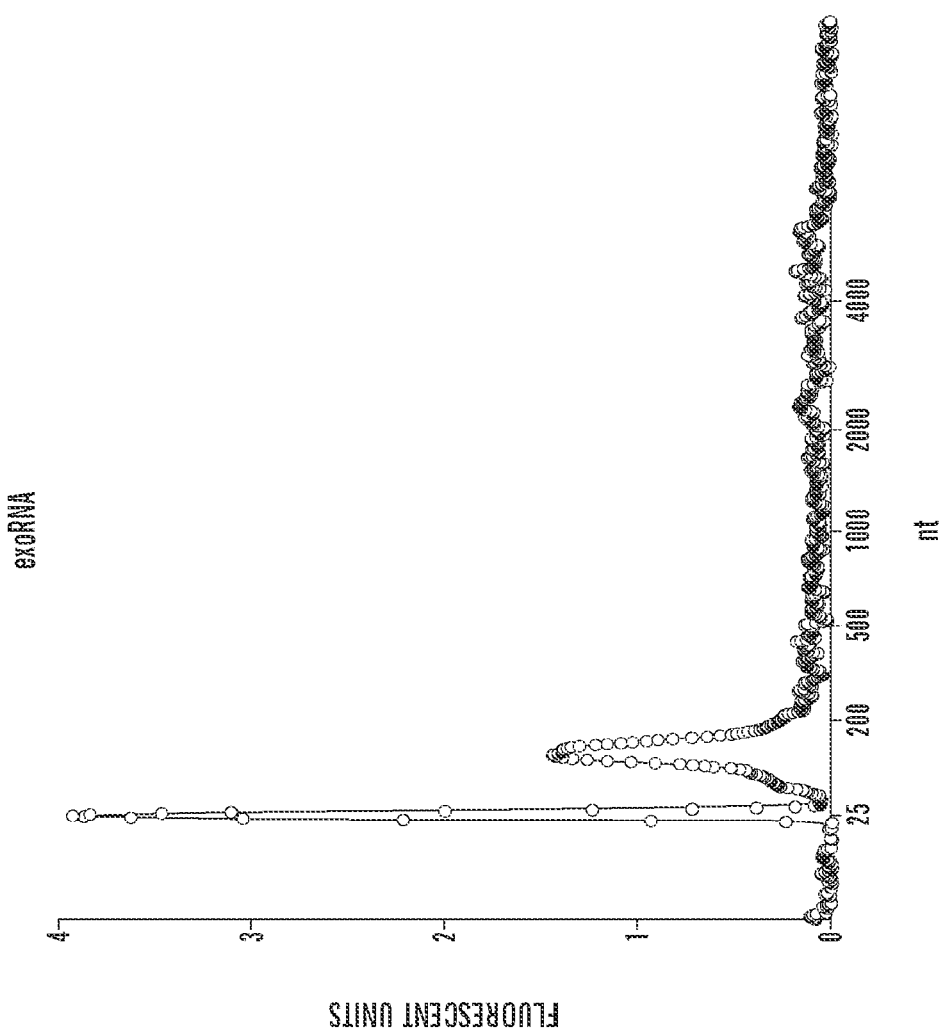

As shown in FIGS. 25A and 25C, the RNA profile varied among cell types and culture conditions, but in general, RNA with intact 18S and 28S ribosomal peaks were isolated from microvesicles.

Figure 25D:
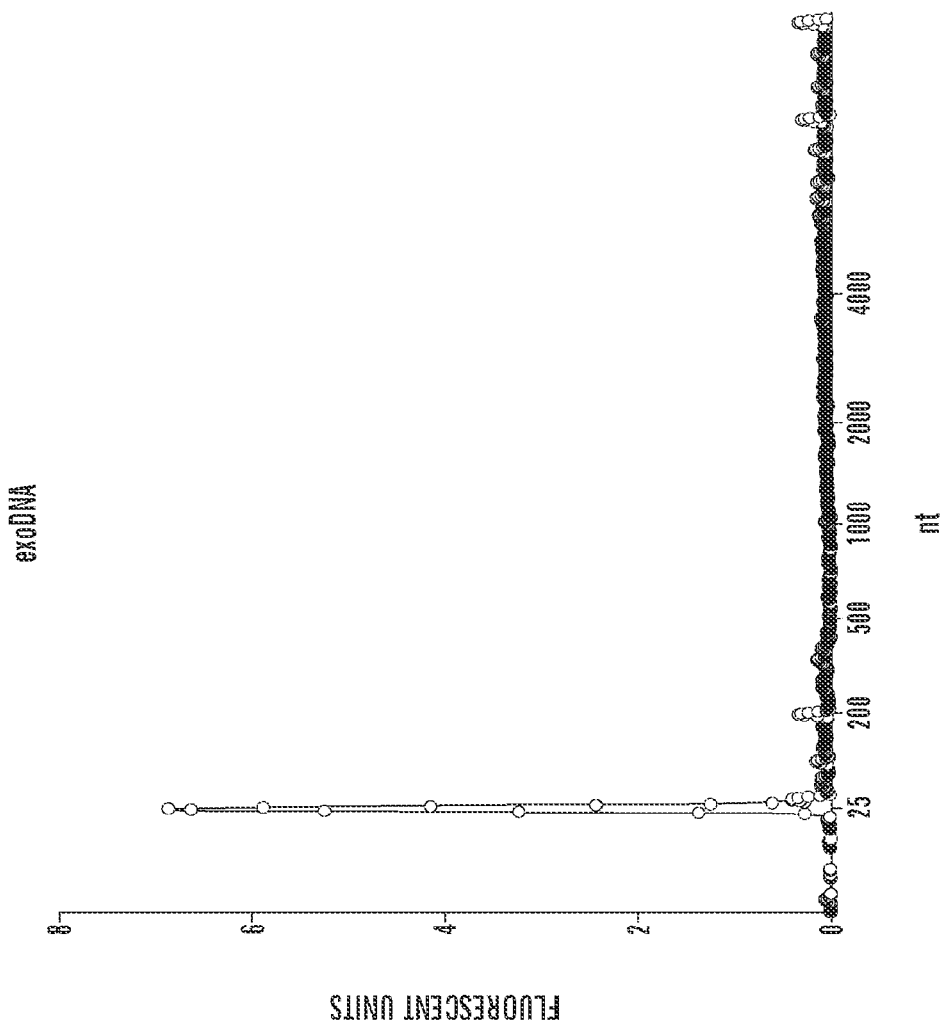

The DNA profile also varied among cell types. ExoDNA was much more abundant in microvesicles secreted by glioblastoma tumor cells (FIG. 25B) as compared to normal fibroblast cells (FIG. 25D).

Figure 26A:
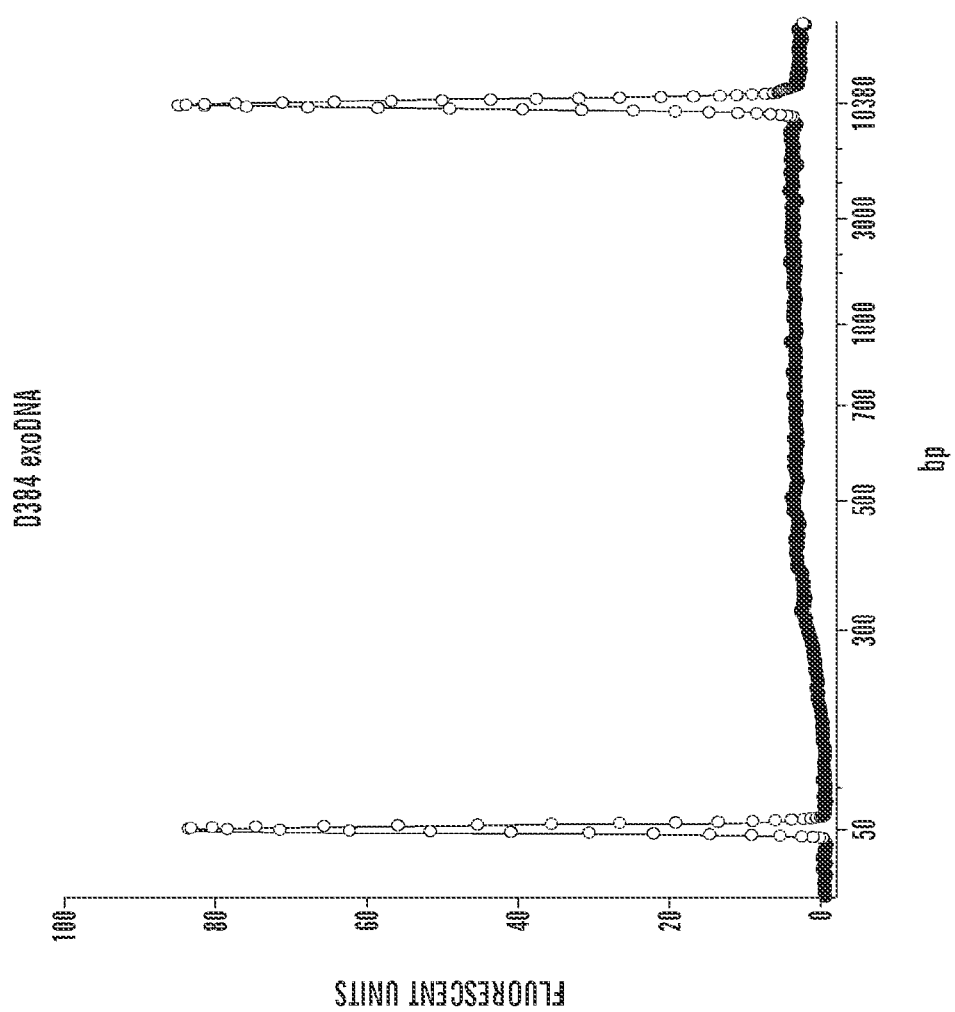
FIGS. 26A and 26B show charts depicting the Bioanalyzer profiles of exoDNA from microvesicles isolated from medulloblastoma D384 cells.
Figure 26B:
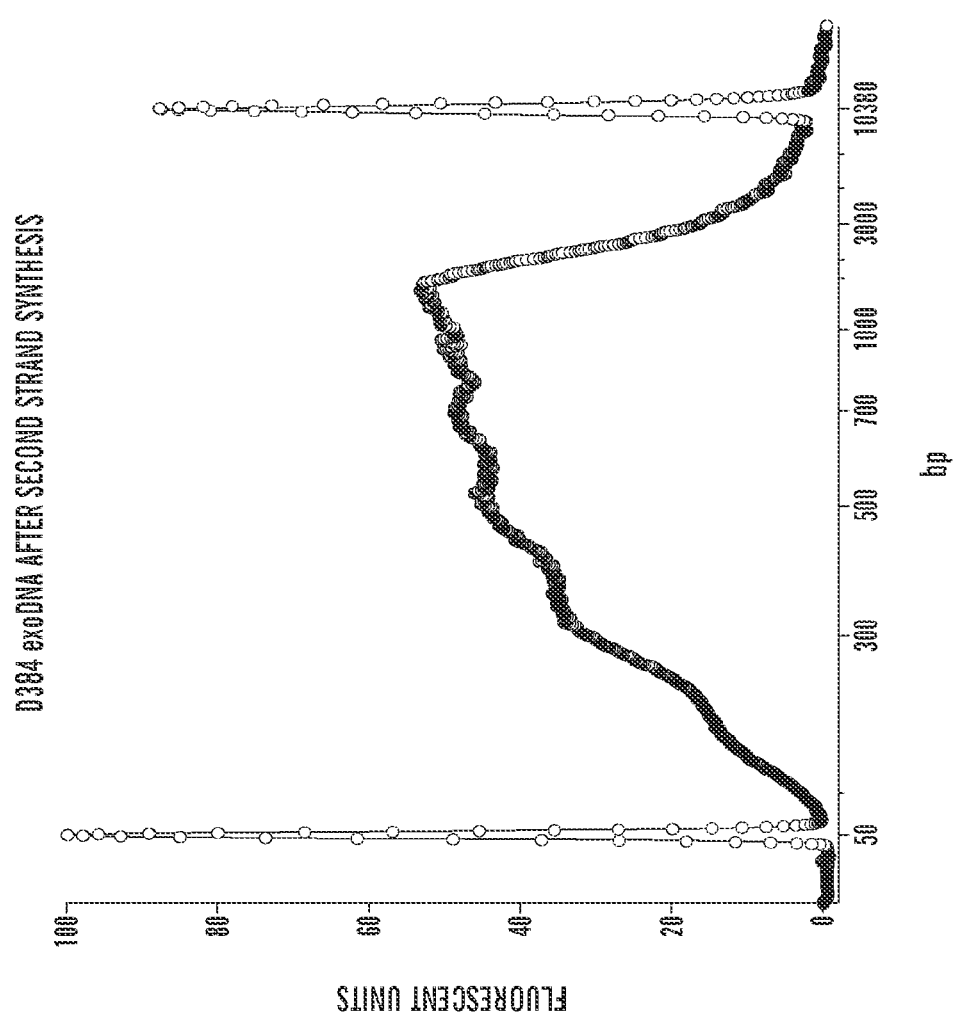

We also found that exoDNA was primarily single stranded. When exoDNA from medulloblastoma tumor cells (D384) was analyzed using a dsDNA detection chip, no DNA was detected (FIG. 26A). However, when this same exoDNA was subjected to second strand synthesis, this same chip detected abundant dsDNA (FIG. 26B). Similar results were obtained with exoDNA extracted from microvesicles secreted by GBM cells (GBM 20/3).

Figure 27:
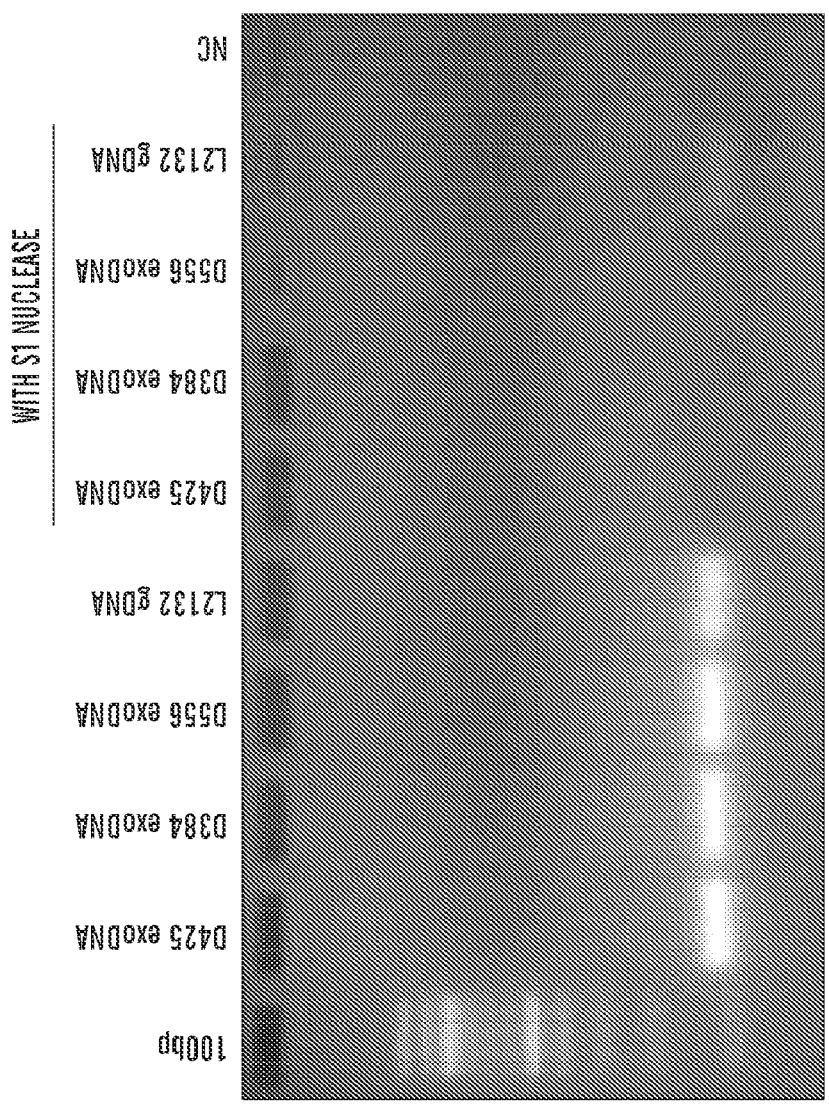
FIG. 27 is an agarose gel picture depicting electrophoresis of GAPDH (112 bp) PCR products using templates from different samples. The different samples were exoDNA samples extracted from microvesicles isolated from three medulloblastoma cell lines (D425, D384 and D556) and genomic DNA extracted from L2132 normal fibroblasts as a control double stranded DNA, all four of which were mock treated or treated with S1 nuclease enzyme which degrades single-stranded nucleic acids.
Figure 28:
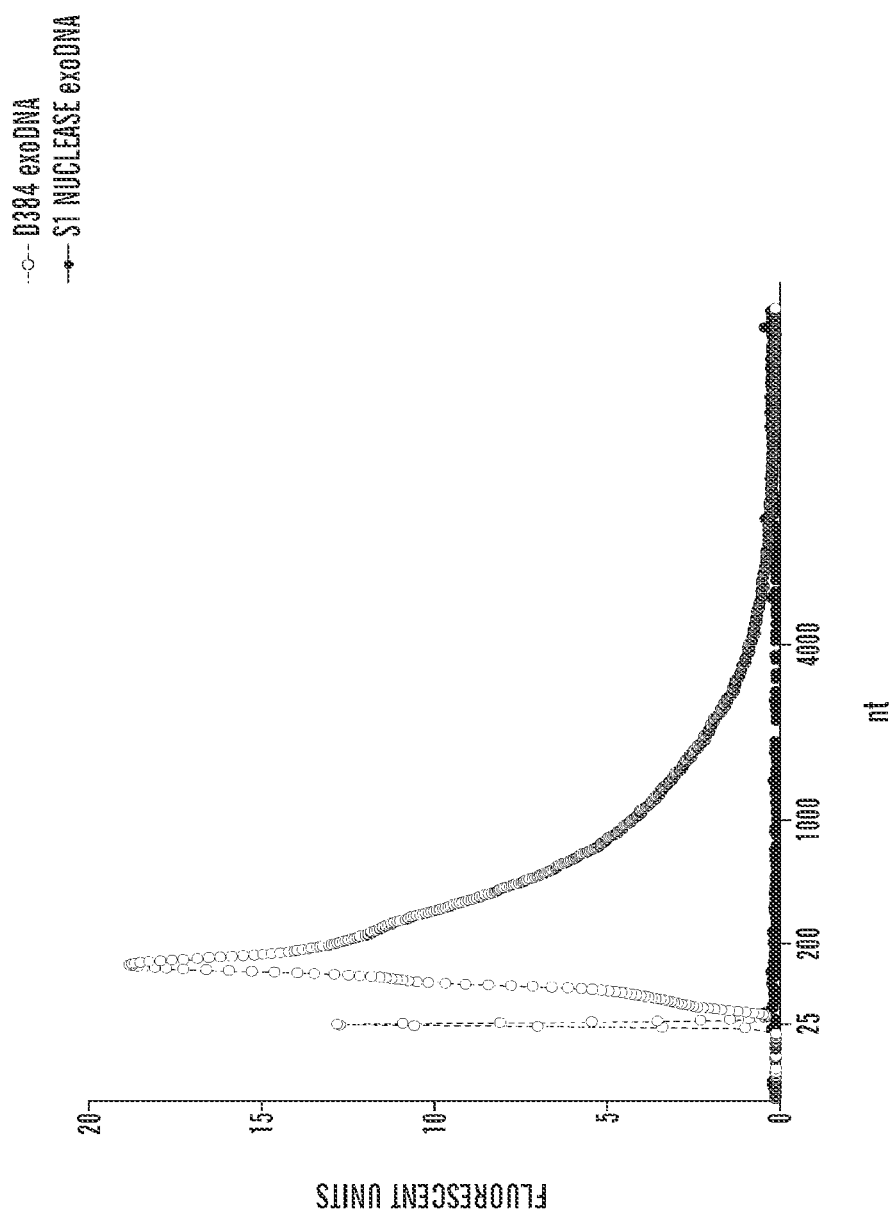
FIG. 28 depicts representative bioanalyzer profiles of exoDNA extracted from medulloblastoma cell line D384 before and after S1 nuclease treatment.

That exoDNA was primarily single stranded DNA was also supported by our S1 exonuclease assays and PicoGreen assays. In the S1 exonuclease assays, we isolated exoDNA from three medulloblastoma cell lines (D435, D384, D556) and gDNA from one normal human fibroblast cell line (L2132). Samples were incubated with S1 nuclease (200 U/ml) at 37° C. for 30 minutes or MOCK treated. PCR for the house-keeping gene GAPDH was then performed on treated and MOCK treated samples. S1 exonuclease specifically digests single stranded nucleic acids. As shown in FIG. 27, without S1 treatment, the bands for exoDNAs extracted from microvesicles secreted by medulloblastoma cell lines (D425 m, D384 and D556) were observed on the gel. In contrast, after S1 treatment, the bands for exoDNAs extracted from microvesicles secreted by medulloblastoma cell lines (D425 m, D384 and D556) did not show up. As a control, the band for the genomic DNA extracted from fibroblast cell line L2132 still showed up after S1 exonuclease digestion. Therefore, exoDNA was sensitive to S1 exonuclease digestion, suggesting that exoDNA is likely to be single stranded DNA.

Further, quantitative analysis of exoDNA using PicoGreen® (Thermo Scientific, Waltham, Mass.), which is a sensitive dsDNA binding fluorescent dye, showed an 18-fold lower amount of nucleic acids in comparison with the amount detected using the Bioanalyzer RNA chip. Since the Bioanalyzer RNA chip detection method can detect only single stranded nucleic acids, the exoDNA extract contained mainly single stranded nucleic acids.

Example 3 c-Myc Oncogene Amplification in Cultured Medulloblastoma Tumor Cells can be Detected in Both exoRNA and exoDNA We detected c-Myc oncogene amplification using either exoRNA or exoDNA from medulloblastoma tumor cells. To measure the amount of c-Myc amplification, we extracted exoRNA and exoDNA, from culture media of three medulloblastoma cell lines (D458, D425 and D384), one atypical teratoid/rhabdoid (AT/RT) tumor cell line NS224, one glioblastoma cell line (11/5), and one normal fibroblast cell line H19 using the same method as detailed in Example 1, respectively. The genomic DNA from each of the same cell lines was extracted according to standard protocols in the art, which can be found in books such as Molecular Cloning: A Laboratory Manual (3-Volume Set) Ed. Joseph Sambrook, David W. Russel, and Joe Sambrook, Cold Spring Harbor Laboratory, 3rd edition (Jan. 15, 2001), ISBN: 0879695773. The extracted nucleic acids were then used in PCR analysis to measure the level of amplifications.

For PCR analysis of exoRNA, total exoRNA (50 ng) was converted into cDNA with the Sensiscript RT Kit (Qiagen) using random primers, according to the manufacturer's instructions, and a 1:20 fraction (corresponding to 2.5 ng reverse transcribed RNA) was used for quantitative PCR (qPCR). For PCR analysis of the gDNA and exoDNA, qPCR was carried out using 10 ng DNA as a template. All reactions were performed in a 25 µl reaction using Power SYBR® Green PCR Master Mix (Applied Biosystems, Foster City, Calif.) and 160 nM of each primer. Amplification conditions consisted of: (1) 1 cycle of 50° C., 2 min; (2) 1 cycle of 95° C., 10 min; (3) 40 cycles of 95° C., 15 sec; and 60° C., 1 min, and (4) a dissociation stage consisting of 1 cycle of 95° C., 15 sec; 60° C., 20 sec; and 95° C., 15 sec on the 7000 ABI Prism PCR system (Applied Biosystems). Cycle threshold ("Ct") values were analyzed in auto mode and manually inspected for accuracy. The Ct values of both RNA and DNA levels were normalized to the housekeeping gene GAPDH in each sample. Primer dimers were excluded by evaluation of dissociation curve and agarose gel electrophoresis.

```
Sequences of the primers used were as follows
n-Myc primers:
1) Forward
                                        (SEQ ID NO: 1)
TCTACCCGGACGAAGATGAC, Reverse
                                        (SEQ ID NO: 2)
AGCTCGTTCTCAAGCAGCAT;
(primers within exon 2)

c-Myc primer:
Forward
                                        (SEQ ID NO: 3)
TCAAGAGGCGAACACACAAC, Reverse
                                        (SEQ ID NO: 4)
TAACTACCTTGGGGGCCTTT;
(both primers in exon 3)
```

-continued c-Myc primer:
Forward
CCTACCCTCTCAACGACAGC, (SEQ ID NO: 5)

Reverse
CTCTGACCTTTTGCCAGGAG. (SEQ ID NO: 6)
(spanning intron 2)

c-Myc human specific primers:
Forward
CAACCCTTGCCGCATCCAC, (SEQ ID NO: 7)

Reverse
AGTCGCGTCCTTGCTCGG. (SEQ ID NO: 8)
(both primers in exon 1)

POU5F1B primers:
Forward
ATCCTGGGGGTTCTATTTGG, (SEQ ID NO: 9)

Reverse
CTCCAGGTTGCCTCTCACTC; (SEQ ID NO: 10)
and

GAPDH primers:
Forward
CTCTGCTCCTCCTGTTCGAC, (SEQ ID NO: 11)
(exon 8)

Reverse
ACGACCAAATCCGTTGACTC. (SEQ ID NO: 12)
(exon 9)

Figure 9:
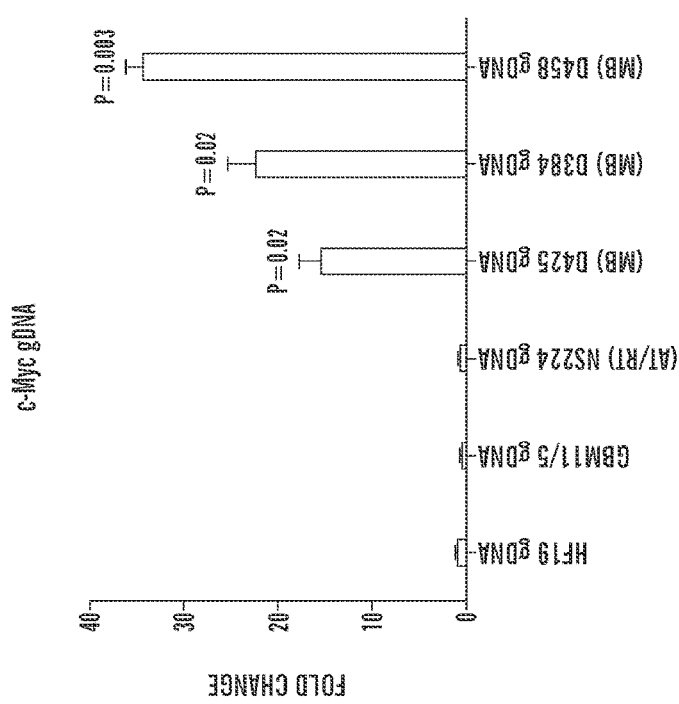
FIG. 9 shows a graph depicting the c-Myc gene yields in terms of genomic DNA extracted from cells of the following cell lines: one normal human fibroblast line (HF19), one GBM line (11/5), one atypical teratoid rhabdoid tumor (AT/RT) line (NS224) and three medulloblastoma (MB) lines (D425, D458 and D384). Quantitative PCR was used to obtain c-Myc Ct values, which were normalized to GAPDH Ct values in the same preparation. The X-axis lists the names of the cell lines tested. The Y-axis is the fold change, represented as the ratio of the Ct value for each cell line to the Ct value for the normal fibroblast cell line HF19. In all cases, the Ct values are expressed as mean±SEM (n=3) and analyzed by a two-tailed t-test.
Figure 10:
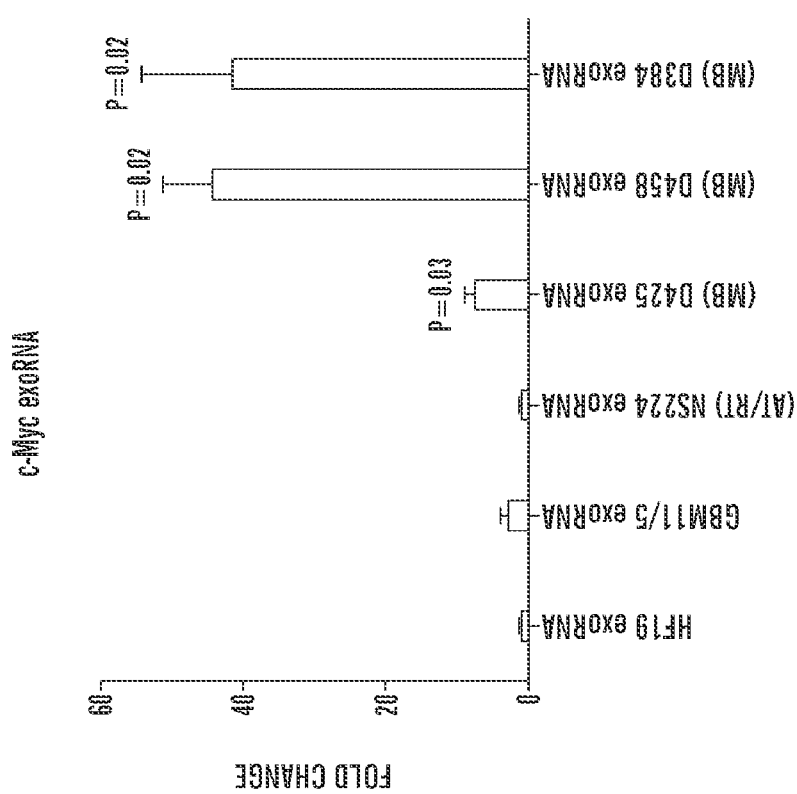
FIG. 10 shows a graph depicting the c-Myc gene yields in terms of RNA extracted from microvesicles secreted by cells of the same cell lines and in the same manner as in FIG. 9. Quantitative Reverse Transcription PCR was used to obtain c-Myc RNA Ct values.
Figure 11:
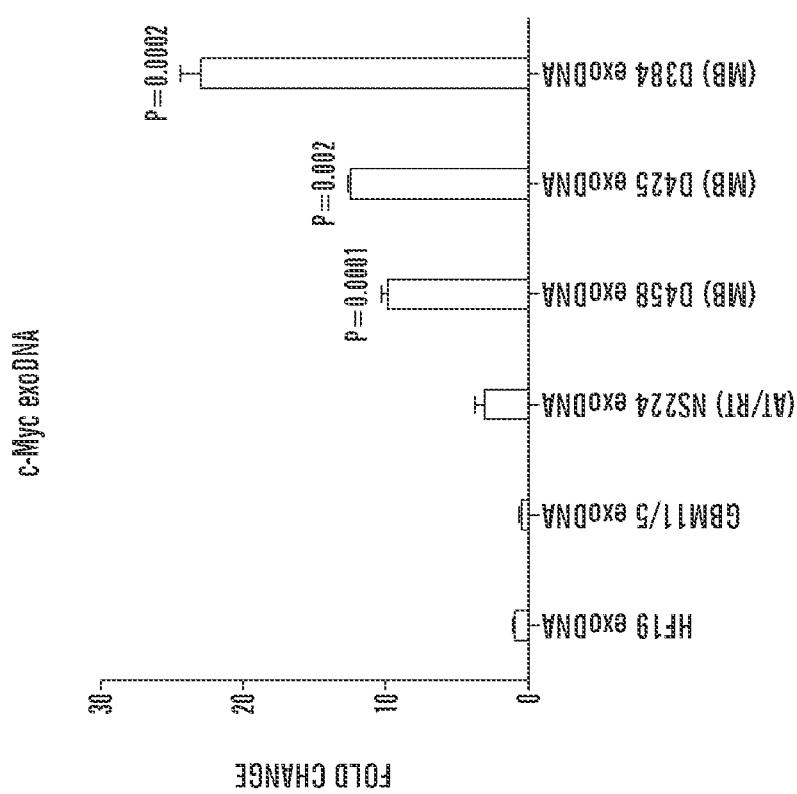
FIG. 11 shows a graph depicting the c-Myc gene yields in terms of DNA extracted from microvesicles secreted by cells of the same cell lines and in the same manner as in FIG. 9. Quantitative PCR was used to obtain c-Myc DNA Ct values.

Levels of c-Myc amplification were measured at the genomic level (gDNA) by qPCR (FIG. 9). All three medulloblastoma cell lines had significant amplifications of c-Myc sequences (16-34-fold) compared to fibroblasts and other tumor cell types. RNA and DNA were extracted from microvesicles shed by these cell lines and quantitated by RT-PCR and PCR respectively, using primers in exon 3 with values for c-Myc sequences normalized to glyceraldehyde 3-phosphate dehydrogenase (GAPDH), a housekeeping gene constitutively expressed in cells and found in exoRNA[14] and here in exoDNA. Microvesicles from all medulloblastoma cell lines showed elevated levels of c-Myc sequences, both for exoRNA (8-45-fold) and exoDNA (10-25 fold), compared to microvesicles from fibroblasts and tumor cells with diploid c-Myc copy numbers (FIGS. 10-11). Also, using primers that span a full intron, we successfully detected a 1.6 kb fragment corresponding to the unspliced c-Myc genomic DNA (verified by sequencing) in exoDNA from all three medulloblastoma cell lines, but not in any of the other cell lines.

Figure 29A:
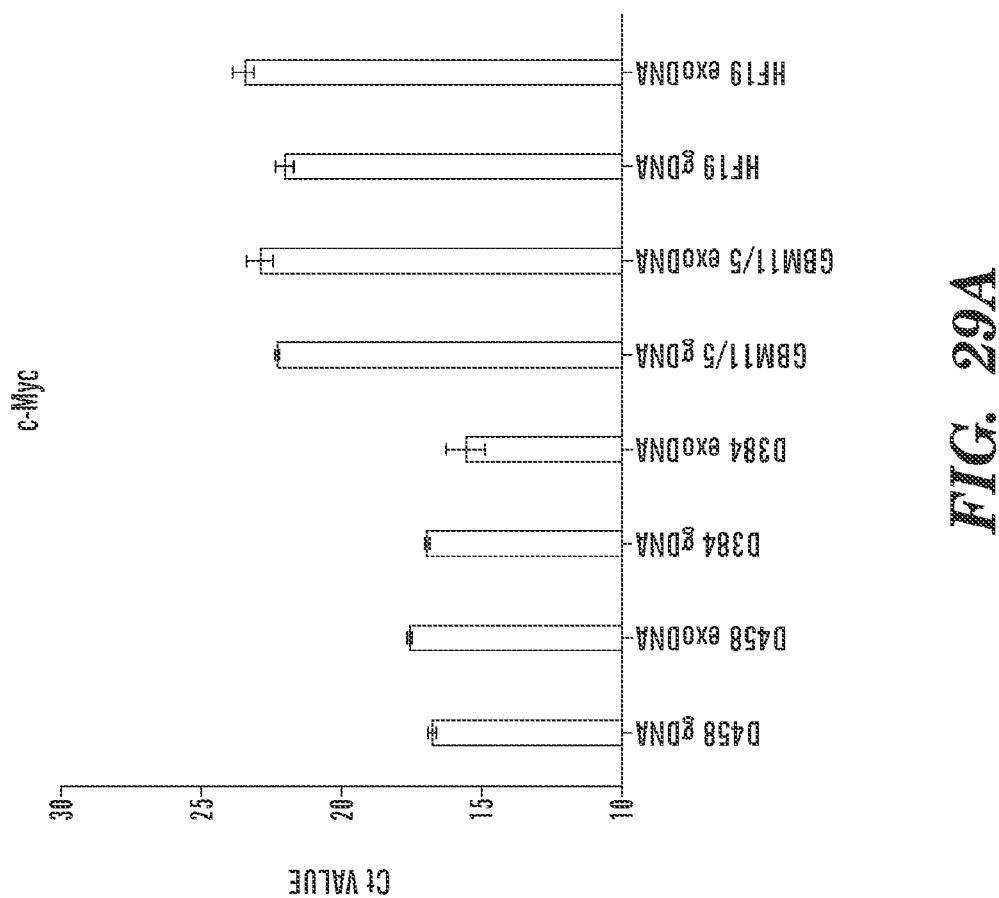
FIGS. 29A and 29B show charts depicting quantitative PCR results of c-Myc and POU5F1B, respectively, using as templates genomic DNA from cells or exoDNA extracted from microvesicles isolated from cells.
Figure 29B:
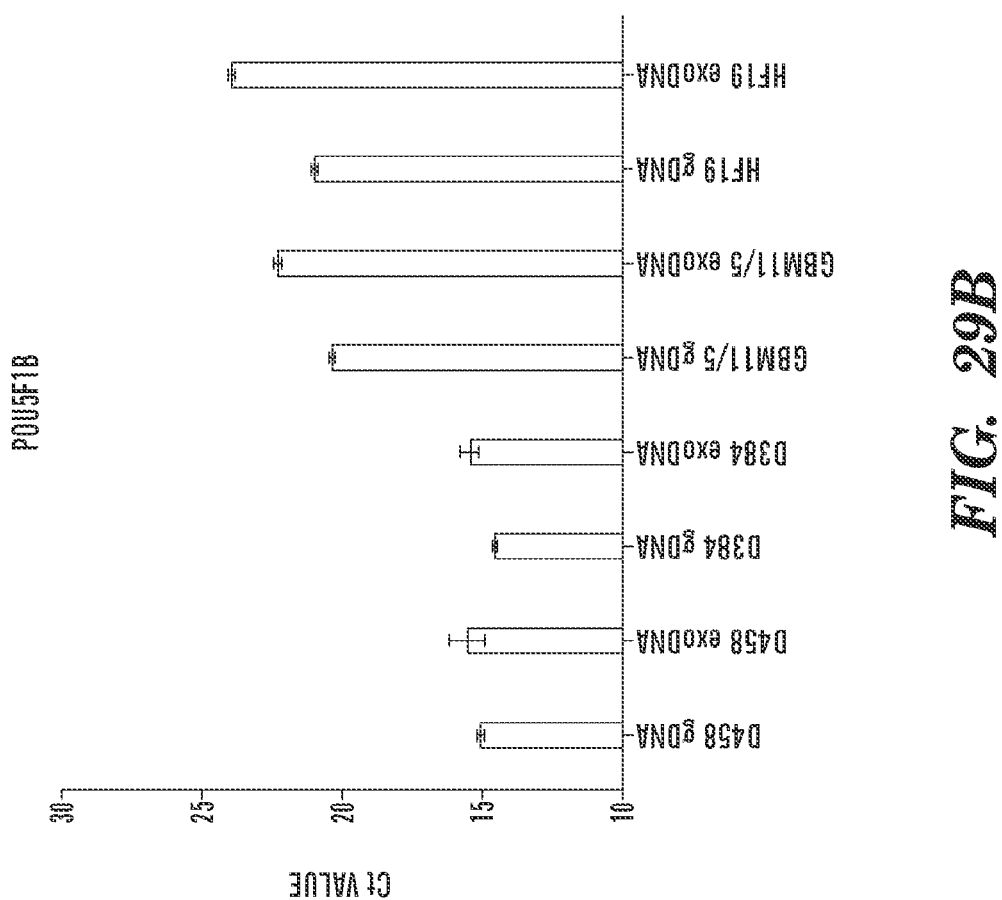

Furthermore, to establish that this genomic fragment of c-Myc in microvesicles was derived from a genomic amplicon, we verified the presence of elevated levels of a flanking gene, POU5F1B gene (Storlazzi et al., 2006) at levels matching those of c-Myc (FIG. 29B). POU5F1B PCR product was also verified by sequencing.

Figure 31A:
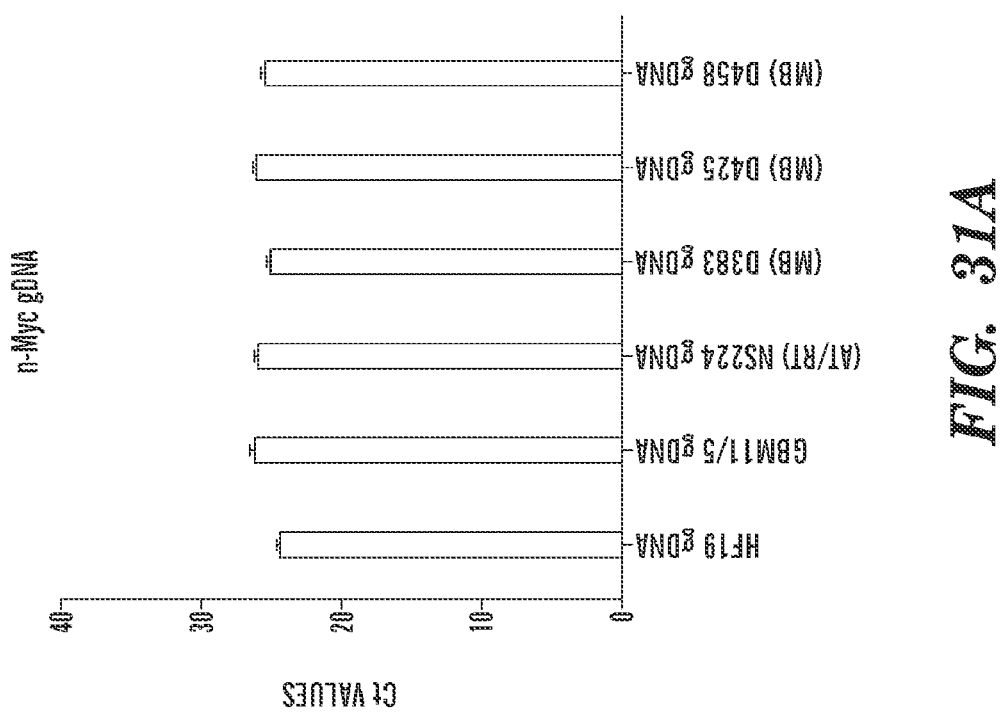
FIGS. 31A and 31B show charts depicting the qPCR results of the n-Myc gene in cells lines medulloblastoma D425, D458 and D384, rhabdoid tumor, GBM, and normal fibroblasts using genomic DNA FIG. 31A or exoDNA FIG. 31B extracted from microvesicles isolated from the cells as templates.
Figure 31B:
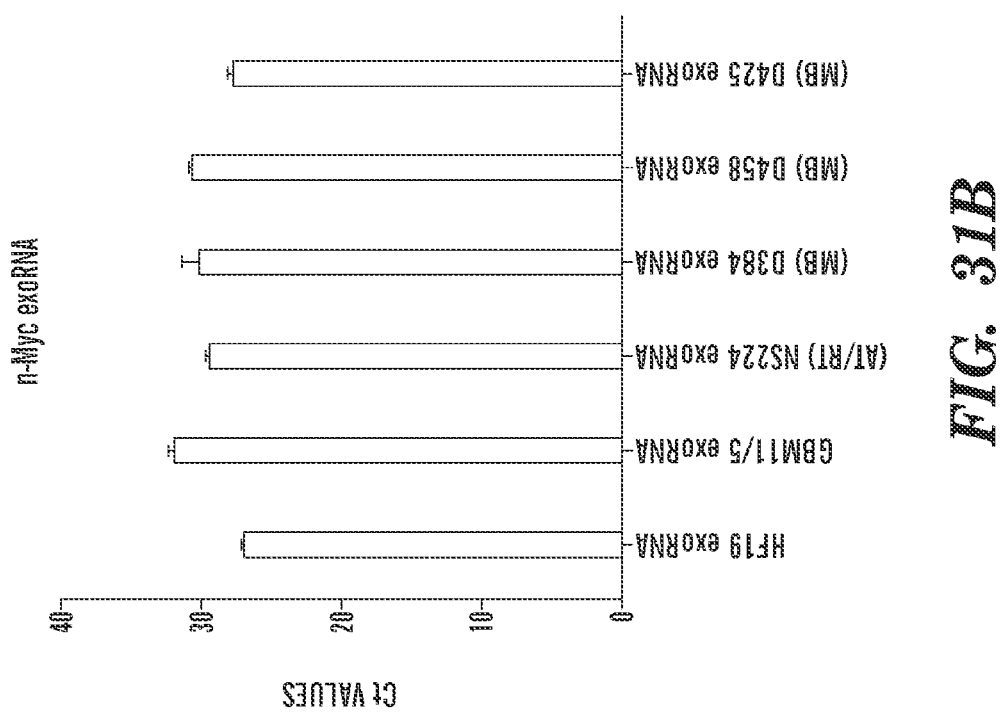

Levels of n-Myc sequences in cellular genomic DNA (gDNA) or exoRNA were also measured by qPCR and qRT-PCR and none of the other tumor types showed genomic amplification of n-Myc sequences or elevated levels of n-Myc exoRNA (FIGS. 31A and B).

The levels of c-Myc DNA quantitated for gDNA and exoDNA/RNA in these medulloblastoma lines were also compared to levels estimated by 250K single nucleotide polymorphism (SNP) analysis. For gene copy number estimation by the SNP array analysis, genomic DNA was extracted from medulloblastoma cell pellets using the Puregene DNA Extraction Kit (Gentra Systems, Minneapolis, Minn.), according to the manufacturer's instructions. To obtain signal intensities and genotype calls, genomic DNA samples were digested, labeled and hybridized to Affymetrix 250K StyI SNP arrays, according to the manufacturer's protocol (Affymetrix, Santa Clara, Calif.). Signal intensities were normalized using rank invariant set normalization, and copy numbers for altered genomic regions were inferred using the GLAD (Gain and Loss of DNA) algorithm available in the Genepattem software package (www.genepattern.org). C-Myc and n-Myc copy numbers were inferred by analyzing the smoothed copy number data at genomic regions ch8q24.12 and ch2p24, respectively.

Figure 30:
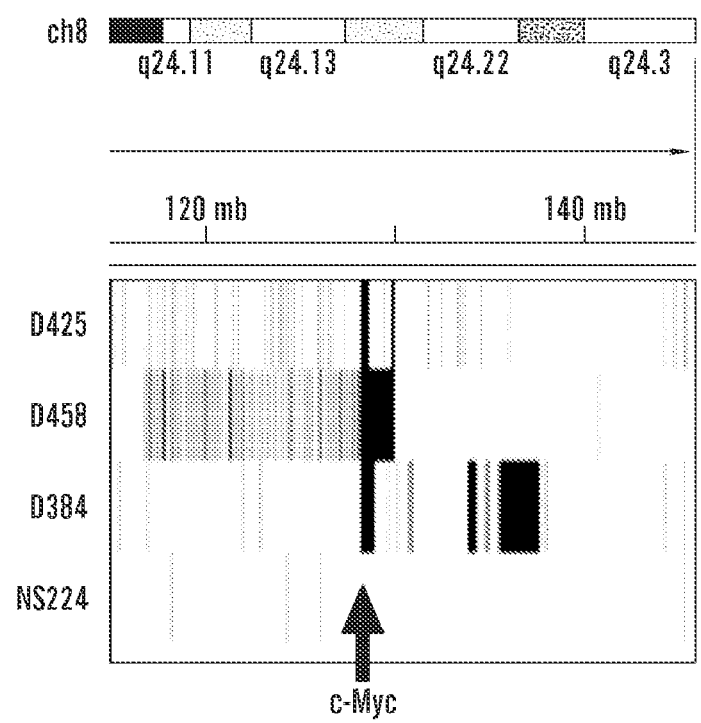
FIG. 30 illustrates the c-Myc copy number analysis results in tumor cell lines using an Affymetrix 250K SNP array. The c-Myc genomic region was analyzed in medulloblastoma lines, D425, D458 and D384, as well as rhabdoid tumor line, NS224.

The results are shown in Table 1 and in FIG. 30 in a representative heat map. Increased levels of c-Myc exoDNA corresponded well to the genomic copy number estimated by 250 k SNP and qPCR in medulloblastoma lines, as compared to normal diploid levels in other cell lines, with correspondingly elevated c-Myc exoRNA in medulloblastoma microvesicles.

TABLE 1

Assessment of c-Myc gene amplification levels in different cell types.

| | Method | c-Myc genomic copy number | c-Myc amount exoRNA[a] | c-Myc amount exoDNA[b] |
| --- | --- | --- | --- | --- |
| D425 | FISH | >25 | | |
| | 250k SNP[c] | 15 | | |
| | qPCR | 8 ± 3.6 | 8 ± 2.0 | 13 ± 0.2 |
| D384 | 250k SNP | 25 | | |
| | qPCR | 12 ± 4.7 | 42 ± 22 | 25 ± 3.7 |
| D458 | 250k SNP | 17 | | |
| | qPCR | 17 ± 3.0 | 45 ± 11 | 10 ± 0.6 |
| NS224 | 250k SNP | 2 | | |
| | qPCR | 2 | 0.8 ± 0.3 | 4.2 ± 0.1 |
| GBM11/5 | qPCR | 2 | 2.8 ± 1.4 | 0.4 ± 0.1 |
| HF19 | qPCR | 2 | 1 | 1 |

[a]2.5 ng reverse transcribed exoRNA and 10 ng of exoDNA were used as template for qPCR.
All values were normalized to GAPDH mRNA.
[b]FISH = Fluorescence in situ hybridization of metaphase chromosome spread.[63]
[c]See representative heat map shown in FIG. 30.

Example 4 c-Myc Oncogene Amplification in Xenografted Medulloblastoma Tumor Cells In Vivo can be Detected with Both exoRNA and exoDNA To assess the potential diagnostic utility of using exoRNA to detect c-Myc amplification in tumors, human medulloblastoma cells (c-Myc amplified) and epidermoid carcinoma tumor cells (non-amplified) were grown as xenograft tumors in nude mice. In the xenograft experiments, two groups of five adult immunodeficient mice (nu/nu NCI) were each injected subcutaneously in both flanks with 5×10[6] medulloblastoma cells (line D425) or epidermoid carcinoma cells (line A431). Tumors were allowed to grow for three weeks; the mice were then sacrificed and blood was drawn by cardiac puncture. Approximately 1 ml of blood was obtained from each mouse and allowed to clot at room temperature for 15 min and then centrifuged at 1300×g for 10 min. The serum was then filtered through a 0.22 μm filter and stored at −80° C. Samples were thawed and centrifuged for 1 hr at 100,000×g to obtain microvesicles for RNA extraction, as described above.

Figure 12:
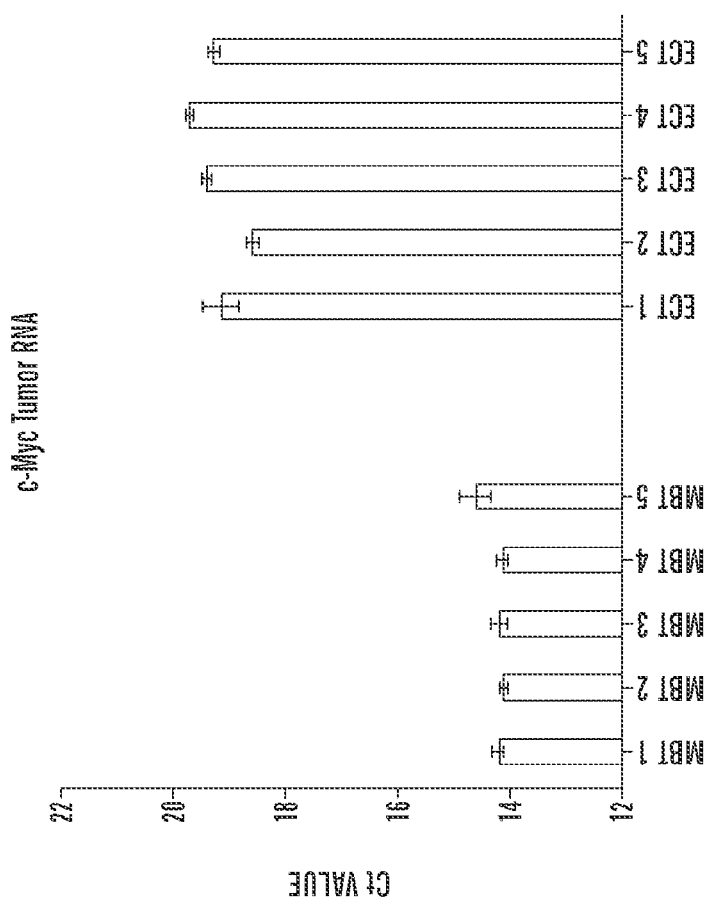
FIG. 12 shows a graph depicting the c-Myc gene yields in terms of RNA extracted from xenograft subcutaneous tumor cells. The subcutaneous tumors were generated by xenografting medulloblastoma cells (MBT; D425 cell line) or epidermoid carcinoma (ECT; A431 cell line) cells in nude mice. The X-axis refers to the different tumor-bearing mice characterized by the type of tumor cell and the tumor mass weight at sacrifice. MBT tumor mass weights are as follows: MBT 1: 3.4 g; MBT 2: 1.7 g; MBT 3: 2.4 g; MBT 4: 2.9 g; and MBT 5: 1.7 g. ECT tumor mass weights are as follows: ECT 1: 1.7 g; ECT 2: 2.3 g; ECT 3: 3.1 g; ECT 4: 1.9 g; and ECT 5: 2.2 g. Ct values were normalized to GAPDH. The Y-axis refers to the Ct values generated by quantitative reverse transcription PCR of the extracted RNA in each sample. For each RNA extract, two replicate qPCR were performed.
Figure 13:
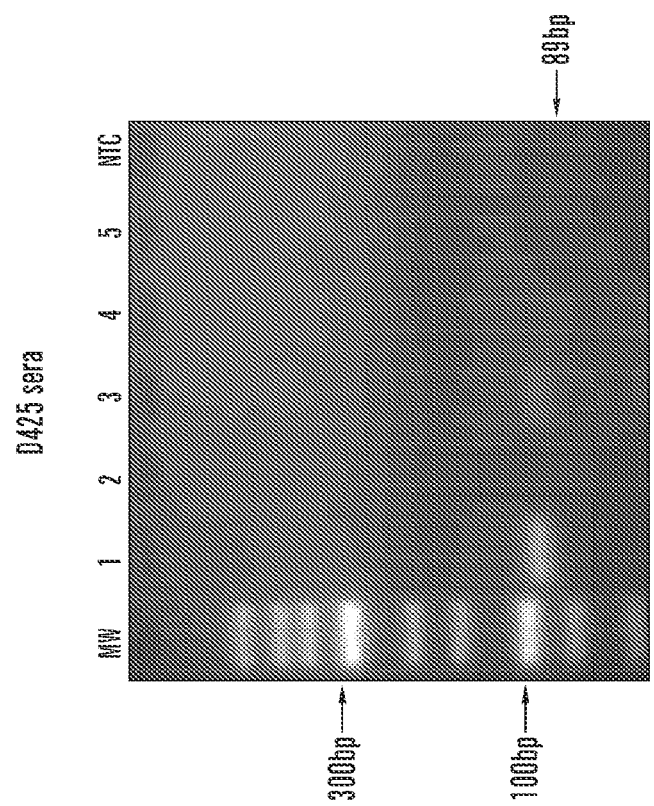
FIG. 13 shows a gel picture depicting the c-Myc gene yields in terms of RNA extracted from serum microvesicles from mice that bear subcutaneous tumors. The subcutaneous tumors were generated by xenografting medulloblastoma cells (MBT; D425 cell line) in nude mice. C-Myc product was amplified by reverse transcription PCR method using human c-Myc specific primers and the RNA extracted from serum microvesicles as templates. The amplified c-Myc product should be 89 bp in length. The amplified c-Myc products were resolved by electrophoresis in a 2% agarose gel and visualized with ethidium bromide staining. The arrow points to the position where an 89 bp product appears on the agarose gel. The lanes are referenced as follows: MW: DNA size marker; 1: MBT tumor mass weight of 3.4 g; 2: MBT tumor mass weight of 1.7 g; 3: MBT tumor mass weight of 2.4 g; 4: MBT tumor mass weight of 2.9 g; 5: MBT tumor mass weight of 1.7 g; NC: negative control where no RNA/cDNA was used.
Figure 14:
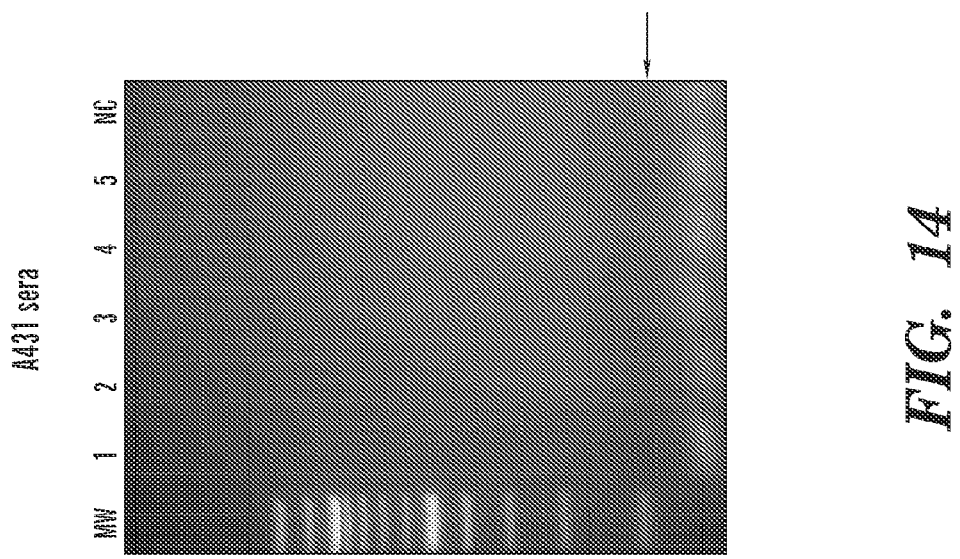
FIG. 14 shows a gel picture depicting the c-Myc gene yields in terms of RNA extracted from serum microvesicles from mice that bear subcutaneous tumors in the same manner as in FIG. 13 except that the subcutaneous tumors were generated by xenografting epidermoid carcinoma (ECT; A431 cell line) in nude mice. The lanes are referenced as follows: MW: DNA size marker; 1: ECT tumor mass weight of 1.7 g; 2: ECT tumor mass weight of 2.3 g; 3: ECT tumor mass weight of 3.1 g; 4: ECT tumor mass weight of 1.9 g; 5: ECT tumor mass weight of 2.2 g; NC: negative control where no RNA/cDNA was used.

As shown in FIG. 12, microvesicles were isolated from serum samples in tumor-bearing mice and exoRNA was extracted from the isolated microvesicles. Human c-Myc was detected in exoRNA s from 2/5 (40%) of the medulloblastoma-bearing mice (FIG. 13) and from 0/5 (0%) of the epidermoid carcinoma-bearing mice (FIG. 14).

Example 5 Retrotransposon Elements are Enriched in Tumor Microvesicles

We analyzed the RNA species in cellular RNA and exoRNA preparations from a low passage GBM line by microarray analysis using a whole genome array (Agilent Technologies). Briefly, RNA was extracted from microvesicles, as described above. RNA (0.5 μg) was used for linear T7-based amplification and Cy-3/Cy-5 labeling (Agilent Low RNA Input Linear Amp Kit, Agilent Technologies) following the manufacturer's protocol. The microarray experiments were performed by Miltenyi Biotec (Auburn, Calif.) using the Agilent whole human genome microarray, 4×44K (44,000 probes), two-color array. The array was performed on two different RNA preparations from primary GBM cells and their microvesicles.

The microarray results have been deposited with a Geo accession number GSE13470. The results indicate the presence of higher transcription levels of a number of retrotransposon sequences in exoRNA extracts as compared to cellular RNA extracts.

From the two-color Agilent array data, we generated MA plots as previously described (Storey and Tibshirani, 2003). The intensities of the expression levels for each transcript were obtained from the array data for both exoRNA extracts from microvesicles and cellular RNA extracts from cells. The intensity of exoRNA is here designated "Microvesicle." The intensity of cellular RNA is here designated "Cell". The log ratio of the intensities of microvesicle/cell is plotted on the Y-axis (M=log$_2$Microvesicle−log$_2$Cell) and the mean log expression of the two on the X-axis (A=0.5× (log$_2$Microvesicle+log$_2$Cell)).

Figure 15:
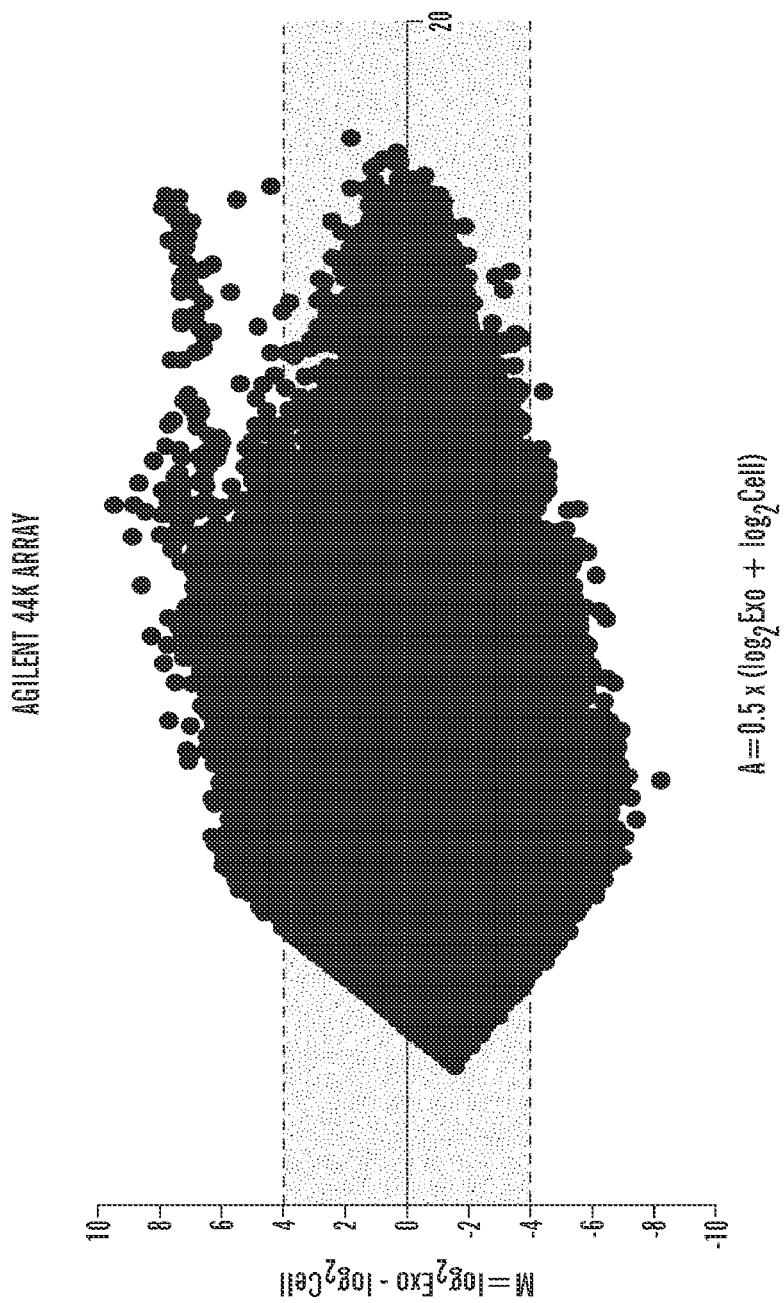
FIG. 15 shows a MA plot depicting relative levels of all represented RNA sequences (using 44,000 RNA probes on the Agilent microarray chip) in cells and microvesicles derived from the cells. The levels of transposon and retrotransposon sequences were compared to the rest of the RNA transcriptome in cells and microvesicles. ExoRNA and cellular RNA were isolated from GBM 20/3 cells and analyzed on an Agilent two-color 44 k array. Y-axis (M)=$\log_2$Exo−$\log_2$Cell, X-axis (A)=0.5×($\log_2$Exo+$\log_2$Cell).

As shown in FIG. 15, the microarray data was represented on a MA plot as the cumulative abundance (in microvesicles and cells) of specific RNAs (X-axis) and the relative ratio of these RNAs in microvesicles versus cells (Y-axis). The Y-axis scale was log 2, so RNAs above 4 or below −4 on the Y-axis have at least a 16-fold different level in the microvesicles vs. cells. There were many RNA species that were at least 16 fold more abundant in microvesicles than in cells (M value above 4). Similarly, there were also many RNA species that were at least 16 fold less abundant in microvesicles than in cells (M value below −4).

Figure 16:
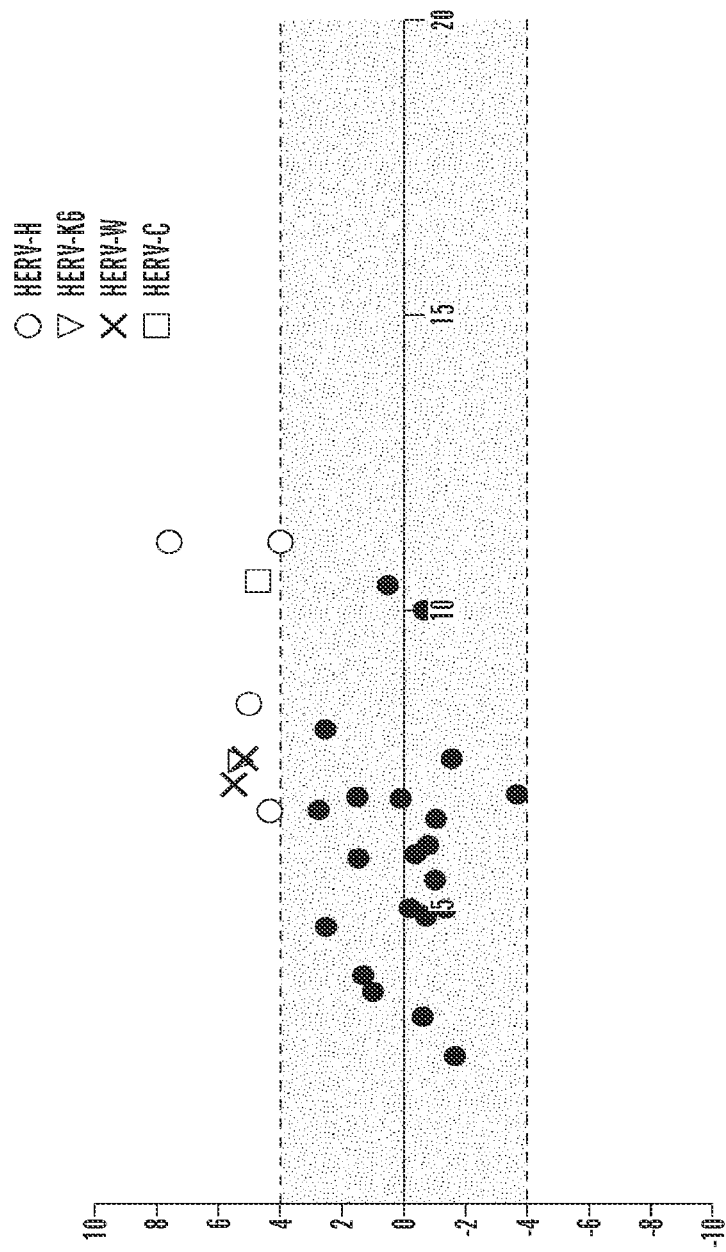
FIG. 16 shows a MA plot similar to the plot in FIG. 15 except that the present plot only depicts relative levels of the following four HERV family sequences: HERV-H, HERV-K6, HERV-W and HERV-C, all of which are enriched in microvesicles more than 16-fold as compared to the host cells, i.e., M≥4.
Figure 17:
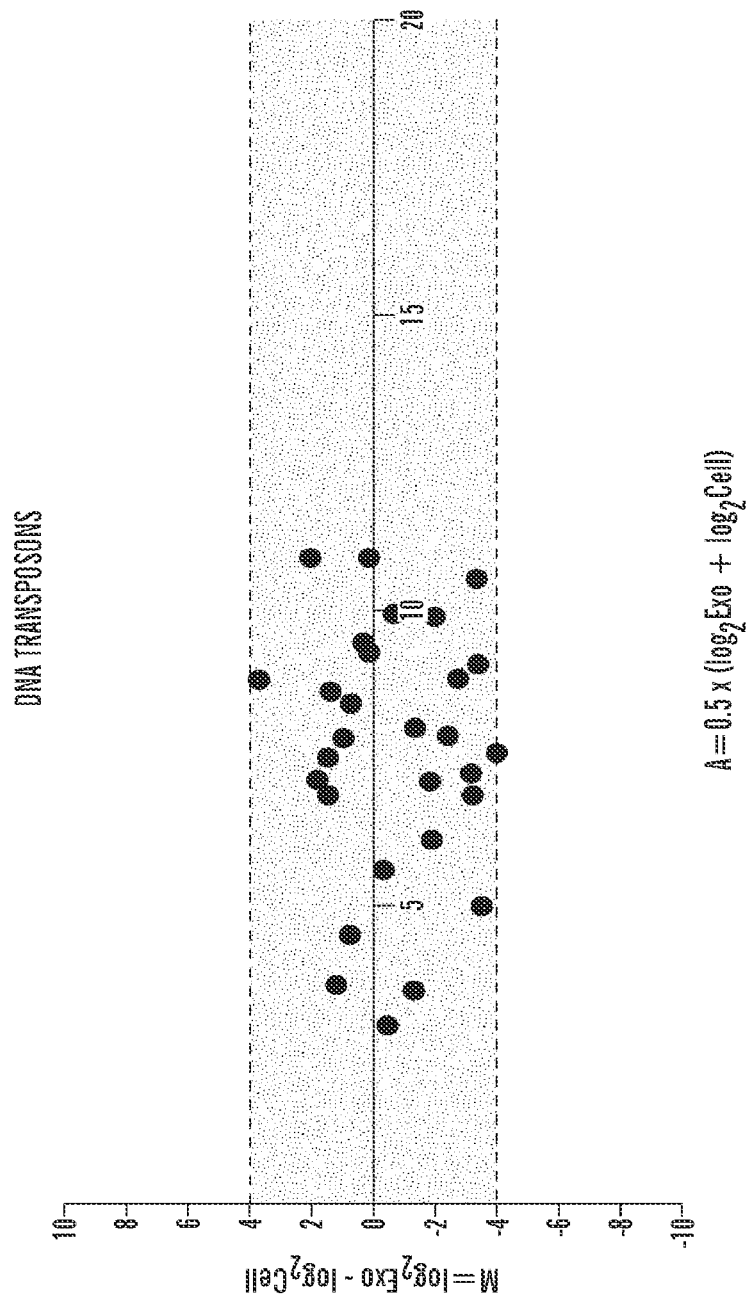
FIG. 17 shows a MA plot similar to the plot in FIG. 15 except that the present plot only depicts relative levels of DNA transposons.
Figure 18:
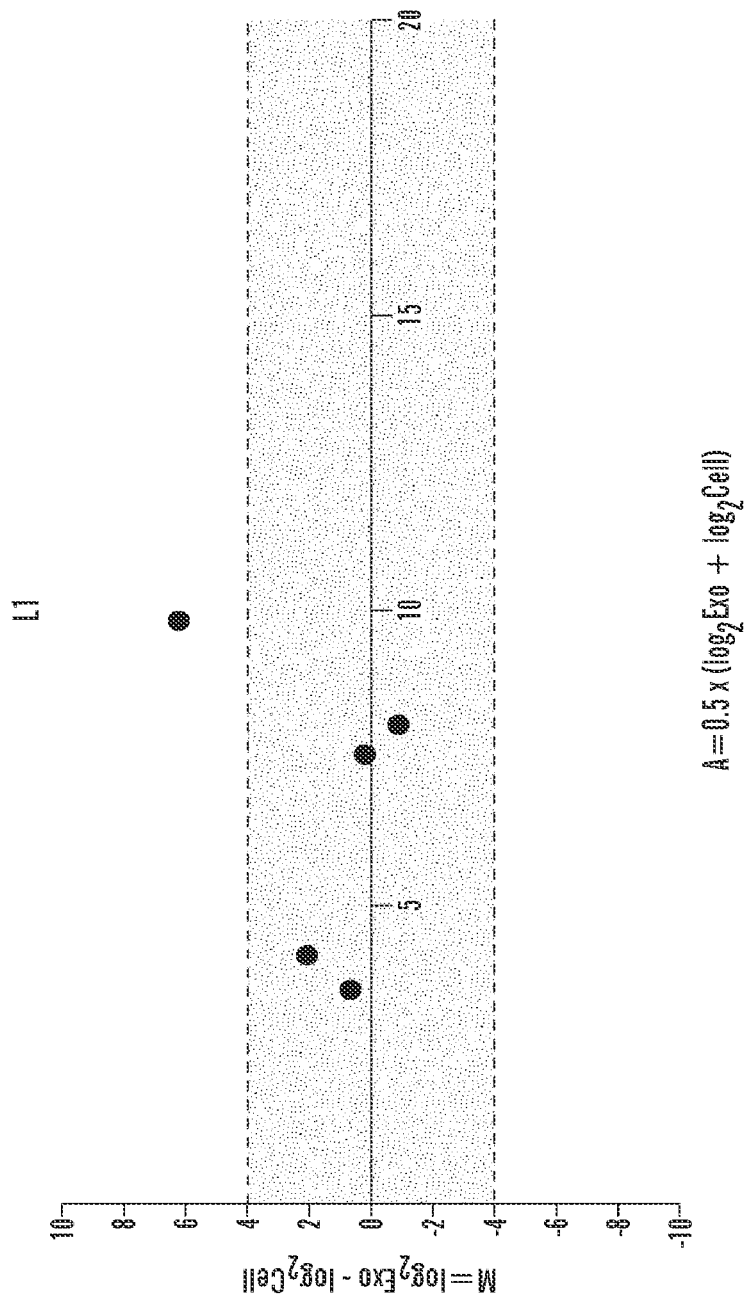
FIG. 18 shows a MA plot similar to the plot in FIG. 15 except that the present plot only depicts relative levels of L1 sequences.
Figure 19:
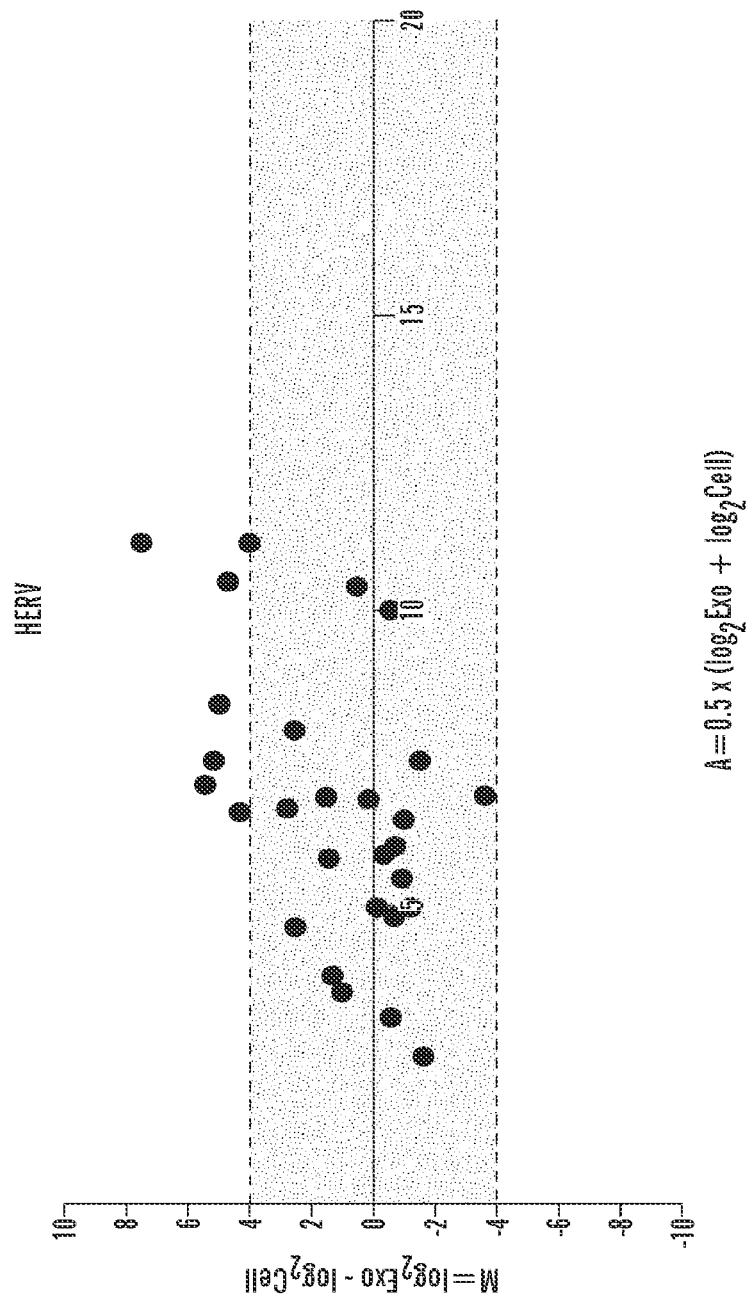
FIG. 19 shows a MA plot similar to the plot in FIG. 15 except that the present plot only depicts relative levels of HERV sequences with HERV-H, HERV-C, HERV-K6 and HERV-W being more than 16 fold enriched.
Figure 20:
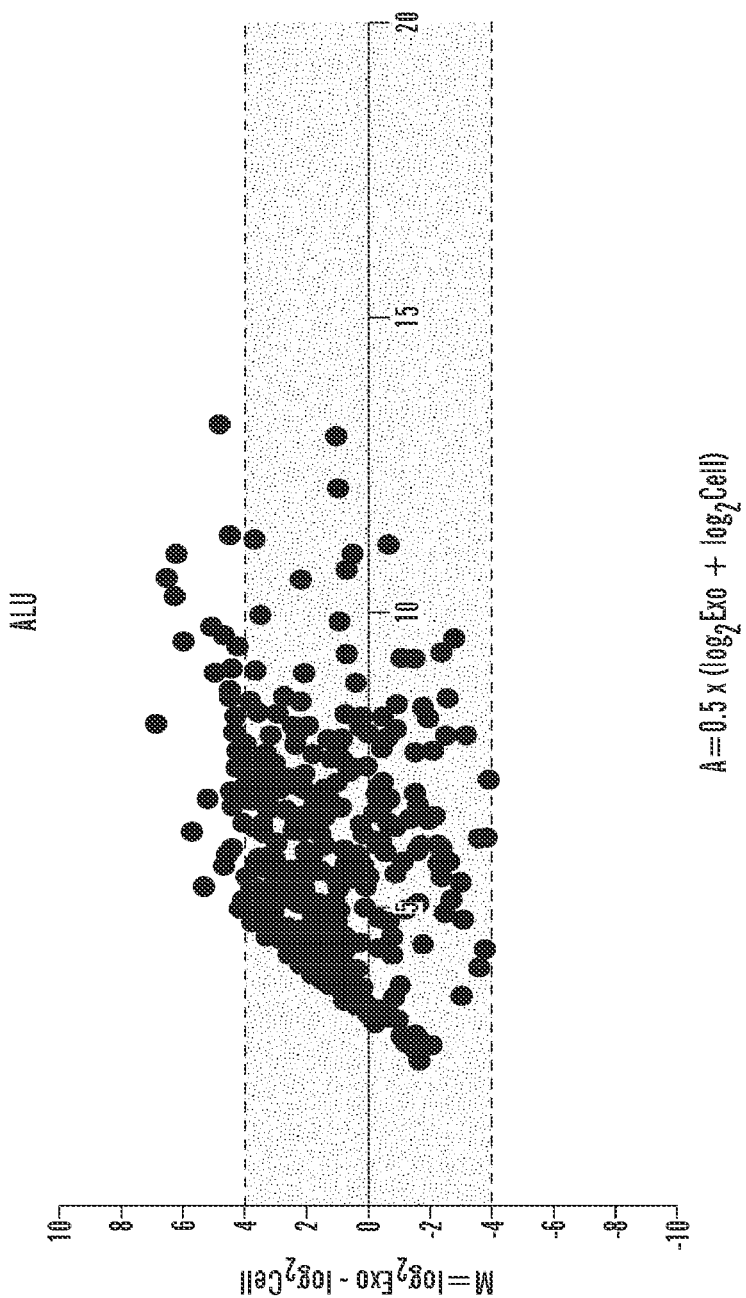
FIG. 20 shows a MA plot similar to the plot in FIG. 15 except that the present plot only depicts relative levels of Alu sequences.

As shown in FIG. 17, RNA from DNA transposons was similar in content in cells and microvesicles with the M values spreading between −4 and 4. In contrast, as shown in FIGS. 18-20, RNA from retrotransposons, e.g. HERV, Alu and L1, was frequently higher in microvesicles than in cells. This was particularly notable for the HERV sequences. As shown in FIG. 16, HERV-H was the most abundant and microvesicle-enriched in these GBM cells, followed by HERV-C, HERV-K6 and HERV-W. Therefore, some retrotransposon RNAs, e.g., HERV RNA, may be selectively packaged or enriched, in tumor microvesicles.

Since only a selected subset of transposon/retrotransposon probes are represented on the Agilent arrays, other retrotransposons that are not represented on the Agilent arrays may be enriched in microvesicles from tumor cells as well.

Figure 21A:
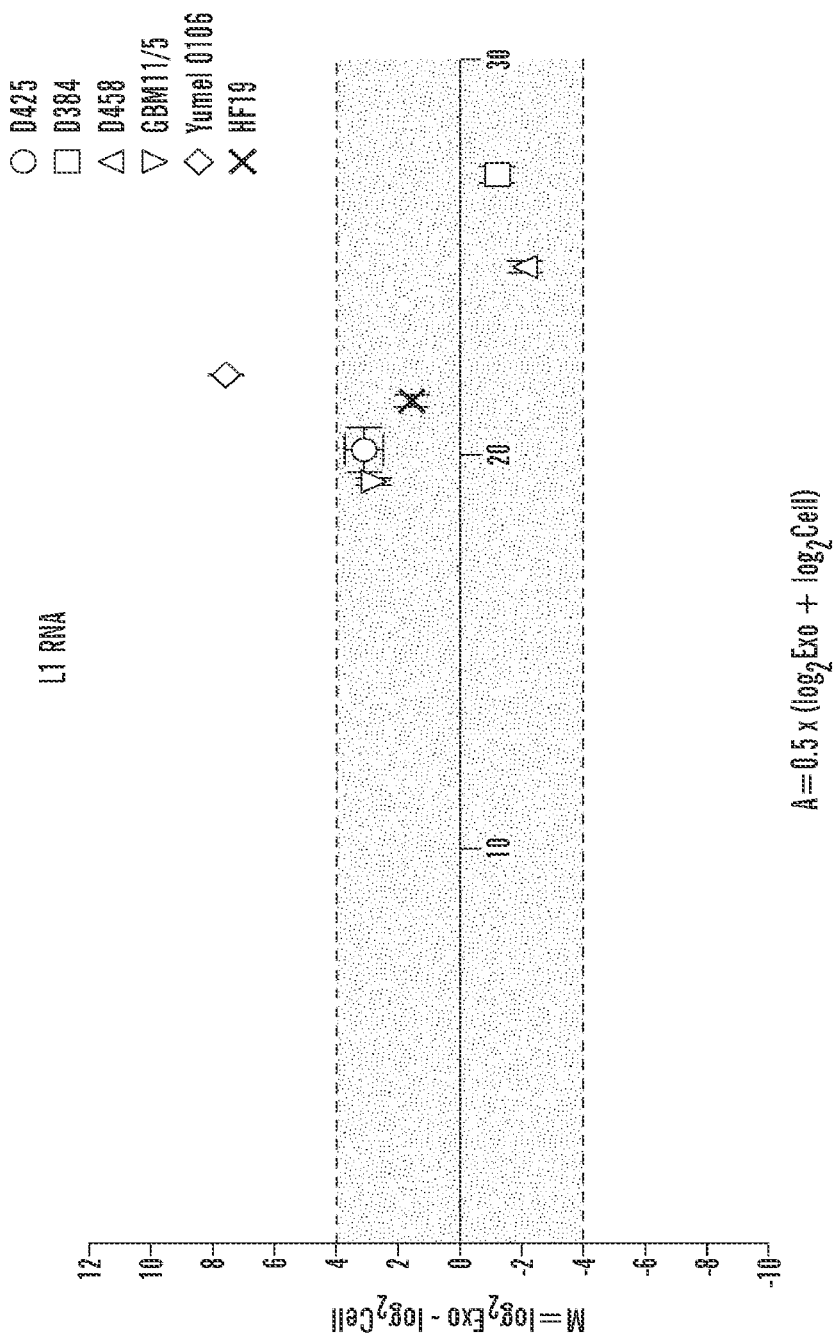
FIGS. 21A, 21B and 21C show MA plots depicting relative expression levels of L1 (FIG. 21A), ALU (FIG. 21B) and HERV-K (FIG. 21C) RNA in cells and microvesicles derived from the cells. qRT-PCR was carried out for retrotransposon elements in cell RNA and exoRNA from three medulloblastoma (D425, D384 and D458), one GBM (11/5), one melanoma (0106) and one human fibroblast (HF19) line. The RNA expression levels were measured and normalized to GAPDH. HERV-K RNA was not detectable in exoRNA from normal human fibroblasts (HF19), so it was given a Ct value of 36 (below detection limit).
Figure 21B:
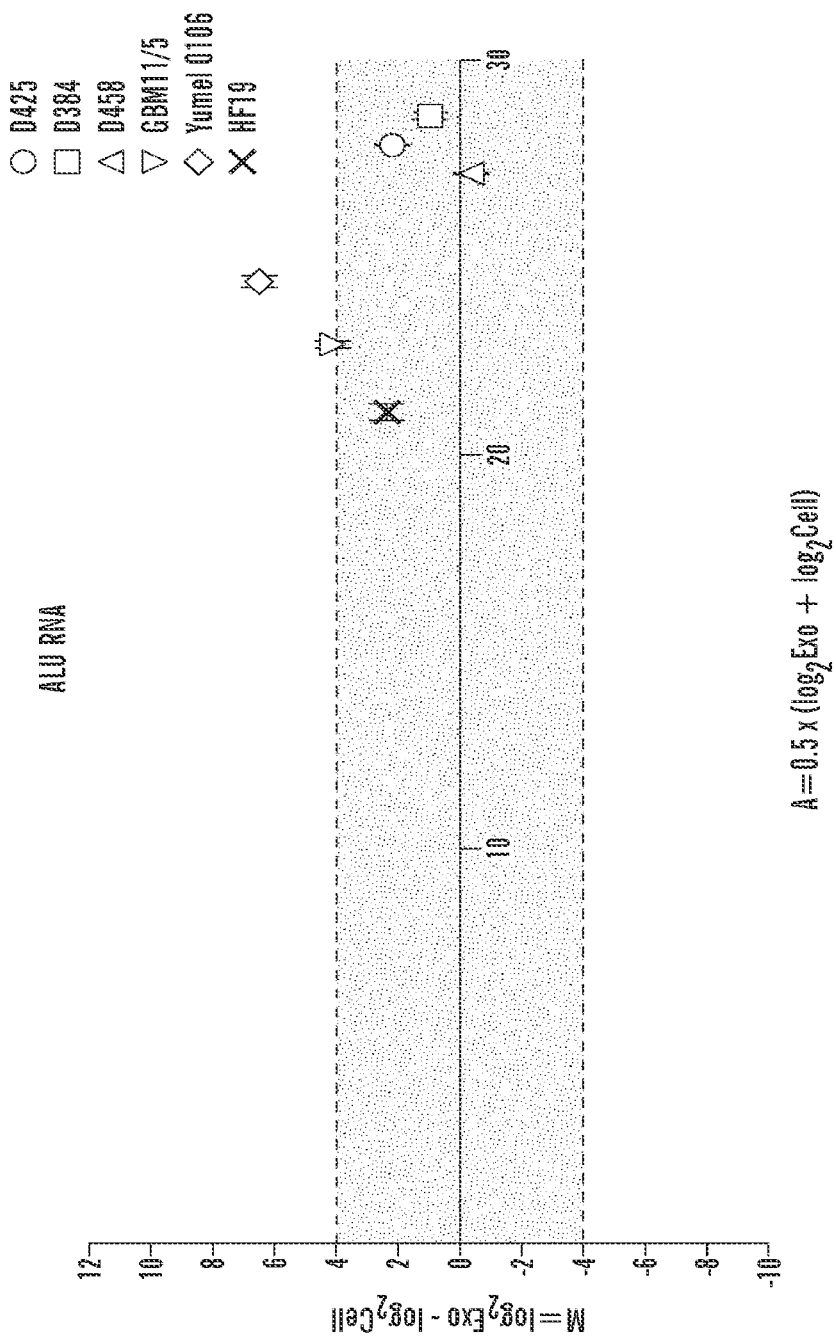
Figure 21C:
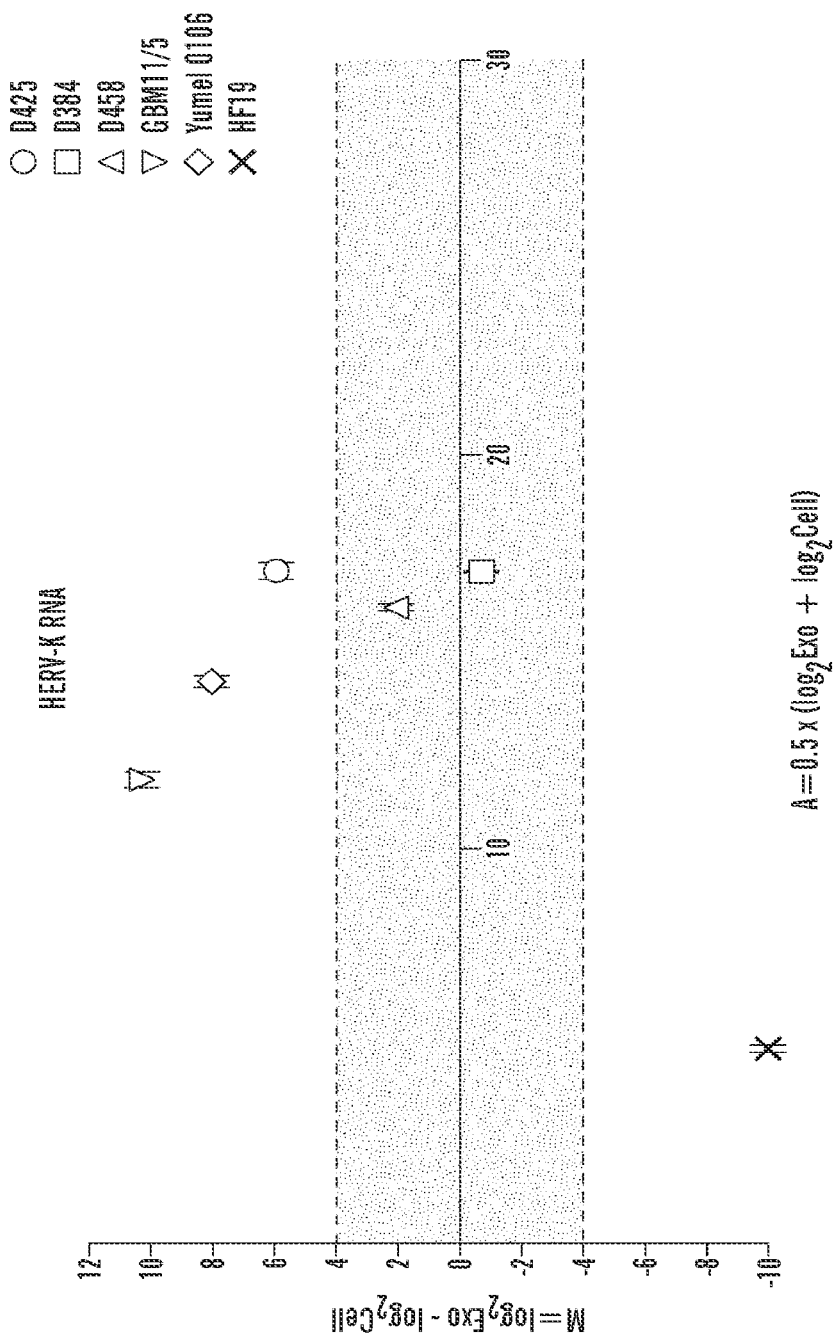

Since L1 and HERV-K retrotransposons, as well as Alu elements (Goodier and Kazazian, 2008), have been implicated in tumor progression, we further assayed their levels in cellular RNA and exoRNA from tumor and normal cells by qRT-PCR (again with the caveat that the primers used only detect a subset of these sequences). See FIGS. 21A-C. The expression levels were normalized to that of the GAPDH mRNA. L1 and Alu sequences were abundant in both cells and microvesicles (high values on the X-axis) and enriched in most of the microvesicles compared to the cells (M>0). The levels of retrotransposon sequences tended to be higher in exoRNA vs. cellular RNA, with HERV-K being relatively high in some tumors. Interestingly, HERV-K RNA was not detectable in exoRNA from normal human fibroblasts (HF19), with a Ct value of 36 (below detection limit). This difference between levels of HERV-K RNA in microvesicles from fibroblasts and tumor cells is shown in the MA plot (FIG. 21C).

Example 6 The Non-Coding 7SL RNA in Microvesicles as Biomarkers for Cancer Cells We found that the expression profiles of the non-coding 7SL RNA in microvesicles from plasma may serve as biomarkers for glioblastoma. We obtained de-identified blood samples from a GBM patient and healthy control from the biobank at Massachusetts General Hospital. We took the serum for each blood sample and isolated microvesicles from the serum using the method as described in Example 1. RNA was extracted from the isolated microvesicles for further analysis. The expression levels of the 7SL RNA, EGFR and GAPDH were determined using qRT-PCR following a procedure as detailed in Example 3. The primers used for the qRT-PCR are as follows: 7SL-RNA:

```
Forward primer
                                      (SEQ ID NO: 13)
5' CAAAACTCCCGTGCTGATCA 3', Reverse primer
                                      (SEQ ID NO: 14)
5' GGCTGGAGTGCAGTGGCTAT 3', Probe (FAM labeled MGB probe),
                                      (SEQ ID NO: 15)
5' TGGGATCGCGCCTGT 3';

EGFR:
Forward primer
                                      (SEQ ID NO: 16)
5' TATGTCCTCATTGCCCTCAACA 3', Reverse primer
                                      (SEQ ID NO: 17)
5' CTGATGATCTGCAGGTTTTCCA 3', Probe (FAM labeled MGB probe),
                                      (SEQ ID NO: 18)
5' AAGGAATTCGCTCCACTG 3';
GAPDH, huGAPDH ID 4326317E from
the vendor Applied Biosystems Inc..
```

The results show that the expression profile of the 7SL RNA in microvesicles correlates with the disease status of the subject from which the microvesicles were isolated (FIG. 34). The expression levels of the 7SL RNA in microvesicles from GBM serum samples were about 200 times higher than the levels from normal serum samples. In contrast, the expression levels of EGFR in microvesicles from GBM serum samples were about 2 times higher than the levels from normal serum samples. Further, the expression levels of GAPDH in microvesicles from GBM serum samples were roughly the same as the levels in normal serum samples.

As such, one aspect of the present invention is directed to the profile of 7SL RNA in microvesicles isolated from a subject, e.g., a human being. The profile of 7SL RNA may be the expression profile of the 7SL RNA. The profile of 7SL RNA may be correlated with the medical condition of the subject wherefrom the microvesicles are isolated.

Another aspect of the present invention is directed to a method of aiding the diagnosis, prognosis or selection of treatment therapy of a medical condition by determining the profile of the 7SL RNA. The determination of the profile of 7SL RNA may be the determination of the expression profile of the 7SL RNA. Since the profile of 7SL RNA may be correlated with the medical condition of the subject wherefrom the microvesicles are isolated, the determination of the profile in microvesicles may therefore aid the diagnosis, prognosis or selection of treatment therapy for the subject.

Example 7 Retrotransposon Elements in Tumor Microvesicles are Transferrable

To determine whether microvesicles could transfer HERV-K RNA to normal cells, human umbilical vein endothelial cells (HUVEC) were exposed to microvesicles from medulloblastoma cells and levels of HERV-K RNA were measured in HUVEC cells over time. Human umbilical vein endothelial cells (HUVEC) cells, kindly provided by Dr. Jonathan Song (Massachusetts General Hospital), were cultured in gelatin-coated flasks in endothelial basal medium (Lonza, Walkersville, Md.) supplemented with hEGF, hydrocortisone, GA-1000 and FBS (Singlequots from Lonza). All cell lines were used over a few passages, as microvesicle yield tended to change over extended passages.

Specifically, HUVEC cells were seeded in 12-well plates at a density of 1.5×10$^5$ cells/well. Microvesicles were isolated from 1.2×10$^7$ D384 cells over a 48 hour period and added to each well in a total volume of 400 µl DMEM. Mock treated cells were incubated in 400 µl exosome-free DMEM. The cells were incubated for 2 hrs at 37° C. and were then replenished with 1.5 ml DMEM (with 5% dFBS). Cells were collected at different time points after the microvesicle exposure and cell RNA was extracted for qRT-PCR analysis. The result is presented as the average±SEM of three independent experiments.

Figure 22:
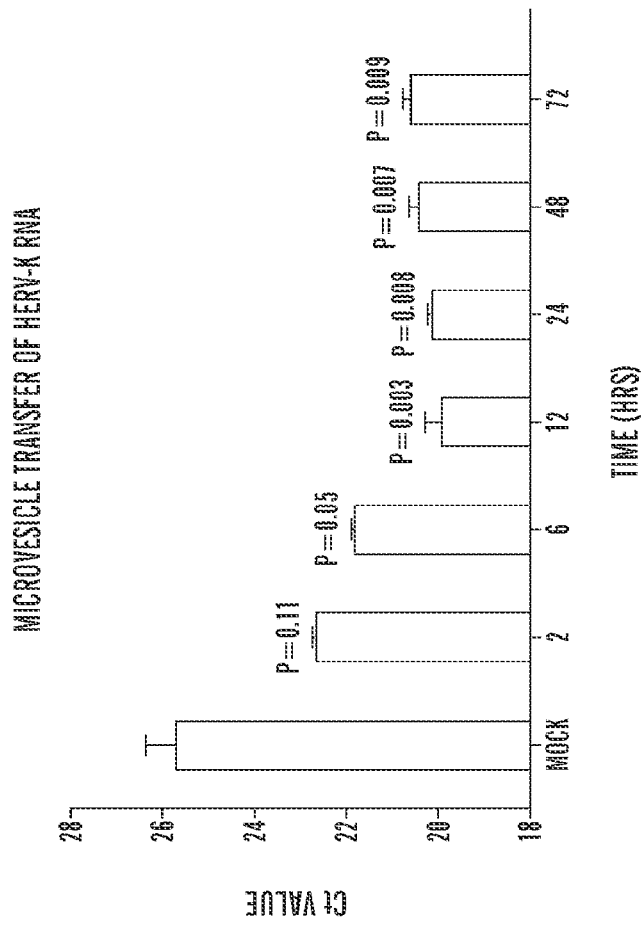
FIG. 22 shows a chart depicting the expression levels of HERV-K at different time points in HUVEC cells. The HUVEC cells were exposed to medulloblastoma D384 microvesicles and their expression level of HERV-K RNA was analyzed by qRT-PCR over 72 hrs following exposure. MOCK is non-exposed cells. HERV-K was normalized to GAPDH. P values were calculated using the two-tailed t-test, comparing levels to MOCK infected cells.

As shown in FIG. 22, HERV-K RNA expression was increased in HUVEC cells at 2, 6, 12, 24, 48 and 72 hours after microvesicle exposure. The increased HERV-K RNA expression in HUVEC cells indicated that the microvesicles contained active HERV-K genes and such genes were transferred to the HUVEC cells.

Example 8 Retrotransposon Elements in the Form of exoDNA were Enriched in Tumor Microvesicles with Elevated RT Activities ExoDNA was also analyzed at the retrotransposon level with qPCR. ExoDNAs were extracted from microvesicles as detailed in Example 2. gDNA were extracted from cells as detailed in Example 3. The primers used for qPCR are as follows:

```
GAPDH primers:
Forward
                                     (SEQ ID NO: 19)
CTCTGCTCCTCCTGTTCGAC,
(exon 8)

Reverse
                                     (SEQ ID NO: 20)
ACGACCAAATCCGTTGACTC;
(exon 9)

L1 primers:
Forward
                                     (SEQ ID NO: 21)
TAAGGGCAGCCAGAGAGAAA, Reverse
                                     (SEQ ID NO: 22)
GCCTGGTGGTGACAAAATCT;

HERV-K6 primers:
Forward
                                     (SEQ ID NO: 23)
GGAGAGAAGCTGTCCTGTGG, Reverse
                                     (SEQ ID NO: 24)
TGACTGGACTTGCACGTAGG;

Alu primers:
Forward
                                     (SEQ ID NO: 25)
CATGTGGGTTAGCCTGGTCT, Reverse
                                     (SEQ ID NO: 26)
TTCCCACATTGCGTCATTTA.
```

Figure 23A:
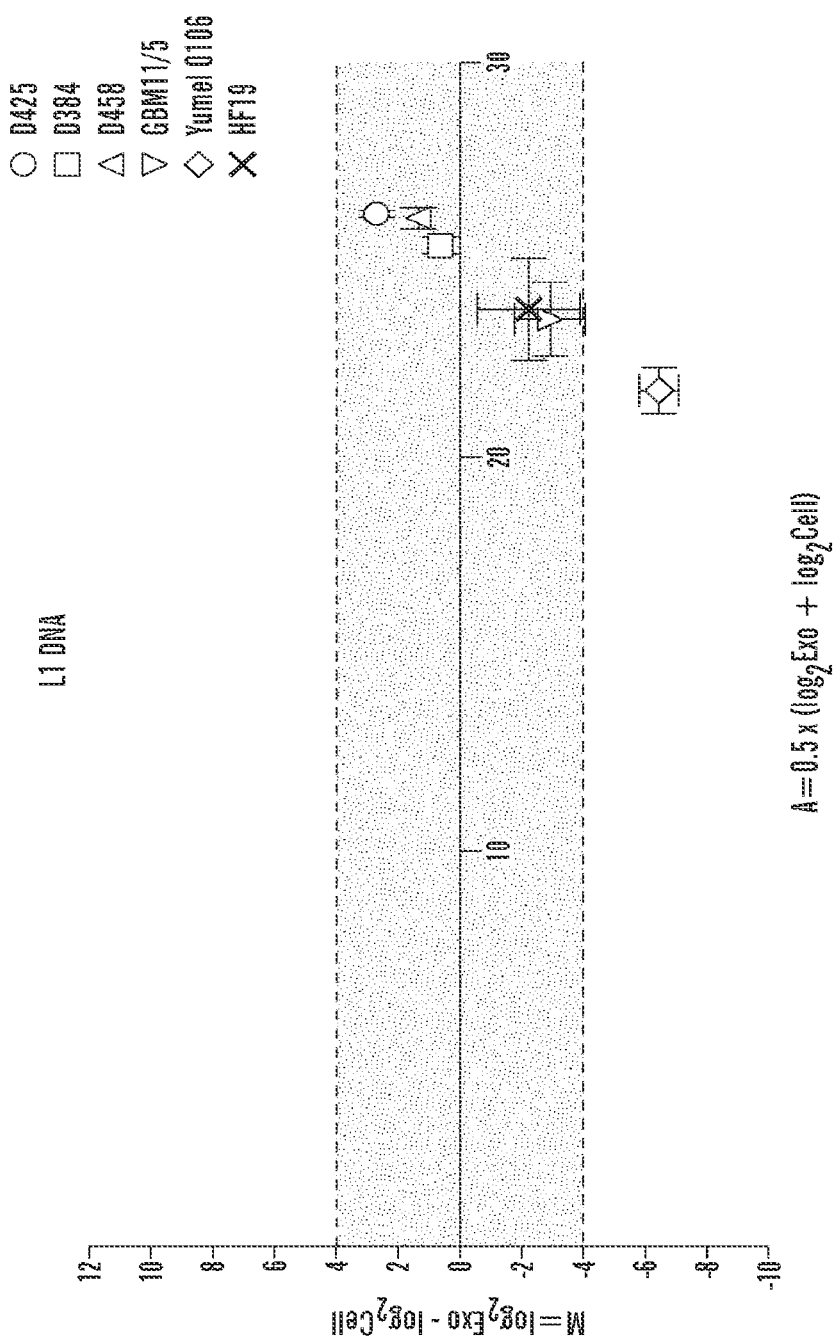
FIGS. 23A, 23B and 23C show MA plots depicting relative levels of L1 (FIG. 23A), ALU (FIG. 23B) and HERV-K (FIG. 23C) DNA in cells and microvesicles derived from the cells. q-PCR was carried out for retrotransposon elements with cell genomic DNA and microvesicle DNA from three medulloblastoma (D425, D384 and D458), one GBM (11/5), one melanoma (0106) and one human fibroblast (HF19) line. The DNA levels were measured and normalized to GAPDH. Results are expressed as average±SEM (n=3).
Figure 23B:
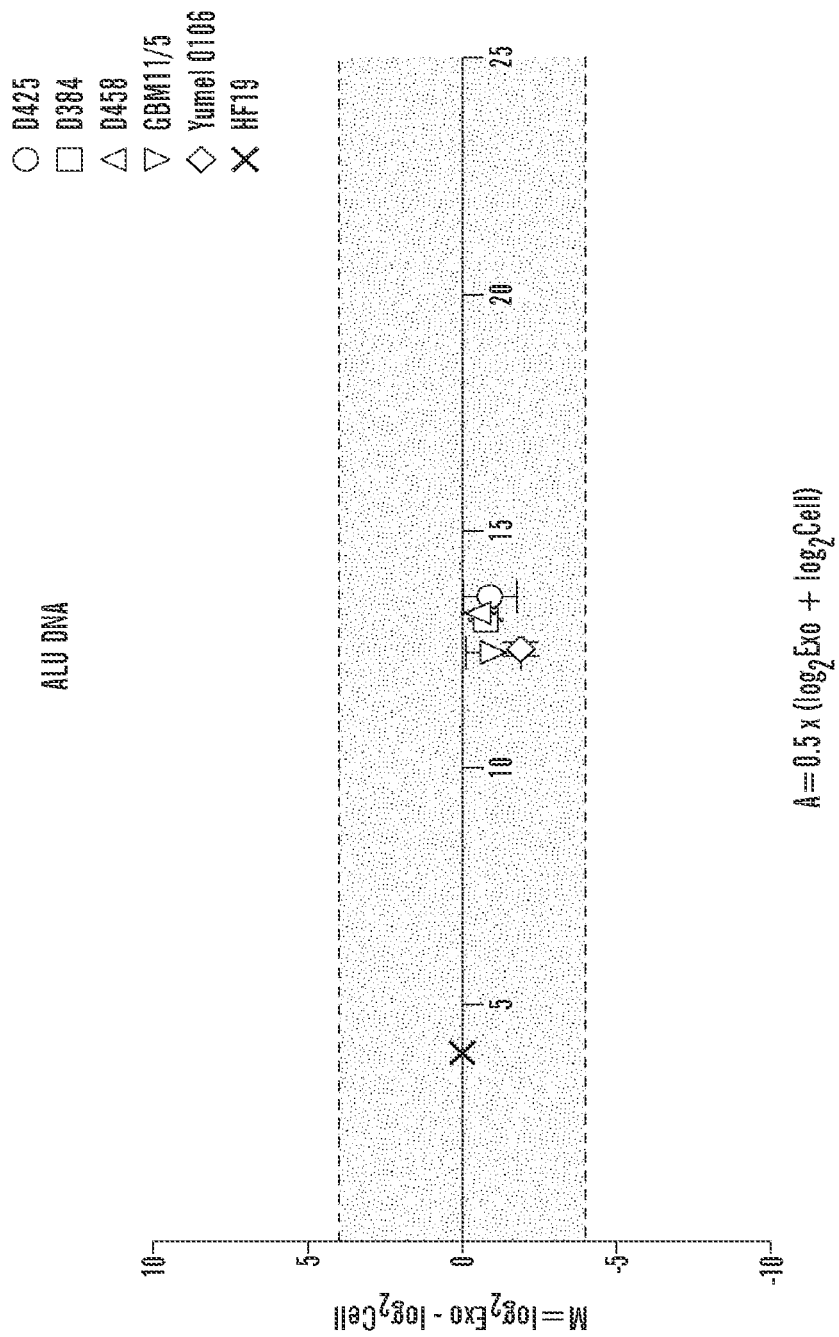
Figure 23C:
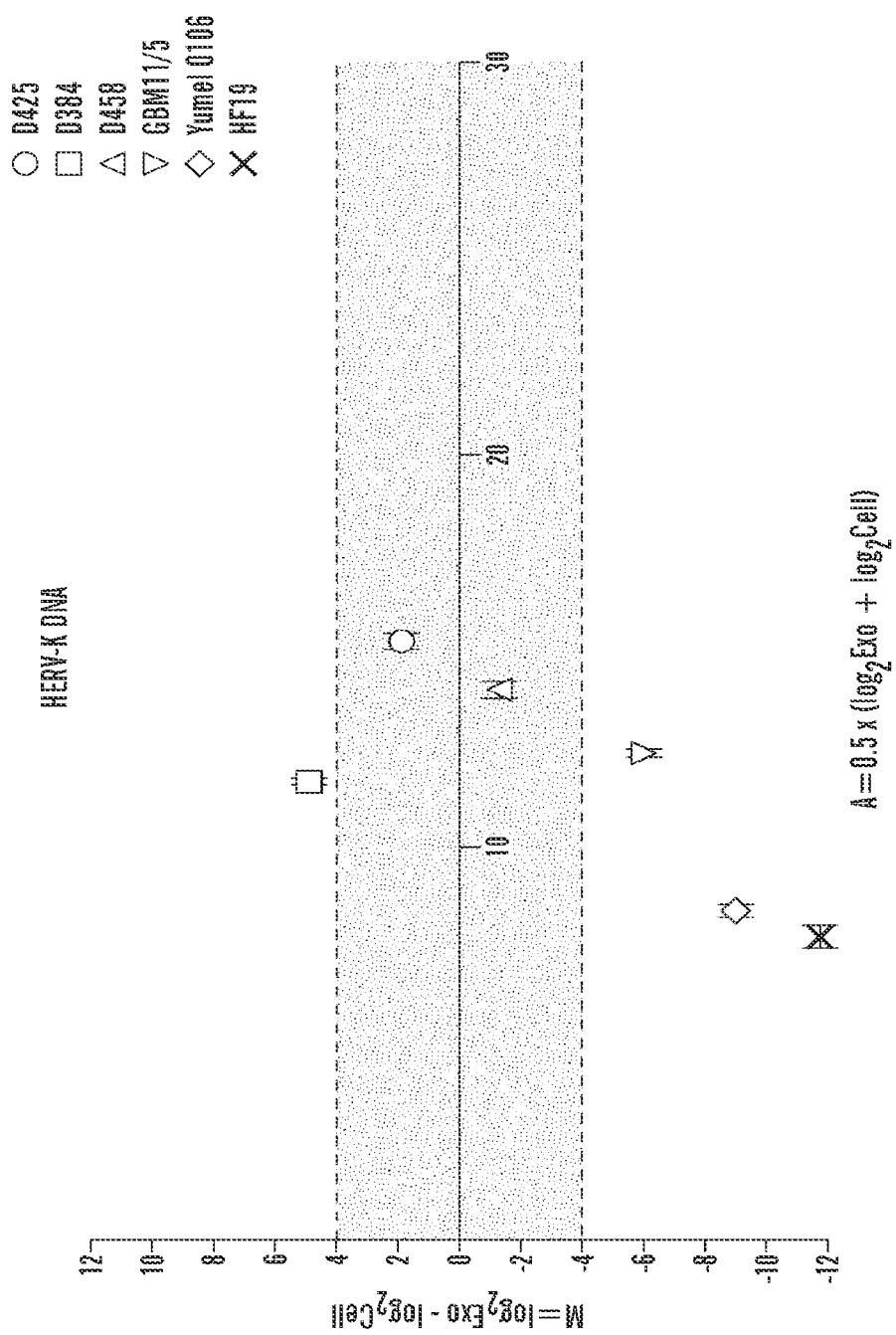

The exoDNA levels were compared to nuclear gDNA isolated from the cells in MA plots. The levels of exoDNA in microvesicles and gDNA in corresponding cells were normalized to levels of GAPDH. The exoDNA (presumably originating from the cytoplasmic compartment) and gDNA (isolated from the nuclear compartment of the cells) showed clearly different patterns (M≠0). L1 was slightly enriched in all medulloblastomas (FIG. 23A). HERV-K DNA was enriched in two of the medulloblastomas (D425 and D384) (FIG. 23C). In contrast, Alu was not enriched in any of the medulloblastoma tested (FIG. 23B).

We further found that the enrichment of the transposable elements at the exoDNA level in the medulloblastoma cell lines corresponded to high levels of endogenous Reverse Transcription (RT) activity in exosomes. To measure RT activities, microvesicles were lysed in RIPA buffer [50 mM Tris-HCl (pH 8); 150 mM NaCl, 2.5% sodium dodecyl sulfate, 2.5% deoxycholic acid, 2.5% Nonidet P-40] for 20 min at 4° C. Exosomal debris was removed by centrifugation at 14,000×g for 15 min. Proteins were quantified by Bradford assay and diluted 1:6 for each RT reaction. The RT assay was performed using the EnzCheck RT assay kit (Invitrogen) on a 25 µL reaction, as described by the manufacturer. Fluorescence signal of the samples was measured before and after the RT incubation. The difference between the two values indicates newly synthesized DNA. Serial dilutions of SuperScript™ III First Strand (Invitrogen) were used as standards. The result is presented as the average±SEM of three independent experiments.

Figure 24:
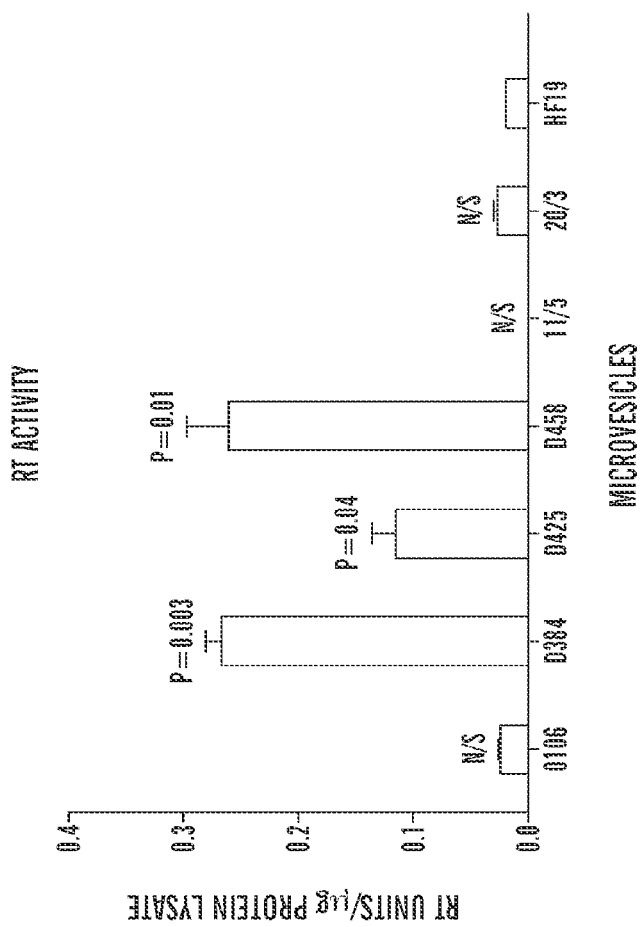
FIG. 24 shows a chart depicting the Reverse Transcriptase (RT) activity in microvesicles secreted by three medulloblastoma (D425, D384 and D458), one GBM (11/5), one melanoma (0106) and one human fibroblast (HF19) line. The RT activity was measured in the microvesicles using the EnzChek RT Assay Kit (Invitrogen) and normalized to protein content. The RT activity is measured as RT units calculated based on the standard curve generated using SuperScript III (Invitrogen). Results are expressed as average±SEM (n=3).

As shown in FIG. 24, RT activities in the 0106, GBM11/5, GBM 20/3 and HF19 cells are significantly less than those in D384, D425 and D458 cells. This decreased RT activities correlate well with the reduced levels of L1 and HERV-K exoDNA in 0106, GBM11/5, GBM 20/3 and HF19 cells (as shown by the negative values on the MA plots in FIGS. 23 A and C). Such correlation suggests that a fraction of exoDNA may be cDNA.

In addition, we found that exoDNA might also include fragments of genomic DNA. We used L-mimosine to inhibit DNA replication and examined whether the inhibition affected the yield of exoDNA. If the exoDNA yield is decreased after inhibition, it is very likely that exoDNA may contain fragments of genomic DNA.

Specifically, D384 cells were plated on 6-well plates (2×106 cells/well) and treated with increasing amounts (200, 400 and 600 µM) of L-mimosine (Sigma-Aldrich, St. Louis, Mo.) which is an inhibitor of DNA replication. The drug was added at one time point and 48 hrs after, the media was collected and processed for the isolation of microvesicles. Cell viability was assessed by cell count using the Countess Automated Cell Counter (Invitogen). SsDNA yields are normalized to one.

Figure 32:
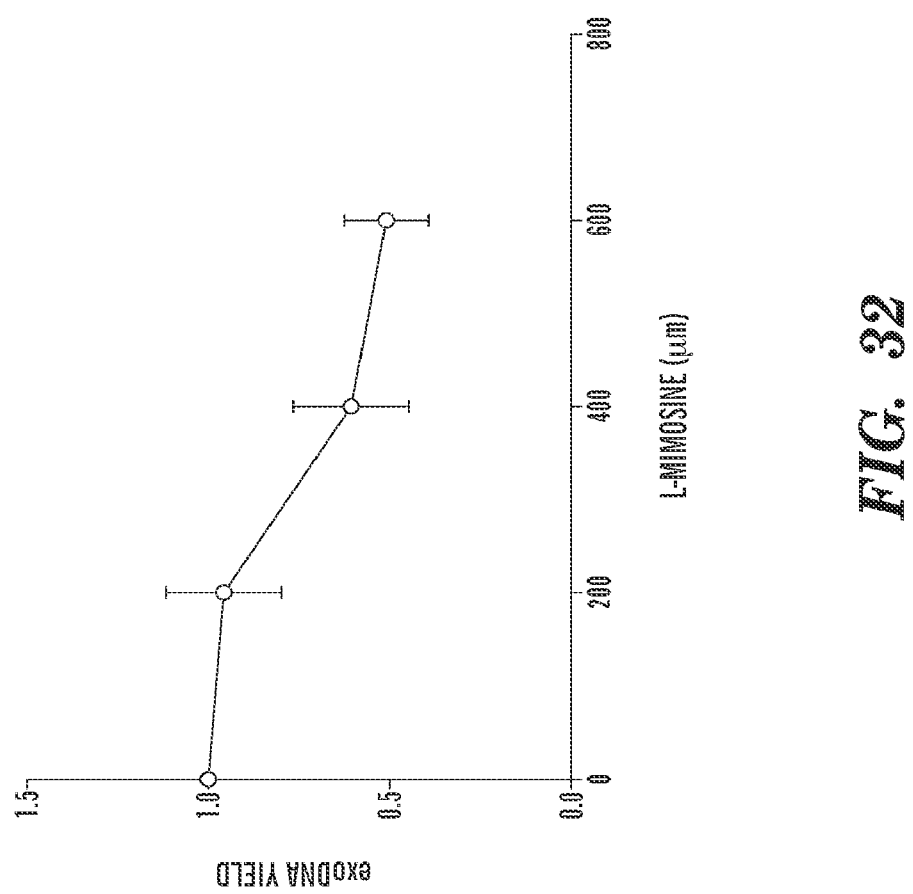
FIG. 32 shows a chart depicting the amount of exoDNA extracted from microvesicles isolated from medulloblastoma D384 cell culture media. D384 cells were seeded in 6-well plates and treated with increasing dosages of L-mimosine (200, 400 and 600 μM) or mock treated. Microvesicles were isolated from the medium after 48 hrs and ssDNA was extracted using the Qiagen PCR purification kit. Single-stranded DNA yields were quantified using the Bioanalyzer and the yields were compared to mock treated cells (normalized to 1.0).
Figure 33:
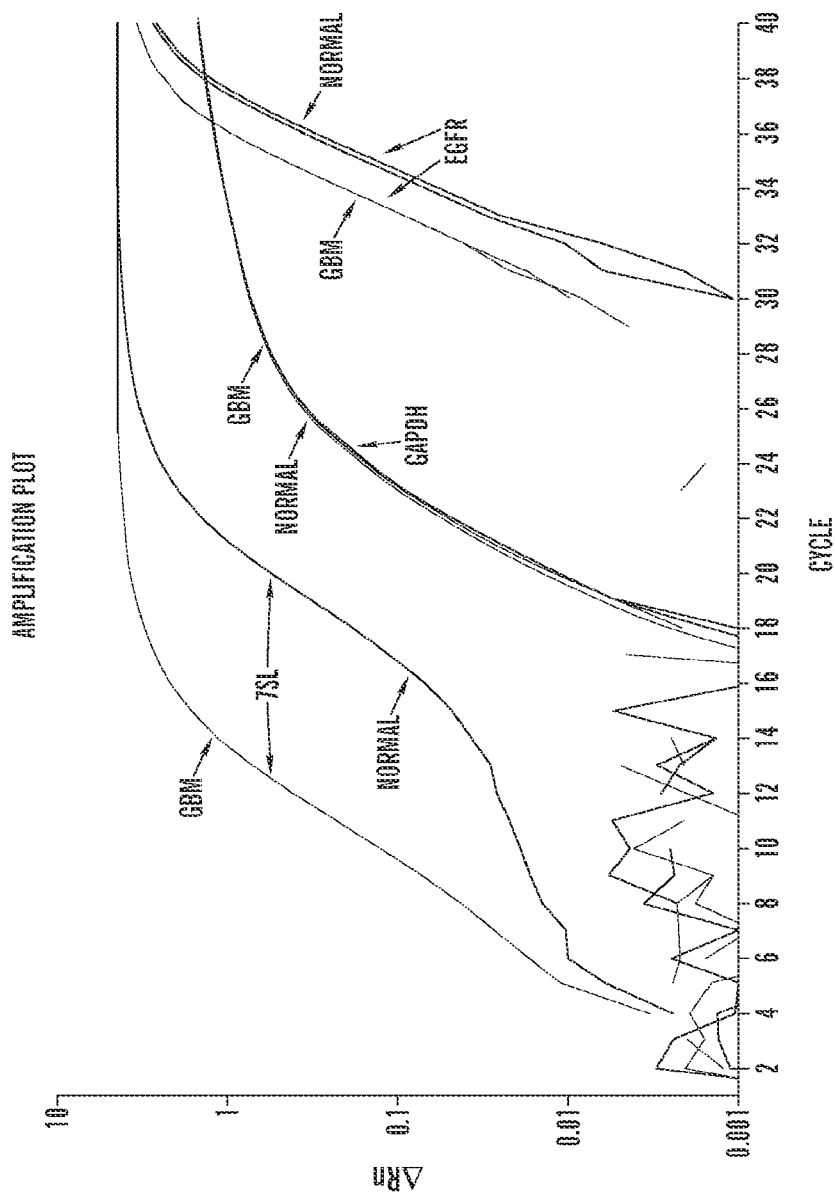
FIG. 33 depicts the results of quantitative RT-PCR analysis of the expression levels of 7SL RNA, EGFR and GAPDH in microvesicles isolated from serum samples obtained from a GBM patient or a normal individual. The X-axis is the number of PCR cycles. The Y-axis is the fluorescent intensity (delta Rn) measured by the ABI7500 machine.

As shown in FIG. 32, the exoDNA yield in microvesicles was decreased by about 50% following inhibition of DNA replication with L-mimosine. Therefore, some of the exoDNA may also be fragments of genomic DNA generated during DNA replication and mitosis.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

TABLE 2

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| ABL1 | 25 | P00519 | 9q34.1 | CML, ALL | — | — | L | Dom | T | BCR, ETV6 |
| ABL2 | 27 | P42684 | 1q24-q25 | AML | — | — | L | Dom | T | ETV6 |
| AF15Q14 | 57082 | NP_065113 | 15q14 | AML | — | — | L | Dom | T | MLL |
| AF1Q | 10962 | Q13015 | 1q21 | ALL | — | — | L | Dom | T | MLL |
| AF3p21 | 51517 | Q9NZQ3 | 3p21 | ALL | — | — | L | Dom | T | MLL |
| AF5q31 | 27125 | NP_055238 | 5q31 | ALL | — | — | L | Dom | T | MLL |
| AKT2 | 208 | P31751 | 19q13.1-q13.2 | Ovarian, pancreatic | — | — | E | Dom | A | — |
| ALK | 238 | Q9UM73 | 2p23 | ALCL | — | — | L | Dom | T | NPM1, TPM3, TFG, TPM4, ATIC, CLTC, MSN, ALO17 |
| ALO17 | 57714 | XP_290769 | 17q25.3 | ALCL | — | — | L | Dom | T | ALK |
| APC | 324 | P25054 | 5q21 | Colorectal, pancreatic, desmoid, hepatoblastoma, glioma, other | Colorectal, pancreatic, desmoid, hepatoblastoma, glioma, other CNS | Adenomatous polyposis coli; Turcot syndrome | E, M, O | Rec | D‡, Mis, N, F, S | — |
| ARHGEF12 | 23365 | NP_056128 | 11q23.3 | AML | — | — | L | Dom | T | MLL |
| ARHH | 399 | Q15669 | 4p13 | NHL | — | — | L | Dom | T | BCL6 |
| ARNT | 405 | P27540 | 1q21 | AML | — | — | L | Dom | T | ETV6 |
| ASPSCR1 | 79058 | NP_076988 | 17q25 | Alveolar soft part sarcoma | — | — | M | Dom | T | TFE3 |
| ATF1 | 466 | P18846 | 12q13 | Malignant melanoma of soft parts, angiomatoid fibrous histiocytoma | — | — | E, M | Dom | T | EWSR1 |
| ATIC | 471 | P31939 | 2q35 | ALCL | — | — | L | Dom | T | ALK |
| ATM | 472 | Q13315 | 11q22.3 | T-PLL | Leukaemia, lymphoma, medulloblastoma, glioma | Ataxia telangiectasia | L, O | Rec | D, Mis, N, F, S | — |
| BCL10 | 8915 | O95999 | 1p22 | MALT | — | — | L | Dom | T | IGHα |
| BCL11A | 53335 | NP_060484 | 2p13 | B-CLL | — | — | L | Dom | T | IGHα |
| BCL11B | 64919 | NP_612808 | 14q32.1 | T-ALL | — | — | L | Dom | T | TLX3 |
| BCL2 | 596 | P10415 | 18q21.3 | NHL, CLL | — | — | L | Dom | T | IGHα |
| BCL3 | 602 | P20749 | 19q13 | CLL | — | — | L | Dom | T | IGHα |
| BCL5 | 603 | 152586 | 17q22 | CLL | — | — | L | Dom | T | MYC |
| BCL6 | 604 | P41182 | 3q27 | NHL, CLL | — | — | L | Dom | T, Mis | IG loci, ZNFN1A1, LCP1, PIM1, TFRC, |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| BCL7A | 605 | NP_066273 | 12q24.1 | B-NHL | — | — | L | Dom | T | MHC2TA, NACA, HSPCB, HSPCA, HIST1H4I, IL21R, POU2AF1, ARHH, EIF4A2 |
| BCL9 | 607 | O00512 | 1q21 | B-ALL | — | — | L | Dom | T | MYC |
| BCR | 613 | P11274 | 22q11.21 | CML, ALL | — | — | L | Dom | T | IGHα, IGLα |
| BHD | 201163 | NP_659434 | 17p11.2 | — | Renal, fibrofolliculomas, trichodiscomas | Birt-Hogg-Dube syndrome | E, M | Rec? | Mis, N, F | ABL1, FGFR1 |
| BIRC3 | 330 | Q13489 | 11q22-q23 | MALT | — | — | L | Dom | T | MALT1 |
| BLM | 641 | P54132 | 15q26.1 | — | Leukaemia, lymphoma, skin squamous cell, other cancers | Bloom Syndrome | L, E | Rec | Mis, N, F | — |
| BMPR1A | 657 | P36894 | 10q22.3 | — | Gastrointestinal polyps | Juvenile polyposis | E | Rec | Mis, N, F | — |
| BRAF | 673 | P15056 | 7q34 | Melanoma, colorectal, papillary thyroid, borderline ovarian, NSCLC, cholangiocarcinoma | — | — | E | Dom | M | — |
| BRCA1 | 672 | P38398 | 17q21 | Ovarian | Breast, ovarian | Hereditary breast/ovarian | E | Rec | D, Mis, N, F, S | — |
| BRCA2 | 675 | P51587 | 13q12 | Breast, ovarian, pancreatic | Breast, ovarian, pancreatic, leukaemia (FANCB, FANCD1) | Hereditary breast/ | L, E ovarian | Rec | D, Mis, N, | — F, S |
| BRD4 | 23476 | O60885 | 19q13.1 | Lethal midline carcinoma of young people | — | — | E | Dom | T | NUT |
| BTG1 | 694 | P31607 | 12q22 | BCLL | — | — | L | Dom | T | MYC |
| CBFA2T1 | 862 | Q06455 | 8q22 | AML | — | — | L | Dom | T | MLL, RUNX1 |
| CBFA2T3 | 863 | NP_005178 | 16q24 | AML | — | — | L | Dom | T | RUNX1 |
| CBFB | 865 | Q13951 | 16q22 | AML | — | — | L | Dom | T | MYH11 |
| CBL | 867 | P22681 | 11q23.3 | CLL, B-ALL, breast | — | — | L | Dom | T | MLL |
| CCND1 | 595 | P24385 | 11q13 | | — | — | L, E | Dom | T | IGHα, FSTL3 |
| CDH1 | 999 | P12830 | 16q22.1 | Lobular breast, gastric | Gastric | Familial gastric carcinoma | E | Rec | Mis, N, F, S | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| CDK4 | 1019 | P11802 | 12q14 | — | Melanoma | Familial malignant melanoma | E | Dom | Mis | — |
| CDKN2A-p14^ARF | 1029 | NP_478102 | 9p21 | Melanoma, multiple other | Melanoma, pancreatic | Familial malignant melanoma | L, E, M, O | Rec | D, S | — |
| CDKN2A-p16^INK4A | 1029 | P42771 | 9p21 | Melanoma, multiple other | Melanoma, pancreatic | Familial malignant melanoma | L, E, M, O | Rec | D, Mis, N, F, S | — |
| CDX2 | 1045 | Q99626 | 13q12.3 | AML | — | — | L | Dom | T | ETV6 |
| CEBPA | 1050 | NP_004355 | 11p15.5 | AML, MDS | — | — | L | Dom | Mis, N, F | — |
| CEP1 | 11064 | NP_008949 | 9q33 | MPD/NHL | — | — | L | Dom | T | FGFR1 |
| CHIC2 | 26511 | NP_036242 | 4q11-q12 | AML | — | — | L | Dom | T | ETV6 |
| CHN1 | 1123 | P15882 | 2q31-q32.1 | Extraskeletal myxoid chondrosarcoma | — | — | M | Dom | T | TAF15 |
| CLTC | 1213 | Q00610 | 17q11-qter | ALCL | — | — | L | Dom | T | ALK |
| COL1A1 | 1277 | P02452 | 17q21.31-q22 | Dermatofibrosarcoma protuberans | — | — | M | Dom | T | PDGFB |
| COPEB | 1316 | Q99612 | 10p15 | Prostatic, glioma | — | — | E, O | Rec | Mis, N | — |
| COX6C | 1345 | P09669 | 8q22-q23 | Uterine leiomyoma | — | — | M | Dom | T | HMGA2 |
| CREBBP | 1387 | Q92793 | 16p13.3 | AL, AML | — | — | L | Dom | T | MLL, MORF, RUNXBP2 |
| CTNNB1 | 1499 | P35222 | 3p22-p21.3 | Colorectal, ovarian, hepatoblastoma, others | — | — | E, M, O | Dom | H, Mis | — |
| CYLD | 1540 | NP_056062 | 16q12-q13 | Cylindroma | Cylindroma | Familial cylindromatosis | E | Rec | Mis, N, F, S | — |
| D10S170 | 8030 | NP_005427 | 10q21 | Papillary thyroid, CML | — | — | E | Dom | T | RET, PDGFB |
| DDB2 | 1643 | Q92466 | 11p12 | — | Skin basal cell, skin squamous cell, melanoma | Xeroderma pigmentosum E | E | Rec | M, N | — |
| DDIT3 | 1649 | P35638 | 12q13.1-q13.2 | Liposarcoma | — | — | M | Dom | T | FUS |
| DDX10 | 1662 | Q13206 | 11q22-q23 | AML^S | — | — | L | Dom | T | NUP98 |
| DEK | 7913 | P35659 | 6p23 | AML | — | — | L | Dom | T | NUP214 |
| EGFR | 1956 | P00533 | 7p12.3-p12.1 | Glioma | — | — | O | Dom | A, O^∥ | — |
| EIF4A2 | 1974 | Q14240 | 3q27.3 | NHL | — | — | L | Dom | T | BCL6 |
| ELKS | 23085 | NP_055879 | 12p13.3 | Papillary thyroid | — | — | E | Dom | T | RET |
| ELL | 8178 | P55199 | 19p13.1 | AL | — | — | L | Dom | T | MLL |
| EP300 | 2033 | Q09472 | 22q13 | Colorectal | — | — | L, E | Rec | T | MLL, RUNXBP2 |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| EPS15 | 2060 | P42566 | 1p32 | breast, pancreatic, AML | — | — | L | Dom | T | MLL |
| ERBB2 | 2064 | P04626 | 17q21.1 | ALL Breast, ovarian, other tumour types | — | — | E | Dom | A | — |
| ERCC2 | 2068 | P18074 | 19q13.2-q13.3 | — | Skin basal cell, skin squamous cell, melanoma | Xeroderma pigmentosum D | E | Rec | M, N, F, S | — |
| ERCC3 | 2071 | P19447 | 2q21 | — | Skin basal cell, skin squamous cell, melanoma | Xeroderma pigmentosum B | E | Rec | M, S | — |
| ERCC4 | 2072 | Q92889 | 16p13.3- | — | Skin basal cell, skin squamous cell, melanoma | Xeroderma pigmentosum F | E | Rec | M, N, F | — |
| ERCC5 | 2073 | P28715 | 13q33 | — | Skin basal cell, skin squamous cell, melanoma | Xeroderma pigmentosum G | E | Rec | M, N, F | — |
| ERG | 2078 | P11308 | 21q22.3 | Ewing's sarcoma | — | — | M | Dom | T | EWSR1 |
| ETV1 | 2115 | P50549 | 7p22 | Ewing's sarcoma | — | — | M | Dom | T | EWSR1 |
| ETV4 | 2118 | P43268 | 17q21 | Ewing's sarcoma | — | — | M | Dom | T | EWSR1 |
| ETV6 | 2120 | P41212 | 12p13 | Congenital fibrosarcoma, multiple leukaemia and lymphoma, secretory breast | — | — | L, E, M | Dom | T | NTRK3, RUNX1, PDGFRB, ABL1, MN1, ABL2, FACL6, CHIC2, ARNT, JAK2, EVI1, CDX2, STL |
| EVI1 | 2122 | Q03112 | 3q26 | AML, CML | — | — | L | Dom | T | RUNX1, ETV6 |
| EWSR1 | 2130 | NP_005234 | 22q12 | Ewing's sarcoma, desmoplastic small round cell, ALL | — | — | L, M | Dom | T | FLI1, ERG, ZNF278, NR4A3, TEC, FEV, ATF1, ETV1, ETV4, WT1, ZNF384 |
| EXT1 | 2131 | NP_000118 | 8q24.11-q24.13 | — | Exostoses, osteosarcoma | Multiple exostoses type 1 | M | Rec | Mis, N, F, S | — |
| EXT2 | 2132 | Q93063 | 11p12-p11 | — | Exostoses; osteosarcoma | Multiple exostoses type 2 | M | Rec | Mis, N, F, S | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| FACL6 | 23305 | NP_056071 | 5q31 | AML, AEL | — | — | L | Dom | T | ETV6 |
| FANCA | 2175 | NP_000126 | 16q24.3 | — | AML, leukaemia | Fanconi anaemia A | L | Rec | D, Mis, N, F, S | — |
| FANCC | 2176 | Q00597 | 9q22.3 | — | AML, leukaemia | Fanconi anaemia C | L | Rec | D, Mis, N, F, S | — |
| FANCD2 | 2177 | NP_149075 | 3p26 | — | AML, leukaemia | Fanconi anaemia D2 | L | Rec | D, Mis, N, F | — |
| FANCE | 2178 | NP_068741 | 6p21-p22 | — | AML, leukaemia | Fanconi anaemia E | L | Rec | N, F, S | — |
| FANCF | 2188 | Q9NPI8 | 11p15 | — | AML, leukaemia | Fanconi anaemia F | L | Rec | N, F | — |
| FANCG | 2189 | O15287 | 9p13 | — | AML, leukaemia | Fanconi anaemia G | L | Rec | Mis, N, F, S | — |
| FEV | 54738 | NP_059991 | 2q36 | Ewing's sarcoma | — | — | M | Dom | T | EWSR1 |
| FGFR1 | 2260 | P11362 | 8p11.2-p11.1 | MPD/NHL | — | — | L | Dom | T | BCR, FOP, ZNF198, CEP1 |
| FGFR1OP | 11116 | NP_008976 | 6q27 | MPD/NHL | — | — | L | Dom | T | FGFR1 |
| FGFR2 | 2263 | P21802 | 10q26 | Gastric | — | — | E | Dom | Mis | — |
| FGFR3 | 2261 | P22607 | 4p16.3 | Bladder, MM | — | — | L, E | Dom | Mis, T | IGHα |
| FH | 2271 | P07954 | 1q42.1 | — | Leiomyomatosis, renal | Hereditary leiomyomatosis and renal-cell cancer | E, M | Rec | Mis, N, F | — |
| FIP1L1 | 81608 | N_112179 | 4q12 | Idiopathic hypereosinophilic syndrome | — | — | L | Dom | T | PDGFRA |
| FLI1 | 2313 | Q01543 | 11q24 | Ewing's sarcoma | — | — | M | Dom | T | EWSR1 |
| FLT3 | 2322 | P36888 | 13q12 | AML, ALL | — | — | L | Dom | Mis, O | — |
| FLT4 | 2324 | P35916 | 5q35.3 | Angiosarcoma | — | — | M | Dom | Mis | — |
| FNBP1 | 23048 | XP_052666 | 9q23 | AML | — | — | L | Dom | T | MLL |
| FOXO1A | 2308 | Q12778 | 13q14.1 | Alveolar rhabdomyosarcomas | — | — | M | Dom | T | PAX3 |
| FOXO3A | 2309 | O43524 | 6q21 | AL | — | — | L | Dom | T | MLL |
| FSTL3 | 10272 | O95633 | 19p13 | B-CLL | — | — | L | Dom | T | CCND1 |
| FUS | 2521 | P35637 | 16p11.2 | Liposarcoma | — | — | M | Dom | T | DDIT3 |
| GAS7 | 8522 | O60861 | 17p | AML$ | — | — | L | Dom | T | MLL |
| GATA1 | 2623 | P15976 | Xp11.23 | Megakaryoblastic leukaemia of Down syndrome | — | — | L | Dom | Mis, F | — |
| GMPS | 8833 | P49915 | 3q24 | AML | — | — | L | Dom | T | MLL |
| GNAS | 2778 | P04895 | 20q13.2 | Pituitary adenoma | — | — | E | Dom | Mis | — |
| GOLGA5 | 9950 | NP_005104 | 14q | Papillary thyroid | — | — | E | Dom | T | RET |
| GPC3 | 2719 | P51654 | Xq26.1 | — | Wilms' tumour | Simpson-Golabi-Behmel O syndrome | O | Rec | T, D, Mis, N, F, S | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| GPHN | 10243 | Q9NQX3 | 14q24 | AL | — | — | L | Dom | T | MLL |
| GRAF | 23092 | NP_055886 | 5q31 | AML, MDS | — | — | L | Dom | T, F, S | MLL |
| HEI10 | 57820 | NP_067001 | 14q11.1 | Uterine leiomyoma | — | — | M | Dom | T | HMGA2 |
| HIP1 | 3092 | O00291 | 7q11.23 | CMML | — | — | L | Dom | T | PDGFRB |
| HIST1H4I | 8294 | NP_003486 | 6p21.3 | NHL | — | — | L | Dom | T | BCL6 |
| HLF | 3131 | Q16534 | 17q22 | ALL | — | — | L | Dom | T | TCF3 |
| HMGA2 | 8091 | P52926 | 12q15 | Lipoma | — | — | M | Dom | T | LHFP, RAD51L1, LPP, HEI10, COX6C |
| HOXA11 | 3207 | P31270 | 7p15-p14.2 | CML | — | — | L | Dom | T | NUP98 |
| HOXA13 | 3209 | P31271 | 7p15-p14.2 | AML | — | — | L | Dom | T | NUP98 |
| HOXA9 | 3205 | P31269 | 7p15-p14.2 | AML$ | — | — | L | Dom | T | NUP98 |
| HOXC13 | 3229 | P31276 | 12q13.3 | AML | — | — | L | Dom | T | NUP98 |
| HOXD11 | 3237 | P31277 | 2q31-q32 | AML | — | — | L | Dom | T | NUP98 |
| HOXD13 | 3239 | P35453 | 2q31-q32 | AML$ | — | — | L | Dom | T | NUP98 |
| HRAS | 3265 | P01112 | 11p15.5 | Infrequent sarcomas, rare other types | — | — | L, M | Dom | Mis | — |
| HRPT2 | 3279 | NP_013522 | 1q21-q31 | Parathyroid adenoma | Parathyroid adenoma, multiple ossifying jaw fibroma | Hyperparathyroidism jaw tumour syndrome | E, M | Rec | Mis, N, F | — |
| HSPCA | 3320 | P07900 | 1q21.2-q22 | NHL | — | — | L | Dom | T | BCL6 |
| HSPCB | 3326 | P08238 | 6p12 | NHL | — | — | L | Dom | T | BCL6 |
| IGHα | 3492 | — | 14q32.33 | MM, Burkitt's lymphoma, NHL, CLL, B-ALL, MALT | — | — | L | Dom | T | MYC, FGFR3, PAX5, IRTA1, IRF4, CCND1, BCL9, BCL6, BCL8, BCL2, BCL3, BCL10, BCL11A. LHX4 |
| IGKα | 50802 | — | 2p12 | Burkitt's lymphoma | — | — | L | Dom | T | MYC |
| IGLα | 3535 | — | 22q11.1-q11.2 | Burkitt's lymphoma | — | — | L | Dom | T | BCL9, MYC |
| IL21R | 50615 | Q9HBE5 | 16p11 | NHL | — | — | L | Dom | T | BCL6 |
| IRF4 | 3662 | Q15306 | 6p25-p23 | MM | — | — | L | Dom | T | IGHα |
| IRTA1 | 83417 | NP_112572 | 1q21 | B-NHL | — | — | L | Dom | T | IGHα |
| JAK2 | 3717 | O60674 | 9p24 | ALL, AML | — | — | L | Dom | T | ETV6 |
| KIT | 3815 | P10721 | 4q12 | GIST, AML, TGCT | GIST, epithelioma | Familial gastrointestinal stromal | L, M, O | Dom | Mis, O | — |
| KRAS2 | 3845 | NP_004976 | 12p12.1 | Pancreatic, colorectal, lung, | — | — | L, E, M, O | Dom | Mis | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| LAF4 | 3899 | P51826 | 2q11.2-q12 | thyroid, AML, others | — | — | L | Dom | T | MLL |
| LASP1 | 3927 | Q14847 | 17q11-q21.3 | ALL | — | — | L | Dom | T | MLL |
| LCK | 3932 | NP_005347 | 1p35-p34.3 | AML | — | — | L | Dom | T | TRBα |
| LCP1 | 3936 | P13796 | 13q14.1-q14.3 | T-ALL | — | — | L | Dom | T | BCL6 |
| LCX | 80312 | XP_167612 | 10q21 | NHL | — | — | L | Dom | T | TML |
| LHFP | 10186 | NP_005771 | 13q12 | AML | — | — | M | Dom | T | HMGA2 |
| LMO1 | 4004 | P25800 | 11p15 | Lipoma | — | — | L | Dom | T | TRDα |
| LMO2 | 4005 | P25791 | 11p13 | T-ALL | — | — | L | Dom | T | TRDα |
| LPP | 4026 | NP_005569 | 3q28 | T-ALL | — | — | L, M | Dom | T | HMGA2, MLL |
| LYL1 | 4066 | P12980 | 19p13.2-p13.1 | Lipoma, leukaemia | — | — | L | Dom | T | TRBα |
| MADH4 | 4089 | Q13485 | 18q21.1 | T-ALL | Gastrointestinal polyps | Juvenile polyposis | E | Rec | D, Mis, N, F | — |
| MALT1 | 10892 | Q9UDY8 | 18q21 | Colorectal, pancreatic, small intestine | — | — | L | Dom | T | BIRC3 |
| MAML2 | 84441 | XP_045716 | 11q22-q23 | MALT | — | — | E | Dom | T | MECT1 |
| MAP2K4 | 6416 | P45985 | 17p11.2 | Salivary-gland mucoepidermoid | — | — | E | Rec | D, Mis, N | — |
| MDS1 | 4197 | Q13465 | 3q26 | Pancreatic, breast, colorectal | — | — | L | Dom | T | RUNX1 |
| MECT1 | 94159 | AAK93832.1 | 19p13 | MDS, AML | — | — | E | Dom | T | MAML2 |
| MEN1 | 4221 | O00255 | 11q13 | Salivary-gland mucoepidermoid | Parathyroid adenoma, pituitary adenoma, pancreatic islet cell, carcinoid | Multiple endocrine neoplasia type 1 | E | Rec | D, Mis, N, F, S | — |
| MET | 4233 | P08581 | 7q31 | Parathyroid | Papillary renal | Familial papillary renal | E | Dom | Mis | — |
| MHC2TA | 4261 | P33076 | 16p13 | Papillary renal, head-neck squamous cell | — | — | L | Dom | T | BCL6 |
| MLF1 | 4291 | P58340 | 3q25.1 | NHL | — | — | L | Dom | T | NPM1 |
| MLH1 | 4292 | P40692 | 3p21.3 | AML | Colorectal, endometrial, ovarian, CNS | Hereditary non-polyposis colorectal, Turcot syndrome | E, O | Rec | D, Mis, N, F, S | — |
| MLL | 4297 | Q03164 | 11q23 | Colorectal, endometrial, ovarian, CNS | — | — | L | Dom | T, O | MLL, MLLT1, MLLT2, MLLT3, MLLT4, MLLT7, |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| MLLT1 | 4298 | Q03111 | 19p13.3 | AL | — | — | L | Dom | T | MLLT10, MLLT6, ELL, EPS15, AF1Q, CREBBP, SH3GL1, FNBP1, PNUTL1, MSF, GPHN, GMPS, SSH3BP1, ARHGEF12, GAS7, FOXO3A, LAF4, LCX, SEPT6, LPP, CBFA2T1, GRAF, EP300, PICALM |
| MLLT10 | 8028 | P55197 | 10p12 | AL | — | — | L | Dom | T | MLL |
| MLLT2 | 4299 | P51825 | 4q21 | AL | — | — | L | Dom | T | MLL, PICALM |
| MLLT3 | 4300 | P42568 | 9p22 | ALL | — | — | L | Dom | T | MLL |
| MLLT4 | 4301 | P55196 | 6q27 | AL | — | — | L | Dom | T | MLL |
| MLLT6 | 4302 | P55198 | 17q21 | AL | — | — | L | Dom | T | MLL |
| MLLT7 | 4303 | NP_005929 | Xq13.1 | AML, meningioma | — | — | L, O | Dom | T | MLL |
| MN1 | 4330 | Q10571 | 22q13 | AML$ | — | — | L | Dom | T | ETV6 |
| MSF | 10801 | NP_006631 | 17q25 | | — | — | L | Dom | T | MLL |
| MSH2 | 4436 | P43246 | 2p22-p21 | Colorectal, endometrial, ovarian | Colorectal, endometrial, ovarian | Hereditary non-polyposis colorectal | E | Rec | D, Mis, N F, S | — |
| MSH6 | 2956 | P52701 | 2p16 | Colorectal | Colorectal, endometrial, ovarian | Hereditary non-polyposis colorectal | E | Rec | Mis, N, F, S | — |
| MSN | 4478 | P26038 | Xq11.2-q12 | ALCL | — | — | L | Dom | T | ALK |
| MUTYH | 4595 | NP_036354 | 1p34.3-1p32.1 | | Colorectal | Adenomatous polyposis coli | E | Rec | Mis, N, F, S | — |
| MYC | 4609 | P01106 | 8q24.12-q24.13 | Burkitt's lymphoma, amplified in other cancers, B-CLL | — | — | L, E | Dom | A, T | IGKα, BCL5, BCL7A, BTG1, TRAα, IGHα |
| MYCL1 | 4610 | P12524 | 1p34.3 | Small cell lung | — | — | E | Dom | A | — |
| MYCN | 4613 | P04198 | 2p24.1 | Neuroblastoma | — | — | O | Dom | A | — |
| MYH11 | 4629 | P35749 | 16p13.13-p13.12 | AML | — | — | L | Dom | T | CBFB |
| MYH9 | 4627 | P35579 | 22q13.1 | ALCL | — | — | L | Dom | T | ALK |
| MYST4 | 23522 | NP_036462 | 10q22 | AML | — | — | L | Dom | T | CREBBP |
| NACA | 4666 | NP_005585 | 12q23-q24.1 | NHL | — | — | L | Dom | T | BCL6 |
| NBS1 | 4683 | NP_002476 | 8q21 | — | NHL, glioma, | Nijmegen | L, E, M, O | Rec | Mis, N, F | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| NCOA2 | 10499 | Q15596 | 8q13.1 | AML | | breakage syndrome | L | Dom | T | RUNXBP2 |
| NCOA4 | 8031 | Q13772 | 10q11.2 | Papillary thyroid | | | E | Dom | T | RET |
| NF1 | 4763 | P21359 | 17q12 | Neurofibroma, glioma | Neurofibroma, glioma | Neurofibromatosis type 1 | O | Rec | D, Mis, N, F, S, O | — |
| NF2 | 4771 | P35240 | 22q12.2 | Meningioma, acoustic neuroma | Meningioma, acoustic neuroma | Neurofibromatosis type 2 | O | Rec | D, Mis, N, F, S, O | — |
| NOTCH1 | 4851 | P46531 | 9q34.3 | T-ALL | | | L | Dom | T | TRBα |
| NPM1 | 4869 | P06748 | 5q35 | NHL, APL, AML | | | L | Dom | T | ALK, RARA, MLF1 |
| NR4A3 | 8013 | Q92570 | 9q22 | Extraskeletal myxoid chondrosarcoma | | | M | Dom | T | EWSR1 |
| NRAS | 4893 | P01111 | 1p13.2 | Melanoma, MM, AML, thyroid | | | L, E | Dom | Mis | — |
| NSD1 | 64324 | NP_071900 | 5q35 | AML | | | L | Dom | T | NUP98 |
| NTRK1 | 4914 | P04629 | 1q21-q22 | Papillary thyroid | | | E | Dom | T | TPM3, TPR, TFG |
| NTRK3 | 4916 | Q16288 | 15q25 | Congenital fibrosarcoma, secretory breast | | | E, M | Dom | T | ETV6 |
| NUMA1 | 4926 | NP_006176 | 11q13 | APL | | | L | Dom | T | RARA |
| NUP214 | 8021 | P35658 | 9q34.1 | AML | | | L | Dom | T | DEK, SET |
| NUP98 | 4928 | P52948 | 11p15 | AML | | | L | Dom | T | HOXA9, NSD1, WHSC1L1, DDX10, TOP1, HOXD13, PMX1, HOXA13, HOXD11, HOXA11, RAP1GDS1 |
| NUT | 256646 | XP_171724 | 15q13 | Lethal midline carcinoma of young people | | | E | Dom | T | BRD4 |
| OLIG2 | 10215 | Q13516 | 21q22.11 | T-ALL | | | L | Dom | T | TRAα |
| PAX3 | 5077 | P23760 | 2q35 | Alveolar rhabdomyosarcoma | | | M | Dom | T | FOXO1A |
| PAX5 | 5079 | Q02548 | 9p13 | NHL | | | L | Dom | T | IGHα |
| PAX7 | 5081 | P23759 | 1p36.2-p36.12 | Alveolar rhabdomyosarcoma | | | M | Dom | T | FOXO1A |
| PAX8 | 7849 | Q06710 | 2q12-q14 | Follicular thyroid | | | E | Dom | T | PPARG |
| PBX1 | 5087 | NP_002576 | 1q23 | Pre-B-ALL | | | L | Dom | T | TCF3 |
| PCM1 | 5108 | NP_006188 | 8p22-p21.3 | Papillary thyroid | | | E | Dom | T | RET |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| PDGFB | 5155 | P01127 | 22q12.3-q13.1 | DFSP | — | — | M | Dom | T | COL1A1 |
| PDGFRA | 5156 | P16234 | 4q11-q13 | GIST | — | — | M, O | Dom | Mis, O | — |
| PDGFRB | 5159 | NP_002600 | 5q31-q32 | MPD, AML, CMML, CML | — | — | L | Dom | T | ETV6, TRIP11, HIP1, RAB5EP, H4 |
| PICALM | 8301 | Q13492 | 11q14 | T-ALL, AML | — | — | L | Dom | T | MLLT10, MLL |
| PIM1 | 5292 | P11309 | 6p21.2 | NHL | — | — | L | Dom | T | BCL6 |
| PML | 5371 | P29590 | 15q22 | APL | — | — | L | Dom | T | RARA |
| PMS1 | 5378 | P54277 | 2q31-q33 | — | Colorectal, endometrial, ovarian | Hereditary non-polyposis colorectal cancer | E | Rec | Mis, N | — |
| PMS2 | 5395 | P54278 | 7p22 | — | Colorectal, endometrial, ovarian, medulloblastoma, glioma | Hereditary non-polyposis colorectal cancer, Turcot syndrome | E | Rec | Mis, N, F | — |
| PMX1 | 5396 | P54821 | 1q24 | AML | — | — | L | Dom | T | NUP98 |
| PNUTL1 | 5413 | NP_002679 | 22q11.2 | AML | — | — | L | Dom | T | MLL |
| POU2AF1 | 5450 | Q16633 | 11q23.1 | NHL | — | — | L | Dom | T | BCL6 |
| PPARG | 5468 | P37231 | 3p25 | Follicular thyroid | — | — | E | Dom | T | PAX8 |
| PRCC | 5546 | Q92733 | 1q21.1 | Papillary renal | — | — | E | Dom | T | TFE3 |
| PRKAR1A | 5573 | P10644 | 17q23-q24 | Papillary thyroid | Myxoma, endocrine, papillary thyroid | Carney complex | E, M | Dom, Rec | T, Mis, N, F, S | RET |
| PRO1073 | 29005 | Q9UHZ2 | 11q31.1 | Renal-cell carcinoma (childhood epithelioid) | — | — | E | Dom | T | TFEB |
| PSIP2 | 11168 | NP_150091 | 9p22.2 | AML | — | — | L | Dom | T | NUP98 |
| PTCH | 5727 | Q13635 | 9q22.3 | Skin basal cell, medulloblastoma | Skin basal cell, medulloblastoma | Nevoid basal-cell carcinoma syndrome | E, M | Rec | Mis, N, F, S | — |
| PTEN | 5728 | O00633 | 10q23.3 | Glioma, prostatic, endometrial | Harmartoma, glioma, prostatic, endometrial | Cowden syndrome, Bannayan-Riley-Ruvalcaba syndrome | L, E, M, O | Rec | D, Mis, N, F, S | — |
| PTPN11 | 5781 | Q06124 | 12q24.1 | JMML, AML, MDS | — | — | L | Dom | Mis | — |
| RAB5EP | 9135 | NP_004694 | 17p13 | CMML | — | — | L | Dom | T | PDGFRB |
| RAD51L1 | 5890 | NP_002868 | 14q23-q24.2 | Lipoma, uterine leiomyoma | — | — | M | Dom | T | HMGA2 |
| RAP1GDS1 | 5910 | P52306 | 4q21-q25 | T-ALL | — | — | L | Dom | T | NUP98 |
| RARA | 5914 | P10276 | 17q12 | APL | — | — | L | Dom | T | PML, ZNF145, |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| RB1 | 5925 | P06400 | 13q14 | Retinoblastoma, sarcoma, breast, small-cell lung | Retinoblastoma, sarcoma, breast, small-cell lung | Familial retinoblastoma | L, E, M, O | Rec | D, Mis, N, F, S | TIF1, NUMA1, NPM1 |
| RECQL4 | 9401 | O94761 | 8q24.3 | — | Osteosarcoma, skin basal and squamous cell | Rothmund-Thompson syndrome | M | Rec | N, F, S | — |
| REL | 5966 | Q04864 | 2p13-p12 | Hodgkin Lymphoma | — | — | L | Dom | A | — |
| RET | 5979 | P07949 | 10q11.2 | Medullary thyroid, papillary thyroid, pheochromocytoma | Medullary thyroid, papillary thyroid, pheochromocytomaneoplasia | Multiple endocrine 2A/2B | E, O | Dom | T, Mis, N, F | H4, PRKAR1A, NCOA4, PCM1, GOLGA5, TRIM33 |
| RPL22 | 6146 | P35268 | 3q26 | AML, CML | — | — | L | Dom | T | RUNX1 |
| RUNX1 | 861 | Q01196 | 21q22.3 | AML, pre-B-ALL | — | — | L | Dom | T | RPL22, MDS1 EVI1, CBFA2T3, CBFA2T1, ETV6 |
| RUNXBP2 | 799 | NP_006757 | 8p11 | AML | — | — | L | Dom | T | CREBBP, NCOA2, EP300 |
| SBDS | 51119 | Q9Y3A5 | 7q11 | — | AML, MDS | Schwachman-Diamond syndrome | L | Rec | Gene conversion | — |
| SDHB | 6390 | P21912 | 1p36.1-p35 | — | Paraganglioma, pheochromocytoma | Familial paraganglioma | O | Rec | Mis, N, F | — |
| SDHC | 6391 | O75609 | 1q21 | — | Paraganglioma, pheochromocytoma | Familial paraganglioma | O | Rec | Mis, N, F | — |
| SDHD | 6392 | O14521 | 11q23 | — | Paraganglioma, pheochromocytoma | Familial paraganglioma | O | Rec | Mis, N, F, S | — |
| SEPT6 | 23157 | N_055944 | Xq24 | AML | — | — | L | Dom | T | MLL |
| SET | 6418 | Q01105 | 9q34 | AML | — | — | L | Dom | T | NUP214 |
| SFPQ | 6421 | P23246 | 1p34.3 | Papillary renal cell | — | — | E | Dom | T | TFE3 |
| SH3GL1 | 6455 | Q99961 | 19p13.3 | AL | — | — | L | Dom | T | MLL |
| SMARCB1 | 6598 | Q12824 | 22q11 | Malignant rhabdoid | Malignant rhabdoid | Rhabdoid predisposition syndrome | M | Rec | D, N, F, S | — |
| SMO | 6608 | Q99835 | 7q31-q32 | Skin basal cell | — | — | E | Dom | Mis | — |
| SS18 | 6760 | Q15532 | 18q11.2 | Synovial sarcoma | — | — | M | Dom | T | SSX1, SSX2 |
| SS18L1 | 26039 | O75177 | 20q13.3 | Synovial sarcoma | — | — | M | Dom | T | SSX1 |
| SSH3BP1 | 10006 | NP_005461 | 10p11.2 | AML | — | — | L | Dom | T | MLL |
| SSX1 | 6756 | Q16384 | Xp11.23-p11.22 | Synovial sarcoma | — | — | M | Dom | T | SS18 |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| SSX2 | 6757 | Q16385 | Xp11.23-p11.22 | Synovial sarcoma | — | — | M | Dom | T | SS18 |
| SSX4 | 6759 | O60224 | Xp11.23 | Synovial sarcoma | — | — | M | Dom | T | SS18 |
| STK11 | 6794 | Q15831 | 19p13.3 | NSCLC | Jejunal harmartoma, ovarian, testicular, pancreatic | Peutz-Jeghers syndrome | E, M, O | Rec | D, Mis, N, | — |
| STL | 7955 | NOPROTEIN | 6q23 | B-ALL | — | — | L | Dom | T | ETV6 |
| SUFU | 51684 | NP_057253 | 10q24.32 | Medulloblastoma | Medulloblastoma | Medulloblastoma predisposition | O | Rec | D, F, S | — |
| TAF15 | 8148 | Q92804 | 17q11.1-q11.2 | Extraskeletal myxoid chondrosarcomas, ALL | — | — | L, M | Dom | T | TEC, CHN1, ZNF384 |
| TAL1 | 6886 | P17542 | 1p32 | Lymphoblastic leukaemia/biphasic | — | — | L | Dom | T | TRDα |
| TAL2 | 6887 | Q16559 | 9q31 | T-ALL | — | — | L | Dom | T | TRBα |
| TCF1 | 6927 | P20823 | 12q24.2 | Hepatic adenoma, hepatocellular carcinoma | Hepatic adenoma, hepatocellular carcinoma | Familial hepatic adenoma | E | Rec | Mis, F | — |
| TCF12 | 6938 | Q99081 | 15q21 | Extraskeletal myxoid chondrosarcoma | — | — | M | Dom | T | TEC |
| TCF3 | 6929 | P15923 | 19p13.3 | pre-B-ALL | — | — | L | Dom | T | PBX1, HLF, TFPT |
| TCL1A | 8115 | NP_068801 | 14q32.1 | T-CLL | — | — | L | Dom | T | TRAα |
| TEC | 7006 | P42680 | 4p12 | Extraskeletal myxoid chondrosarcoma | — | — | M | Dom | T | EWSR1, TAF15, TCF12 |
| TFE3 | 7030 | P19532 | Xp11.22 | Papillary renal, alveolar soft part sarcoma | — | — | E | Dom | T | SFPQ, ASPSCR1, PRCC |
| TFEB | 7942 | P19484 | 6p21 | Renal (childhood epithelioid) | — | — | E, M | Dom | T | ALPHA |
| TFG | 10342 | NP_006061 | 3q11-q12 | Papillary thyroid, ALCL | — | — | E, L | Dom | T | NTRK1, ALK |
| TFPT | 29844 | NP_037474 | 19q13 | Pre-B-ALL | — | — | L | Dom | T | TCF3 |
| TFRC | 7037 | P02786 | 3q29 | NHL | — | — | L | Dom | T | BCL6 |
| TIF1 | 8805 | O15164 | 7q32-q34 | APL | — | — | L | Dom | T | RARA |
| TLX1 | 3195 | P31314 | 10q24 | T-ALL | — | — | L | Dom | T | TRBα, TRDα |
| TLX3 | 30012 | O43711 | 5q35.1 | T-ALL | — | — | L | Dom | T | BCL11B |
| TNFRSF6 | 355 | P25445 | 10q24.1 | TGCT, nasal NK/T lymphoma, skin squamous-cell carcinoma (burn-scar related) | — | — | L, E, O | Rec | Mis | — |
| TOP1 | 7150 | P11387 | 20q12-q13.1 | AMl§ | — | — | L | Dom | T | NUP98 |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| TP53 | 7157 | P04637 | 17p13 | Breast, colorectal, lung, sarcoma, adrenocortical, glioma, multiple other types | Breast, sarcoma, adrenocortical carcinoma, glioma, multiple other types | Li-Fraumeni syndrome | L, E, M, O | Rec | Mis, N, F | — |
| TPM3 | 7170 | P06753 | 1q22-q23 | Papillary thyroid, ALCL | — | — | E, L | Dom | T | NTRK1, ALK |
| TPM4 | 7171 | P07226 | 19p13.1 | ALCL | — | — | L | Dom | T | ALK |
| TPR | 7175 | P12270 | 1q25 | Papillary thyroid | — | — | E | Dom | T | NTRK1 |
| TRAα | 6955 | — | 14q11.2 | T-ALL | — | — | L | Dom | T | ATL, OLIG2, MYC, TCL1A |
| TRBα | 6957 | — | 7q35 | T-ALL | — | — | L | Dom | T | HOX11, LCK, NOTCH1, TAL2, LYL1 |
| TRDα | 6964 | — | 14q11 | T-cell leukaemia | — | — | L | Dom | T | TAL1, HOX11, TLX1, LMO1, LMO2 |
| TRIM33 | 51592 | Q9UPN9 | 1p13 | Papillary thyroid | — | — | E | Dom | T | RET |
| TRIP11 | 9321 | NP_004230 | 14q31-q32 | AML | — | — | L | Dom | T | PDGFRB |
| TSC1 | 7248 | Q92574 | 9q34 | — | Hamartoma, renal cell | Tuberous sclerosis 1 | E, O | Rec | D, Mis, N, F, S | — |
| TSC2 | 7249 | P49815 | 16p13.3 | — | Hamartoma, renal cell | Tuberous sclerosis 2 | E, O | Rec | D, Mis, N, F, S | — |
| TSHR | 7253 | P16473 | 14q31 | Toxic thyroid adenoma | Thyroid adenoma | — | E | Dom | Mis | — |
| VHL | 7428 | P40337 | 3p25 | Renal, hemangioma, pheochromocytoma | Renal, hemangioma, pheochromocytoma | von Hippel-Lindau syndrome | E, M, O | Rec | D, Mis, N, F, S | — |
| WAS | 7454 | P42768 | Xp11.23-p11.22 | — | Lymphoma | Wiskott-Aldrich syndrome | L | Rec | Mis, N, F, S | — |
| WHSC1L1 | 54904 | NP_060248 | 8p12 | AML | — | — | L | Dom | T | NUP98 |
| WRN | 7486 | Q14191 | 8p12-p11.2 | — | Osteosarcoma, meningioma, others | Werner syndrome | L, E, M, O | Rec | Mis, N, F, S | — |
| WT1 | 7490 | NP_000369 | 11p13 | Wilms', desmoplastic small round cell | Wilms' | Denys-Drash syndrome, Frasier syndrome, Familial Wilms' tumour | O | Rec | D, Mis, N, F, S | EWSR1 |
| XPA | 7507 | P23025 | 9q22.3 | — | Skin basal cell, skin squamous cell, melanoma | Xeroderma pigmentosum A | E | Rec | Mis, N, F, S | — |
| XPC | 7508 | Q01831 | 3p25 | — | Skin basal cell, skin squamous cell, | Xeroderma pigmentosum C | E | Rec | Mis, N, F, S | — |

TABLE 2-continued

Cancer Genes.

| Symbol | Locuslink ID | Protein ID* | Chromosome band | Tumour types (somatic) | Tumour types (germline) | Cancer syndrome | Tissue type | Cancer molecular genetics | Mutation type | Translocation partner |
|---|---|---|---|---|---|---|---|---|---|---|
| | | | | melanoma | | | | | | |
| ZNF145 | 7704 | Q05516 | 11q23.1 | APL | — | — | L | Dom | T | RARA |
| ZNF198 | 7750 | Q9UBW7 | 13q11-q12 | MPD/NHL | — | — | L | Dom | T | FGFR1 |
| ZNF278 | 23598 | NP_055138 | 22q12-q14 | Ewing's sarcoma | — | — | M | Dom | T | EWSR1 |
| ZNF384 | 171017 | NP_597733 | 12p13 | ALL | — | — | L | Dom | T | EWSR1, TAF15 |
| ZNFN1A1 | 10320 | NP_006051 | 7p12 | ALL, DLBCL | — | — | L | Dom | T | BCL6 |

*From Swiss-Prot/Refseq.

†D (large deletion) covers the abnormalities that result in allele loss/loss of heterozygosity at many recessive cancer genes.

‡Refers to cases of acute myeloid leukaemia that are associated with treatment.

§O (other) in the 'mutation type' column refers primarily to small in-frame deletions/insertions as found in FLT3 and EGFR. Note that where an inversion/large deletion has been shown to result in a fusions protein, these have been listed under translocations. The Wellcome Trust Sanger Institute web version of the cancer-gene set can be found at http://www.sanger.ac.uk/genetics/CPG/Census/.

A, amplification; AEL, acute eosinophilic leukaemia; AL, acute leukaemia; ALCL, anaplastic large-cell lymphoma; ALL, acute lymphocytic leukaemia; AML, acute myelogenous leukaemia; APL, acute promyelocytic leukaemia; B-ALL, B-cell acute lymphocytic leukaemia; B-CLL, B-cell lymphocytic leukaemia; B-NHL, B-cell non-Hodgkin's lymphoma; CLL, chronic lymphatic leukaemia; CML, chronic myeloid leukaemia; CMML, chronic myelomonocytic leukaemia; CNS, central nervous system; D, large deletion; DFSP, dermatofibrosarcoma protuberans; DLBCL, diffuse large B-cell lymphoma; Dom, dominant; E, epithelial; F, frameshift; GIST, gastrointestinal stromal tumour; JMML, juvenile myelomonocytic leukaemia; L, leukaemia/lymphoma; M, mesenchymal; MALT, mucosa-associated lymphoid tissue; MDS, myelodysplastic syndrome; MM, multiple myeloma; Mis, missense; N, nonsense; NHL, non-Hodgkin's lymphoma; NK/T, natural killer T cell; NSCLC, non-small-cell lung cancer; O, other; pre-B-ALL, pre-B-cell acute lymphoblastic leukaemia; Rec, recessive; S, splice site; T, translocation; T-ALL, T-cell acute lymphoblastic leukaemia; T-CLL, T-cell chronic lymphocytic leukaemia; TGCT, testicular germ-cell tumour; T-PLL, T-cell prolymphocytic leukaemia.

TABLE 3

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| 39340 | A1BG | A1CF | A2BP1 | A2LD1 |
| A2M | A2ML1 | A2RRG4_HUMAN | A3GALT2 | A4D198_HUMAN |
| A4D226_HUMAN | A4GALT | A4GNT | AAAS | AACS |
| AADAC | AADACL2 | AADACL3 | AADACL4 | AADAT |
| AAGAB | AAK1 | AAMP | AANAT | AARS |
| AARS2 | AARSD1 | AASDH | AASDHPPT | AASS |
| AATF | AATK | AB019437_1 | ABAT | ABBA-1 |
| ABCA1 | ABCA10 | ABCA12 | ABCA13 | ABCA2 |
| ABCA3 | ABCA4 | ABCA5 | ABCA6 | ABCA7 |
| ABCA8 | ABCA9 | ABCB1 | ABCB10 | ABCB11 |
| ABCB4 | ABCB5 | ABCB6 | ABCB7 | ABCB8 |
| ABCB9 | ABCC1 | ABCC10 | ABCC11 | ABCC12 |
| ABCC2 | ABCC3 | ABCC4 | ABCC5 | ABCC6 |
| ABCC8 | ABCC9 | ABCD1 | ABCD2 | ABCD3 |
| ABCD4 | ABCE1 | ABCF1 | ABCF2 | ABCF3 |
| ABCG1 | ABCG2 | ABCG4 | ABCG5 | ABCG8 |
| ABHD1 | ABHD10 | ABHD11 | ABHD12 | ABHD12B |
| ABHD13 | ABHD14A | ABHD14B | ABHD15 | ABHD2 |
| ABHD3 | ABHD4 | ABHD5 | ABHD6 | ABHD8 |
| ABI1 | ABI2 | ABI3 | ABI3BP | ABL1 |
| ABL2 | ABLIM1 | ABLIM3 | ABO | ABP1 |
| ABR | ABRA | ABT1 | ABTB1 | ABTB2 |
| AC002472.13 | AC007731_16 | AC008537_5-2 | AC008969.1 | AC010872_2 |
| AC012100.1 | AC013469_8-2 | AC021593.2 | AC022098.2 | AC023469_1 |
| AC027369_8 | AC068473.1 | AC079612.1 | AC092070_2 | AC093393.1 |
| AC097374_3 | AC099524.1 | AC103710_2 | AC112491_4 | AC114273.2 |
| AC120042.2 | AC127391_4 | AC142381_2 | AC142381_2_ENST00000356559 | ACAA1 |
| ACAA2 | ACACA | ACACB | ACAD10 | ACAD11 |
| ACAD8 | ACAD9 | ACADL | ACADM | ACADS |
| ACADSB | ACADVL | ACAN | ACAP1 | ACAP2 |
| ACAP3 | ACAT1 | ACAT2 | ACBD3 | ACBD4 |
| ACBD5 | ACBD6 | ACBD7 | ACCN1 | ACCN2 |
| ACCN3 | ACCN4 | ACCN5 | ACCS | ACCSL |
| ACD | ACE | ACE2 | ACER1 | ACER2 |
| ACER3 | ACHE | ACIN1 | ACLY | ACMSD |
| ACN9 | ACO1 | ACO2 | ACOT1 | ACOT11 |
| ACOT12 | ACOT13 | ACOT2 | ACOT4 | ACOT6 |
| ACOT7 | ACOT8 | ACOT9 | ACOX1 | ACOX2 |
| ACOX3 | ACOXL | ACP1 | ACP2 | ACP5 |
| ACP6 | ACPL2 | ACPP | ACPT | ACR |
| ACRBP | ACRC | ACRV1 | ACSBG1 | ACSBG2 |
| ACSF2 | ACSF3 | ACSL1 | ACSL3 | ACSL4 |
| ACSL5 | ACSL6 | ACSM1 | ACSM2A | ACSM2B |
| ACSM3 | ACSM5 | ACSS1 | ACSS2 | ACSS3 |
| ACTA1 | ACTA2 | ACTB | ACTBL2 | ACTC1 |
| ACTG1 | ACTG2 | ACTL6A | ACTL6B | ACTL7A |
| ACTL7B | ACTL8 | ACTL9 | ACTN1 | ACTN2 |
| ACTN3 | ACTN4 | ACTR10 | ACTR1A | ACTR1B |
| ACTR2 | ACTR3 | ACTR3B | ACTR5 | ACTR6 |
| ACTR8 | ACTRT1 | ACTRT2 | ACVR1 | ACVR1B |
| ACVR1C | ACVR2A | ACVR2B | ACVRL1 | ACY1 |
| ACY3 | ACYP1 | ACYP2 | ADA | ADAD1 |
| ADAD2 | ADAL | ADAM10 | ADAM11 | ADAM12 |
| ADAM15 | ADAM17 | ADAM18 | ADAM19 | ADAM2 |
| ADAM20 | ADAM21 | ADAM22 | ADAM22_ENST00000315984 | ADAM23 |
| ADAM28 | ADAM29 | ADAM30 | ADAM32 | ADAM33 |
| ADAM7 | ADAM8 | ADAM9 | ADAMDEC1 | ADAMTS1 |
| ADAMTS10 | ADAMTS12 | ADAMTS13 | ADAMTS14 | ADAMTS15 |
| ADAMTS16 | ADAMTS16_ENST00000274181 | ADAMTS17 | ADAMTS18 | ADAMTS19 |
| ADAMTS2 | ADAMTS20 | ADAMTS3 | ADAMTS4 | ADAMTS5 |
| ADAMTS6 | ADAMTS6_ENST00000381055 | ADAMTS7 | ADAMTS8 | ADAMTS9 |
| ADAMTSL1 | ADAMTSL1_ENST00000380548 | ADAMTSL2 | ADAMTSL3 | ADAMTSL4 |
| ADAMTSL5 | ADAP1 | ADAP2 | ADAR | ADARB1 |
| ADARB2 | ADAT1 | ADAT2 | ADAT3 | ADC |
| ADCK1 | ADCK2 | ADCK4 | ADCK5 | ADCY1 |
| ADCY10 | ADCY2 | ADCY3 | ADCY4 | ADCY5 |
| ADCY6 | ADCY7 | ADCY8 | ADCY9 | ADCYAP1 |
| ADCYAP1R1 | ADD1 | ADD2 | ADD3 | ADH1A |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ADH1B | ADH4 | ADH5 | ADH6 | ADH7 |
| ADHFE1 | ADI1 | ADIPOQ | ADIPOR1 | ADIPOR2 |
| ADK | ADM | ADM2 | ADNP | ADNP2 |
| ADO | ADORA1 | ADORA2A | ADORA2B | ADORA3 |
| ADPGK | ADPRH | ADPRHL1 | ADPRHL2 | ADRA1A |
| ADRA1B | ADRA1D | ADRA2A | ADRA2B | ADRA2C |
| ADRB1 | ADRB2 | ADRB3 | ADRBK1 | ADRBK2 |
| ADRM1 | ADSL | ADSS | ADSSL1 | AEBP1 |
| AEN | AES | AFAP1 | AFAP1L1 | AFAP1L2 |
| AFF1 | AFF2 | AFF3 | AFF4 | AFG3L2 |
| AFM | AFMID | AFP | AFTPH | AGA |
| AGAP1 | AGAP2 | AGAP3 | AGAP4 | AGAP5 |
| AGAP7 | AGAP8 | AGBL2 | AGBL4 | AGBL5 |
| AGC1 | AGER | AGFG1 | AGFG2 | AGGF1 |
| AGK | AGL | AGMAT | AGPAT1 | AGPAT2 |
| AGPAT3 | AGPAT4 | AGPAT5 | AGPAT6 | AGPAT9 |
| AGPHD1 | AGPS | AGR2 | AGR3 | AGRN |
| AGRP | AGT | AGTPBP1 | AGTR1 | AGTR2 |
| AGTRAP | AGXT | AGXT2 | AGXT2L1 | AGXT2L2 |
| AHCTF1 | AHCTF1P | AHCY | AHCYL1 | AHCYL2 |
| AHDC1 | AHI1 | AHNAK | AHNAK2 | AHR |
| AHRR | AHSA1 | AHSA2 | AHSG | AHSP |
| AICDA | AIDA | AIF1 | AIF1L | AIF1_ENST00000376051 |
| AIFM1 | AIFM2 | AIFM3 | AIG1 | AIM1 |
| AIM1L | AIM2 | AIMP1 | AIMP2 | AIP |
| AIPL1 | AIRE | AJAP1 | AK1 | AK2 |
| AK3 | AK3L1 | AK5 | AK7 | AKAP1 |
| AKAP10 | AKAP11 | AKAP12 | AKAP13 | AKAP14 |
| AKAP2 | AKAP3 | AKAP4 | AKAP5 | AKAP6 |
| AKAP7 | AKAP8 | AKAP9 | AKAP9_NM_005751 | AKD1 |
| AKIRIN1 | AKIRIN2 | AKNA | AKNAD1 | AKR1A1 |
| AKR1B1 | AKR1B10 | AKR1B1P8 | AKR1C1 | AKR1C2 |
| AKR1C3 | AKR1C4 | AKR1CL1 | AKR1D1 | AKR1E2 |
| AKR7A2 | AKR7A3 | AKR7L | AKT1 | AKT1S1 |
| AKT2 | AKT3 | AKTIP | AL121675_36-2 | AL122001_32 |
| AL161645_14 | AL512274_9 | ALAD | ALAS1 | ALAS2 |
| ALB | ALCAM | ALDH16A1 | ALDH18A1 | ALDH1A1 |
| ALDH1A2 | ALDH1A3 | ALDH1B1 | ALDH1L1 | ALDH1L2 |
| ALDH2 | ALDH3A1 | ALDH3A2 | ALDH3B2 | ALDH4A1 |
| ALDH5A1 | ALDH6A1 | ALDH7A1 | ALDH8A1 | ALDH9A1 |
| ALDOA | ALDOB | ALDOC | ALG1 | ALG10 |
| ALG10B | ALG11 | ALG12 | ALG13 | ALG14 |
| ALG1L | ALG2 | ALG5 | ALG6 | ALG8 |
| ALG9 | ALK | ALKBH1 | ALKBH2 | ALKBH3 |
| ALKBH4 | ALKBH5 | ALKBH6 | ALKBH7 | ALKBH8 |
| ALLC | ALMS1 | ALOX12 | ALOX12B | ALOX12P2 |
| ALOX15 | ALOX15B | ALOX5 | ALOX5AP | ALOXE3 |
| ALPI | ALPK1 | ALPK2 | ALPK2_ENST00000361673 | ALPK3 |
| ALPL | ALPP | ALPPL2 | ALS2 | ALS2CL |
| ALS2CR11 | ALS2CR12 | ALS2CR8 | ALX1 | ALX3 |
| ALX4 | AMAC1 | AMAC1L2 | AMACR | AMBN |
| AMBP | AMBRA1 | AMD1 | AMDHD1 | AMDHD2 |
| AMELX | AMELY | AMFR | AMH | AMHR2 |
| AMICA1 | AMIGO1 | AMIGO2 | AMIGO3 | AMMECR1 |
| AMMECR1L | AMN | AMOT | AMOTL1 | AMOTL2 |
| AMPD1 | AMPD2 | AMPD2_ENST00000393689 | AMPD3 | AMPH |
| AMT | AMTN | AMY1A | AMY1B | AMY1C |
| AMY2A | AMY2B | AMZ1 | AMZ2 | ANAPC1 |
| ANAPC10 | ANAPC11 | ANAPC13 | ANAPC2 | ANAPC4 |
| ANAPC5 | ANAPC7 | ANG | ANGEL1 | ANGEL2 |
| ANGPT1 | ANGPT2 | ANGPT4 | ANGPTL1 | ANGPTL2 |
| ANGPTL3 | ANGPTL4 | ANGPTL5 | ANGPTL6 | ANGPTL7 |
| ANK1 | ANK2 | ANK3 | ANKAR | ANKDD1A |
| ANKFN1 | ANKFY1 | ANKH | ANKHD1 | ANKHD1-EIF4EBP3 |
| ANKK1 | ANKLE2 | ANKMY1 | ANKMY2 | ANKRA2 |
| ANKRD1 | ANKRD10 | ANKRD11 | ANKRD12 | ANKRD13A |
| ANKRD13B | ANKRD13C | ANKRD13D | ANKRD16 | ANKRD17 |
| ANKRD18A | ANKRD2 | ANKRD20A1 | ANKRD20A2 | ANKRD20A3 |
| ANKRD20A4 | ANKRD20A5 | ANKRD22 | ANKRD23 | ANKRD24 |
| ANKRD26 | ANKRD27 | ANKRD28 | ANKRD29 | ANKRD30A |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ANKRD31 | ANKRD32 | ANKRD33 | ANKRD34A | ANKRD34B |
| ANKRD35 | ANKRD37 | ANKRD39 | ANKRD40 | ANKRD42 |
| ANKRD43 | ANKRD44 | ANKRD45 | ANKRD46 | ANKRD49 |
| ANKRD5 | ANKRD50 | ANKRD52 | ANKRD53 | ANKRD54 |
| ANKRD55 | ANKRD56 | ANKRD57 | ANKRD58 | ANKRD6 |
| ANKRD60 | ANKRD7 | ANKRD9 | ANKS1A | ANKS3 |
| ANKS4B | ANKS6 | ANKZF1 | ANLN | ANO10 |
| ANO2 | ANO3 | ANO4 | ANO5 | ANO6 |
| ANO7 | ANO8 | ANO9 | ANP32B | ANP32C |
| ANP32D | ANP32E | ANPEP | ANTXR1 | ANTXRL |
| ANUBL1 | ANXA1 | ANXA10 | ANXA11 | ANXA13 |
| ANXA2 | ANXA3 | ANXA4 | ANXA5 | ANXA6 |
| ANXA7 | ANXA8 | ANXA8L1 | ANXA8L2 | ANXA9 |
| AOAH | AOC2 | AOC3 | AOF2 | AOX1 |
| AP001011.2_ENST00000261598 | AP001011.3_ENST00000320876 | AP005901_2 | AP1AR | AP1B1 |
| AP1G1 | AP1G2 | AP1M1 | AP1M2 | AP1S1 |
| AP1S2 | AP1S3 | AP2A1 | AP2A2 | AP2B1 |
| AP2M1 | AP2S1 | AP3B1 | AP3B2 | AP3D1 |
| AP3M1 | AP3M2 | AP3S1 | AP3S2 | AP4B1 |
| AP4E1 | AP4M1 | AP4S1 | APAF1 | APBA1 |
| APBA2 | APBA3 | APBB1 | APBB1IP | APBB2 |
| APBB3 | APC | APC2 | APCDD1 | APCDD1L |
| APCS | APEH | APEX1 | APEX2 | APH1A |
| APH1B | API5 | APIP | APITD1 | APLF |
| APLN | APLNR | APLP1 | APLP2 | APOA1 |
| APOA1BP | APOA2 | APOA4 | APOA5 | APOB |
| APOB48R | APOBEC1 | APOBEC2 | APOBEC3A | APOBEC3B |
| APOBEC3C | APOBEC3D | APOBEC3F | APOBEC3G | APOBEC3H |
| APOBEC4 | APOC1 | APOC2 | APOC3 | APOC4 |
| APOD | APOE | APOH | APOL1 | APOL2 |
| APOL3 | APOL4 | APOL5 | APOL6 | APOLD1 |
| APOM | APOO | APOOL | APP | APPBP2 |
| APPL1 | APPL2 | APRT | APTX | AQP1 |
| AQP10 | AQP11 | AQP12A | AQP2 | AQP3 |
| AQP4 | AQP5 | AQP6 | AQP7 | AQP8 |
| AQP9 | AQR | AR | ARAF | ARAP1 |
| ARAP2 | ARAP3 | ARC | ARCN1 | ARD1B |
| AREG | ARF1 | ARF3 | ARF4 | ARF5 |
| ARF6 | ARFGAP1 | ARFGAP2 | ARFGAP3 | ARFGEF1 |
| ARFGEF2 | ARFIP1 | ARFIP2 | ARFRP1 | ARG1 |
| ARG2 | ARGFX | ARGLU1 | ARHGAP1 | ARHGAP10 |
| ARHGAP11A | ARHGAP11B | ARHGAP12 | ARHGAP15 | ARHGAP17 |
| ARHGAP18 | ARHGAP19 | ARHGAP19_ENST00000358531 | ARHGAP20 | ARHGAP21 |
| ARHGAP22 | ARHGAP23 | ARHGAP24 | ARHGAP25 | ARHGAP26 |
| ARHGAP27 | ARHGAP28 | ARHGAP29 | ARHGAP30 | ARHGAP31 |
| ARHGAP32 | ARHGAP32_ENST00000310343 | ARHGAP33 | ARHGAP36 | ARHGAP4 |
| ARHGAP5 | ARHGAP6 | ARHGAP8 | ARHGAP9 | ARHGDIA |
| ARHGDIB | ARHGDIG | ARHGEF1 | ARHGEF10 | ARHGEF10L |
| ARHGEF10_ENST00000398564 | ARHGEF11 | ARHGEF12 | ARHGEF15 | ARHGEF16 |
| ARHGEF17 | ARHGEF18 | ARHGEF19 | ARHGEF2 | ARHGEF3 |
| ARHGEF4 | ARHGEF5 | ARHGEF5L | ARHGEF6 | ARHGEF7 |
| ARHGEF9 | ARID1A | ARID1B | ARID2 | ARID3A |
| ARID3B | ARID3C | ARID4A | ARID4B | ARID4B_ENST00000264183 |
| ARID5A | ARID5B | ARIH1 | ARIH2 | ARL1 |
| ARL10 | ARL11 | ARL13A | ARL13B | ARL14 |
| ARL15 | ARL17B | ARL2 | ARL2BP | ARL3 |
| ARL4A | ARL4C | ARL4D | ARL4P | ARL5A |
| ARL5B | ARL5C | ARL6 | ARL6IP1 | ARL6IP4 |
| ARL6IP5 | ARL6IP6 | ARL8A | ARL8B | ARL9 |
| ARMC1 | ARMC10 | ARMC2 | ARMC3 | ARMC4 |
| ARMC6 | ARMC7 | ARMC8 | ARMC9 | ARMCX1 |
| ARMCX2 | ARMCX3 | ARMCX4 | ARMCX5 | ARMCX6 |
| ARNT | ARNT2 | ARNTL | ARNTL2 | ARPC1A |
| ARPC1B | ARPC2 | ARPC3 | ARPC4 | ARPC5 |
| ARPC5L | ARPM1 | ARPP-21 | ARPP19 | ARR3 |
| ARRB1 | ARRB2 | ARRDC1 | ARRDC2 | ARRDC3 |
| ARRDC4 | ARSA | ARSB | ARSD | ARSE |
| ARSF | ARSG | ARSH | ARSI | ARSJ |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ARSK | ART1 | ART3 | ART4 | ART5 |
| ARTN | ARV1 | ARVCF | ARX | AS3MT |
| ASAH1 | ASAH2 | ASAH2B | ASAM | ASAP1 |
| ASAP2 | ASAP3 | ASB1 | ASB10 | ASB11 |
| ASB12 | ASB13 | ASB14 | ASB15 | ASB16 |
| ASB17 | ASB18 | ASB2 | ASB3 | ASB4 |
| ASB5 | ASB6 | ASB7 | ASB8 | ASB9 |
| ASCC1 | ASCC2 | ASCC3 | ASCL1 | ASCL2 |
| ASCL3 | ASCL4 | ASF1B | ASGR1 | ASGR1_ENST00000380920 |
| ASGR2 | ASH1L | ASH2L | ASIP | ASL |
| ASMT | ASMTL | ASNA1 | ASNS | ASNSD1 |
| ASNS_ENST00000394309 | ASPA | ASPDH | ASPH | ASPHD1 |
| ASPHD2 | ASPM | ASPN | ASPRV1 | ASPSCR1 |
| ASRGL1 | ASS1 | ASTE1 | ASTL | ASTN1 |
| ASTN2 | ASXL1 | ASXL2 | ASXL3 | ASZ1 |
| ATAD1 | ATAD2 | ATAD2B | ATAD2B_ENST00000238789 | ATAD3A |
| ATAD3B | ATAD3B_ENST00000378741 | ATAD5 | ATCAY | ATE1 |
| ATF1 | ATF2 | ATF3 | ATF4 | ATF5 |
| ATF6 | ATF6B | ATF7IP | ATF7IP2 | ATG10 |
| ATG12 | ATG16L1 | ATG16L2 | ATG2A | ATG2B |
| ATG3 | ATG4A | ATG4A_ENST00000372232 | ATG4C | ATG4D |
| ATG5 | ATG7 | ATG9A | ATG9B | ATHL1 |
| ATIC | ATL1 | ATL2 | ATL3 | ATM |
| ATMIN | ATN1 | ATOH1 | ATOH7 | ATOH8 |
| ATP10A | ATP10B | ATP10D | ATP11A | ATP11B |
| ATP11C | ATP12A | ATP13A1 | ATP13A2 | ATP13A3 |
| ATP13A4 | ATP13A5 | ATP1A1 | ATP1A2 | ATP1A3 |
| ATP1A4 | ATP1B1 | ATP1B2 | ATP1B3 | ATP1B4 |
| ATP2A1 | ATP2A2 | ATP2A3 | ATP2B1 | ATP2B2 |
| ATP2B3 | ATP2B3_ENST00000370186 | ATP2B4 | ATP2C1 | ATP2C2 |
| ATP4A | ATP4B | ATP5A1 | ATP5B | ATP5C1 |
| ATP5D | ATP5E | ATP5F1 | ATP5G1 | ATP5G2 |
| ATP5G3 | ATP5H | ATP5I | ATP5J | ATP5J2 |
| ATP5L | ATP5O | ATP5S | ATP5SL | ATP6AP1 |
| ATP6AP1L | ATP6AP2 | ATP6V0A1 | ATP6V0A2 | ATP6V0A4 |
| ATP6V0B | ATP6V0C | ATP6V0D1 | ATP6V0D2 | ATP6V0E1 |
| ATP6V0E2L | ATP6V1A | ATP6V1B1 | ATP6V1B2 | ATP6V1C1 |
| ATP6V1C2 | ATP6V1D | ATP6V1E1 | ATP6V1E2 | ATP6V1F |
| ATP6V1G1 | ATP6V1G2 | ATP6V1G3 | ATP6V1H | ATP7A |
| ATP7B | ATP8A1 | ATP8A2 | ATP8B1 | ATP8B2 |
| ATP8B4 | ATP9A | ATP9B | ATPAF1 | ATPAF2 |
| ATPBD3 | ATPBD4 | ATPGD1 | ATPIF1 | ATR |
| ATRIP | ATRN | ATRNL1 | ATRX | ATXN1 |
| ATXN10 | ATXN2 | ATXN2L | ATXN3 | ATXN3L |
| ATXN7 | ATXN7L1 | ATXN7L2 | ATXN7L3 | AUH |
| AUP1 | AURKA | AURKAIP1 | AURKB | AURKC |
| AUTS2 | AVEN | AVIL | AVL9 | AVP |
| AVPI1 | AVPR1A | AVPR1B | AVPR2 | AWAT1 |
| AWAT2 | AXIN1 | AXIN2 | AXL | AZGP1 |
| AZI1 | AZI2 | AZIN1 | AZU1 | B2M |
| B3GALNT1 | B3GALNT2 | B3GALT1 | B3GALT2 | B3GALT4 |
| B3GALT5 | B3GALT6 | B3GALTL | B3GAT1 | B3GAT2 |
| B3GAT3 | B3GNT1 | B3GNT2 | B3GNT3 | B3GNT4 |
| B3GNT5 | B3GNT6 | B3GNT7 | B3GNT8 | B3GNTL1 |
| B3Gn-T6 | B4GALNT1 | B4GALNT2 | B4GALNT3 | B4GALNT4 |
| B4GALT1 | B4GALT2 | B4GALT3 | B4GALT4 | B4GALT5 |
| B4GALT6 | B4GALT7 | B7 | B9D1 | B9D2 |
| BAALC | BAAT | BACE1 | BACE2 | BACH1 |
| BACH2 | BAD | BAG1 | BAG2 | BAG3 |
| BAG4 | BAG5 | BAHD1 | BAI1 | BAI2 |
| BAI3 | BAIAP2 | BAIAP2L1 | BAIAP2L2 | BAIAP3 |
| BAK1 | BAMBI | BANF1 | BANF2 | BANK1 |
| BANP | BAP1 | BARD1 | BARHL1 | BARHL2 |
| BARX1 | BARX2 | BASP1 | BAT1 | BAT2 |
| BAT2D1 | BAT2D1_ENST00000392078 | BAT3 | BAT4 | BAT5 |
| BATF | BATF2 | BATF3 | BAX | BAZ1A |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| BAZ1B | BAZ2A | BAZ2B | BBC3 | BBOX1 |
| BBS1 | BBS10 | BBS12 | BBS2 | BBS4 |
| BBS5 | BBS7 | BBS9 | BBX | BCAM |
| BCAN | BCAP29 | BCAP31 | BCAR1 | BCAR3 |
| BCAS1 | BCAS2 | BCAS3 | BCAS4 | BCAS4_ENST00000358791 |
| BCAT1 | BCAT2 | BCCIP | BCDIN3D | BCHE |
| BCKDHA | BCKDHB | BCKDK | BCL10 | BCL11A |
| BCL11B | BCL2 | BCL2A1 | BCL2L1 | BCL2L10 |
| BCL2L11 | BCL2L12 | BCL2L13 | BCL2L14 | BCL2L15 |
| BCL2L2 | BCL3 | BCL6 | BCL6B | BCL7A |
| BCL7B | BCL7C | BCL9 | BCL9L | BCLAF1 |
| BCMO1 | BCO2 | BCOR | BCORL1 | BCORL2 |
| BCR | BCS1L | BDH1 | BDH2 | BDKRB1 |
| BDKRB2 | BDNF | BDP1 | BECN1 | BEGAIN |
| BEND2 | BEND3 | BEND4 | BEND5 | BEND6 |
| BEND7 | BEST1 | BEST2 | BEST3 | BEST4 |
| BET1 | BET1L | BEX1 | BEX2 | BEX4 |
| BEX5 | BFAR | BFSP1 | BFSP2 | BGLAP |
| BGN | BHLHA15 | BHLHB9 | BHLHE22 | BHLHE23 |
| BHLHE40 | BHLHE41 | BHMT | BHMT2 | BICC1 |
| BICD1 | BICD2 | BID | BIK | BIN1 |
| BIN2 | BIRC2 | BIRC3 | BIRC5 | BIRC6 |
| BIRC7 | BIRC8 | BIVM | BLCAP | BLID |
| BLK | BLM | BLMH | BLNK | BLOC1S1 |
| BLOC1S2 | BLOC1S3 | BLVRA | BLVRB | BLYM_HUMAN |
| BLZF1 | BMF | BMI1 | BMP1 | BMP10 |
| BMP15 | BMP2 | BMP2K | BMP2KL | BMP2K_ENST00000335016 |
| BMP3 | BMP4 | BMP5 | BMP6 | BMP7 |
| BMP8A | BMP8B | BMPER | BMPR1A | BMPR1B |
| BMPR2 | BMS1 | BMX | BNC1 | BNC2 |
| BNIP1 | BNIP2 | BNIP3 | BNIP3L | BNIPL |
| BOC | BOD1 | BOD1L | BOK | BOLA1 |
| BOLA2 | BOLA2B | BOLA3 | BOLL | BOP1 |
| BPGM | BPHL | BPI | BPIL1 | BPIL2 |
| BPIL3 | BPNT1 | BPTF | BPY2B | BPY2C |
| BRAF | BRAP | BRCA1 | BRCA2 | BRCC3 |
| BRD1 | BRD2 | BRD2_ENST00000395289 | BRD3 | BRD3_ENST00000303407 |
| BRD4 | BRD4_ENST00000263377 | BRD7 | BRD8 | BRD9 |
| BRDT | BRE | BRF1 | BRF2 | BRI3 |
| BRI3BP | BRIP1 | BRIX1 | BRMS1 | BRMS1L |
| BRP44 | BRP44L | BRPF1 | BRPF3 | BRS3 |
| BRSK1 | BRSK2 | BRWD1 | BRWD3 | BSCL2 |
| BSDC1 | BSG | BSN | BSND | BSPRY |
| BST1 | BST2 | BSX | BTAF1 | BTBD1 |
| BTBD10 | BTBD11 | BTBD12 | BTBD16 | BTBD17 |
| BTBD2 | BTBD3 | BTBD6 | BTBD7 | BTBD8 |
| BTBD9 | BTBD9_ENST00000403056 | BTC | BTD | BTF3 |
| BTF3L1 | BTF3L3 | BTF3L4 | BTG1 | BTG2 |
| BTG3 | BTG4 | BTK | BTLA | BTN1A1 |
| BTN2A1 | BTN2A2 | BTN2A3 | BTN3A1 | BTN3A2 |
| BTN3A3 | BTNL2 | BTNL8 | BTNL9 | BTRC |
| BUB1 | BUB1B | BUB3 | BUD13 | BUD31 |
| BVES | BYSL | BZRAP1 | BZW1 | BZW2 |
| C10orf10 | C10orf104 | C10orf107 | C10orf11 | C10orf111 |
| C10orf113 | C10orf113_ENST00000377118 | C10orf114 | C10orf116 | C10orf118 |
| C10orf119 | C10orf12 | C10orf120 | C10orf125 | C10orf128 |
| C10orf129 | C10orf131 | C10orf137 | C10orf18 | C10orf2 |
| C10orf25 | C10orf26 | C10orf27 | C10orf28 | C10orf31 |
| C10orf32 | C10orf35 | C10orf4 | C10orf46 | C10orf47 |
| C10orf53 | C10orf54 | C10orf57 | C10orf58 | C10orf6 |
| C10orf61 | C10orf62 | C10orf64 | C10orf68 | C10orf71 |
| C10orf71_ENST00000374144 | C10orf72 | C10orf76 | C10orf78 | C10orf79 |
| C10orf81 | C10orf82 | C10orf84 | C10orf88 | C10orf90 |
| C10orf91 | C10orf92 | C10orf93 | C10orf95 | C10orf96 |
| C10orf99 | C11orf1 | C11orf10 | C11orf16 | C11orf17 |
| C11orf2 | C11orf24 | C11orf30 | C11orf34 | C11orf35 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| C11orf40 | C11orf41 | C11orf42 | C11orf44 | C11orf45 |
| C11orf46 | C11orf47 | C11orf48 | C11orf49 | C11orf51 |
| C11orf52 | C11orf53 | C11orf54 | C11orf57 | C11orf58 |
| C11orf59 | C11orf60 | C11orf61 | C11orf63 | C11orf65 |
| C11orf66 | C11orf67 | C11orf68 | C11orf70 | C11orf73 |
| C11orf74 | C11orf75 | C11orf76 | C11orf77 | C11orf82 |
| C11orf83 | C11orf84 | C11orf85 | C11orf86 | C11orf87 |
| C11orf88 | C11orf9 | C11orf92 | C12orf10 | C12orf11 |
| C12orf12 | C12orf23 | C12orf24 | C12orf26 | C12orf28 |
| C12orf29 | C12orf32 | C12orf34 | C12orf35 | C12orf36 |
| C12orf37 | C12orf39 | C12orf4 | C12orf40 | C12orf42 |
| C12orf43 | C12orf44 | C12orf45 | C12orf48 | C12orf49 |
| C12orf5 | C12orf50 | C12orf52 | C12orf54 | C12orf55 |
| C12orf56 | C12orf57 | C12orf59 | C12orf60 | C12orf61 |
| C12orf62 | C12orf63 | C12orf64 | C12orf65 | C12orf66 |
| C12orf67 | C12orf68 | C12orf69 | C12orf72 | C12orf74 |
| C12orf76 | C13orf1 | C13orf15 | C13orf16 | C13orf23 |
| C13orf26 | C13orf27 | C13orf28 | C13orf30 | C13orf31 |
| C13orf33 | C13orf34 | C13orf35 | C13orf36 | C13orf37 |
| C13orf39 | C13orf40 | C14orf1 | C14orf100 | C14orf101 |
| C14orf102 | C14orf104 | C14orf105 | C14orf106 | C14orf109 |
| C14orf115 | C14orf118 | C14orf119 | C14orf126 | C14orf128 |
| C14orf129 | C14orf135 | C14orf138 | C14orf142 | C14orf143 |
| C14orf145 | C14orf147 | C14orf148 | C14orf149 | C14orf153 |
| C14orf156 | C14orf159 | C14orf166 | C14orf167 | C14orf173 |
| C14orf174 | C14orf177 | C14orf178 | C14orf179 | C14orf180 |
| C14orf181 | C14orf182 | C14orf183 | C14orf2 | C14orf20 |
| C14orf21 | C14orf23 | C14orf28 | C14orf37 | C14orf38 |
| C14orf39 | C14orf4 | C14orf43 | C14orf45 | C14orf48 |
| C14orf49 | C14orf50 | C14orf68 | C14orf73 | C14orf79 |
| C14orf80 | C14orf93 | C15orf17 | C15orf2 | C15orf23 |
| C15orf24 | C15orf26 | C15orf27 | C15orf29 | C15orf32 |
| C15orf33 | C15orf38 | C15orf39 | C15orf40 | C15orf42 |
| C15orf43 | C15orf44 | C15orf48 | C15orf52 | C15orf53 |
| C15orf54 | C15orf55 | C15orf56 | C15orf57 | C15orf58 |
| C15orf59 | C15orf63 | C16orf11 | C16orf13 | C16orf3 |
| C16orf35 | C16orf38 | C16orf42 | C16orf45 | C16orf46 |
| C16orf48 | C16orf5 | C16orf53 | C16orf54 | C16orf55 |
| C16orf57 | C16orf58 | C16orf59 | C16orf61 | C16orf62 |
| C16orf63 | C16orf65 | C16orf68 | C16orf7 | C16orf70 |
| C16orf71 | C16orf72 | C16orf73 | C16orf75 | C16orf78 |
| C16orf79 | C16orf80 | C16orf85 | C16orf87 | C16orf88 |
| C16orf89 | C16orf91 | C16orf92 | C16orf93 | C17orf101 |
| C17orf102 | C17orf103 | C17orf28 | C17orf37 | C17orf38 |
| C17orf39 | C17orf42 | C17orf46 | C17orf47 | C17orf48 |
| C17orf49 | C17orf50 | C17orf53 | C17orf55 | C17orf56 |
| C17orf57 | C17orf58 | C17orf59 | C17orf60 | C17orf61 |
| C17orf62 | C17orf64 | C17orf65 | C17orf66 | C17orf67 |
| C17orf68 | C17orf70 | C17orf71 | C17orf74 | C17orf76 |
| C17orf77 | C17orf79 | C17orf80 | C17orf81 | C17orf82 |
| C17orf85 | C17orf87 | C17orf90 | C17orf91 | C17orf92 |
| C17orf97 | C17orf98 | C18orf1 | C18orf10 | C18orf19 |
| C18orf21 | C18orf22 | C18orf25 | C18orf26 | C18orf32 |
| C18orf34 | C18orf45 | C18orf54 | C18orf55 | C18orf56 |
| C18orf62 | C18orf8 | C19orf10 | C19orf12 | C19orf16 |
| C19orf18 | C19orf2 | C19orf20 | C19orf21 | C19orf22 |
| C19orf24 | C19orf26 | C19orf28 | C19orf29 | C19orf29_ENST00000429344 |
| C19orf33 | C19orf35 | C19orf36 | C19orf39 | C19orf40 |
| C19orf41 | C19orf42 | C19orf43 | C19orf44 | C19orf45 |
| C19orf46 | C19orf47 | C19orf48 | C19orf50 | C19orf51 |
| C19orf52 | C19orf53 | C19orf56 | C19orf57 | C19orf59 |
| C19orf6 | C19orf60 | C19orf61 | C19orf63 | C19orf67 |
| C19orf75 | C1D | C1GALT1 | C1GALT1C1 | C1QA |
| C1QB | C1QBP | C1QC | C1QL1 | C1QL2 |
| C1QL3 | C1QL4 | C1QTNF1 | C1QTNF2 | C1QTNF3 |
| C1QTNF4 | C1QTNF5 | C1QTNF6 | C1QTNF7 | C1QTNF8 |
| C1QTNF9 | C1RL | C1S | C1orf100 | C1orf101 |
| C1orf103 | C1orf105 | C1orf106 | C1orf107 | C1orf109 |
| C1orf111 | C1orf112 | C1orf113 | C1orf114 | C1orf115 |
| C1orf116 | C1orf122 | C1orf123 | C1orf124 | C1orf125 |
| C1orf127 | C1orf128 | C1orf129 | C1orf130 | C1orf131 |
| C1orf135 | C1orf14 | C1orf141 | C1orf144 | C1orf146 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| C1orf147 | C1orf150 | C1orf151 | C1orf156 | C1orf158 |
| C1orf161 | C1orf162 | C1orf163 | C1orf164 | C1orf167 |
| C1orf168 | C1orf170 | C1orf172 | C1orf173 | C1orf174 |
| C1orf175 | C1orf177 | C1orf182 | C1orf183 | C1orf186 |
| C1orf187 | C1orf189 | C1orf190 | C1orf192 | C1orf194 |
| C1orf198 | C1orf201 | C1orf21 | C1orf210 | C1orf212 |
| C1orf213 | C1orf216 | C1orf218 | C1orf220 | C1orf222 |
| C1orf227 | C1orf229 | C1orf25 | C1orf26 | C1orf31 |
| C1orf34 | C1orf35 | C1orf38 | C1orf43 | C1orf49 |
| C1orf50 | C1orf51 | C1orf52 | C1orf54 | C1orf55 |
| C1orf56 | C1orf57 | C1orf58 | C1orf59 | C1orf61 |
| C1orf63 | C1orf64 | C1orf65 | C1orf66 | C1orf67 |
| C1orf68 | C1orf69 | C1orf74 | C1orf77 | C1orf83 |
| C1orf84 | C1orf85 | C1orf86 | C1orf87 | C1orf88 |
| C1orf89 | C1orf9 | C1orf91 | C1orf92 | C1orf93 |
| C1orf94 | C1orf95 | C1orf96 | C2 | C20orf103 |
| C20orf106 | C20orf107 | C20orf108 | C20orf11 | C20orf111 |
| C20orf112 | C20orf114 | C20orf118 | C20orf133 | C20orf134 |
| C20orf134_ENST00000330271 | C20orf135 | C20orf141 | C20orf144 | C20orf151 |
| C20orf152 | C20orf160 | C20orf165 | C20orf166 | C20orf177 |
| C20orf185 | C20orf186 | C20orf187 | C20orf191 | C20orf194 |
| C20orf195 | C20orf196 | C20orf197 | C20orf20 | C20orf200 |
| C20orf201 | C20orf24 | C20orf26 | C20orf27 | C20orf29 |
| C20orf3 | C20orf30 | C20orf4 | C20orf43 | C20orf46 |
| C20orf54 | C20orf62 | C20orf7 | C20orf70 | C20orf71 |
| C20orf72 | C20orf74 | C20orf78 | C20orf79 | C20orf80 |
| C20orf85 | C20orf94 | C20orf95 | C20orf96 | C21orf105 |
| C21orf124 | C21orf13 | C21orf15 | C21orf2 | C21orf29 |
| C21orf33 | C21orf34 | C21orf45 | C21orf56 | C21orf57 |
| C21orf58 | C21orf59 | C21orf62 | C21orf63 | C21orf66 |
| C21orf7 | C21orf70 | C21orf74 | C21orf88 | C21orf89 |
| C21orf9 | C21orf91 | C22orf13 | C22orf15 | C22orf23 |
| C22orf24 | C22orf25 | C22orf26 | C22orf28 | C22orf29 |
| C22orf30 | C22orf31 | C22orf32 | C22orf33 | C22orf36 |
| C22orf39 | C22orf40 | C22orf42 | C22orf43 | C22orf9 |
| C2CD2 | C2CD2L | C2CD3 | C2CD4A | C2CD4B |
| C2orf15 | C2orf16 | C2orf18 | C2orf24 | C2orf27A |
| C2orf27B | C2orf28 | C2orf29 | C2orf3 | C2orf34 |
| C2orf39 | C2orf40 | C2orf42 | C2orf43 | C2orf44 |
| C2orf47 | C2orf48 | C2orf49 | C2orf50 | C2orf51 |
| C2orf52 | C2orf53 | C2orf54 | C2orf55 | C2orf56 |
| C2orf57 | C2orf60 | C2orf61 | C2orf62 | C2orf63 |
| C2orf63_ENST00000407122 | C2orf64 | C2orf65 | C2orf66 | C2orf67 |
| C2orf68 | C2orf69 | C2orf7 | C2orf70 | C2orf71 |
| C2orf76 | C2orf77 | C2orf79 | C2orf80 | C2orf82 |
| C2orf83 | C2orf84 | C2orf85 | C2orf86 | C2orf88 |
| C3 | C3AR1 | C3P1 | C3orf1 | C3orf14 |
| C3orf15 | C3orf17 | C3orf18 | C3orf19 | C3orf20 |
| C3orf21 | C3orf22 | C3orf23 | C3orf24 | C3orf25 |
| C3orf26 | C3orf27 | C3orf28 | C3orf30 | C3orf31 |
| C3orf32 | C3orf33 | C3orf34 | C3orf35 | C3orf36 |
| C3orf37 | C3orf38 | C3orf39 | C3orf43 | C3orf45 |
| C3orf46 | C3orf49 | C3orf53 | C3orf54 | C3orf57 |
| C3orf58 | C3orf59 | C3orf62 | C3orf63 | C3orf64 |
| C3orf67 | C3orf70 | C3orf72 | C3orf75 | C3orf77 |
| C4A | C4B | C4BPA | C4BPB | C4orf14 |
| C4orf17 | C4orf19 | C4orf21 | C4orf22 | C4orf23 |
| C4orf26 | C4orf27 | C4orf31 | C4orf32 | C4orf33 |
| C4orf34 | C4orf35 | C4orf36 | C4orf37 | C4orf39 |
| C4orf40 | C4orf41 | C4orf42 | C4orf43 | C4orf44 |
| C4orf46 | C4orf49 | C4orf50 | C4orf6 | C4orf7 |
| C5 | C5AR1 | C5orf13 | C5orf15 | C5orf22 |
| C5orf23 | C5orf24 | C5orf28 | C5orf30 | C5orf32 |
| C5orf33 | C5orf34 | C5orf35 | C5orf36 | C5orf37 |
| C5orf38 | C5orf39 | C5orf4 | C5orf40 | C5orf41 |
| C5orf42 | C5orf43 | C5orf45 | C5orf46 | C5orf48 |
| C5orf49 | C5orf5 | C5orf50 | C5orf51 | C5orf53 |
| C5orf54 | C5orf56 | C6 | C6orf1 | C6orf10 |
| C6orf103 | C6orf105 | C6orf106 | C6orf108 | C6orf114 |
| C6orf115 | C6orf118 | C6orf12 | C6orf120 | C6orf124 |
| C6orf125 | C6orf129 | C6orf130 | C6orf134 | C6orf136 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| C6orf138 | C6orf142 | C6orf145 | C6orf146 | C6orf15 |
| C6orf150 | C6orf153 | C6orf154 | C6orf162 | C6orf163_ENST00000369574 |
| C6orf165 | C6orf167 | C6orf168 | C6orf170 | C6orf173 |
| C6orf174 | C6orf182 | C6orf186 | C6orf191 | C6orf192 |
| C6orf195 | C6orf201 | C6orf203 | C6orf204 | C6orf211 |
| C6orf213 | C6orf218 | C6orf221 | C6orf222 | C6orf223 |
| C6orf224 | C6orf225 | C6orf227 | C6orf25 | C6orf26 |
| C6orf27 | C6orf35 | C6orf47 | C6orf48 | C6orf49 |
| C6orf57 | C6orf58 | C6orf62 | C6orf64 | C6orf70 |
| C6orf72 | C6orf81 | C6orf87 | C6orf89 | C6orf94 |
| C6orf97 | C6orf98 | C7 | C7orf11 | C7orf16 |
| C7orf20 | C7orf23 | C7orf25 | C7orf26 | C7orf27 |
| C7orf28A | C7orf28B | C7orf29 | C7orf30 | C7orf31 |
| C7orf33 | C7orf34 | C7orf36 | C7orf41 | C7orf42 |
| C7orf43 | C7orf44 | C7orf45 | C7orf46 | C7orf47 |
| C7orf49 | C7orf50 | C7orf51 | C7orf52 | C7orf53 |
| C7orf54 | C7orf55 | C7orf58 | C7orf59 | C7orf60 |
| C7orf62 | C7orf63 | C7orf64 | C7orf66 | C7orf68 |
| C7orf69 | C7orf70 | C7orf72_ENST00000297001 | C8A | C8B |
| C8G | C8orf12 | C8orf13 | C8orf14 | C8orf30A |
| C8orf31 | C8orf33 | C8orf34 | C8orf37 | C8orf38 |
| C8orf4 | C8orf40 | C8orf41 | C8orf44 | C8orf45 |
| C8orf46 | C8orf47 | C8orf55 | C8orf58 | C8orf59 |
| C8orf76 | C8orf79 | C8orf8 | C8orf80 | C8orf82 |
| C8orf84 | C8orf85 | C8orf86 | C9 | C9orf100 |
| C9orf102 | C9orf103 | C9orf106 | C9orf11 | C9orf114 |
| C9orf116 | C9orf117 | C9orf119 | C9orf123 | C9orf125 |
| C9orf128 | C9orf129 | C9orf131 | C9orf135 | C9orf139 |
| C9orf140 | C9orf142 | C9orf144 | C9orf150 | C9orf152 |
| C9orf153 | C9orf156 | C9orf16 | C9orf163 | C9orf164 |
| C9orf167 | C9orf170 | C9orf171 | C9orf21 | C9orf23 |
| C9orf24 | C9orf25 | C9orf3 | C9orf30 | C9orf37 |
| C9orf4 | C9orf40 | C9orf41 | C9orf43 | C9orf46 |
| C9orf47 | C9orf48 | C9orf5 | C9orf50 | C9orf51 |
| C9orf56 | C9orf6 | C9orf62 | C9orf64 | C9orf66 |
| C9orf68 | C9orf7 | C9orf71 | C9orf72 | C9orf75 |
| C9orf78 | C9orf79 | C9orf80 | C9orf82 | C9orf84 |
| C9orf85 | C9orf86 | C9orf89 | C9orf9 | C9orf91 |
| C9orf93 | C9orf95 | C9orf96 | C9orf98 | C9orf98_ENST00000298545 |
| CA1 | CA10 | CA11 | CA12 | CA13 |
| CA14 | CA2 | CA3 | CA4 | CA5A |
| CA5B | CA5BP | CA6 | CA7 | CA8 |
| CA9 | CAB39 | CAB39L | CABC1 | CABIN1 |
| CABLES1 | CABLES2 | CABP1 | CABP2 | CABP4 |
| CABP5 | CABP7 | CABYR | CACHD1 | CACNA1A |
| CACNA1A_ENST00000357018 | CACNA1B | CACNA1C | CACNA1D | CACNA1E |
| CACNA1F | CACNA1G | CACNA1H | CACNA1H_ENST00000358590 | CACNA1I |
| CACNA1S | CACNA2D1 | CACNA2D2 | CACNA2D3 | CACNB1 |
| CACNB2 | CACNB3 | CACNG1 | CACNG2 | CACNG3 |
| CACNG4 | CACNG5 | CACNG6 | CACNG7 | CACNG8 |
| CACYBP | CAD | CADM1 | CADM2 | CADM3 |
| CADM4 | CADPS | CADPS2 | CAGE1 | CALB1 |
| CALB2 | CALCA | CALCB | CALCOCO1 | CALCOCO2 |
| CALCR | CALCRL | CALD1 | CALHM1 | CALHM2 |
| CALM1 | CALM2 | CALM3 | CALML3 | CALML4 |
| CALML5 | CALML6 | CALN1 | CALR | CALR3 |
| CALU | CALY | CAMK1 | CAMK1D | CAMK1G |
| CAMK2A | CAMK2B | CAMK2D | CAMK2G | CAMK2N1 |
| CAMK2N2 | CAMK4 | CAMKK1 | CAMKK2 | CAMKV |
| CAMKV_ENST00000477224 | CAMLG | CAMP | CAMSAP1 | CAMSAP1L1 |
| CAMTA1 | CAMTA2 | CAND1 | CAND2 | CANT1 |
| CANX | CAP1 | CAP2 | CAPG | CAPN1 |
| CAPN10 | CAPN11 | CAPN12 | CAPN13 | CAPN2 |
| CAPN3 | CAPN5 | CAPN6 | CAPN7 | CAPN9 |
| CAPNS1 | CAPRIN1 | CAPRIN2 | CAPS | CAPS2 |
| CAPSL | CAPZA1 | CAPZA2 | CAPZA3 | CAPZB |
| CARD10 | CARD11 | CARD14 | CARD16 | CARD17 |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| CARD18 | CARD6 | CARD8 | CARD9 | CARHSP1 |
| CARKD | CARM1 | CARS | CARS2 | CARTPT |
| CASC1 | CASC3 | CASC4 | CASC5 | CASD1 |
| CASK | CASKIN1 | CASKIN2 | CASP1 | CASP10 |
| CASP14 | CASP2 | CASP3 | CASP4 | CASP5 |
| CASP6 | CASP7 | CASP8 | CASP9 | CASQ1 |
| CASQ2 | CASR | CASS4 | CAST | CASZ1 |
| CAT | CATSPER1 | CATSPER2 | CATSPER3 | CATSPER4 |
| CATSPERB | CATSPERG | CAV1 | CAV2 | CAV3 |
| CBARA1 | CBFA2T2 | CBFA2T3 | CBFB | CBL |
| CBLB | CBLC | CBLL1 | CBLN1 | CBLN2 |
| CBLN3 | CBLN4 | CBR1 | CBR3 | CBR4 |
| CBS | CBWD1 | CBWD2 | CBWD3 | CBWD5 |
| CBWD6 | CBX1 | CBX2 | CBX3 | CBX4 |
| CBX5 | CBX6 | CBX7 | CBX8 | CBY1 |
| CC2D1A | CC2D1B | CC2D2A | CC2D2B | CCAR1 |
| CCBE1 | CCBL1 | CCBL2 | CCBL2_ENST00000370491 | CCBP2 |
| CCDC101 | CCDC102A | CCDC102B | CCDC103 | CCDC104 |
| CCDC105 | CCDC106 | CCDC107 | CCDC108 | CCDC109A |
| CCDC109B | CCDC11 | CCDC110 | CCDC111 | CCDC112 |
| CCDC113 | CCDC114 | CCDC115 | CCDC116 | CCDC117 |
| CCDC12 | CCDC120 | CCDC121 | CCDC122 | CCDC123 |
| CCDC124 | CCDC125 | CCDC126 | CCDC127 | CCDC128 |
| CCDC13 | CCDC130 | CCDC132 | CCDC132_ENST00000305866 | CCDC134 |
| CCDC135 | CCDC137 | CCDC138 | CCDC14 | CCDC140 |
| CCDC141 | CCDC142 | CCDC144B | CCDC144NL | CCDC146 |
| CCDC147 | CCDC148 | CCDC149 | CCDC15 | CCDC151 |
| CCDC153 | CCDC155 | CCDC157 | CCDC158 | CCDC160 |
| CCDC18 | CCDC19 | CCDC21 | CCDC22 | CCDC23 |
| CCDC24 | CCDC25 | CCDC27 | CCDC28A | CCDC28B |
| CCDC29 | CCDC3 | CCDC30 | CCDC33 | CCDC34 |
| CCDC35 | CCDC36 | CCDC37 | CCDC38 | CCDC39 |
| CCDC40 | CCDC41 | CCDC42 | CCDC46 | CCDC47 |
| CCDC48 | CCDC50 | CCDC51 | CCDC52 | CCDC54 |
| CCDC55 | CCDC56 | CCDC58 | CCDC59 | CCDC6 |
| CCDC60 | CCDC62 | CCDC63 | CCDC64 | CCDC65 |
| CCDC66 | CCDC67 | CCDC68 | CCDC69 | CCDC7 |
| CCDC70 | CCDC71 | CCDC72 | CCDC73 | CCDC74A |
| CCDC74B | CCDC76 | CCDC77 | CCDC78 | CCDC8 |
| CCDC80 | CCDC81 | CCDC82 | CCDC83 | CCDC84 |
| CCDC85A | CCDC85B | CCDC86 | CCDC87 | CCDC88A |
| CCDC88B | CCDC89 | CCDC9 | CCDC90A | CCDC90B |
| CCDC91 | CCDC92 | CCDC93 | CCDC94 | CCDC96 |
| CCDC97 | CCDC99 | CCHCR1 | CCIN | CCK |
| CCKAR | CCKBR | CCL1 | CCL11 | CCL13 |
| CCL14 | CCL15 | CCL16 | CCL17 | CCL18 |
| CCL19 | CCL2 | CCL20 | CCL21 | CCL22 |
| CCL23 | CCL24 | CCL25 | CCL26 | CCL27 |
| CCL28 | CCL3 | CCL3L1 | CCL3L3 | CCL4 |
| CCL4L1 | CCL4L2 | CCL5 | CCL7 | CCL8 |
| CCM2 | CCNA1 | CCNA2 | CCNB1 | CCNB1IP1 |
| CCNB2 | CCNB3 | CCNB3_ENST00000376042 | CCNC | CCND1 |
| CCND2 | CCND3 | CCNDBP1 | CCNE1 | CCNE2 |
| CCNF | CCNG1 | CCNG2 | CCNH | CCNI |
| CCNI2 | CCNJ | CCNJL | CCNL1 | CCNL2 |
| CCNO | CCNT1 | CCNT2 | CCNY | CCNYL1 |
| CCNYL2 | CCPG1 | CCR1 | CCR10 | CCR2 |
| CCR3 | CCR4 | CCR5 | CCR6 | CCR7 |
| CCR8 | CCR9 | CCRL1 | CCRL2 | CCRN4L |
| CCS | CCT2 | CCT3 | CCT4 | CCT5 |
| CCT6A | CCT6B | CCT7 | CCT8 | CCT8L1 |
| CCT8L2 | CD101 | CD109 | CD14 | CD151 |
| CD160 | CD163 | CD163L1 | CD164 | CD164L2 |
| CD180 | CD19 | CD1A | CD1B | CD1C |
| CD1D | CD1E | CD2 | CD200 | CD200R1 |
| CD200R1L | CD207 | CD209 | CD22 | CD226 |
| CD244 | CD247 | CD248 | CD27 | CD274 |
| CD276 | CD28 | CD2AP | CD2BP2 | CD300A |
| CD300C | CD300E | CD300LB | CD300LD | CD300LF |
| CD300LG | CD302 | CD320 | CD33 | CD34 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| CD36 | CD36_ENST00000433696 | CD37 | CD38 | CD3D |
| CD3E | CD3EAP | CD3G | CD4 | CD40 |
| CD40LG | CD44 | CD46 | CD47 | CD48 |
| CD5 | CD52 | CD53 | CD55 | CD58 |
| CD59 | CD5L | CD6 | CD63 | CD68 |
| CD69 | CD7 | CD70 | CD72 | CD74 |
| CD79A | CD79B | CD80 | CD81 | CD82 |
| CD83 | CD84 | CD86 | CD8A | CD8B |
| CD9 | CD93 | CD96 | CD97 | CD99 |
| CD99L2 | CDA | CDADC1 | CDAN1 | CDC123 |
| CDC14A | CDC14B | CDC16 | CDC20 | CDC20B |
| CDC23 | CDC25A | CDC25B | CDC25C | CDC26 |
| CDC27 | CDC2L2 | CDC34 | CDC37 | CDC37L1 |
| CDC37P1 | CDC40 | CDC42 | CDC42BPA | CDC42BPB |
| CDC42BPG | CDC42EP1 | CDC42EP2 | CDC42EP3 | CDC42EP4 |
| CDC42EP5 | CDC42SE1 | CDC42SE2 | CDC45L | CDC5L |
| CDC6 | CDC7 | CDC73 | CDCA2 | CDCA3 |
| CDCA4 | CDCA5 | CDCA7 | CDCA7L | CDCA8 |
| CDCP1 | CDCP2 | CDH1 | CDH10 | CDH11 |
| CDH12 | CDH13 | CDH15 | CDH16 | CDH17 |
| CDH18 | CDH19 | CDH2 | CDH20 | CDH22 |
| CDH23 | CDH24 | CDH26 | CDH3 | CDH4 |
| CDH5 | CDH6 | CDH7 | CDH8 | CDH9 |
| CDHR1 | CDHR5 | CDIPT | CDK1 | CDK10 |
| CDK11B | CDK12 | CDK13 | CDK14 | CDK15 |
| CDK16 | CDK17 | CDK18 | CDK19 | CDK1_ENST00000395284 |
| CDK2 | CDK20 | CDK2AP1 | CDK2AP2 | CDK3 |
| CDK4 | CDK5 | CDK5R1 | CDK5R2 | CDK5RAP1 |
| CDK5RAP2 | CDK5RAP3 | CDK6 | CDK7 | CDK8 |
| CDK9 | CDKAL1 | CDKL1 | CDKL2 | CDKL3 |
| CDKL4 | CDKL5 | CDKN1A | CDKN1B | CDKN1C |
| CDKN2A | CDKN2AIP | CDKN2AIPNL | CDKN2B | CDKN2C |
| CDKN2D | CDKN2a(p14) | CDKN3 | CDNF | CDO1 |
| CDON | CDR1 | CDR2 | CDRT1 | CDRT15 |
| CDRT4 | CDS1 | CDS2 | CDSN | CDT1 |
| CDV3 | CDX1 | CDX2 | CDX4 | CDY1 |
| CDY1B | CDY2A | CDY2B | CDYL | CDYL2 |
| CEACAM1 | CEACAM18 | CEACAM18_ENST00000451626 | CEACAM19 | CEACAM20 |
| CEACAM3 | CEACAM4 | CEACAM5 | CEACAM6 | CEACAM7 |
| CEACAM8 | CEBPA | CEBPB | CEBPE | CEBPG |
| CEBPZ | CECR1 | CECR2 | CECR5 | CECR6 |
| CEL | CELA1 | CELA2A | CELA2B | CELA3A |
| CELA3B | CELF1 | CELF2 | CELF3 | CELF4 |
| CELF5 | CELF6 | CELP | CELSR1 | CELSR2 |
| CELSR3 | CEMP1 | CEND1 | CENPA | CENPB |
| CENPC1 | CENPE | CENPF | CENPH | CENPI |
| CENPJ | CENPK | CENPL | CENPM | CENPN |
| CENPO | CENPP | CENPQ | CENPT | CENPV |
| CEP110 | CEP120 | CEP135 | CEP152 | CEP164 |
| CEP170 | CEP170L | CEP192 | CEP250 | CEP290 |
| CEP55 | CEP57 | CEP63 | CEP68 | CEP70 |
| CEP72 | CEP76 | CEP78 | CEP97 | CEPT1 |
| CER1 | CERCAM | CERK | CERKL | CES1 |
| CES1_ENST00000360526 | CES2 | CES3 | CES7 | CES8 |
| CETN1 | CETN2 | CETN3 | CETP | CFB |
| CFC1 | CFC1B | CFD | CFDP1 | CFH |
| CFHR1 | CFHR2 | CFHR3 | CFHR4 | CFHR5 |
| CFI | CFL1 | CFL2 | CFLAR | CFP |
| CFTR | CGA | CGB | CGB1 | CGB2 |
| CGB5 | CGB7 | CGB8 | CGGBP1 | CGI-77 |
| CGN | CGNL1 | CGREF1 | CGRRF1 | CH25H |
| CHAC1 | CHAC2 | CHAD | CHADL | CHAF1A |
| CHAF1B | CHAT | CHCHD1 | CHCHD10 | CHCHD2 |
| CHCHD3 | CHCHD4 | CHCHD5 | CHCHD6 | CHCHD7 |
| CHCHD8 | CHCHD9 | CHD1 | CHD1L | CHD2 |
| CHD3 | CHD4 | CHD5 | CHD6 | CHD7 |
| CHD8 | CHD9 | CHDH | CHEK1 | CHEK2 |
| CHERP | CHFR | CHGA | CHGB | CHI3L1 |
| CHI3L2 | CHIA | CHIC1 | CHIC2 | CHID1 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| CHIT1 | CHKA | CHKB | CHL1 | CHM |
| CHML | CHMP2A | CHMP2B | CHMP4A | CHMP4B |
| CHMP4C | CHMP5 | CHMP6 | CHMP7 | CHN1 |
| CHN2 | CHODL | CHORDC1 | CHP | CHP2 |
| CHPF | CHPF2 | CHPT1 | CHRAC1 | CHRD |
| CHRDL1 | CHRDL2 | CHRFAM7A | CHRM1 | CHRM2 |
| CHRM3 | CHRM5 | CHRNA1 | CHRNA10 | CHRNA2 |
| CHRNA3 | CHRNA4 | CHRNA5 | CHRNA6 | CHRNA7 |
| CHRNA9 | CHRNB1 | CHRNB2 | CHRNB3 | CHRNB4 |
| CHRND | CHRNE | CHRNG | CHST1 | CHST10 |
| CHST11 | CHST12 | CHST13 | CHST14 | CHST15 |
| CHST2 | CHST3 | CHST4 | CHST5 | CHST6 |
| CHST7 | CHST8 | CHST9 | CHSY1 | CHSY3 |
| CHTF18 | CHTF8 | CHUK | CHURC1 | CIAO1 |
| CIAPIN1 | CIB1 | CIB2 | CIB3 | CIB4 |
| CIC | CIDEA | CIDEB | CIDEC | CIITA |
| CILP | CILP2 | CINP | CIR1 | CIRBP |
| CIRH1A | CISD1 | CISD1B | CISD2 | CISH |
| CIT | CITED1 | CITED2 | CITED4 | CIZ1 |
| CKAP2 | CKAP2L | CKAP4 | CKAP5 | CKB |
| CKLF | CKM | CKMT1A | CKMT1B | CKMT2 |
| CKS1B | CKS2 | CLASP1 | CLASP2 | CLC |
| CLCA1 | CLCA2 | CLCA3P | CLCA4 | CLCC1 |
| CLCF1 | CLCN1 | CLCN2 | CLCN3 | CLCN4 |
| CLCN5 | CLCN6 | CLCN7 | CLCNKA | CLCNKB |
| CLDN1 | CLDN10 | CLDN11 | CLDN12 | CLDN14 |
| CLDN15 | CLDN16 | CLDN17 | CLDN18 | CLDN19 |
| CLDN2 | CLDN20 | CLDN22 | CLDN3 | CLDN4 |
| CLDN5 | CLDN6 | CLDN7 | CLDN8 | CLDN9 |
| CLDND1 | CLDND2 | CLEC10A | CLEC11A | CLEC12A |
| CLEC12B | CLEC14A | CLEC16A | CLEC18A | CLEC18B |
| CLEC18C | CLEC1A | CLEC1B | CLEC2B | CLEC2D |
| CLEC3A | CLEC3B | CLEC4A | CLEC4C | CLEC4D |
| CLEC4E | CLEC4F | CLEC4G | CLEC4M | CLEC5A |
| CLEC6A | CLEC7A | CLEC9A | CLECL1 | CLGN |
| CLIC1 | CLIC2 | CLIC3 | CLIC4 | CLIC5 |
| CLIC6 | CLIP1 | CLIP2 | CLIP3 | CLIP4 |
| CLK1 | CLK2 | CLK3 | CLK4 | CLLU1 |
| CLLU1OS | CLMN | CLN3 | CLN5 | CLN6 |
| CLN8 | CLNS1A | CLOCK | CLP1 | CLPB |
| CLPP | CLPS | CLPTM1 | CLPTM1L | CLPX |
| CLRN1 | CLRN2 | CLRN3 | CLSPN | CLSTN1 |
| CLSTN2 | CLSTN3 | CLTA | CLTB | CLTC |
| CLTCL1 | CLU | CLUAP1 | CLUL1 | CLVS2 |
| CLYBL | CMA1 | CMAS | CMBL | CMC1 |
| CMKLR1 | CMPK1 | CMPK2 | CMTM1 | CMTM2 |
| CMTM3 | CMTM4 | CMTM5 | CMTM6 | CMTM7 |
| CMTM8 | CMYA5 | CNBP | CNDP1 | CNDP2 |
| CNFN | CNGA1 | CNGA2 | CNGA3 | CNGA4 |
| CNGB1 | CNGB3 | CNIH | CNIH2 | CNIH3 |
| CNIH4 | CNKSR1 | CNKSR2 | CNKSR3 | CNN1 |
| CNN2 | CNN3 | CNNM1 | CNNM2 | CNNM3 |
| CNNM4 | CNO | CNOT1 | CNOT10 | CNOT2 |
| CNOT3 | CNOT4 | CNOT6 | CNOT6L | CNOT7 |
| CNOT8 | CNP | CNPY1 | CNPY2 | CNPY3 |
| CNPY4 | CNR1 | CNR2 | CNRIP1 | CNST |
| CNTD1 | CNTD2 | CNTF | CNTFR | CNTLN |
| CNTN1 | CNTN2 | CNTN3 | CNTN4 | CNTN5 |
| CNTN6 | CNTNAP1 | CNTNAP2 | CNTNAP3 | CNTNAP4 |
| CNTNAP5 | CNTROB | COASY | COBL | COBLL1 |
| COBRA1 | COCH | COE4_HUMAN | COG1 | COG2 |
| COG3 | COG4 | COG5 | COG6 | COG7 |
| COG8 | COIL | COL10A1 | COL11A1 | COL11A2 |
| COL12A1 | COL13A1 | COL14A1 | COL15A1 | COL16A1 |
| COL17A1 | COL18A1 | COL19A1 | COL1A1 | COL1A2 |
| COL20A1 | COL22A1 | COL23A1 | COL24A1 | COL25A1 |
| COL27A1 | COL28A1 | COL2A1 | COL3A1 | COL4A1 |
| COL4A2 | COL4A3 | COL4A3BP | COL4A4 | COL4A5 |
| COL4A6 | COL5A1 | COL5A2 | COL5A3 | COL6A1 |
| COL6A2 | COL6A3 | COL6A6 | COL7A1 | COL8A1 |
| COL8A2 | COL9A1 | COL9A2 | COL9A3 | COLEC10 |
| COLEC11 | COLEC12 | COLQ | COMMD1 | COMMD10 |
| COMMD2 | COMMD3 | COMMD4 | COMMD5 | COMMD6 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| COMMD7 | COMMD8 | COMMD9 | COMP | COMT |
| COMTD1 | COPA | COPB1 | COPB2 | COPE |
| COPG | COPS2 | COPS3 | COPS4 | COPS5 |
| COPS6 | COPS7A | COPS7B | COPS8 | COPZ1 |
| COQ10A | COQ10B | COQ2 | COQ3 | COQ4 |
| COQ5 | COQ6 | COQ7 | COQ9 | CORIN |
| CORO1A | CORO1B | CORO1C | CORO2A | CORO2B |
| CORO6 | CORO7 | CORT | COTL1 | COX10 |
| COX11 | COX15 | COX16 | COX17 | COX18 |
| COX19 | COX4I1 | COX4I2 | COX4NB | COX5A |
| COX5B | COX6A1 | COX6A2 | COX6B1 | COX6B1_ENST00000392201 |
| COX6B2 | COX6BP3 | COX6C | COX7A1 | COX7A2 |
| COX7A2L | COX7AP2 | COX7B | COX7B2 | COX7C |
| COX8A | COX8C | CP | CP110 | CPA1 |
| CPA2 | CPA3 | CPA4 | CPA5 | CPA6 |
| CPAMD8 | CPB1 | CPB2 | CPD | CPE |
| CPEB1 | CPEB2 | CPEB3 | CPEB4 | CPLX2 |
| CPLX3 | CPLX4 | CPM | CPN1 | CPN2 |
| CPNE1 | CPNE2 | CPNE3 | CPNE4 | CPNE5 |
| CPNE6 | CPNE7 | CPNE8 | CPNE9 | CPO |
| CPOX | CPPED1 | CPS1 | CPSF1 | CPSF2 |
| CPSF3 | CPSF3L | CPSF4 | CPSF4L | CPSF6 |
| CPSF7 | CPT1A | CPT1B | CPT1C | CPT2 |
| CPVL | CPXCR1 | CPXM1 | CPXM2 | CPZ |
| CR1 | CR1L | CR2 | CRABP1 | CRABP2 |
| CRADD | CRAT | CRB1 | CRB2 | CRB3 |
| CRBN | CRCP | CRCT1 | CREB1 | CREB3 |
| CREB3L1 | CREB3L2 | CREB3L3 | CREB3L4 | CREB5 |
| CREBBP | CREBL2 | CREBZF | CREG1 | CREG2 |
| CRELD1 | CRELD2 | CREM | CREM_ENST00000395887 | CRH |
| CRHBP | CRHR1 | CRHR2 | CRIM1 | CRIP1 |
| CRIP2 | CRIP3 | CRIPAK | CRIPT | CRISP1 |
| CRISP2 | CRISP3 | CRISPLD1 | CRISPLD2 | CRK |
| CRKL | CRLF1 | CRLF2 | CRLF3 | CRLS1 |
| CRMP1 | CRNKL1 | CRNN | CROCC | CROT |
| CRP | CRSP3 | CRTAC1 | CRTAM | CRTAP |
| CRTC1 | CRTC2 | CRTC3 | CRX | CRY1 |
| CRY2 | CRYAA | CRYAB | CRYBA1 | CRYBA2 |
| CRYBA4 | CRYBB1 | CRYBB2 | CRYBB3 | CRYBG3 |
| CRYGA | CRYGB | CRYGC | CRYGD | CRYGN |
| CRYGS | CRYL1 | CRYM | CRYZ | CRYZL1 |
| CS | CSAD | CSAG1 | CSAG2 | CSAG3 |
| CSAG4 | CSDA | CSDC2 | CSDE1 | CSE1L |
| CSF1 | CSF1R | CSF2 | CSF2RA | CSF2RB |
| CSF3 | CSF3R | CSGALNACT1 | CSGALNACT2 | CSH1 |
| CSH2 | CSHL1 | CSK | CSMD1 | CSMD1_ENST00000318252 |
| CSMD2 | CSMD3 | CSN2 | CSN3 | CSNK1A1 |
| CSNK1A1L | CSNK1D | CSNK1E | CSNK1E_ENST00000403904 | CSNK1G1 |
| CSNK1G2 | CSNK1G3 | CSNK2A1 | CSNK2A2 | CSNK2B |
| CSPG4 | CSPG5 | CSPP1 | CSRNP1 | CSRNP2 |
| CSRNP3 | CSRP1 | CSRP2 | CSRP2BP | CSRP3 |
| CST1 | CST11 | CST2 | CST3 | CST4 |
| CST5 | CST6 | CST7 | CST8 | CST9 |
| CST9L | CSTA | CSTB | CSTF1 | CSTF2 |
| CSTF2T | CSTF3 | CSTL1 | CT45-1 | CT45A2 |
| CT45A3 | CT45A4 | CT45A5 | CT45A6 | CT47A1 |
| CT47A10 | CT47A11 | CT47A2 | CT47A3 | CT47A4 |
| CT47A5 | CT47A6 | CT47A7 | CT47A8 | CT47A9 |
| CTAG1A | CTAG1B | CTAG2 | CTAG2_ENST00000247306 | CTAGE5 |
| CTBP1 | CTBP2 | CTBS | CTCF | CTCFL |
| CTD-2267G17_3 | CTDP1 | CTDSP1 | CTDSP2 | CTDSPL |
| CTDSPL2 | CTF1 | CTGF | CTH | CTHRC1 |
| CTLA4 | CTNNA1 | CTNNA2 | CTNNA2_ENST00000466387 | CTNNA3 |
| CTNNAL1 | CTNNB1 | CTNNBIP1 | CTNNBL1 | CTNND1 |
| CTNND2 | CTNS | CTPS | CTPS2 | CTR9 |
| CTRB1 | CTRB2 | CTRC | CTRL | CTSA |
| CTSB | CTSC | CTSD | CTSE | CTSF |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| CTSG | CTSH | CTSK | CTSL1 | CTSL2 |
| CTSL3 | CTSO | CTSS | CTSW | CTSZ |
| CTTN | CTTNBP2 | CTTNBP2NL | CTU2 | CTXN1 |
| CTXN3 | CU041_HUMAN | CU085_HUMAN | CUBN | CUEDC1 |
| CUEDC2 | CUL1 | CUL2 | CUL3 | CUL4A |
| CUL4B | CUL4B_ENST00000371322 | CUL5 | CUL7 | CUL9 |
| CUTA | CUTC | CUX1 | CUX1_ENST00000292538 | CUX2 |
| CUZD1 | CWC22 | CWC27 | CWF19L1 | CWF19L2 |
| CWH43 | CX3CL1 | CX3CR1 | CXADR | CXCL1 |
| CXCL10 | CXCL11 | CXCL12 | CXCL13 | CXCL14 |
| CXCL16 | CXCL17 | CXCL2 | CXCL3 | CXCL5 |
| CXCL6 | CXCL9 | CXCR1 | CXCR2 | CXCR3 |
| CXCR4 | CXCR5 | CXCR6 | CXCR7 | CXXC1 |
| CXXC4 | CXXC5 | CXorf1 | CXorf15 | CXorf19 |
| CXorf21 | CXorf22 | CXorf23 | CXorf24 | CXorf25 |
| CXorf26 | CXorf27 | CXorf28 | CXorf29 | CXorf30 |
| CXorf31 | CXorf35 | CXorf36 | CXorf38 | CXorf40A |
| CXorf40B | CXorf41 | CXorf42 | CXorf48 | CXorf56 |
| CXorf57 | CXorf58 | CXorf59 | CXorf61 | CXorf62 |
| CXorf65 | CXorf66 | CXorf67 | CYB561 | CYB561D1 |
| CYB561D2 | CYB5A | CYB5B | CYB5D1 | CYB5D2 |
| CYB5R1 | CYB5R2 | CYB5R3 | CYB5R4 | CYBA |
| CYBASC3 | CYBB | CYBRD1 | CYC1 | CYCS |
| CYCSP52 | CYFIP1 | CYFIP2 | CYGB | CYHR1 |
| CYLC1 | CYLC2 | CYLD | CYP11A1 | CYP11B1 |
| CYP11B2 | CYP17A1 | CYP19A1 | CYP1A1 | CYP1A2 |
| CYP1B1 | CYP20A1 | CYP21A2 | CYP24A1 | CYP26A1 |
| CYP26B1 | CYP26C1 | CYP27A1 | CYP27B1 | CYP27C1 |
| CYP2A13 | CYP2A6 | CYP2A7 | CYP2B6 | CYP2B7P1 |
| CYP2C18 | CYP2C19 | CYP2C8 | CYP2C9 | CYP2D6 |
| CYP2E1 | CYP2F1 | CYP2J2 | CYP2R1 | CYP2S1 |
| CYP2U1 | CYP2W1 | CYP39A1 | CYP3A4 | CYP3A43 |
| CYP3A5 | CYP3A7 | CYP46A1 | CYP4A11 | CYP4A22 |
| CYP4B1 | CYP4F11 | CYP4F12 | CYP4F2 | CYP4F22 |
| CYP4F3 | CYP4F8 | CYP4V2 | CYP4X1 | CYP4Z1 |
| CYP51A1 | CYP7A1 | CYP7B1 | CYP8B1 | CYR61 |
| CYS1 | CYSLTR1 | CYSLTR2 | CYTH1 | CYTH2 |
| CYTH3 | CYTH4 | CYTIP | CYTL1 | CYTSA |
| CYTSB | CYYR1 | CYorf15B | CaMK1b | D2HGDH |
| D4S234E | DAAM1 | DAAM2 | DAB1 | DAB2 |
| DAB2IP | DACH1 | DACH2 | DACH2_ENST00000373131 | DACT1 |
| DACT2 | DAD1 | DAG1 | DAGLA | DAGLB |
| DAK | DALRD3 | DAMS_HUMAN | DAND5 | DAO |
| DAOA | DAP | DAP3 | DAPK1 | DAPK2 |
| DAPK3 | DAPL1 | DAPP1 | DARC | DARS |
| DARS2 | DAXX | DAZ2 | DAZ3 | DAZAP1 |
| DAZAP2 | DAZL | DBC1 | DBF4 | DBF4B |
| DBF4B_ENST00000315005 | DBH | DBI | DBN1 | DBNDD1 |
| DBNDD2 | DBNL | DBP | DBR1 | DBT |
| DBX1 | DBX2 | DCAF10 | DCAF12 | DCAF12L1 |
| DCAF12L2 | DCAF13 | DCAF15 | DCAF16 | DCAF17 |
| DCAF4 | DCAF4L1 | DCAF4L2 | DCAF5 | DCAF6 |
| DCAF7 | DCAF8 | DCAF8L1 | DCAF8L2 | DCAKD |
| DCBLD1 | DCBLD2 | DCC | DCD | DCDC1 |
| DCDC2 | DCDC5 | DCHS1 | DCHS2 | DCI |
| DCK | DCLK1 | DCLK2 | DCLK3 | DCLRE1A |
| DCLRE1B | DCLRE1C | DCLRE1C_ENST00000378278 | DCN | DCP1A |
| DCP1B | DCP2 | DCPS | DCST1 | DCST2 |
| DCT | DCTD | DCTN1 | DCTN3 | DCTN4 |
| DCTN5 | DCTN6 | DCTPP1 | DCUN1D1 | DCUN1D2 |
| DCUN1D3 | DCUN1D4 | DCUN1D5 | DCX | DCXR |
| DDA1 | DDAH1 | DDAH2 | DDB1 | DDB2 |
| DDC | DDHD1 | DDHD2 | DDI1 | DDI2 |
| DDIT3 | DDIT4 | DDIT4L | DDN | DDO |
| DDOST | DDR1 | DDR2 | DDRGK1 | DDT |
| DDTL | DDX1 | DDX10 | DDX11 | DDX12 |
| DDX12_ENST00000432996 | DDX17 | DDX18 | DDX19A | DDX19B |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| DDX20 | DDX21 | DDX23 | DDX24 | DDX25 |
| DDX26B | DDX27 | DDX28 | DDX31 | DDX39 |
| DDX3X | DDX3Y | DDX4 | DDX41 | DDX42 |
| DDX43 | DDX46 | DDX47 | DDX49 | DDX5 |
| DDX50 | DDX51 | DDX52 | DDX53 | DDX54 |
| DDX55 | DDX56 | DDX58 | DDX59 | DDX6 |
| DDX60 | DDX60L | DDX60_ENST00000393743 | DEAF1 | 01-Dec |
| DECR1 | DECR2 | DEDD | DEDD2 | DEF6 |
| DEF8 | DEFA1 | DEFA1B | DEFA3 | DEFA4 |
| DEFA5 | DEFA6 | DEFB1 | DEFB103A | DEFB103B |
| DEFB104A | DEFB104B | DEFB105A | DEFB105B | DEFB106A |
| DEFB106B | DEFB107A | DEFB107B | DEFB108B | DEFB110 |
| DEFB111 | DEFB112 | DEFB113 | DEFB114 | DEFB115 |
| DEFB116 | DEFB118 | DEFB119 | DEFB121 | DEFB123 |
| DEFB124 | DEFB125 | DEFB126 | DEFB127 | DEFB128 |
| DEFB129 | DEFB130 | DEFB131 | DEFB132 | DEFB134 |
| DEFB135 | DEFB136 | DEFB4A | DEGS1 | DEGS2 |
| DEK | DEM1 | DENND1A | DENND1B | DENND1C |
| DENND2A | DENND2C | DENND2D | DENND3 | DENND4A |
| DENND4B | DENND4C | DENND5A | DENND5B | DEPDC1 |
| DEPDC1B | DEPDC4 | DEPDC5 | DEPDC6 | DEPDC7 |
| DERL1 | DERL2 | DERL3 | DES | DET1 |
| DEXI | DFFA | DFFB | DFNA5 | DFNB31 |
| DFNB59 | DGAT1 | DGAT2 | DGAT2L6 | DGCR14 |
| DGCR2 | DGCR6 | DGCR6L | DGCR8 | DGKA |
| DGKB | DGKD | DGKE | DGKG | DGKH |
| DGKI | DGKK | DGKQ | DGKZ | DGUOK |
| DHCR24 | DHCR7 | DHDDS | DHDH | DHDPSL |
| DHFR | DHFRL1 | DHH | DHODH | DHPS |
| DHRS1 | DHRS11 | DHRS12 | DHRS13 | DHRS2 |
| DHRS3 | DHRS4 | DHRS4L2 | DHRS7 | DHRS7B |
| DHRS9 | DHRSX | DHTKD1 | DHX15 | DHX16 |
| DHX29 | DHX30 | DHX32 | DHX33 | DHX34 |
| DHX35 | DHX36 | DHX37 | DHX38 | DHX40 |
| DHX57 | DHX58 | DHX8 | DHX9 | DIABLO |
| DIAPH1 | DIAPH2 | DIAPH3 | DICER1 | DIDO1 |
| DIMT1L | DIO1 | DIO3 | DIP2B | DIP2C |
| DIRAS1 | DIRAS2 | DIRAS3 | DIRC1 | DIRC2 |
| DIS3 | DIS3L | DIS3L2 | DISC1 | DISP1 |
| DISP2 | DIXDC1 | DKC1 | DKFZP434P1750 | DKFZP564O0823 |
| DKFZP566M114 | DKK1 | DKK2 | DKK3 | DKK4 |
| DKKL1 | DLAT | DLC1 | DLC1_ENST00000316609 | DLD |
| DLEC1 | DLEU2L | DLG1 | DLG2 | DLG3 |
| DLG4_ENST00000293813 | DLG5 | DLGAP1 | DLGAP2 | DLGAP2_ENST00000356067 |
| DLGAP3 | DLGAP4 | DLGAP5 | DLK1 | DLK2 |
| DLL1 | DLL3 | DLL4 | DLST | DLX1 |
| DLX2 | DLX3 | DLX4 | DLX5 | DLX6 |
| DMAP1 | DMBT1 | DMBX1 | DMC1 | DMD |
| DMD_ENST00000378687 | DMGDH | DMKN | DMP1 | DMPK |
| DMRT1 | DMRT2 | DMRT2_ENST00000302441 | DMRT3 | DMRTA1 |
| DMRTB1 | DMRTC1 | DMRTC1B | DMRTC2 | DMTF1 |
| DMWD | DMXL1 | DMXL2 | DNA2L | DNAH1 |
| DNAH10 | DNAH10_same_name | DNAH11 | DNAH12L | DNAH14 |
| DNAH17 | DNAH1_ENST00000420323 | DNAH2 | DNAH3 | DNAH5 |
| DNAH6 | DNAH7 | DNAH8 | DNAH9 | DNAI1 |
| DNAI2 | DNAJA1 | DNAJA2 | DNAJA3 | DNAJA4 |
| DNAJB1 | DNAJB11 | DNAJB12 | DNAJB13 | DNAJB14 |
| DNAJB2 | DNAJB4 | DNAJB5 | DNAJB6 | DNAJB7 |
| DNAJB8 | DNAJB9 | DNAJC1 | DNAJC10 | DNAJC11 |
| DNAJC12 | DNAJC13 | DNAJC14 | DNAJC15 | DNAJC16 |
| DNAJC17 | DNAJC18 | DNAJC19 | DNAJC2 | DNAJC21 |
| DNAJC22 | DNAJC24 | DNAJC25 | DNAJC25-GNG10 | DNAJC27 |
| DNAJC28 | DNAJC3 | DNAJC30 | DNAJC4 | DNAJC5 |
| DNAJC5B | DNAJC5G | DNAJC6 | DNAJC7 | DNAJC8 |
| DNAJC9 | DNAL4 | DNALI1 | DNAPTP6 | DNASE1 |
| DNASE1L1 | DNASE1L2 | DNASE1L3 | DNASE2 | DNASE2B |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| DND1 | DNER | DNHD1_ ENST00000254579 | DNHL1 | DNLZ |
| DNM1 | DNM1L | DNM2 | DNM3 | DNMBP |
| DNMT1 | DNMT3A | DNMT3B | DNMT3L | DNPEP |
| DNTT | DNTTIP1 | DOC2A | DOCK1 | DOCK10 |
| DOCK10_ ENST00000373702 | DOCK11 | DOCK2 | DOCK3 | DOCK3_ ENST00000266037 |
| DOCK4 | DOCK5 | DOCK6 | DOCK7 | DOCK8 |
| DOCK9 | DOHH | DOK1 | DOK2 | DOK3 |
| DOK4 | DOK5 | DOK6 | DOK7 | DOLK |
| DOLPP1 | DOM3Z | DONSON | DOPEY1 | DOPEY2 |
| DOT1L | DPAGT1 | DPCR1 | DPEP1 | DPEP2 |
| DPEP3 | DPF1 | DPF2 | DPH1 | DPH1-OVCA2 |
| DPH2 | DPH3 | DPH3B | DPH5 | DPM1 |
| DPM2 | DPM3 | DPP10 | DPP3 | DPP4 |
| DPP6 | DPP7 | DPP8 | DPP9 | DPPA2 |
| DPPA3 | DPPA4 | DPPA5 | DPRX | DPT |
| DPY19L1 | DPY19L2 | DPY19L3 | DPY19L4 | DPY30 |
| DPYD | DPYS | DPYSL2 | DPYSL3 | DPYSL4 |
| DPYSL5 | DQX1 | DR1 | DRAM1 | DRAM2 |
| DRAP1 | DRD1 | DRD2 | DRD3 | DRD4 |
| DRD5 | DRD5P1 | DRG1 | DRG2 | DRP2 |
| DSC1 | DSC2 | DSC3 | DSCAM | DSCAML1 |
| DSCC1 | DSCR3 | DSCR4 | DSCR6 | DSE |
| DSEL | DSG1 | DSG2 | DSG3 | DSG4 |
| DSN1 | DSP | DSPP | DST | DSTN |
| DSTYK | DST_ ENST00000370754 | DST_ ENST00000370769 | DTD1 | DTHD1 |
| DTL | DTNA | DTNB | DTNBP1 | DTWD1 |
| DTWD2 | DTX1 | DTX2 | DTX3 | DTX3L |
| DTX4 | DTYMK | DULLARD | DUOX1 | DUOX2 |
| DUOXA1 | DUOXA2 | DUPD1 | DUS1L | DUS2L |
| DUS3L | DUS4L | DUSP1 | DUSP10 | DUSP11 |
| DUSP12 | DUSP13 | DUSP13_ ENST00000356369 | DUSP14 | DUSP15 |
| DUSP16 | DUSP18 | DUSP19 | DUSP2 | DUSP21 |
| DUSP22 | DUSP23 | DUSP26 | DUSP27 | DUSP28 |
| DUSP3 | DUSP4 | DUSP5 | DUSP5P | DUSP6 |
| DUSP7 | DUSP8 | DUSP9 | DUT | DUXA |
| DVL1 | DVL2 | DVL3 | DYDC1 | DYDC2 |
| DYM | DYNC1H1 | DYNC1I1 | DYNC1I2 | DYNC1LI1 |
| DYNC1LI2 | DYNC2H1 | DYNC2H1_ ENST00000398093 | DYNC2LI1 | DYNLL1 |
| DYNLL2 | DYNLRB1 | DYNLRB2 | DYNLT1 | DYNLT3 |
| DYRK1A | DYRK1B | DYRK2 | DYRK3 | DYRK4 |
| DYSF | DYSFIP1 | DYX1C1 | DZIP1 | DZIP1L |
| DZIP3 | E2F1 | E2F2 | E2F3 | E2F4 |
| E2F5 | E2F6 | E2F7 | E2F8 | E4F1 |
| EAF1 | EAF2 | EAPP | EARS2 | EBAG9 |
| EBF1 | EBF3 | EBI3 | EBNA1BP2 | EBP |
| EBPL | ECD | ECE1 | ECE2 | ECEL1 |
| ECH1 | ECHDC1 | ECHDC2 | ECHDC3 | ECHS1 |
| ECM1 | ECM2 | ECOP | ECSIT | ECT2 |
| ECT2L | EDA | EDA2R | EDAR | EDARADD |
| EDC3 | EDC4 | EDDM3A | EDDM3B | EDEM1 |
| EDEM2 | EDEM3 | EDF1 | EDG6 | EDIL3 |
| EDN1 | EDN2 | EDN3 | EDNRA | EDNRB |
| EEA1 | EED | EEF1A1 | EEF1A1P11 | EEF1A2 |
| EEF1B2 | EEF1D | EEF1E1 | EEF2 | EEF2K |
| EEFSEC | EEPD1 | EFCAB1 | EFCAB2 | EFCAB3 |
| EFCAB4A | EFCAB4B | EFCAB5 | EFCAB6 | EFCAB7 |
| EFEMP1 | EFEMP2 | EFHA1 | EFHA2 | EFHB |
| EFHC1 | EFHC2 | EFHD1 | EFHD2 | EFNA1 |
| EFNA2 | EFNA3 | EFNA4 | EFNA5 | EFNB1 |
| EFNB2 | EFNB3 | EFR3A | EFS | EFTUD1 |
| EFTUD2 | EGF | EGFL4 | EGFL6 | EGFL7 |
| EGFL8 | EGFLAM | EGFR | EGFR_ ENST00000344576 | EGLN1 |
| EGLN2 | EGLN3 | EGR1 | EGR2 | EGR3 |
| EGR4 | EHBP1 | EHBP1L1 | EHD1 | EHD2 |
| EHD3 | EHD4 | EHF | EHHADH | EHMT1 |
| EHMT2 | EI24 | EID1 | EID2 | EID2B |
| EIF1 | EIF1AD | EIF1AX | EIF1AY | EIF1B |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| EIF2A | EIF2AK1 | EIF2AK2 | EIF2AK3 | EIF2AK4 |
| EIF2A_ ENST00000487799 | EIF2B1 | EIF2B2 | EIF2B3 | EIF2B4 |
| EIF2B5 | EIF2C1 | EIF2C2 | EIF2C3 | EIF2C4 |
| EIF2S1 | EIF2S2 | EIF2S3 | EIF3A | EIF3B |
| EIF3C | EIF3CL | EIF3D | EIF3E | EIF3EIP |
| EIF3F | EIF3G | EIF3H | EIF3I | EIF3J |
| EIF3K | EIF3M | EIF3S8 | EIF4A1 | EIF4A2 |
| EIF4A3 | EIF4B | EIF4E | EIF4E2 | EIF4E3 |
| EIF4EBP1 | EIF4EBP2 | EIF4EBP3 | EIF4ENIF1 | EIF4G1 |
| EIF4G2 | EIF4G3 | EIF4H | EIF5 | EIF5A |
| EIF5A2 | EIF5B | EIF6 | ELAC1 | ELAC2 |
| ELANE | ELAVL1 | ELAVL2 | ELAVL3 | ELAVL4 |
| ELF1 | ELF2 | ELF3 | ELF4 | ELF5 |
| ELFN2 | ELK1 | ELK3 | ELK4 | ELL |
| ELL2 | ELL3 | ELMO1 | ELMO2 | ELMO3 |
| ELMOD2 | ELMOD3 | ELN | ELOF1 | ELOVL1 |
| ELOVL2 | ELOVL3 | ELOVL4 | ELOVL5 | ELOVL6 |
| ELOVL7 | ELP2 | ELP3 | ELP4 | ELSPBP1 |
| ELTD1 | EMB | EMCN | EMD | EME1 |
| EME2 | EMID1 | EMID2 | EMILIN1 | EMILIN2 |
| EMILIN3 | EML1 | EML2 | EML3 | EML4 |
| EML5 | EMP1 | EMP2 | EMP3 | EMR1 |
| EMR2 | EMR3 | EMR4 | EMX1 | EMX2 |
| EN1 | EN2 | ENAH | ENAM | ENC1 |
| ENDOD1 | ENDOG | ENDOU | ENG | ENGASE |
| ENHO | ENKUR | ENO1 | ENO2 | ENO3 |
| ENO4 | ENOPH1 | ENOSF1 | ENOX1 | ENOX2 |
| ENPEP | ENPP1 | ENPP2 | ENPP3 | ENPP4 |
| ENPP5 | ENPP6 | ENPP7 | ENSA | ENSG00000038102 |
| ENSG00000064489 | ENSG00000068650 | ENSG00000101152 | ENSG00000102445 | ENSG00000104880 |
| ENSG00000106232 | ENSG00000107816 | ENSG00000115339 | ENSG00000117540 | ENSG00000118519 |
| ENSG00000118928 | ENSG00000123257 | ENSG00000124224 | ENSG00000124677 | ENSG00000124854 |
| ENSG00000124915 | ENSG00000125631 | ENSG00000125822 | ENSG00000125881 | ENSG00000125964 |
| ENSG00000126002 | ENSG00000126217 | ENSG00000128422 | ENSG00000128563 | ENSG00000129973 |
| ENSG00000130225 | ENSG00000130241 | ENSG00000131484 | ENSG00000135213 | ENSG00000135702 |
| ENSG00000135749 | ENSG00000137021 | ENSG00000137746 | ENSG00000139239 | ENSG00000140209 |
| ENSG00000142832 | ENSG00000142951 | ENSG00000143910 | ENSG00000144396 | ENSG00000145642 |
| ENSG00000146736 | ENSG00000147113 | ENSG00000148667 | ENSG00000148713 | ENSG00000148805 |
| ENSG00000149618 | ENSG00000149658 | ENSG00000150980 | ENSG00000153081 | ENSG00000154732 |
| ENSG00000156367 | ENSG00000156509 | ENSG00000157819 | ENSG00000157999 | ENSG00000158185 |
| ENSG00000158301 | ENSG00000158403 | ENSG00000159239 | ENSG00000161643 | ENSG00000162568 |
| ENSG00000162621 | ENSG00000162644 | ENSG00000162734 | ENSG00000162767 | ENSG00000162872 |
| ENSG00000163144 | ENSG00000163182 | ENSG00000163612 | ENSG00000164159 | ENSG00000164236 |
| ENSG00000164241 | ENSG00000164500 | ENSG00000164845 | ENSG00000164860 | ENSG00000164946 |
| ENSG00000165114 | ENSG00000165124 | ENSG00000165429 | ENSG00000165851 | ENSG00000165935 |
| ENSG00000166013 | ENSG00000166329 | ENSG00000166492 | ENSG00000166593 | ENSG00000166707 |
| ENSG00000167281 | ENSG00000167390 | ENSG00000167433 | ENSG00000167442 | ENSG00000167475 |
| ENSG00000168038 | ENSG00000168113 | ENSG00000168561 | ENSG00000169664 | ENSG00000169697 |
| ENSG00000170238 | ENSG00000170817 | ENSG00000170987 | ENSG00000171084 | ENSG00000171459 |
| ENSG00000171841 | ENSG00000171878 | ENSG00000171995 | ENSG00000172070 | ENSG00000172212 |
| ENSG00000172261 | ENSG00000172764 | ENSG00000172786 | ENSG00000172823 | ENSG00000172895 |
| ENSG00000172899 | ENSG00000172900 | ENSG00000172963 | ENSG00000173115 | ENSG00000173213 |
| ENSG00000173609 | ENSG00000173671 | ENSG00000173679 | ENSG00000173774 | ENSG00000173780 |
| ENSG00000173820 | ENSG00000173863 | ENSG00000173961 | ENSG00000173968 | ENSG00000174028 |
| ENSG00000174057 | ENSG00000174104 | ENSG00000174121 | ENSG00000174126 | ENSG00000174144 |
| ENSG00000174398 | ENSG00000174440 | ENSG00000174459 | ENSG00000174483 | ENSG00000174658 |
| ENSG00000174681 | ENSG00000174880 | ENSG00000175117 | ENSG00000175143 | ENSG00000175267 |
| ENSG00000175822 | ENSG00000175856 | ENSG00000176050 | ENSG00000176207 | ENSG00000176220 |
| ENSG00000176757 | ENSG00000176819 | ENSG00000176900 | ENSG00000176937 | ENSG00000176951 |
| ENSG00000176960 | ENSG00000177111 | ENSG00000177634 | ENSG00000177835 | ENSG00000177858 |
| ENSG00000177863 | ENSG00000178006 | ENSG00000178225 | ENSG00000178322 | ENSG00000178510 |
| ENSG00000178546 | ENSG00000178585 | ENSG00000179294 | ENSG00000179312 | ENSG00000179326 |
| ENSG00000179360 | ENSG00000179574 | ENSG00000179702 | ENSG00000179755 | ENSG00000179824 |
| ENSG00000179851 | ENSG00000180150 | ENSG00000180494 | ENSG00000180518 | ENSG00000180519 |
| ENSG00000180649 | ENSG00000180715 | ENSG00000180882 | ENSG00000181437 | ENSG00000181669 |
| ENSG00000181882 | ENSG00000181922 | ENSG00000182053 | ENSG00000182065 | ENSG00000182150 |
| ENSG00000182553 | ENSG00000182625 | ENSG00000182729 | ENSG00000182933 | ENSG00000182957 |
| ENSG00000183000 | ENSG00000183059 | ENSG00000183096 | ENSG00000183122 | ENSG00000183144 |
| ENSG00000183190 | ENSG00000183239 | ENSG00000183317 | ENSG00000183355 | ENSG00000183397 |
| ENSG00000183405 | ENSG00000183445 | ENSG00000183455 | ENSG00000183514 | ENSG00000183627 |
| ENSG00000183817 | ENSG00000183851 | ENSG00000183920 | ENSG00000183981 | ENSG00000183983 |
| ENSG00000184008 | ENSG00000184064 | ENSG00000184100 | ENSG00000184263 | ENSG00000184352 |
| ENSG00000184353 | ENSG00000184391 | ENSG00000184490 | ENSG00000184493 | ENSG00000184521 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ENSG00000184543 | ENSG00000184653 | ENSG00000184673 | ENSG00000184844 | ENSG00000184888 |
| ENSG00000184902 | ENSG00000185034 | ENSG00000185055 | ENSG00000185082 | ENSG00000185095 |
| ENSG00000185319 | ENSG00000185448 | ENSG00000185467 | ENSG00000185636 | ENSG00000185641 |
| ENSG00000185685 | ENSG00000185758 | ENSG00000185834 | ENSG00000185863 | ENSG00000185929 |
| ENSG00000185945 | ENSG00000185956 | ENSG00000186218 | ENSG00000186259 | ENSG00000186381 |
| ENSG00000186400 | ENSG00000186414 | ENSG00000186483 | ENSG00000186659 | ENSG00000186663 |
| ENSG00000186709 | ENSG00000186728 | ENSG00000186743 | ENSG00000186756 | ENSG00000186773 |
| ENSG00000186787 | ENSG00000187042 | ENSG00000187072 | ENSG00000187080 | ENSG00000187522 |
| ENSG00000187534 | ENSG00000187544 | ENSG00000187600 | ENSG00000187615 | ENSG00000187653 |
| ENSG00000187661 | ENSG00000187686 | ENSG00000187791 | ENSG00000187809 | ENSG00000187828 |
| ENSG00000187851 | ENSG00000187900 | ENSG00000187938 | ENSG00000187963 | ENSG00000187988 |
| ENSG00000187999 | ENSG00000188013 | ENSG00000188023 | ENSG00000188031 | ENSG00000188075 |
| ENSG00000188082 | ENSG00000188144 | ENSG00000188292 | ENSG00000188405 | ENSG00000188423 |
| ENSG00000188438 | ENSG00000188447 | ENSG00000188463 | ENSG00000188469 | ENSG00000188604 |
| ENSG00000188668 | ENSG00000188683 | ENSG00000188796 | ENSG00000188831 | ENSG00000188841 |
| ENSG00000188873 | ENSG00000188890 | ENSG00000188912 | ENSG00000188926 | ENSG00000188974 |
| ENSG00000188985 | ENSG00000188989 | ENSG00000189118 | ENSG00000189119 | ENSG00000189128 |
| ENSG00000189244 | ENSG00000189258 | ENSG00000189279 | ENSG00000189290 | ENSG00000189311 |
| ENSG00000189378 | ENSG00000189384 | ENSG00000196076 | ENSG00000196094 | ENSG00000196115 |
| ENSG00000196121 | ENSG00000196183 | ENSG00000196230 | ENSG00000196285 | ENSG00000196292 |
| ENSG00000196306 | ENSG00000196454 | ENSG00000196527 | ENSG00000196681 | ENSG00000196690 |
| ENSG00000196926 | ENSG00000196930 | ENSG00000196940 | ENSG00000196960 | ENSG00000197023 |
| ENSG00000197049 | ENSG00000197149 | ENSG00000197185 | ENSG00000197218 | ENSG00000197246 |
| ENSG00000197320 | ENSG00000197335 | ENSG00000197369 | ENSG00000197407 | ENSG00000197438 |
| ENSG00000197450 | ENSG00000197475 | ENSG00000197481 | ENSG00000197490 | ENSG00000197526 |
| ENSG00000197575 | ENSG00000197585 | ENSG00000197608 | ENSG00000197630 | ENSG00000197680 |
| ENSG00000197799 | ENSG00000197825 | ENSG00000197865 | ENSG00000197883 | ENSG00000198059 |
| ENSG00000198079 | ENSG00000198107 | ENSG00000198154 | ENSG00000198179 | ENSG00000198229 |
| ENSG00000198273 | ENSG00000198322 | ENSG00000198326 | ENSG00000198475 | ENSG00000198544 |
| ENSG00000198615 | ENSG00000198649 | ENSG00000198684 | ENSG00000198694 |  |
| ENSG00000198706 | ENSG00000198725 | ENSG00000198726 | ENSG00000198731 | ENSG00000198760 |
| ENSG00000198778 | ENSG00000198789 | ENSG00000198801 | ENSG00000198810 | ENSG00000198902 |
| ENSG00000198921 | ENSG00000198957 | ENSG00000198965 | ENTHD1 | ENTPD1 |
| ENTPD2 | ENTPD3 | ENTPD4 | ENTPD5 | ENTPD6 |
| ENTPD7 | ENTPD8 | ENY2 | EOMES | EP300 |
| EP400 | EPAS1 | EPB41 | EPB41L1 | EPB41L2 |
| EPB41L3 | EPB41L4A | EPB41L4B | EPB41L5 | EPB42 |
| EPB49 | EPC1 | EPC2 | EPCAM | EPDR1 |
| EPGN | EPHA1 | EPHA10 | EPHA2 | EPHA3 |
| EPHA4 | EPHA5 | EPHA6 | EPHA7 | EPHA8 |
| EPHB1 | EPHB1_ENST00000398015 | EPHB2 | EPHB3 | EPHB4 |
| EPHB6 | EPHX1 | EPHX2 | EPHX3 | EPHX4 |
| EPM2A | EPN2 | EPN3 | EPO | EPOR |
| EPRS | EPS15 | EPS15L1 | EPS8 | EPS8L1 |
| EPS8L2 | EPS8L3 | EPSTI1 | EPX | EPYC |
| ERAL1 | ERAP1 | ERAP2 | ERAS | ERBB2 |
| ERBB2IP | ERBB3 | ERBB3_ENST00000267101 | ERBB4 | ERC1 |
| ERCC1 | ERCC2 | ERCC3 | ERCC4 | ERCC5 |
| ERCC6 | ERCC6L | ERCC8 | EREG | ERF |
| ERG | ERGIC1 | ERGIC2 | ERGIC3 | ERH |
| ERI1 | ERI2 | ERI3 | ERICH1 | ERLEC1 |
| ERLIN2 | ERMAP | ERMN | ERMP1 | ERN1 |
| ERN2 | ERO1L | ERO1LB | ERP27 | ERP29 |
| ERP44 | ERRFI1 | ERVFC1 | ERVWE1 | ESAM |
| ESCO1 | ESCO2 | ESD | ESF1 | ESM1 |
| ESPL1 | ESPN | ESPNL | ESR1 | ESR2 |
| ESRP1 | ESRP2 | ESRRA | ESRRB | ESRRG |
| ESSPL | ESX1 | ESYT1 | ESYT2 | ESYT3 |
| ETAA1 | ETF1 | ETFA | ETFB | ETFDH |
| ETHE1 | ETNK1 | ETNK2 | ETS1 | ETS2 |
| ETV1 | ETV2 | ETV3 | ETV3L | ETV4 |
| ETV5 | ETV6 | ETV7 | EVC | EVC2 |
| EVI2A | EVI2B | EVI5 | EVI5L | EVL |
| EVPL | EVX1 | EVX2 | EWSR1 | EXD1 |
| EXD3 | EXDL2 | EXO1 | EXOC1 | EXOC2 |
| EXOC3 | EXOC3L | EXOC3L2 | EXOC4 | EXOC5 |
| EXOC6 | EXOC6B | EXOC7 | EXOC8 | EXOG |
| EXOSC1 | EXOSC10 | EXOSC2 | EXOSC3 | EXOSC4 |
| EXOSC5 | EXOSC6 | EXOSC7 | EXOSC8 | EXOSC9 |
| EXPH5 | EXT1 | EXT2 | EXTL1 | EXTL2 |
| EXTL3 | EYA1 | EYA2 | EYAS | EYA4 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| EYS | EZH1 | EZH2 | EZH2_ENST00000350995 | EZR |
| F10 | F11 | F11R | F12 | F13A1 |
| F13B | F2 | F2R | F2RL1 | F2RL2 |
| F2RL3 | F3 | F5 | F7 | F8 |
| F8A1 | F8A2 | F8A3 | F8_ENST000000360256 | F9 |
| FA2H | FA87B_HUMAN | FAAH | FAAH2 | FABP1 |
| FABP12 | FABP2 | FABP3 | FABP4 | FABP5 |
| FABP6 | FABP7 | FABP9 | FABPE_HUMAN | FADD |
| FADS1 | FADS2 | FADS3 | FADS6 | FAF1 |
| FAF2 | FAH | FAHD1 | FAHD2A | FAHD2B |
| FAIM | FAIM2 | FAIM3 | FAM100A | FAM100B |
| FAM101A | FAM102A | FAM102B | FAM103A1 | FAM104B |
| FAM105A | FAM105B | FAM107A | FAM107B | FAM108A1 |
| FAM108A3 | FAM108B1 | FAM109A | FAM109B | FAM110A |
| FAM110B | FAM110C | FAM111A | FAM111B | FAM113A |
| FAM113B | FAM114A1 | FAM114A2 | FAM115A | FAM115C |
| FAM116A | FAM117A | FAM117B | FAM118A | FAM118B |
| FAM119A | FAM119B | FAM120A | FAM120AOS | FAM120B |
| FAM120C | FAM122A | FAM122B | FAM122C | FAM123A |
| FAM123B | FAM123C | FAM124A | FAM124B | FAM125A |
| FAM125B | FAM126A | FAM126B | FAM127A | FAM127B |
| FAM127C | FAM128A | FAM128B | FAM129A | FAM129B |
| FAM129C | FAM131A | FAM131B | FAM131C | FAM132A |
| FAM133A | FAM134A | FAM134B | FAM134C | FAM135A |
| FAM135B | FAM136A | FAM13A1 | FAM13C | FAM149A |
| FAM150A | FAM151A | FAM151B | FAM153A | FAM153B |
| FAM153C | FAM154A | FAM154B | FAM155A | FAM155B |
| FAM156A | FAM156B | FAM158A | FAM159A | FAM160A2 |
| FAM160B1 | FAM161A | FAM161B | FAM162A | FAM162B |
| FAM163A | FAM163B | FAM164A | FAM164C | FAM165B |
| FAM166A | FAM167B | FAM168A | FAM168B | FAM169A |
| FAM170A | FAM171A1 | FAM171B | FAM172A | FAM173A |
| FAM173B | FAM174A | FAM174B | FAM175A | FAM175B |
| FAM176A | FAM176B | FAM177A1 | FAM177B | FAM178B |
| FAM179A | FAM179B | FAM180A | FAM181A | FAM181B |
| FAM184A | FAM184B | FAM186A | FAM186B | FAM187B |
| FAM188A | FAM188B | FAM189A1 | FAM189A2 | FAM189B |
| FAM18B | FAM18B2 | FAM190A | FAM190B | FAM192A |
| FAM193A | FAM194A | FAM194B | FAM195A | FAM196A |
| FAM198A | FAM198B | FAM199X | FAM19A2 | FAM19A3 |
| FAM19A4 | FAM19A5 | FAM200A | FAM20A | FAM20B |
| FAM21A | FAM21C | FAM22A | FAM22D | FAM22F |
| FAM22G | FAM23A | FAM23B | FAM24A | FAM24B |
| FAM26A | FAM26D | FAM26E | FAM26F | FAM32A |
| FAM33A | FAM35A | FAM36A | FAM38B | FAM39B |
| FAM3A | FAM3B | FAM3C | FAM3D | FAM40A |
| FAM40B | FAM43A | FAM43B | FAM45A | FAM45B |
| FAM46A | FAM46B | FAM46C | FAM46D | FAM47A |
| FAM47B | FAM47C | FAM48A | FAM48B1 | FAM48B2 |
| FAM49A | FAM49B | FAM50A | FAM50B | FAM53A |
| FAM53B | FAM53C | FAM54A | FAM54B | FAM55A |
| FAM55C | FAM55D | FAM57A | FAM57B | FAM58A |
| FAM58B | FAM59A | FAM5B | FAM5C | FAM60A |
| FAM63A | FAM63B | FAM64A | FAM65A | FAM65B |
| FAM65C | FAM69B | FAM69C | FAM70A | FAM70B |
| FAM71A | FAM71B | FAM71C | FAM71E1 | FAM71F1 |
| FAM72A | FAM72B | FAM73A | FAM73B | FAM74A3 |
| FAM75A1 | FAM75A2 | FAM75A6 | FAM75A7 | FAM76A |
| FAM76B | FAM78A | FAM78B | FAM81A | FAM81B |
| FAM82A1 | FAM82A2 | FAM82B | FAM83A | FAM83B |
| FAM83C | FAM83D | FAM83E | FAM83F | FAM83G |
| FAM83H | FAM84A | FAM84B | FAM86A | FAM86C |
| FAM87B | FAM89A | FAM89B | FAM8A1 | FAM90A1 |
| FAM90A20 | FAM91A1 | FAM92B | FAM96A | FAM98A |
| FAM98B | FAM98C | FAM9A | FAM9B | FAM9C |
| FANCA | FANCB | FANCC | FANCD2 | FANCE |
| FANCF | FANCG | FANCI | FANCL | FANCM |
| FANK1 | FAP | FAR1 | FAR2 | FARP1 |
| FARP2 | FARS2 | FARSA | FARSB | FAS |
| FASLG | FASN | FASTK | FASTKD1 | FASTKD2 |
| FASTKD3 | FASTKD5 | FAT | FAT1 | FAT2 |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

Figure 4:
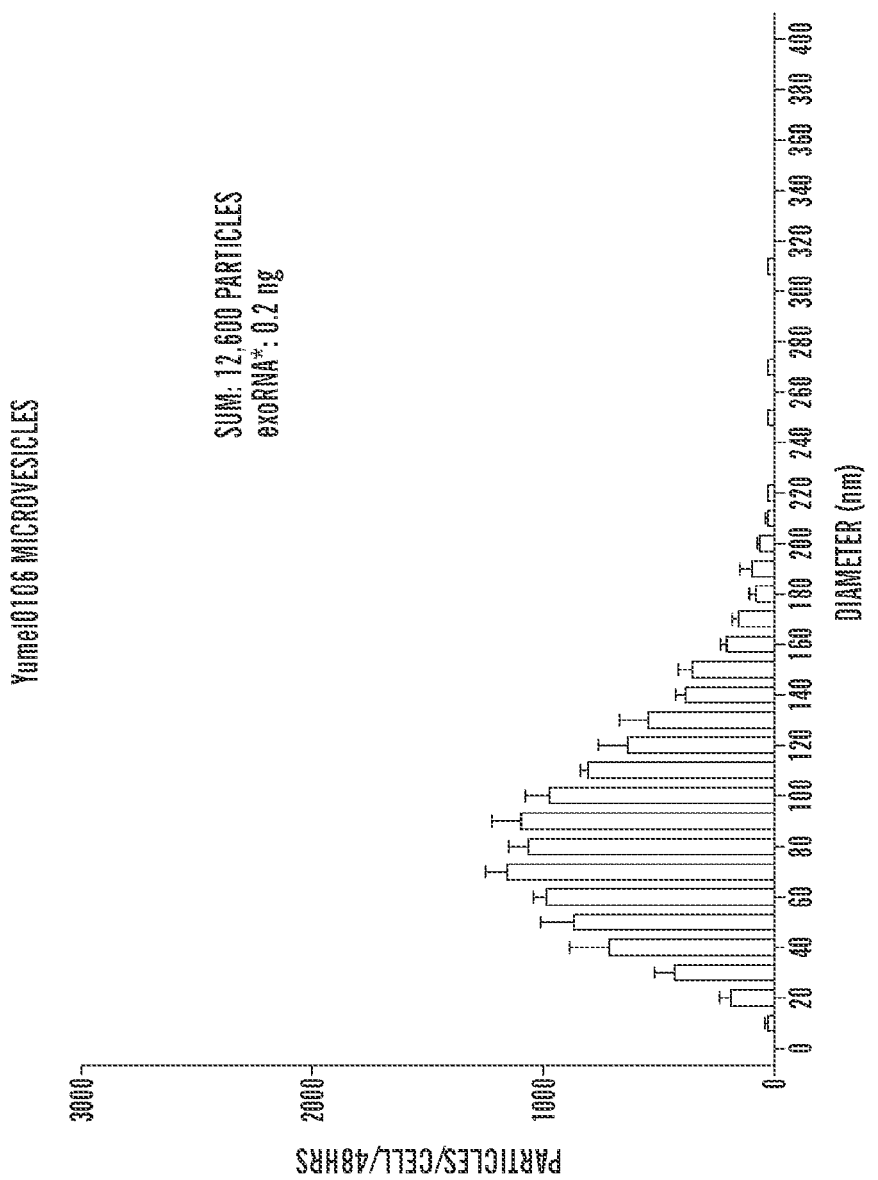
FIG. 4 shows a graph depicting the quantification, size distribution and RNA yield of microvesicles purified from the melanoma cell line Yumel 0106 in the same manner as in FIG. 1.

| HGNC Gene Name | HGNC Gene Name | HGNC Gene Name | HGNC Gene Name | HGNC Gene Name |
|---|---|---|---|---|
| FAT3 | FAT4 | FAT4_ENST00000394329 | FATE1 | FAU |
| FBF1 | FBL | FBLIM1 | FBLN1 | FBLN2 |
| FBLN2_ENST00000492059 | FBLN5 | FBLN7 | FBN1 | FBN2 |
| FBN3 | FBP1 | FBP2 | FBRSL1 | FBXL12 |
| FBXL13 | FBXL14 | FBXL15 | FBXL16 | FBXL17 |
| FBXL18 | FBXL19 | FBXL2 | FBXL20 | FBXL21 |
| FBXL21_ENST00000297158 | FBXL22 | FBXL3 | FBXL4 | FBXL5 |
| FBXL6 | FBXL7 | FBXL8 | FBXO10 | FBXO11 |
| FBXO15 | FBXO16 | FBXO17 | FBXO18 | FBXO2 |
| FBXO21 | FBXO22 | FBXO24 | FBXO25 | FBXO27 |
| FBXO28 | FBXO3 | FBXO30 | FBXO31 | FBXO32 |
| FBXO33 | FBXO34 | FBXO36 | FBXO38 | FBXO39 |
| FBXO4 | FBXO40 | FBXO41 | FBXO42 | FBXO43 |
| FBXO44 | FBXO45 | FBXO46 | FBXO47 | FBXO48 |
| FBXO5 | FBXO6 | FBXO7 | FBXO8 | FBXO9 |
| FBXW10 | FBXW11 | FBXW12 | FBXW2 | FBXW4 |
| FBXW5 | FBXW7 | FBXW7_NM_018315_2 | FBXW8 | FBXW9 |
| FCAMR | FCAR | FCER1A | FCER1G | FCER2 |
| FCF1 | FCGBP | FCGR1A | FCGR1B | FCGR2A |
| FCGR2B | FCGR3A | FCGR3B | FCGRT | FCHO1 |
| FCHSD1 | FCHSD2 | FCN1 | FCN2 | FCN3 |
| FCRL1 | FCRL2 | FCRL3 | FCRL4 | FCRL5 |
| FCRL6 | FCRLA | FCRLB | FDFT1 | FDPS |
| FDX1 | FDX1L | FDXR | FECH | FEM1A |
| FEM1B | FEM1C | FEN1 | FER | FER1L6 |
| FERD3L | FERMT1 | FERMT2 | FERMT3 | FES |
| FETUB | FEV | FEZ1 | FEZF1 | FEZF2 |
| FFAR1 | FFAR2 | FFAR3 | FGA | FGB |
| FGD1 | FGD2 | FGD3 | FGD4 | FGD5 |
| FGD6 | FGF1 | FGF10 | FGF11 | FGF12 |
| FGF13 | FGF14 | FGF16 | FGF17 | FGF18 |
| FGF19 | FGF2 | FGF20 | FGF21 | FGF22 |
| FGF23 | FGF3 | FGF4 | FGF5 | FGF6 |
| FGF7 | FGF7P2 | FGF8 | FGF9 | FGFBP1 |
| FGFBP2 | FGFBP3 | FGFR1 | FGFR1OP | FGFR1OP2 |
| FGFR1_ENST00000425967 | FGFR2 | FGFR3 | FGFR4 | FGFR4_ENST00000292408 |
| FGFRL1 | FGG | FGGY | FGL1 | FGL2 |
| FGR | FH | FHAD1 | FHDC1 | FHIT |
| FHL1 | FHL2 | FHL3 | FHL5 | FHOD1 |
| FHOD3 | FIBCD1 | FIBIN | FIBP | FICD |
| FIG4 | FIGF | FIGN | FIGNL1 | FILIP1 |
| FILIP1L | FIP1L1 | FIS1 | FITM1 | FITM2 |
| FIZ1 | FKBP10 | FKBP11 | FKBP14 | FKBP1A |
| FKBP1B | FKBP1C | FKBP2 | FKBP3 | FKBP4 |
| FKBP5 | FKBP6 | FKBP7 | FKBP8 | FKBP9 |
| FKBP9L | FKBPL | FKRP | FKTN | FLAD1 |
| FLCN | FLG | FLG2 | FLI1 | FLII |
| FLJ10357 | FLJ10404 | FLJ10490 | FLJ13236 | FLJ13855 |
| FLJ14075 | FLJ14627 | FLJ14775 | FLJ16165 | FLJ16171 |
| FLJ16331 | FLJ16360 | FLJ16369 | FLJ16542 | FLJ20184 |
| FLJ20273 | FLJ20366 | FLJ20584 | FLJ23356 | FLJ23584 |
| FLJ25006 | FLJ25917 | FLJ31132 | FLJ34521 | FLJ35880 |
| FLJ38348 | FLJ38451 | FLJ38576 | FLJ39257 | FLJ39369 |
| FLJ41131 | FLJ41603 | FLJ42177 | FLJ42418 | FLJ42957 |
| FLJ43374 | FLJ43806 | FLJ43980 | FLJ44048 | FLJ44060 |
| FLJ44216 | FLJ44635 | FLJ44817 | FLJ44874 | FLJ45224 |
| FLJ45422 | FLJ45455 | FLJ45831 | FLJ45910 | FLJ45983 |
| FLJ46321 | FLJ90650 | FLNA | FLNB | FLNC |
| FLOT1 | FLOT2 | FLRT1 | FLRT2 | FLRT3 |
| FLT1 | FLT3 | FLT3LG | FLT4 | FLT4_ENST00000261937 |
| FLVCR1 | FLVCR2 | FLYWCH1 | FLYWCH2 | FMN2 |
| FMNL1 | FMNL2 | FMNL3 | FMO1 | FMO2 |
| FMO3 | FMO4 | FMO5 | FMO6P | FMOD |
| FMR1 | FMR1NB | FN1 | FN3K | FN3KRP |
| FNBP1L | FNBP1_ENST00000372416 | FNBP4 | FNDC1 | FNDC3A |
| FNDC3B | FNDC4 | FNDC5 | FNDC7 | FNDC8 |
| FNIP1 | FNIP2 | FNTA | FNTB | FOLH1 |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| FOLH1B | FOLR1 | FOLR2 | FOS | FOSB |
| FOSL1 | FOSL2 | FOXA1 | FOXA2 | FOXA3 |
| FOXB1 | FOXB2 | FOXC1 | FOXC2 | FOXD2 |
| FOXD3 | FOXD4 | FOXD4L1 | FOXD4L2 | FOXD4L3 |
| FOXD4L4 | FOXD4L6 | FOXE1 | FOXE3 | FOXF1 |
| FOXF2 | FOXG1 | FOXH1 | FOXI1 | FOXI2 |
| FOXI3 | FOXJ1 | FOXJ2 | FOXJ3 | FOXK1 |
| FOXK2 | FOXL1 | FOXL2 | FOXM1 | FOXN1 |
| FOXN2 | FOXN3 | FOXN4 | FOXO1 | FOXO3 |
| FOXO4 | FOXP1 | FOXP2 | FOXP3 | FOXP4 |
| FOXQ1 | FOXR1 | FOXR2 | FOXRED1 | FOXRED2 |
| FOXS1 | FPGS | FPGT | FPR1 | FPR2 |
| FPR3 | FRAG1 | FRAS1 | FRAS1_ENST00000325942 | FRAT1 |
| FRAT2 | FREM1 | FREM2 | FREM3 | FRG1 |
| FRG2 | FRG2C | FRK | FRMD1 | FRMD3 |
| FRMD4A | FRMD4B | FRMD5 | FRMD6 | FRMD7 |
| FRMD8 | FRMPD1 | FRMPD2 | FRMPD2L1 | FRMPD2L2 |
| FRMPD3 | FRMPD4 | FRRS1 | FRS2 | FRS3 |
| FRY | FRYL | FRZB | FSCB | FSCN1 |
| FSCN3 | FSD1 | FSD2 | FSHB | FSHR |
| FSIP1 | FST | FSTL1 | FSTL3 | FSTL4 |
| FSTL5 | FTCD | FTH1 | FTHL17 | FTHL19 |
| FTL | FTLP2 | FTMT | FTO | FTSJ1 |
| FTSJ2 | FTSJ3 | FTSJD1 | FTSJD2 | FUBP1 |
| FUBP3 | FUCA1 | FUCA2 | FUK | FUNDC1 |
| FUNDC2 | FUNDC2P1 | FURIN | FUS | FUSIP1 |
| FUT1 | FUT10 | FUT11 | FUT2 | FUT3 |
| FUT4 | FUT5 | FUT6 | FUT7 | FUT8 |
| FUT9 | FUZ | FXC1 | FXN | FXR1 |
| FXYD1 | FXYD2 | FXYD3 | FXYD4 | FXYD5 |
| FXYD6 | FXYD7 | FXYD8 | FYCO1 | FYN |
| FYTTD1 | FZD1 | FZD10 | FZD2 | FZD3 |
| FZD4 | FZD5 | FZD6 | FZD7 | FZD8 |
| FZD9 | FZR1 | G0S2 | G2E3 | G3BP1 |
| G3BP2 | G6PC | G6PC2 | G6PC3 | G6PD |
| GAA | GAB1 | GAB2 | GAB3 | GAB4 |
| GABARAP | GABARAPL1 | GABARAPL2 | GABARAPL3 | GABBR1 |
| GABBR2 | GABPA | GABPB1 | GABPB2 | GABRA1 |
| GABRA2 | GABRA3 | GABRA4 | GABRA5 | GABRA6 |
| GABRB1 | GABRB2 | GABRB3 | GABRD | GABRE |
| GABRG1 | GABRG2 | GABRP | GABRQ | GABRR1 |
| GABRR2 | GABRR3 | GAD1 | GAD2 | GADD45A |
| GADD45B | GADD45G | GADD45GIP1 | GADL1 | GAGE1 |
| GAGE10 | GAGE12C | GAGE12E | GAGE12F | GAGE12G |
| GAGE12H | GAGE12J | GAGE2C | GAGE2D | GAGE2E |
| GAK | GAL | GAL3ST1 | GAL3ST2 | GAL3ST3 |
| GAL3ST4 | GALC | GALE | GALK1 | GALK2 |
| GALM | GALNS | GALNT1 | GALNT10 | GALNT11 |
| GALNT12 | GALNT13 | GALNT14 | GALNT2 | GALNT3 |
| GALNT5 | GALNT6 | GALNT7 | GALNT8 | GALNT9 |
| GALNTL1 | GALNTL2 | GALNTL4 | GALNTL5 | GALNTL6 |
| GALP | GALR1 | GALR2 | GALR3 | GALT |
| GAMT | GAN | GANAB | GANC | GAP43 |
| GAPDH | GAPDHS | GAPT | GAPVD1 | GAR1 |
| GARNL3 | GARS | GART | GAS1 | GAS2 |
| GAS2L1 | GAS2L2 | GAS2L3 | GAS6 | GAS7 |
| GAS8 | GAST | GATA1 | GATA2 | GATA3 |
| GATA4 | GATA5 | GATA6 | GATAD1 | GATAD2A |
| GATAD2B | GATC | GATM | GATS | GATSL3 |
| GBA | GBA2 | GBAP | GBAS | GBF1 |
| GBG5L_HUMAN | GBGT1 | GBP1 | GBP2 | GBP3 |
| GBP4 | GBP5 | GBP6 | GBP7 | GBX1 |
| GBX2 | GC | GCA | GCAT | GCC1 |
| GCC2 | GCDH | GCET2 | GCH1 | GCHFR |
| GCK | GCKR | GCLC | GCLM | GCM1 |
| GCM2 | GCN1L1 | GCNT1 | GCNT2 | GCNT3 |
| GCNT4 | GCOM1 | GCSH | GDA | GDAP1 |
| GDAP1L1 | GDAP2 | GDE1 | GDF1 | GDF10 |
| GDF11 | GDF15 | GDF2 | GDF3 | GDF5 |
| GDF6 | GDF7 | GDF9 | GDI1 | GDI2 |
| GDNF | GDPD1 | GDPD2 | GDPD3 | GDPD4 |
| GDPD5 | GEFT | GEM | GEMIN4 | GEMIN5 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| GEMIN6 | GEMIN7 | GEMIN8 | GEN1 | GFAP |
| GFER | GFI1 | GFI1B | GFM1 | GFM2 |
| GFOD1 | GFOD2 | GFPT1 | GFPT2 | GFRA1 |
| GFRA3 | GFRA4 | GFRAL | GGA1 | GGA2 |
| GGA3 | GGCT | GGCX | GGH | GGN |
| GGNBP2 | GGPS1 | GGT1 | GGT5 | GGT6 |
| GGT7 | GGTLA4 | GGTLC1 | GGTLC2 | GH1 |
| GH2 | GHDC | GHITM | GHR | GHRH |
| GHRHR | GHRL | GHSR | GIF | GIGYF1 |
| GIGYF2 | GIMAP1 | GIMAP2 | GIMAP4 | GIMAP5 |
| GIMAP6 | GIMAP7 | GIMAP8 | GIN1 | GINS1 |
| GINS2 | GINS3 | GINS4 | GIOT-1 | GIP |
| GIPC1 | GIPC2 | GIPC3 | GIPR | GIT1 |
| GIT2 | GIYD1 | GIYD2 | GJA1 | GJA10 |
| GJA3 | GJA4 | GJA5 | GJA8 | GJA9 |
| GJB1 | GJB2 | GJB3 | GJB4 | GJB5 |
| GJB6 | GJB7 | GJC1 | GJC2 | GJC3 |
| GJD2 | GJD4 | GK | GK2 | GK3P |
| GK5 | GKAP1 | GKN1 | GKN2 | GLA |
| GLB1 | GLB1L | GLB1L2 | GLB1L3 | GLCCI1 |
| GLCE | GLDC | GLDN | GLE1 | GLE1L |
| GLG1 | GLI1 | GLI2 | GLI3 | GLI4 |
| GLIPR1 | GLIPR1L1 | GLIPR1L2 | GLIPR2 | GLIS1 |
| GLIS2 | GLIS3 | GLMN | GLO1 | GLOD4 |
| GLOD5 | GLP1R | GLP2R | GLRA1 | GLRA2 |
| GLRA3 | GLRA4 | GLRB | GLRX | GLRX2 |
| GLRX3 | GLRX5 | GLRXP3 | GLS | GLS2 |
| GLT1D1 | GLT25D1 | GLT25D2 | GLT28D1 | GLT6D1 |
| GLT8D1 | GLT8D2 | GLTP | GLTPD1 | GLTPD2 |
| GLTSCR2 | GLUD1 | GLUD2 | GLUL | GLYAT |
| GLYATL1 | GLYATL2 | GLYCTK | GLYR1 | GM2A |
| GMCL1 | GMDS | GMEB1 | GMEB2 | GMFB |
| GMFG | GMIP | GML | GMNN | GMPPA |
| GMPPB | GMPR | GMPR2 | GMPS | GNA11 |
| GNA12 | GNA13 | GNA14 | GNA15 | GNAI1 |
| GNAI2 | GNAI3 | GNAL | GNAO1 | GNAQ |
| GNAS | GNAS_ENST00000371100 | GNAS_NM_016592_1 | GNAT1 | GNAT2 |
| GNAZ | GNB1 | GNB1L | GNB2 | GNB2L1 |
| GNB3 | GNB4 | GNB5 | GNE | GNG10 |
| GNG11 | GNG12 | GNG13 | GNG2 | GNG3 |
| GNG4 | GNG5 | GNG7 | GNG8 | GNGT1 |
| GNGT2 | GNL1 | GNL2 | GNL3 | GNL3L |
| GNLY | GNMT | GNPAT | GNPDA1 | GNPDA2 |
| GNPNAT1 | GNPTAB | GNPTG | GNRH1 | GNRH2 |
| GNRHR | GNRHR2 | GNS | GOLGA1 | GOLGA2 |
| GOLGA2B | GOLGA3 | GOLGA4 | GOLGA5 | GOLGA6A |
| GOLGA7 | GOLGA7B | GOLGA8A | GOLGA8E | GOLGA8G |
| GOLGB1 | GOLIM4 | GOLM1 | GOLPH3 | GOLPH3L |
| GOLT1A | GOLT1B | GON4L | GOPC | GORAB |
| GORASP1 | GORASP2 | GOSR1 | GOSR2 | GOT1 |
| GOT2 | GP1BB | GP2 | GP5 | GP6 |
| GP9 | GPA33 | GPAA1 | GPAM | GPAT2 |
| GPATCH1 | GPATCH2 | GPATCH3 | GPATCH4 | GPATCH8 |
| GPBP1 | GPBP1L1 | GPC1 | GPC2 | GPC3 |
| GPC4 | GPC5 | GPC6 | GPCPD1 | GPD1 |
| GPD1L | GPD2 | GPER | GPHA2 | GPHB5 |
| GPHN | GPI | GPIHBP1 | GPKOW | GPLD1 |
| GPM6A | GPM6B | GPN1 | GPN2 | GPN3 |
| GPNMB | GPR1 | GPR101 | GPR107 | GPR108 |
| GPR109A | GPR110 | GPR111 | GPR112 | GPR113 |
| GPR114 | GPR115 | GPR116 | GPR119 | GPR12 |
| GPR120 | GPR123 | GPR124 | GPR125 | GPR126 |
| GPR128 | GPR132 | GPR133 | GPR135 | GPR137 |
| GPR137B | GPR137C | GPR139 | GPR141 | GPR142 |
| GPR143 | GPR146 | GPR148 | GPR149 | GPR15 |
| GPR150 | GPR151 | GPR152 | GPR153 | GPR155 |
| GPR156 | GPR157 | GPR158 | GPR160 | GPR161 |
| GPR162 | GPR165P | GPR17 | GPR171 | GPR172A |
| GPR172B | GPR173 | GPR174 | GPR176 | GPR179 |
| GPR18 | GPR180 | GPR182 | GPR183 | GPR19 |
| GPR20 | GPR21 | GPR22 | GPR25 | GPR26 |
| GPR27 | GPR3 | GPR31 | GPR32 | GPR34 |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| GPR35 | GPR37 | GPR37L1 | GPR39 | GPR4 |
| GPR42 | GPR44 | GPR45 | GPR50 | GPR52 |
| GPR55 | GPR56 | GPR6 | GPR61 | GPR62 |
| GPR63 | GPR64 | GPR65 | GPR68 | GPR75 |
| GPR77 | GPR78 | GPR81 | GPR82 | GPR82_ENST00000302548 |
| GPR83 | GPR84 | GPR85 | GPR87 | GPR88 |
| GPR89A | GPR89B | GPR97 | GPR98 | GPRASP1 |
| GPRASP2 | GPRC5A | GPRC5B | GPRC5C | GPRC5D |
| GPRC6A | GPRIN1 | GPRIN2 | GPRIN3 | GPS1 |
| GPS2 | GPSM1 | GPSM2 | GPSM3 | GPT |
| GPT2 | GPX1 | GPX2 | GPX3 | GPX4 |
| GPX5 | GPX6 | GPX7 | GPX8 | GRAMD1A |
| GRAMD1B | GRAMD1C | GRAMD2 | GRAMD3 | GRAMD4 |
| GRAP | GRAP2 | GRASP | GRB10 | GRB14 |
| GRB2 | GRB7 | GREB1 | GREB1_ENST00000381486 | GREM1 |
| GREM2 | GRHL1 | GRHL2 | GRHL3 | GRHPR |
| GRIA1 | GRIA2 | GRIA3 | GRIA3_ENST00000264357 | GRIA4 |
| GRID1 | GRID2 | GRIK1 | GRIK2 | GRIK2_ENST00000421544 |
| GRIK3 | GRIK4 | GRIK5 | GRIN1 | GRIN2A |
| GRIN2B | GRIN2C | GRIN2D | GRIN3A | GRIN3B |
| GRINA | GRINL1A | GRINL1B | GRIP1 | GRIP2 |
| GRIPAP1 | GRK1 | GRK4 | GRK5 | GRK6 |
| GRK7 | GRLF1 | GRM1 | GRM2 | GRM3 |
| GRM4 | GRM4_ENST00000374177 | GRM5 | GRM6 | GRM7 |
| GRM8 | GRN | GRP | GRPEL1 | GRPEL2 |
| GRPR | GRRP1 | GRTP1 | GRWD1 | GRXCR1 |
| GRXCR2 | GSC | GSC2 | GSDMA | GSDMB |
| GSDMC | GSDMD | GSG1 | GSG1L | GSG2 |
| GSK3A | GSK3B | GSN | GSPT1 | GSPT2 |
| GSR | GSS | GSTA1 | GSTA2 | GSTA3 |
| GSTA4 | GSTA5 | GSTCD | GSTK1 | GSTM1 |
| GSTM2 | GSTM3 | GSTM4 | GSTM5 | GSTO1 |
| GSTO2 | GSTP1 | GSTT1 | GSTT2 | GSTT2B |
| GSTZ1 | GSX1 | GSX2 | GTDC1 | GTF2A1 |
| GTF2A2 | GTF2B | GTF2E1 | GTF2E2 | GTF2F1 |
| GTF2F2 | GTF2H1 | GTF2H2 | GTF2H2C | GTF2H3 |
| GTF2H4 | GTF2H5 | GTF2I | GTF2IRD1 | GTF2IRD2 |
| GTF2IRD2B | GTF3C1 | GTF3C2 | GTF3C3 | GTF3C4 |
| GTF3C5 | GTF3C6 | GTPBP1 | GTPBP10 | GTPBP2 |
| GTPBP3 | GTPBP4 | GTPBP5 | GTPBP6 | GTPBP8 |
| GTSE1 | GTSF1 | GTSF1L | GUCA1A | GUCA1B |
| GUCA1C | GUCA2A | GUCA2B | GUCY1A2 | GUCY1A3 |
| GUCY2C | GUCY2D | GUCY2F | GUF1 | GUK1 |
| GUK1_ENST00000366719 | GULP1 | GUSB | GUSL1_HUMAN | GXYLT1 |
| GYG1 | GYG2 | GYLTL1B | GYPA | GYPB |
| GYPC | GYS1 | GYS2 | GZF1 | GZMA |
| GZMB | GZMH | GZMK | GZMM | H19 |
| H1F0 | H1FNT | H1FOO | H1FX | H2AFB1 |
| H2AFB2 | H2AFB3 | H2AFJ | H2AFV | H2AFX |
| H2AFY | H2AFY2 | H2AFZ | H2AFZP2 | H2BFM |
| H2BFWT | H3F3A | H3F3B | H3F3C | H6PD |
| HAAO | HABP2 | HABP4 | HACE1 | HACL1 |
| HADH | HADHA | HADHB | HAGH | HAGHL |
| HAL | HAMP | HAND1 | HAND2 | HAO1 |
| HAO2 | HAP1 | HAPLN1 | HAPLN2 | HAPLN3 |
| HAPLN4 | HARBI1 | HARS | HARS2 | HAS1 |
| HAS2 | HAS3 | HAT1 | HAUS1 | HAUS2 |
| HAUS3 | HAUS4 | HAUS5 | HAUS6 | HAUS7 |
| HAUS8 | HAVCR1 | HAVCR2 | HAX1 | HBA1 |
| HBA2 | HBB | HBD | HBE1 | HBEGF |
| HBG1 | HBG2 | HBM | HBP1 | HBQ1 |
| HBS1L | HBXIP | HBZ | HCCS | HCFC1 |
| HCFC1R1 | HCFC2 | HCG9 | HCK | HCLS1 |
| HCN1 | HCN2 | HCN3 | HCN4 | HCP1 |
| HCP5 | HCRT | HCRTR1 | HCRTR2 | HCST |
| HDAC1 | HDAC10 | HDAC11 | HDAC2 | HDAC3 |
| HDAC4 | HDAC5 | HDAC6 | HDAC7 | HDAC8 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| HDAC9 | HDC | HDDC2 | HDDC3 | HDGF |
| HDGF2 | HDGFL1 | HDGFRP3 | HDHD1A | HDHD2 |
| HDHD3 | HDLBP | HDX | HEATR1 | HEATR2 |
| HEATR3 | HEATR4 | HEATR5B | HEATR6 | HEATR7B1 |
| HEATR7B2 | HEBP1 | HEBP2 | HECA | HECTD1 |
| HECTD2 | HECTD3 | HECTD3_ENST00000372172 | HECW1 | HECW2 |
| HEG1 | HEJ1 | HELB | HELLS | HELQ |
| HELT | HELZ | HEMGN | HEMK1 | HEPACAM |
| HEPACAM2 | HEPH | HEPHL1 | HERC1 | HERC2 |
| HERC2P3 | HERC3 | HERC4 | HERC5 | HERC6 |
| HERPUD1 | HERPUD2 | HERV-FRD | HES1 | HES2 |
| HES3 | HES4 | HESS | HES6 | HES7 |
| HESX1 | HEXA | HEXB | HEXDC | HEXIM1 |
| HEXIM2 | HEY1 | HEY2 | HEYL | HFE |
| HFE2 | HFM1 | HGD | HGF | HGFAC |
| HGS | HGSNAT | HGSNAT_ENST00000458501 | HHAT | HHATL |
| HHEX | HHIP | HHIPL1 | HHIPL2 | HHLA3 |
| HIAT1 | HIATL1 | HIATL2 | HIBADH | HIBCH |
| HIC1 | HIC2 | HIF1A | HIF1AN | HIF3A |
| HIGD1A | HIGD1B | HIGD2A | HIGD2BP | HIN1L_HUMAN |
| HINFP | HINT1 | HINT2 | HINT3 | HIP1 |
| HIP1R | HIPK1 | HIPK2 | HIPK3 | HIPK4 |
| HIRA | HIRIP3 | HIST1H1A | HIST1H1B | HIST1H1C |
| HIST1H1D | HIST1H1E | HIST1H1T | HIST1H2AA | HIST1H2AB |
| HIST1H2AC | HIST1H2AD | HIST1H2AE | HIST1H2AG | HIST1H2AH |
| HIST1H2AI | HIST1H2AJ | HIST1H2AK | HIST1H2AL | HIST1H2AM |
| HIST1H2BA | HIST1H2BB | HIST1H2BC | HIST1H2BD | HIST1H2BE |
| HIST1H2BF | HIST1H2BG | HIST1H2BH | HIST1H2BI | HIST1H2BJ |
| HIST1H2BK | HIST1H2BL | HIST1H2BM | HIST1H2BN | HIST1H2BO |
| HIST1H3A | HIST1H3B | HIST1H3C | HIST1H3D | HIST1H3E |
| HIST1H3F | HIST1H3G | HIST1H3H | HIST1H3I | HIST1H3J |
| HIST1H4A | HIST1H4B | HIST1H4C | HIST1H4D | HIST1H4E |
| HIST1H4F | HIST1H4G | HIST1H4H | HIST1H4I | HIST1H4J |
| HIST1H4K | HIST1H4L | HIST2H2AA3 | HIST2H2AA4 | HIST2H2AB |
| HIST2H2AC | HIST2H2BE | HIST2H2BF | HIST2H3A | HIST2H3C |
| HIST2H3D | HIST2H4A | HIST2H4B | HIST3H2A | HIST3H2BB |
| HIST3H3 | HIST4H4 | HIVEP1 | HIVEP2 | HIVEP3 |
| HJURP | HK1 | HK2 | HK3 | HKDC1 |
| HKR1 | HLA-A | HLA-B | HLA-C | HLA-DMA |
| HLA-DMB | HLA-DOA | HLA-DOB | HLA-DPA1 | HLA-DPB1 |
| HLA-DQA1 | HLA-DQA2 | HLA-DQB1 | HLA-DRA | HLA-DRB5 |
| HLA-E | HLA-F | HLA-G | HLCS | HLF |
| HLTF | HLX | HM13 | HMBOX1 | HMBS |
| HMCN1 | HMG1L10 | HMG20A | HMG20B | HMGA1 |
| HMGA2 | HMGB1 | HMGB1L1 | HMGB2 | HMGB3 |
| HMGB4 | HMGCL | HMGCLL1 | HMGCR | HMGCS1 |
| HMGCS2 | HMGN1 | HMGN2 | HMGN3 | HMGN4 |
| HMGN5 | HMGXB3 | HMGXB4 | HMHA1 | HMHB1 |
| HMMR | HMOX1 | HMOX2 | HMP19 | HMX2 |
| HMX3 | HN1 | HN1L | HNF1A | HNF1B |
| HNF4A | HNF4G | HNMT | HNRNPA0 | HNRNPA1 |
| HNRNPA1L2 | HNRNPA2B1 | HNRNPA3 | HNRNPAB | HNRNPC |
| HNRNPCL1 | HNRNPD | HNRNPF | HNRNPH1 | HNRNPH2 |
| HNRNPH3 | HNRNPK | HNRNPL | HNRNPM | HNRNPR |
| HNRNPU | HNRNPUL1 | HNRNPUL2 | HNRPD | HNRPDL |
| HNRPF | HNRPH1 | HNRPL | HNRPLL | HNRPR |
| HNRPU | HOMER1 | HOMER2 | HOMER3 | HOOK1 |
| HOOK2 | HOOK3 | HOPX | HORMAD1 | HOXA1 |
| HOXA10 | HOXA11 | HOXA13 | HOXA2 | HOXA3 |
| HOXA4 | HOXA5 | HOXA6 | HOXA7 | HOXA9 |
| HOXB1 | HOXB13 | HOXB2 | HOXB3 | HOXB4 |
| HOXB5 | HOXB6 | HOXB7 | HOXB8 | HOXB9 |
| HOXC10 | HOXC11 | HOXC12 | HOXC13 | HOXC4 |
| HOXC5 | HOXC6 | HOXC8 | HOXC9 | HOXD1 |
| HOXD10 | HOXD11 | HOXD13 | HOXD3 | HOXD4 |
| HOXD8 | HOXD9 | HP | HP1BP3 | HPCA |
| HPCAL1 | HPCAL4 | HPD | HPDL | HPGD |
| HPGDS | HPN | HPR | HPRT1 | HPS1 |
| HPS3 | HPS4 | HPS5 | HPS6 | HPSE |
| HPSE2 | HPX | HR | HRAS | HRASLS |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| HRASLS2 | HRASLS5 | HRAS_ENST00000397594 | HRC | HRCT1 |
| HRG | HRH1 | HRH2 | HRH3 | HRH4 |
| HRK | HRNR | HRSP12 | HS1BP3 | HS2ST1 |
| HS3ST1 | HS3ST2 | HS3ST3A1 | HS3ST3B1 | HS3ST4 |
| HS3ST5 | HS6ST1 | HS6ST1P | HS6ST2 | HS6ST3 |
| HSCB | HSD11B1 | HSD11B1L | HSD11B2 | HSD17B1 |
| HSD17B10 | HSD17B11 | HSD17B12 | HSD17B13 | HSD17B14 |
| HSD17B2 | HSD17B3 | HSD17B4 | HSD17B6 | HSD17B7 |
| HSD17B8 | HSD3B1 | HSD3B2 | HSD3B3 | HSDL1 |
| HSDL2 | HSF1 | HSF2 | HSF2BP | HSF4 |
| HSF5 | HSFX1 | HSFY1 | HSFY2 | HSP90AA1 |
| HSP90AA2 | HSP90AB1 | HSP90AB2P | HSP90AB6P | HSP90B1 |
| HSPA12A | HSPA12B | HSPA13 | HSPA14 | HSPA1A |
| HSPA1B | HSPA1L | HSPA2 | HSPA4 | HSPA4L |
| HSPA5 | HSPA6 | HSPA8 | HSPA9 | HSPB1 |
| HSPB11 | HSPB2 | HSPB3 | HSPB6 | HSPB7 |
| HSPB8 | HSPB9 | HSPBAP1 | HSPBP1 | HSPC159 |
| HSPD1 | HSPE1 | HSPG2 | HSPH1 | HTATIP2 |
| HTATSF1 | HTN1 | HTN3 | HTR1A | HTR1B |
| HTR1D | HTR1E | HTR1F | HTR2A | HTR2B |
| HTR2C | HTR3A | HTR3B | HTR3C | HTR3D |
| HTR3E | HTR4 | HTR5A | HTR6 | HTR7 |
| HTRA1 | HTRA2 | HTRA3 | HTRA4 | HTT |
| HUMPPA | HUNK | HUS1 | HUS1B | HUWE1 |
| HVCN1 | HYAL1 | HYAL2 | HYAL3 | HYAL4 |
| HYDIN | HYI | HYLS1 | HYOU1 | IAH1 |
| IAPP | IARS | IARS2 | IBSP | IBTK |
| ICA1 | ICA1L | ICAM1 | ICAM2 | ICAM3 |
| ICAM4 | ICAM5 | ICK | ICMT | ICOS |
| ICOSLG | ICT1 | ID1 | ID2 | ID2B |
| ID3 | ID4 | IDE | IDH1 | IDH2 |
| IDH3A | IDH3B | IDH3G | IDI1 | IDI2 |
| IDO1 | IDS | IDUA | IER2 | IER3 |
| IER3IP1 | IER5 | IER5L | IFFO1 | IFI16 |
| IFI27 | IFI27L1 | IFI27L2 | IFI30 | IFI35 |
| IFI44 | IFI44L | IFI6 | IFIH1 | IFIT1 |
| IFIT1L | IFIT2 | IFIT3 | IFIT5 | IFITM2 |
| IFITM3 | IFITM5 | IFLTD1 | IFNA1 | IFNA10 |
| IFNA13 | IFNA14 | IFNA16 | IFNA17 | IFNA2 |
| IFNA21 | IFNA4 | IFNA5 | IFNA6 | IFNA7 |
| IFNA8 | IFNAR1 | IFNAR2 | IFNB1 | IFNE |
| IFNG | IFNGR1 | IFNGR2 | IFNK | IFNW1 |
| IFRD1 | IFRD2 | IFT122 | IFT140 | IFT172 |
| IFT20 | IFT52 | IFT57 | IFT74 | IFT80 |
| IFT81 | IFT88 | IGBP1 | IGDCC3 | IGDCC4 |
| IGF1 | IGF1R | IGF2 | IGF2AS | IGF2BP1 |
| IGF2BP2 | IGF2BP3 | IGF2R | IGFALS | IGFBP1 |
| IGFBP2 | IGFBP3 | IGFBP4 | IGFBP5 | IGFBP6 |
| IGFBP7 | IGFBPL1 | IGFL3 | IGFL4 | IGFN1 |
| IGHMBP2 | IGHV1OR15-1 | IGHV1OR15-5 | IGJ | IGLL1 |
| IGLL3 | IGSF1 | IGSF10 | IGSF11 | IGSF21 |
| IGSF22 | IGSF3 | IGSF5 | IGSF6 | IGSF8 |
| IGSF9 | IGSF9B | IHH | IK | IKBIP |
| IKBKAP | IKBKB | IKBKE | IKBKG | IKZF1 |
| IKZF2 | IKZF3 | IKZF4 | IKZF4_ENST00000262032 | IKZF5 |
| IL10 | IL10RA | IL10RB | IL11 | IL11RA |
| IL12A | IL12B | IL12RB1 | IL12RB2 | IL13 |
| IL13RA1 | IL13RA2 | IL15 | IL15RA | IL16 |
| IL17A | IL17B | IL17C | IL17D | IL17F |
| IL17RA | IL17RB | IL17RC | IL17RD | IL17RE |
| IL17REL | IL18 | IL18BP | IL18R1 | IL18RAP |
| IL19 | IL1A | IL1B | IL1F10 | IL1F5 |
| IL1F6 | IL1F7 | IL1F8 | IL1F9 | IL1R1 |
| IL1R2 | IL1RAP | IL1RAPL1 | IL1RAPL2 | IL1RL1 |
| IL1RL2 | IL1RN | IL2 | IL20 | IL20RA |
| IL20RB | IL21 | IL21R | IL22 | IL22RA1 |
| IL22RA2 | IL23A | IL23R | IL24 | IL25 |
| IL26 | IL27 | IL27RA | IL28A | IL28B |
| IL28RA | IL29 | IL2RA | IL2RB | IL2RG |
| IL2RG_ENST00000374202 | IL3 | IL31 | IL31RA | IL32 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| IL33 | IL34 | IL3RA | IL4 | IL4I1 |
| IL4R | IL5 | IL5RA | IL6 | IL6R |
| IL6ST | IL7 | IL7R | IL8 | IL9 |
| IL9R | ILDR1 | ILDR2 | ILF2 | ILF3 |
| ILK | ILKAP | ILK__ENST00000299421 | ILVBL | IMMP1L |
| IMMP2L | IMMT | IMP3 | IMP4 | IMP5 |
| IMPA1 | IMPA2 | IMPACT | IMPAD1 | IMPDH1 |
| IMPDH2 | IMPG1 | IMPG2 | INA | INADL |
| INCA1 | INCENP | INE1 | INF2 | INF2__NEW |
| ING1 | ING2 | ING3 | ING4 | ING5 |
| INGX | INHA | INHBA | INHBB | INHBC |
| INHBE | INMT | INO80 | INO80B | INO80C |
| INO80D | INO80E | INOC1 | INPP1 | INPP4A |
| INPP4B | INPP5A | INPP5B | INPP5B__ENST00000373026 | INPP5D |
| INPP5E | INPP5F | INPP5J | INPP5K | INPPL1 |
| INS | INS-IGF2 | INSC | INSIG1 | INSIG2 |
| INSL3 | INSL4 | INSL5 | INSL6 | INSM1 |
| INSM2 | INSR | INSRR | INTS10 | INTS12 |
| INTS2 | INTS3 | INTS4 | INTS5 | INTS6 |
| INTS7 | INTS8 | INTS9 | INTU | INVS |
| IP6K1 | IP6K2 | IP6K3 | IPCEF1 | IPMK |
| IPO11 | IPO13 | IPO4 | IPO5 | IPO7 |
| IPO8 | IPO9 | IPP | IPPK | IQCB1 |
| IQCC | IQCD | IQCE | IQCF1 | IQCF2 |
| IQCG | IQCH | IQCK | IQGAP1 | IQGAP2 |
| IQGAP3 | IQSEC1 | IQSEC2 | IQSEC3 | IQUB |
| IRAK1 | IRAK1BP1 | IRAK2 | IRAK3 | IRAK4 |
| IREB2 | IRF1 | IRF2 | IRF2BP1 | IRF2BP2 |
| IRF3 | IRF4 | IRF5 | IRF6 | IRF7 |
| IRF8 | IRF9 | IRGC | IRGQ | IRS1 |
| IRS2 | IRS4 | IRX1 | IRX2 | IRX3 |
| IRX4 | IRX5 | IRX6 | ISCA1 | ISCA2 |
| ISCU | ISG15 | ISG20 | ISG20L2 | ISL1 |
| ISL2 | ISLR | ISLR2 | ISM1 | ISM2 |
| ISOC1 | ISOC2 | ISX | ISY1 | ISYNA1 |
| ITCH | ITFG1 | ITFG2 | ITFG3 | ITGA1 |
| ITGA10 | ITGA11 | ITGA2 | ITGA2B | ITGA3 |
| ITGA4 | ITGA5 | ITGA6 | ITGA7 | ITGA8 |
| ITGA9 | ITGAD | ITGAE | ITGAL | ITGAM |
| ITGAV | ITGAX | ITGB1 | ITGB1BP1 | ITGB1BP2 |
| ITGB1BP3 | ITGB2 | ITGB3 | ITGB3BP | ITGB4 |
| ITGB5 | ITGB6 | ITGB7 | ITGB8 | ITGBL1 |
| ITIH1 | ITIH2 | ITIH3 | ITIH4 | ITIH5 |
| ITIH5L | ITK | ITLN1 | ITLN2 | ITM2A |
| ITM2B | ITM2C | ITPA | ITPK1 | ITPKA |
| ITPKB | ITPKC | ITPR1 | ITPR2 | ITPR3 |
| ITPRIP | ITPRIPL1 | ITPRIPL2 | ITSN1 | ITSN2 |
| IVD | IVL | IVNS1ABP | IWS1 | IYD |
| IZUMO1 | JAG1 | JAG2 | JAGN1 | JAK1 |
| JAK2 | JAK3 | JAKMIP1 | JAKMIP2 | JAKMIP3 |
| JAM2 | JAM3 | JARID2 | JAZF1 | JDP2 |
| JHDM1D | JMJD1C | JMJD4 | JMJD5 | JMJD6 |
| JMJD7-PLA2G4B | JMY | JOSD1 | JOSD2 | JPH1 |
| JPH2 | JPH3 | JPH4 | JRKL | JSRP1 |
| JTB | JUB | JUN | JUNB | JUND |
| JUP | K0087__HUMAN | K0401__HUMAN | KAAG1 | KAL1 |
| KALRN | KANK1 | KANK2 | KANK3 | KANK4 |
| KARCA1 | KARS | KAT2A | KAT2B | KAT5 |
| KATNA1 | KATNAL1 | KATNAL2 | KATNB1 | KAZALD1 |
| KBTBD10 | KBTBD11 | KBTBD2 | KBTBD3 | KBTBD4 |
| KBTBD5 | KBTBD6 | KBTBD7 | KBTBD8 | KCNA1 |
| KCNA10 | KCNA2 | KCNA3 | KCNA4 | KCNA5 |
| KCNA6 | KCNA7 | KCNAB1 | KCNAB2 | KCNAB3 |
| KCNB1 | KCNB2 | KCNC1 | KCNC2 | KCNC3 |
| KCNC4 | KCND1 | KCND2 | KCND3 | KCNE1 |
| KCNE1L | KCNE2 | KCNE3 | KCNE4 | KCNF1 |
| KCNG1 | KCNG2 | KCNG3 | KCNG4 | KCNH1 |
| KCNH2 | KCNH3 | KCNH4 | KCNH5 | KCNH6 |
| KCNH7 | KCNH8 | KCNIP1 | KCNIP2 | KCNIP3 |
| KCNIP4 | KCNJ1 | KCNJ10 | KCNJ11 | KCNJ12 |
| KCNJ13 | KCNJ14 | KCNJ15 | KCNJ16 | KCNJ2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| KCNJ3 | KCNJ4 | KCNJ5 | KCNJ6 | KCNJ8 |
| KCNJ9 | KCNK1 | KCNK10 | KCNK12 | KCNK13 |
| KCNK15 | KCNK16 | KCNK17 | KCNK18 | KCNK2 |
| KCNK3 | KCNK4 | KCNK5 | KCNK6 | KCNK7 |
| KCNK9 | KCNMA1 | KCNMB1 | KCNMB2 | KCNMB3 |
| KCNMB4 | KCNN1 | KCNN1_ENST00000222249 | KCNN2 | KCNN3 |
| KCNN4 | KCNQ1 | KCNQ2 | KCNQ3 | KCNQ4 |
| KCNQ5 | KCNRG | KCNS1 | KCNS2 | KCNS3 |
| KCNT1 | KCNT2 | KCNV1 | KCNV2 | KCP |
| KCTD1 | KCTD10 | KCTD11 | KCTD12 | KCTD13 |
| KCTD14 | KCTD15 | KCTD16 | KCTD17 | KCTD18 |
| KCTD19 | KCTD2 | KCTD20 | KCTD21 | KCTD3 |
| KCTD4 | KCTD5 | KCTD6 | KCTD7 | KCTD8 |
| KCTD9 | KCTD9L | KDELC1 | KDELC2 | KDELR1 |
| KDELR2 | KDELR3 | KDM1A | KDM1B | KDM2A |
| KDM2B | KDM3A | KDM3B | KDM4A | KDM4B |
| KDM4C | KDM4D | KDM5A | KDM5B | KDM5C |
| KDM5D | KDM6A | KDM6B | KDR | KDSR |
| KEAP1 | KEL | KERA | KHDC1 | KHDRBS1 |
| KHDRBS2 | KHDRBS3 | KHK | KHNYN | KHSRP |
| KIAA0020 | KIAA0090 | KIAA0100 | KIAA0101 | KIAA0141 |
| KIAA0146 | KIAA0174 | KIAA0182 | KIAA0195 | KIAA0196 |
| KIAA0226 | KIAA0226_ENST00000273582 | KIAA0232 | KIAA0240 | KIAA0247 |
| KIAA0284 | KIAA0317 | KIAA0319 | KIAA0319L | KIAA0355 |
| KIAA0368 | KIAA0391 | KIAA0406 | KIAA0408 | KIAA0415 |
| KIAA0415_ENST00000450194 | KIAA0427 | KIAA0430 | KIAA0467 | KIAA0467_ENST00000372442 |
| KIAA0494 | KIAA0513 | KIAA0528 | KIAA0556 | KIAA0562 |
| KIAA0564 | KIAA0649 | KIAA0664 | KIAA0664_ENST00000322335 | KIAA0672 |
| KIAA0701 | KIAA0746 | KIAA0748 | KIAA0753 | KIAA0776 |
| KIAA0802 | KIAA0831 | KIAA0892 | KIAA0895 | KIAA0895L |
| KIAA0895_ENST00000338533 | KIAA0907 | KIAA0913 | KIAA0922 | KIAA0947 |
| KIAA0953 | KIAA1009 | KIAA1012 | KIAA1024 | KIAA1033 |
| KIAA1045 | KIAA1109 | KIAA1143 | KIAA1147 | KIAA1161 |
| KIAA1191 | KIAA1199 | KIAA1210 | KIAA1211 | KIAA1217 |
| KIAA1244 | KIAA1267 | KIAA1274 | KIAA1279 | KIAA1324 |
| KIAA1324L | KIAA1328 | KIAA1377 | KIAA1404 | KIAA1407 |
| KIAA1409 | KIAA1429 | KIAA1430 | KIAA1432 | KIAA1443 |
| KIAA1462 | KIAA1467 | KIAA1468 | KIAA1486 | KIAA1509 |
| KIAA1522 | KIAA1524 | KIAA1529 | KIAA1530 | KIAA1539 |
| KIAA1542 | KIAA1543 | KIAA1549 | KIAA1586 | KIAA1598 |
| KIAA1609 | KIAA1614 | KIAA1618 | KIAA1632 | KIAA1644 |
| KIAA1671 | KIAA1683 | KIAA1688 | KIAA1704 | KIAA1712 |
| KIAA1715 | KIAA1737 | KIAA1751 | KIAA1755 | KIAA1772 |
| KIAA1797 | KIAA1804 | KIAA1826 | KIAA1841 | KIAA1853 |
| KIAA1875 | KIAA1913 | KIAA1919 | KIAA1949 | KIAA1958 |
| KIAA1967 | KIAA1984 | KIAA2013 | KIAA2018 | KIAA2022 |
| KIAA2026 | KIDINS220 | KIF11 | KIF12 | KIF13A |
| KIF13B | KIF14 | KIF15 | KIF16B | KIF17 |
| KIF18A | KIF18B | KIF19 | KIF1A | KIF1B |
| KIF1C | KIF20A | KIF20B | KIF21A | KIF21B |
| KIF22 | KIF23 | KIF25 | KIF27 | KIF2A |
| KIF2B | KIF2C | KIF3A | KIF3B | KIF3C |
| KIF4A | KIF5A | KIF5B | KIF5C | KIF6 |
| KIF7 | KIF9 | KIFAP3 | KIFC1 | KIFC2 |
| KIFC3 | KIN | KIR2DL1 | KIR2DL3 | KIR2DL4 |
| KIR2DS4 | KIR3DL1 | KIR3DL2 | KIR3DL3 | KIR3DX1 |
| KIRREL | KIRREL2 | KIRREL3 | KISS1 | KISS1R |
| KIT | KITLG | KL | KLB | KLC1 |
| KLC2 | KLC3 | KLC4 | KLF1 | KLF10 |
| KLF11 | KLF12 | KLF13 | KLF14 | KLF15 |
| KLF16 | KLF17 | KLF2 | KLF3 | KLF4 |
| KLF5 | KLF6 | KLF7 | KLF8 | KLF9 |
| KLHDC1 | KLHDC10 | KLHDC2 | KLHDC3 | KLHDC4 |
| KLHDC5 | KLHDC6 | KLHDC7A | KLHDC7B | KLHDC8A |
| KLHDC8B | KLHDC9 | KLHL1 | KLHL10 | KLHL11 |
| KLHL12 | KLHL13 | KLHL14 | KLHL15 | KLHL17 |
| KLHL18 | KLHL2 | KLHL20 | KLHL21 | KLHL22 |
| KLHL23 | KLHL24 | KLHL25 | KLHL26 | KLHL28 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| KLHL29 | KLHL3 | KLHL31 | KLHL32 | KLHL34 |
| KLHL36 | KLHL38 | KLHL4 | KLHL5 | KLHL6 |
| KLHL7 | KLHL8 | KLHL9 | KLK1 | KLK10 |
| KLK11 | KLK12 | KLK13 | KLK14 | KLK15 |
| KLK2 | KLK3 | KLK4 | KLK5 | KLK6 |
| KLK7 | KLK8 | KLK9 | KLKB1 | KLRA1 |
| KLRB1 | KLRC1 | KLRC2 | KLRC3 | KLRC4 |
| KLRD1 | KLRF1 | KLRG1 | KLRG2 | KLRK1 |
| KMO | KNDC1 | KNG1 | KNTC1 | KPNA1 |
| KPNA2 | KPNA3 | KPNA4 | KPNA5 | KPNA6 |
| KPNA7 | KPNB1 | KPRP | KPTN | KRAS |
| KRBA1 | KRBA2 | KRCC1 | KREMEN1 | KREMEN2 |
| KRI1 | KRIT1 | KRR1 | KRT1 | KRT10 |
| KRT12 | KRT13 | KRT14 | KRT15 | KRT16 |
| KRT17 | KRT18 | KRT19 | KRT2 | KRT20 |
| KRT222 | KRT23 | KRT24 | KRT25 | KRT26 |
| KRT27 | KRT28 | KRT3 | KRT31 | KRT32 |
| KRT33A | KRT33B | KRT34 | KRT35 | KRT36 |
| KRT37 | KRT38 | KRT39 | KRT4 | KRT40 |
| KRT5 | KRT6A | KRT6B | KRT6C | KRT7 |
| KRT71 | KRT72 | KRT73 | KRT74 | KRT75 |
| KRT76 | KRT77 | KRT78 | KRT79 | KRT8 |
| KRT80 | KRT81 | KRT82 | KRT83 | KRT84 |
| KRT85 | KRT86 | KRT9 | KRTAP1-1 | KRTAP1-3 |
| KRTAP10-1 | KRTAP10-10 | KRTAP10-11 | KRTAP10-12 | KRTAP10-2 |
| KRTAP10-3 | KRTAP10-4 | KRTAP10-5 | KRTAP10-6 | KRTAP10-8 |
| KRTAP11-1 | KRTAP12-1 | KRTAP12-3 | KRTAP12-4 | KRTAP13-1 |
| KRTAP13-2 | KRTAP13-3 | KRTAP13-4 | KRTAP15-1 | KRTAP17-1 |
| KRTAP19-1 | KRTAP19-2 | KRTAP19-3 | KRTAP19-4 | KRTAP19-5 |
| KRTAP19-6 | KRTAP19-7 | KRTAP19-8 | KRTAP2-1 | KRTAP2-4 |
| KRTAP20-1 | KRTAP20-2 | KRTAP21-1 | KRTAP21-2 | KRTAP22-1 |
| KRTAP23-1 | KRTAP24-1 | KRTAP26-1 | KRTAP27-1 | KRTAP3-1 |
| KRTAP3-2 | KRTAP3-3 | KRTAP4-12 | KRTAP4-2 | KRTAP4-3 |
| KRTAP4-4 | KRTAP4-5 | KRTAP5-1 | KRTAP5-10 | KRTAP5-11 |
| KRTAP5-2 | KRTAP5-3 | KRTAP5-5 | KRTAP5-6 | KRTAP5-7 |
| KRTAP5-8 | KRTAP6-1 | KRTAP6-2 | KRTAP8-1 | KRTAP9-2 |
| KRTAP9-3 | KRTAP9-4 | KRTAP9-8 | KRTAP9L2 | KRTCAP2 |
| KRTCAP3 | KRTDAP | KSR1 | KSR2 | KTELC1 |
| KTI12 | KTN1 | KYNU | Klkbl4 | L1CAM |
| L1TD1 | L2HGDH | L3MBTL | L3MBTL2 | L3MBTL3 |
| L3MBTL4 | LACE1 | LACRT | LACTB | LACTB2 |
| LAD1 | LAG3 | LAGE3 | LAIR1 | LAIR2 |
| LALBA | LAMA1 | LAMA2 | LAMA3 | LAMA4 |
| LAMA5 | LAMB1 | LAMB2 | LAMB3 | LAMB4 |
| LAMC1 | LAMC2 | LAMC3 | LAMP1 | LAMP2 |
| LAMP3 | LANCL1 | LANCL2 | LANCL3 | LAP3 |
| LAPTM4A | LAPTM4B | LAPTM5 | LARGE | LARP1 |
| LARP1B | LARP4 | LARP4B | LARP6 | LARP7 |
| LARS | LARS2 | LAS1L | LASP1 | LASS1 |
| LASS2 | LASS3 | LASS4 | LASS5 | LASS6 |
| LAT | LAT2 | LATS1 | LATS2 | LAX1 |
| LAYN | LBH | LBP | LBR | LBX1 |
| LBX2 | LBXCOR1 | LCA5 | LCA5L | LCAP |
| LCAT | LCE1A | LCE1B | LCE1C | LCE1D |
| LCE1E | LCE1F | LCE2A | LCE2B | LCE2C |
| LCE2D | LCE3A | LCE3B | LCE3C | LCE3D |
| LCE3E | LCE4A | LCE5A | LCK | LCLAT1 |
| LCMT1 | LCMT2 | LCN1 | LCN10 | LCN12 |
| LCN15 | LCN2 | LCN6 | LCN8 | LCN9 |
| LCOR | LCORL | LCP1 | LCT | LCTL |
| LDB1 | LDB2 | LDB3 | LDHA | LDHAL6A |
| LDHAL6B | LDHB | LDHC | LDHD | LDLR |
| LDLRAD1 | LDLRAD2 | LDLRAD3 | LDLRAP1 | LDOC1 |
| LDOC1L | LEAP2 | LECT1 | LECT2 | LEF1 |
| LEFTY1 | LEFTY2 | LEKR1 | LELP1 | LEMD1 |
| LEMD2 | LEMD3 | LENEP | LENG1 | LENG8 |
| LENG9 | LEO1 | LEP | LEPR | LEPRE1 |
| LEPREL1 | LEPREL2 | LEPROT | LEPROTL1 | LETM1 |
| LETM2 | LETMD1 | LFNG | LGALS1 | LGALS12 |
| LGALS13 | LGALS14 | LGALS2 | LGALS3 | LGALS3BP |
| LGALS4 | LGALS7 | LGALS8 | LGALS9 | LGALS9B |
| LGALS9C | LGI1 | LGI2 | LGI3 | LGI4 |
| LGMN | LGR4 | LGR5 | LGR6 | LGSN |

TABLE 3-continued

List of genes which contain cancer-related somatic mutations. The list was adapted from Sanger
Center's COSMIC database(Bamford et al, 2004; Forbes et al., 2008; Forbes et al.; Forbes
et al.; Friedberg; Pleasance et al.). The gene names are uniquely assigned by HUGO Gene Nomenclature
Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| LGTN | LHB | LHCGR | LHFP | LHFPL1 |
| LHFPL2 | LHFPL4 | LHFPL5 | LHPP | LHX1 |
| LHX2 | LHX3 | LHX4 | LHX5 | LHX6 |
| LHX8 | LHX9 | LIAS | LIF | LIFR |
| LIG1 | LIG3 | LIG4 | LILRA1 | LILRA2 |
| LILRA3 | LILRA4 | LILRA5 | LILRA6 | LILRB1 |
| LILRB2 | LILRB3 | LILRB4 | LILRB5 | LIM2 |
| LIMA1 | LIMCH1 | LIMD1 | LIMD2 | LIME1 |
| LIMK1 | LIMK2 | LIMS1 | LIMS2 | LIMS3 |
| LIN28 | LIN28B | LIN52 | LIN54 | LIN7A |
| LIN7B | LIN7C | LIN9 | LINGO1 | LINGO2 |
| LINGO4 | LINS1 | LIPA | LIPC | LIPE |
| LIPF | LIPG | LIPH | LIPI | LIPJ |
| LIPM | LIPT1 | LIPT2 | LITAF | LIX1 |
| LIX1L | LL0XNC01-209G1_2 | LL0XNC01-237H1_1 | LLGL1 | LLGL2 |
| LLPH | LMAN1 | LMAN1L | LMAN2 | LMAN2L |
| LMBR1 | LMBR1L | LMBRD1 | LMBRD2 | LMCD1 |
| LMF1 | LMF2 | LMLN | LMNA | LMNB1 |
| LMNB2 | LMO1 | LMO2 | LMO3 | LMO4 |
| LMO7 | LMOD1 | LMOD2 | LMTK2 | LMTK3 |
| LMX1A | LMX1B | LNP1 | LNPEP | LNX1 |
| LNX2 | LOC114984 | LOC120364 | LOC133308 | LOC139116 |
| LOC139249 | LOC139263 | LOC139431 | LOC139516 | LOC139542 |
| LOC145814 | LOC148213 | LOC152485 | LOC153328 | LOC157567 |
| LOC158572 | LOC158730 | LOC158825 | LOC158957 | LOC165186 |
| LOC168850 | LOC200420 | LOC203510 | LOC203604 | LOC220686 |
| LOC223075 | LOC257106 | LOC283232 | LOC283398 | LOC283412 |
| LOC283849 | LOC284023 | LOC284100 | LOC284288 | LOC286404 |
| LOC286408 | LOC286411 | LOC286467 | LOC286478 | LOC286512 |
| LOC286528 | LOC339123 | LOC340096 | LOC340549 | LOC340571 |
| LOC340578 | LOC340581 | LOC341457 | LOC342541 | LOC344165 |
| LOC345630 | LOC347376 | LOC347381 | LOC347411 | LOC347421 |
| LOC347424 | LOC347549 | LOC349136 | LOC387867 | LOC388972 |
| LOC389669 | LOC389841 | LOC389842 | LOC389846 | LOC389848 |
| LOC389858 | LOC389873 | LOC389888 | LOC389895 | LOC389899 |
| LOC389900 | LOC389901 | LOC389904 | LOC390335 | LOC390956 |
| LOC391370 | LOC392434 | LOC392439 | LOC392459 | LOC392467 |
| LOC392473 | LOC392487 | LOC392512 | LOC392528 | LOC392529 |
| LOC392531 | LOC392533 | LOC392539 | LOC392546 | LOC392549 |
| LOC392554 | LOC392556 | LOC392559 | LOC401052 | LOC401584 |
| LOC401588 | LOC401599 | LOC401605 | LOC401611 | LOC401613 |
| LOC401616 | LOC401621 | LOC402120 | LOC402414 | LOC402418 |
| LOC439951 | LOC440055 | LOC440345 | LOC440354 | LOC440917 |
| LOC440925 | LOC440944 | LOC441344 | LOC441480 | LOC441481 |
| LOC441483 | LOC441485 | LOC441486 | LOC441488 | LOC441493 |
| LOC441494 | LOC441496 | LOC441497 | LOC441498 | LOC441499 |
| LOC441504 | LOC441507 | LOC441510 | LOC441511 | LOC441513 |
| LOC441515 | LOC441526 | LOC441795 | LOC442425 | LOC442439 |
| LOC442444 | LOC442447 | LOC442451 | LOC442452 | LOC442454 |
| LOC442456 | LOC442461 | LOC442464 | LOC442465 | LOC442466 |
| LOC442470 | LOC493829 | LOC51058 | LOC51059 | LOC51123 |
| LOC51321 | LOC541473 | LOC55954 | LOC56901 | LOC57149 |
| LOC642755 | LOC643751 | LOC645864 | LOC646049 | LOC646625 |
| LOC646853 | LOC646870 | LOC646871 | LOC649445 | LOC649587 |
| LOC649618 | LOC649930 | LOC650875 | LOC65121 | LOC651271 |
| LOC651503 | LOC651746 | LOC652153 | LOC652737 | LOC653192 |
| LOC653698 | LOC653720 | LOC728194 | LOC728350 | LOC728378 |
| LOC729903 | LOC730029 | LOC730445 | LOC730735 | LOC731028 |
| LOC731173 | LOC731740 | LOC731796 | LOC731890 | LOC81691 |
| LOC88523 | LOC91461 | LOC91807 | LOC92249 | LOC93081 |
| LOH12CR1 | LONP1 | LONP2 | LONRF1 | LONRF2 |
| LONRF3 | LOR | LOX | LOXL1 | LOXL2 |
| LOXL3 | LOXL4 | LPA | LPAL2 | LPAR1 |
| LPAR2 | LPAR3 | LPAR4 | LPAR5 | LPAR6 |
| LPCAT1 | LPCAT2 | LPCAT3 | LPCAT4 | LPGAT1 |
| LPHN1 | LPHN2 | LPHN3 | LPIN1 | LPIN2 |
| LPIN3 | LPL | LPO | LPP | LPPR2 |
| LPPR4 | LPXN | LRAT | LRBA | LRCH1 |
| LRCH2 | LRCH3 | LRCH4 | LRDD | LRFN1 |
| LRFN2 | LRFN3 | LRFN4 | LRFN5 | LRG1 |
| LRGUK | LRIG1 | LRIG2 | LRIG3 | LRIT1 |
| LRIT2 | LRIT3 | LRMP | LRP1 | LRP10 |
| LRP11 | LRP12 | LRP1B | LRP2 | LRP2BP |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| LRP3 | LRP4 | LRP5 | LRP5L | LRP6 |
| LRP8 | LRPAP1 | LRPPRC | LRRC1 | LRRC10 |
| LRRC14 | LRRC14B | LRRC15 | LRRC16A | LRRC16B |
| LRRC17 | LRRC18 | LRRC19 | LRRC2 | LRRC20 |
| LRRC23 | LRRC24 | LRRC25 | LRRC26 | LRRC27 |
| LRRC28 | LRRC29 | LRRC3 | LRRC30 | LRRC31 |
| LRRC32 | LRRC33 | LRRC34 | LRRC36 | LRRC37A |
| LRRC37A2 | LRRC37A3 | LRRC37B | LRRC39 | LRRC3B |
| LRRC4 | LRRC40 | LRRC41 | LRRC42 | LRRC43 |
| LRRC45 | LRRC46 | LRRC47 | LRRC49 | LRRC4B |
| LRRC4C | LRRC50 | LRRC52 | LRRC55 | LRRC56 |
| LRRC57 | LRRC59 | LRRC6 | LRRC61 | LRRC66 |
| LRRC67 | LRRC68 | LRRC7 | LRRC8A | LRRC8B |
| LRRC8C | LRRC8D | LRRC8E | LRRCC1 | LRRFIP1 |
| LRRFIP1_ENST00000392000 | LRRFIP2 | LRRIQ1 | LRRIQ3 | LRRK1 |
| LRRK2 | LRRK2_ENST00000298910 | LRRN1 | LRRN2 | LRRN3 |
| LRRN4 | LRRN4CL | LRRTM1 | LRRTM3 | LRRTM4 |
| LRSAM1 | LRTM1 | LRTM2 | LRTOMT | LRWD1 |
| LSAMP | LSG1 | LSM1 | LSM10 | LSM11 |
| LSM12 | LSM14A | LSM14B | LSM2 | LSM3 |
| LSM4 | LSM5 | LSM6 | LSMD1 | LSP1 |
| LSR | LSS | LST1 | LTA | LTA4H |
| LTB | LTB4R | LTB4R2 | LTBP1 | LTBP2 |
| LTBP3 | LTBP4 | LTBR | LTC4S | LTF |
| LTK | LTV1 | LUC7L | LUC7L2 | LUC7L3 |
| LUM | LUZP1 | LUZP2 | LUZP4 | LXN |
| LY6D | LY6E | LY6G5B | LY6G5C | LY6G6C |
| LY6G6D | LY6G6F | LY6H | LY6K | LY75 |
| LY86 | LY9 | LY96 | LYAR | LYG1 |
| LYG2 | LYL1 | LYN | LYNX1 | LYNX1_ENST00000317543 |
| LYPD1 | LYPD2 | LYPD3 | LYPD4 | LYPD5 |
| LYPD6 | LYPLA1 | LYPLA2 | LYPLAL1 | LYRM1 |
| LYRM2 | LYRM4 | LYRM5 | LYRM7 | LYSMD1 |
| LYSMD2 | LYSMD3 | LYSMD4 | LYST | LYVE1 |
| LYZ | LYZL1 | LYZL2 | LYZL4 | LYZL6 |
| LZIC | LZTFL1 | LZTR1 | LZTS1 | LZTS2 |
| M6PR | MAB21L1 | MAB21L2 | MACC1 | MACF1 |
| MACF1_ENST00000361689 | MACROD1 | MACROD2 | MAD1L1 | MAD2L1 |
| MAD2L1BP | MAD2L2 | MADCAM1 | MADD | MAEA |
| MAEL | MAF | MAF1 | MAFA | MAFB |
| MAFF | MAFG | MAFK | MAG | MAGEA1 |
| MAGEA10 | MAGEA11 | MAGEA12 | MAGEA13P | MAGEA2 |
| MAGEA2B | MAGEA3 | MAGEA4 | MAGEA5 | MAGEA6 |
| MAGEA8 | MAGEA9 | MAGEA9B | MAGEB1 | MAGEB10 |
| MAGEB16 | MAGEB17 | MAGEB18 | MAGEB2 | MAGEB3 |
| MAGEB4 | MAGEB5 | MAGEB6 | MAGEB6B | MAGEC1 |
| MAGEC2 | MAGEC3 | MAGED1 | MAGED2 | MAGED4B |
| MAGEE1 | MAGEE2 | MAGEF1 | MAGEH1 | MAGI1 |
| MAGI1_ENST00000402939 | MAGI2 | MAGI3 | MAGIX | MAGOH |
| MAGOHB | MAGT1 | MAK | MAK16 | MAL |
| MALL | MALT1 | MAMDC2 | MAMDC4 | MAML1 |
| MAML2 | MAMLD1 | MAMSTR | MAN1A1 | MAN1A2 |
| MAN1B1 | MAN1C1 | MAN2A1 | MAN2A2 | MAN2B1 |
| MAN2B2 | MAN2C1 | MANBA | MANBAL | MANEA |
| MANEAL | MANSC1 | MAOA | MAOB | MAP1A |
| MAP1B | MAP1D | MAP1LC3A | MAP1LC3B | MAP1LC3B2 |
| MAP1LC3C | MAP1S | MAP2 | MAP2K1 | MAP2K2 |
| MAP2K3 | MAP2K4 | MAP2K5 | MAP2K6 | MAP2K7 |
| MAP3K1 | MAP3K10 | MAP3K11 | MAP3K12 | MAP3K13 |
| MAP3K14 | MAP3K15 | MAP3K2 | MAP3K3 | MAP3K4 |
| MAP3K5 | MAP3K6 | MAP3K6_ENST00000374040 | MAP3K7 | MAP3K8 |
| MAP3K9 | MAP4 | MAP4K1 | MAP4K2 | MAP4K3 |
| MAP4K4 | MAP4K5 | MAP6 | MAP6D1 | MAP7 |
| MAP7D1 | MAP7D2 | MAP7D3 | MAP9 | MAPK1 |
| MAPK10 | MAPK11 | MAPK12 | MAPK13 | MAPK14 |
| MAPK15 | MAPK1IP1L | MAPK3 | MAPK4 | MAPK6 |
| MAPK7 | MAPK8 | MAPK8IP1 | MAPK8IP2 | MAPK8IP3 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| MAPK9 | MAPKAP1 | MAPKAPK2 | MAPKAPK3 | MAPKAPK5 |
| MAPKBP1 | MAPKSP1 | MAPRE1 | MAPRE2 | MAPRE3 |
| MAPT | 01-Mar | 10-Mar | 02-Mar | 03-Mar |
| 04-Mar | 05-Mar | 06-Mar | 07-Mar | 08-Mar |
| 09-Mar | MARCKS | MARCKSL1 | MARCO | MARK1 |
| MARK2 | MARK3 | MARK4 | MARS | MARS2 |
| MARVELD2 | MARVELD3 | MAS1 | MAS1L | MASP1 |
| MASP2 | MAST1 | MAST2 | MAST2_ENST00000361297 | MAST3 |
| MAST4 | MASTL | MAT1A | MAT2A | MAT2B |
| MATK | MATN1 | MATN4 | MATR3 | MAVS |
| MAX | MAZ | MB | MB3L2_HUMAN | MBD1 |
| MBD2 | MBD3 | MBD3L1 | MBD3L2 | MBD4 |
| MBD5 | MBD6 | MBIP | MBL2 | MBLAC1 |
| MBLAC2 | MBNL1 | MBNL1_ENST00000282488 | MBNL2 | MBNL3 |
| MBOAT1 | MBOAT2 | MBOAT4 | MBOAT7 | MBP |
| MBTD1 | MBTPS1 | MBTPS2 | MC2R | MC3R |
| MC4R | MC5R | MCAM | MCART1 | MCART2 |
| MCART6 | MCAT | MCC | MCCC1 | MCCC2 |
| MCCD1 | MCC_ENST00000408903 | MCEE | MCF2 | MCF2L |
| MCF2L2 | MCFD2 | MCHR1 | MCHR2 | MCL1 |
| MCM10 | MCM2 | MCM3 | MCM3AP | MCM4 |
| MCM5 | MCM6 | MCM7 | MCM8 | MCM9 |
| MCOLN1 | MCOLN2 | MCOLN3 | MCPH1 | MCRS1 |
| MCTP1 | MCTP2 | MCTS1 | MDC1 | MDFI |
| MDFIC | MDGA1 | MDGA2 | MDH1 | MDH1B |
| MDH2 | MDK | MDM1 | MDM2 | MDM4 |
| MDN1 | MDP1 | MDS1 | MDS2 | ME1 |
| ME2 | ME3 | MEA1 | MEAF6 | MECOM |
| MECP2 | MECR | MED1 | MED10 | MED11 |
| MED12 | MED12L | MED13 | MED13L | MED14 |
| MED15 | MED16 | MED17 | MED18 | MED19 |
| MED20 | MED21 | MED22 | MED23 | MED24 |
| MED25 | MED26 | MED27 | MED28 | MED29 |
| MED30 | MED31 | MED4 | MED6 | MED7 |
| MED8 | MED9 | MEF2B | MEF2C | MEF2D |
| MEFV | MEGF10 | MEGF11 | MEGF6 | MEI1 |
| MEIG1 | MEIS1 | MEIS2 | MEIS3 | MELK |
| MEMO1 | MEMO1P | MEN1 | MEOX1 | MEOX2 |
| MEP1A | MEP1B | MEPCE | MEPE | MERTK |
| MESDC1 | MESDC2 | MESP1 | MESP2 | MEST |
| MET | METAP2 | METRN | METRNL | METT10D |
| METT11D1 | METT5D1 | METTL1 | METTL10 | METTL11A |
| METTL12 | METTL13 | METTL14 | METTL2A | METTL2B |
| METTL3 | METTL4 | METTL5 | METTL6 | METTL7A |
| METTL7B | METTL8 | METTL9 | MEX3A | MEX3B |
| MEX3C | MEX3D | MFAP1 | MFAP2 | MFAP3 |
| MFAP3L | MFAP4 | MFAP5 | MFF | MFGE8 |
| MFHAS1 | MFI2 | MFN1 | MFN2 | MFNG |
| MFRP | MFSD1 | MFSD10 | MFSD11 | MFSD2A |
| MFSD3 | MFSD4 | MFSD5 | MFSD6 | MFSD6L |
| MFSD7 | MFSD8 | MFSD9 | MGA | MGAM |
| MGAM_ENST00000473011 | MGAT1 | MGAT2 | MGAT3 | MGAT4A |
| MGAT4B | MGAT4C | MGAT5 | MGAT5B | MGC15476 |
| MGC17624 | MGC33414 | MGC33530 | MGC42105 | MGC57359 |
| MGC99813 | MGEA5 | MGLL | MGMT | MGP |
| MGRN1 | MGST1 | MGST2 | MGST3 | MIA |
| MIA2 | MIA3 | MIB1 | MIB2 | MICA3_HUMAN |
| MICAL1 | MICAL2 | MICAL3 | MICALCL | MICALL1 |
| MICALL2 | MICB | MID1 | MID1IP1 | MID2 |
| MIDN | MIER1 | MIER2 | MIER3 | MIF |
| MIF4GD | MIIP | MINA | MINK1 | MINPP1 |
| MIOS | MIOX | MIP | MIPEP | MIPOL1 |
| MIS12 | MITD1 | MITF | MIXL1 | MKI67 |
| MKI67IP | MKKS | MKL1 | MKL2 | MKLN1 |
| MKNK1 | MKNK2 | MKNK2_ENST00000250896 | MKRN1 | MKRN2 |
| MKRN3 | MKRN4P | MKS1 | MKX | MLANA |
| MLC1 | MLEC | MLF1 | MLF1IP | MLF2 |
| MLH1 | MLH3 | MLKL | MLL | MLL2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| MLL3 | MLL4 | MLL5 | MLLT1 | MLLT10 |
| MLLT11 | MLLT3 | MLLT4 | MLLT6 | MLN |
| MLNR | MLPH | MLST8 | MLST8_ENST00000301724 | MLX |
| MLXIP | MLXIPL | MLYCD | MMAA | MMAB |
| MMACHC | MMADHC | MMD | MMD2 | MME |
| MMEL1 | MMGT1 | MMP1 | MMP10 | MMP11 |
| MMP12 | MMP13 | MMP14 | MMP15 | MMP16 |
| MMP17 | MMP19 | MMP2 | MMP20 | MMP21 |
| MMP23B | MMP25 | MMP26 | MMP27 | MMP28 |
| MMP3 | MMP7 | MMP8 | MMP9 | MMPL1 |
| MMRN1 | MMRN2 | MN1 | MNAT1 | MND1 |
| MNDA | MNS1 | MNT | MNX1 | MOAP1 |
| MOBKL1A | MOBKL1B | MOBKL2A | MOBKL2B | MOBKL2C |
| MOBKL3 | MOBP | MOCOS | MOCS1 | MOCS2 |
| MOCS3 | MOG | MOGAT1 | MOGAT2 | MOGAT3 |
| MOGS | MON1A | MON1B | MON2 | MORC1 |
| MORC2 | MORC3 | MORC4 | MORF4L1 | MORF4L2 |
| MORN1 | MORN3 | MORN4 | MORN5 | MOS |
| MOSC1 | MOSC2 | MOSPD1 | MOSPD2 | MOSPD3 |
| MOV10 | MOV10L1 | MOXD1 | MOXD1_ENST00000336749 | MPDU1 |
| MPDZ | MPEG1 | MPG | MPHOSPH10 | MPHOSPH6 |
| MPHOSPH8 | MPHOSPH9 | MPI | MPL | MPND |
| MPO | MPP1 | MPP2 | MPP3 | MPP4 |
| MPP5 | MPP6 | MPP7 | MPPE1 | MPPED2 |
| MPRIP | MPST | MPV17 | MPV17L | MPV17L2 |
| MPZ | MPZL1 | MPZL2 | MPZL3 | MR1 |
| MRAP | MRAP2 | MRAS | MRC1 | MRC1L1 |
| MRC2 | MRE11A | MREG | MRFAP1 | MRFAP1L1 |
| MRGPRD | MRGPRE | MRGPRF | MRGPRG | MRGPRX1 |
| MRGPRX2 | MRGPRX3 | MRGPRX4 | MRI1 | MRM1 |
| MRO | MRP63 | MRPL1 | MRPL10 | MRPL11 |
| MRPL12 | MRPL13 | MRPL14 | MRPL15 | MRPL16 |
| MRPL17 | MRPL18 | MRPL19 | MRPL2 | MRPL20 |
| MRPL21 | MRPL22 | MRPL23 | MRPL24 | MRPL27 |
| MRPL28 | MRPL3 | MRPL30 | MRPL32 | MRPL33 |
| MRPL34 | MRPL35 | MRPL36 | MRPL37 | MRPL39 |
| MRPL4 | MRPL40 | MRPL41 | MRPL42 | MRPL43 |
| MRPL44 | MRPL45 | MRPL46 | MRPL47 | MRPL49 |
| MRPL50 | MRPL51 | MRPL52 | MRPL53 | MRPL54 |
| MRPL55 | MRPL9 | MRPS10 | MRPS11 | MRPS12 |
| MRPS14 | MRPS15 | MRPS16 | MRPS17 | MRPS18A |
| MRPS18B | MRPS18C | MRPS2 | MRPS21 | MRPS22 |
| MRPS23 | MRPS24 | MRPS25 | MRPS26 | MRPS27 |
| MRPS28 | MRPS30 | MRPS31 | MRPS33 | MRPS34 |
| MRPS35 | MRPS36 | MRPS5 | MRPS6 | MRPS7 |
| MRPS9 | MRRF | MRRFP1 | MRS2 | MRTO4 |
| MRVI1 | MS4A1 | MS4A10 | MS4A12 | MS4A13 |
| MS4A14 | MS4A15 | MS4A2 | MS4A3 | MS4A4A |
| MS4A5 | MS4A6A | MS4A6E | MS4A7 | MS4A8B |
| MSC | MSGN1 | MSH2 | MSH3 | MSH4 |
| MSH5 | MSH6 | MSI1 | MSI2 | MSL1 |
| MSL2 | MSL3 | MSLN | MSLNL | MSMB |
| MSMP | MSN | MSR1 | MSRA | MSRB2 |
| MSRB3 | MST1 | MST1R | MST4 | MSTN |
| MSTO1 | MSX1 | MSX2 | MT1A | MT1B |
| MT1E | MT1F | MT1G | MT1H | MT1M |
| MT1P2 | MT1X | MT2A | MT3 | MT4 |
| MTA1 | MTA2 | MTAC2D1 | MTAP | MTBP |
| MTCH1 | MTCH2 | MTCP1 | MTDH | MTERF |
| MTERFD1 | MTERFD2 | MTERFD3 | MTF1 | MTF2 |
| MTFR1 | MTG1 | MTHFD1 | MTHFD1L | MTHFD2 |
| MTHFD2L | MTHFR | MTHFS | MTHFSD | MTIF2 |
| MTIF3 | MTL5 | MTM1 | MTMR1 | MTMR10 |
| MTMR11 | MTMR12 | MTMR14 | MTMR15 | MTMR2 |
| MTMR3 | MTMR3_ENST00000401950 | MTMR4 | MTMR6 | MTMR7 |
| MTMR8 | MTMR9 | MTNR1A | MTNR1B | MTO1 |
| MTOR | MTP18 | MTPAP | MTPN | MTR |
| MTRF1 | MTRF1L | MTRR | MTSS1 | MTTP |
| MTUS1 | MTUS2 | MTUS2_ENST00000431530 | MTX1 | MTX2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| MUC1 | MUC13 | MUC15 | MUC16 | MUC16_ENST00000331986 |
| MUC17 | MUC2 | MUC21 | MUC4 | MUC4_ENST00000405167 |
| MUC5AC | MUC7 | MUCL1 | MUDENG | MUL1 |
| MUM1 | MUM1L1 | MURC | MUS81 | MUSK |
| MUT | MUTED | MUTYH | MVD | MVK |
| MVP | MX1 | MX2 | MXD1 | MXD3 |
| MXD4 | MXI1 | MXRA5 | MXRA7 | MXRA8 |
| MYADM | MYADML2 | MYB | MYBBP1A | MYBL1 |
| MYBL2 | MYBPC1 | MYBPC2 | MYBPC3 | MYBPH |
| MYBPHL | MYB_ENST00000341911 | MYC | MYCBP | MYCBP2 |
| MYCBPAP | MYCL1 | MYCL1_ENST00000397332 | MYCL2 | MYCN |
| MYCT1 | MYD88 | MYEF2 | MYEOV | MYEOV2 |
| MYF5 | MYF6 | MYH1 | MYH10 | MYH11 |
| MYH14 | MYH15 | MYH16 | MYH2 | MYH3 |
| MYH4 | MYH6 | MYH7 | MYH7B | MYH8 |
| MYH9 | MYL1 | MYL10 | MYL12A | MYL12B |
| MYL2 | MYL3 | MYL4 | MYL5 | MYL6 |
| MYL6B | MYL7 | MYL9 | MYLIP | MYLK |
| MYLK2 | MYLK3 | MYLK4 | MYLPF | MYNN |
| MYO10 | MYO15A | MYO16 | MYO18A | MYO18B |
| MYO1A | MYO1B | MYO1C | MYO1D | MYO1E |
| MYO1F | MYO1G | MYO3A | MYO3B | MYO5A |
| MYO5B | MYO5C | MYO6 | MYO7A | MYO9A |
| MYO9B | MYO9B_ENST00000319396 | MYOC | MYOCD | MYOD1 |
| MYOF | MYOG | MYOHD1 | MYOM1 | MYOM2 |
| MYOM3 | MYOT | MYOZ1 | MYOZ2 | MYOZ3 |
| MYPN | MYPOP | MYRIP | MYSM1 | MYST1 |
| MYST2 | MYST3 | MYST4 | MYT1 | MYT1L |
| MZF1 | Magmas | N4BP1 | N4BP2 | N4BP2L1 |
| N4BP2L2 | N4BP3 | N6AMT1 | N6AMT2 | NAA10 |
| NAA15 | NAA16 | NAA20 | NAA25 | NAA30 |
| NAA35 | NAA38 | NAA40 | NAA50 | NAAA |
| NAALAD2 | NAALADL1 | NAB1 | NAB2 | NACA |
| NACA2 | NACA3P | NACC1 | NACC2 | NADK |
| NADSYN1 | NAE1 | NAF1 | NAG6 | NAGA |
| NAGK | NAGLU | NAGPA | NAGS | NAIF1 |
| NAIP | NALCN | NALP6 | NAMPT | NANOG |
| NANOGP1 | NANOS1 | NANOS2 | NANOS3 | NANP |
| NANS | NAP1L1 | NAP1L2 | NAP1L3 | NAP1L4 |
| NAP1L5 | NAP1L6 | NAPA | NAPB | NAPEPLD |
| NAPRT1 | NAPSA | NAPSB | NARF | NARFL |
| NARG2 | NARS | NARS2 | NASP | NAT1 |
| NAT10 | NAT14 | NAT2 | NAT6 | NAT8 |
| NAT8L | NAT9 | NAV1 | NAV2 | NAV3 |
| NBAS | NBEA | NBEAL1 | NBEAL1_ENST00000449802 | NBEAL2 |
| NBL1 | NBN | NBPF11 | NBPF14 | NBPF15 |
| NBPF16 | NBPF3 | NBPF5 | NBPF7 | NBR1 |
| NCALD | NCAM2 | NCAN | NCAPD2 | NCAPD3 |
| NCAPG | NCAPG2 | NCAPH | NCAPH2 | NCBP1 |
| NCBP2 | NCBP2L | NCCRP1 | NCDN | NCEH1 |
| NCF1 | NCF2 | NCF4 | NCK1 | NCK2 |
| NCKAP1 | NCKAP1L | NCKAP5L | NCKAP5_ENST00000405974 | NCKIPSD |
| NCL | NCLN | NCOA1 | NCOA2 | NCOA3 |
| NCOA4 | NCOA5 | NCOA6 | NCOA7 | NCOR1 |
| NCOR2 | NCR1 | NCR2 | NCR3 | NCRNA00086 |
| NCRNA00103 | NCRNA00105 | NCRNA00169 | NCRNA00174 | NCRNA00175 |
| NCRNA00176 | NCRNA00188 | NCS1 | NCSTN | ND4 |
| NDC80 | NDE1 | NDEL1 | NDFIP1 | NDFIP2 |
| NDN | NDNL2 | NDOR1 | NDP | NDRG1 |
| NDRG2 | NDRG3 | NDRG4 | NDST1 | NDST2 |
| NDST3 | NDST4 | NDUFA1 | NDUFA10 | NDUFA11 |
| NDUFA12 | NDUFA13 | NDUFA2 | NDUFA3 | NDUFA4 |
| NDUFA4L2 | NDUFA5 | NDUFA6 | NDUFA7 | NDUFA8 |
| NDUFA9 | NDUFAB1 | NDUFAF1 | NDUFAF2 | NDUFAF3 |
| NDUFAF4 | NDUFB1 | NDUFB10 | NDUFB11 | NDUFB2 |
| NDUFB3 | NDUFB4 | NDUFB5 | NDUFB6 | NDUFB7 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| NDUFB8 | NDUFB9 | NDUFC1 | NDUFC2 | NDUFS1 |
| NDUFS2 | NDUFS3 | NDUFS4 | NDUFS5 | NDUFS6 |
| NDUFS7 | NDUFS8 | NDUFV1 | NDUFV2 | NDUFV3 |
| NEB | NEBL | NECAB1 | NECAB2 | NECAB3 |
| NECAP1 | NECAP2 | NEDD1 | NEDD4 | NEDD4L |
| NEDD8 | NEDD9 | NEFH | NEFL | NEFM |
| NEGR1 | NEIL1 | NEIL2 | NEIL3 | NEK1 |
| NEK10 | NEK11 | NEK2 | NEK3 | NEK4 |
| NEK5 | NEK6 | NEK7 | NEK8 | NEK9 |
| NELF | NELL1 | NELL2 | NENF | NEO1 |
| NES | NET1 | NETO1 | NETO2 | NEU1 |
| NEU2 | NEU4 | NEURL | NEURL2 | NEURL3 |
| NEURL4 | NEURL4_ENST00000315614 | NEUROD1 | NEUROD2 | NEUROD4 |
| NEUROD6 | NEUROG1 | NEUROG2 | NEUROG3 | NEXN |
| NF1 | NF2 | NFAM1 | NFASC | NFAT5 |
| NFATC1 | NFATC2 | NFATC2IP | NFATC3 | NFATC4 |
| NFE2 | NFE2L1 | NFE2L2 | NFE2L3 | NFIA |
| NFIB | NFIB_ENST00000397581 | NFIC | NFIL3 | NFIX |
| NFKB1 | NFKB2 | NFKBIA | NFKBIB | NFKBID |
| NFKBIE | NFKBIL1 | NFKBIL2 | NFKBIZ | NFRKB |
| NFS1 | NFU1 | NFX1 | NFXL1 | NFYA |
| NFYB | NFYC | NGB | NGDN | NGEF |
| NGF | NGFR | NGFRAP1 | NGLY1 | NGRN |
| NHEDC1 | NHEDC2 | NHEJ1 | NHLH1 | NHLH2 |
| NHLRC1 | NHLRC2 | NHLRC3 | NHP2 | NHP2L1 |
| NHS | NHSL1 | NHSL2 | NICN1 | NID1 |
| NID2 | NIF3L1 | NIN | NINJ1 | NINJ2 |
| NINL | NIP7 | NIPA1 | NIPA2 | NIPAL1 |
| NIPAL2 | NIPAL3 | NIPAL4 | NIPBL | NIPSNAP1 |
| NIPSNAP3A | NIPSNAP3B | NISCH | NIT1 | NIT2 |
| NKAIN1 | NKAIN2 | NKAIN4 | NKAP | NKAPL |
| NKD1 | NKD2 | NKG7 | NKIRAS1 | NKIRAS2 |
| NKPD1 | NKRF | NKTR | NKX2-1 | NKX2-2 |
| NKX2-3 | NKX2-4 | NKX2-5 | NKX2-6 | NKX2-8 |
| NKX3-1 | NKX3-2 | NKX6-1 | NKX6-2 | NKX6-3 |
| NLE1 | NLGN1 | NLGN2 | NLGN3 | NLGN4X |
| NLGN4Y | NLK | NLN | NLRC3 | NLRC4 |
| NLRC5 | NLRP1 | NLRP10 | NLRP11 | NLRP12 |
| NLRP13 | NLRP14 | NLRP2 | NLRP3 | NLRP4 |
| NLRP5 | NLRP6 | NLRP7 | NLRP8 | NLRP9 |
| NLRX1 | NMB | NMBR | NMD3 | NME1 |
| NME1-NME2 | NME2 | NME2P1 | NME3 | NME4 |
| NME5 | NME6 | NME7 | NMI | NMNAT1 |
| NMNAT2 | NMNAT3 | NMRAL1 | NMS | NMT1 |
| NMT2 | NMU | NMUR1 | NMUR2 | NM0010129842 |
| NM_001013679 | NM_001031_4 | NM_001039690_2 | NM_001080470_1 | NM024534 |
| NM_024588_3 | NM_032947_3 | NM_198455_2 | NNAT | NNMT |
| NNT | NOB1 | NOBOX | NOC2L | NOC3L |
| NOC4L | NOD1 | NOD2 | NODAL | NOG |
| NOL11 | NOL12 | NOL3 | NOL4 | NOL6 |
| NOL7 | NOL9 | NOLC1 | NOM1 | NOMO1 |
| NOMO2 | NOMO3 | NONO | NOP10 | NOP14 |
| NOP16 | NOP2 | NOP56 | NOP58 | NOS1 |
| NOS1AP | NOS1AP_ENST00000361897 | NOS2 | NOS3 | NOSIP |
| NOSTRIN | NOTCH1 | NOTCH2 | NOTCH2NL | NOTCH3 |
| NOTCH4 | NOTUM | NOV | NOVA1 | NOVA2 |
| NOX1 | NOX3 | NOX4 | NOX5 | NOXA1 |
| NOXO1 | NP12_HUMAN | NPAS1 | NPAS2 | NPAS3 |
| NPAS4 | NPAT | NPB | NPBWR1 | NPBWR2 |
| NPC1 | NPC1L1 | NPC2 | NPDC1 | NPEPPS |
| NPFF | NPFFR1 | NPFFR2 | NPHP1 | NPHP3 |
| NPHP4 | NPHS1 | NPHS2 | NPIP | NPIPL1 |
| NPIPL2 | NPL | NPLOC4 | NPM1 | NPM2 |
| NPM3 | NPNT | NPPA | NPPB | NPPC |
| NPR1 | NPR2 | NPR3 | NPS | NPSR1 |
| NPTN | NPTX1 | NPTX2 | NPTXR | NPVF |
| NPW | NPY | NPY1R | NPY2R | NPY5R |
| NPY6R | NP_001073948_1 | NQO1 | NQO2 | NR0B1 |
| NR0B2 | NR1D1 | NR1D2 | NR1H2 | NR1H3 |
| NR1H4 | NR1I2 | NR1I3 | NR2C1 | NR2C2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| NR2C2AP | NR2E1 | NR2E3 | NR2F1 | NR2F2 |
| NR2F6 | NR3C1 | NR3C2 | NR4A1 | NR4A2 |
| NR4A3 | NR5A1 | NR5A2 | NR6A1 | NRAP |
| NRARP | NRAS | NRBF2 | NRBP1 | NRBP2 |
| NRCAM | NRD1 | NRF1 | NRG1 | NRG2 |
| NRG3 | NRG4 | NRGN | NRIP1 | NRIP2 |
| NRIP3 | NRK | NRL | NRM | NRN1 |
| NRN1L | NRP1 | NRP2 | NRSN1 | NRSN2 |
| NRTN | NRXN1 | NRXN2 | NRXN3 | NR_002168_1 |
| NR_002217_1 | NR_002453_4 | NR_002730_1 | NR_002733_1 | NR_002781_1 |
| NR_002938_2 | NR_003034_1 | NR_003148_2 | NR_003276_1 | NSA2 |
| NSD1 | NSDHL | NSF | NSFL1C | NSL1 |
| NSMAF | NSMCE1 | NSMCE2 | NSMCE4A | NSUN2 |
| NSUN3 | NSUN4 | NSUN5 | NSUN5P1 | NSUN5P2 |
| NSUN6 | NSUN7 | NT5C | NT5C1A | NT5C1B |
| NT5C2 | NT5C3 | NT5C3L | NT5DC1 | NT5DC2 |
| NT5DC3 | NT5E | NT5M | NTAN1 | NTF3 |
| NTF4 | NTHL1 | NTM | NTN1 | NTN3 |
| NTN4 | NTN5 | NTNG1 | NTNG2 | NTRK1 |
| NTRK2 | NTRK3 | NTS | NTSR1 | NTSR2 |
| NUAK1 | NUAK2 | NUB1 | NUBP1 | NUBP2 |
| NUBPL | NUCB1 | NUCB2 | NUCKS1 | NUDC |
| NUDCD1 | NUDCD2 | NUDCD3 | NUDT1 | NUDT10 |
| NUDT11 | NUDT12 | NUDT13 | NUDT14 | NUDT15 |
| NUDT16 | NUDT16L1 | NUDT17 | NUDT19 | NUDT2 |
| NUDT21 | NUDT22 | NUDT3 | NUDT4 | NUDT5 |
| NUDT6 | NUDT7 | NUDT8 | NUDT9 | NUF2 |
| NUFIP1 | NUFIP2 | NUMA1 | NUMB | NUMBL |
| NUP107 | NUP133 | NUP153 | NUP155 | NUP160 |
| NUP188 | NUP205 | NUP210 | NUP210L | NUP214 |
| NUP35 | NUP37 | NUP43 | NUP50 | NUP54 |
| NUP62 | NUP62CL | NUP85 | NUP88 | NUP93 |
| NUP98 | NUPL1 | NUPL2 | NUPR1 | NUS1 |
| NUTF2 | NVL | NWD1 | NXF1 | NXF2 |
| NXF2B | NXF3 | NXF4 | NXF5 | NXN |
| NXNL1 | NXNL2 | NXPH1 | NXPH2 | NXPH3 |
| NXPH4 | NXT1 | NXT2 | NYNRIN | NYX |
| O00434_HUMAN | O10D4_HUMAN | O10J6_HUMAN | O52L2_HUMAN | O5AK3_HUMAN |
| O60374_HUMAN | O60384_HUMAN | O60411_HUMAN | O75863_HUMAN | O95014_HUMAN |
| O95431_HUMAN | OAF | OAS1 | OAS2 | OAS3 |
| OASL | OAT | OAZ1 | OBFC1 | OBFC2A |
| OBFC2B | OBP2A | OBP2B | OBSCN | OBSCN_ENST00000359599 |
| OBSL1 | OC90 | OC90_ENST00000262283 | OCA2 | OCEL1 |
| OCIAD1 | OCIAD2 | OCLN | OCM | OCM2 |
| OCRL | ODAM | ODC1 | ODF1 | ODF2 |
| ODF2L | ODF3 | ODF3B | ODF3L1 | ODF3L2 |
| ODF4 | ODZ1 | ODZ2 | OFCC1 | OFD1 |
| OGDH | OGDHL | OGFOD1 | OGFOD2 | OGFR |
| OGFRL1 | OGG1 | OGN | OGT | OGT_ENST00000373719 |
| OIP5 | OIT3 | OLA1 | OLAH | OLFM1 |
| OLFM2 | OLFM3 | OLFM4 | OLFML1 | OLFML2A |
| OLFML2B | OLFML3 | OLIG1 | OLIG2 | OLIG3 |
| OLR1 | OMA1 | OMD | OMG | ONECUT1 |
| ONECUT2 | OPA1 | OPA3 | OPALIN | OPCML |
| OPHN1 | OPLAH | OPN1LW | OPN1MW | OPN1MW2 |
| OPN1SW | OPN3 | OPN4 | OPN5 | OPRD1 |
| OPRK1 | OPRL1 | OPRM1 | OPTC | OPTN |
| OR10A2 | OR10A3 | OR10A4 | OR10A5 | OR10A6 |
| OR10A7 | OR10AD1 | OR10AG1 | OR10C1 | OR10G2 |
| OR10G3 | OR10G4 | OR10G6 | OR10G7 | OR10G8 |
| OR10G9 | OR10H1 | OR10H2 | OR10H3 | OR10H4 |
| OR10H5 | OR10J1 | OR10J3 | OR10J5 | OR10K1 |
| OR10K2 | OR10P1 | OR10Q1 | OR10R2 | OR10R3P |
| OR10S1 | OR10T2 | OR10V1 | OR10W1 | OR10X1 |
| OR10Z1 | OR11A1 | OR11G2 | OR11H1 | OR11H12 |
| OR11H4 | OR11H6 | OR11L1 | OR12D2 | OR12D3 |
| OR13A1 | OR13C2 | OR13C3 | OR13C4 | OR13C5 |
| OR13C8 | OR13C9 | OR13D1 | OR13F1 | OR13G1 |
| OR13H1 | OR13J1 | OR14A16 | OR14C36 | OR14I1 |
| OR14J1 | OR1A1 | OR1A2 | OR1B1 | OR1C1 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| OR1D2 | OR1D4 | OR1E1 | OR1E2 | OR1F1 |
| OR1G1 | OR1I1 | OR1J1 | OR1J2 | OR1J4 |
| OR1K1 | OR1L1 | OR1L3 | OR1L4 | OR1L6 |
| OR1L8 | OR1M1 | OR1N1 | OR1N2 | OR1Q1 |
| OR1S1 | OR1S2 | OR2A12 | OR2A14 | OR2A2 |
| OR2A25 | OR2A4 | OR2A5 | OR2AE1 | OR2AG1 |
| OR2AG2 | OR2AJ1 | OR2AK2 | OR2AP1 | OR2AT4 |
| OR2B11 | OR2B2 | OR2B3P | OR2B6 | OR2C1 |
| OR2C3 | OR2D2 | OR2D3 | OR2F1 | OR2F2 |
| OR2G2 | OR2G3 | OR2G6 | OR2H1 | OR2H2 |
| OR2J1 | OR2J2 | OR2J3 | OR2J3_HUMAN | OR2K2 |
| OR2L13 | OR2L1P | OR2L2 | OR2L3 | OR2L8 |
| OR2M1P | OR2M2 | OR2M3 | OR2M4 | OR2M5 |
| OR2M7 | OR2S2 | OR2T1 | OR2T10 | OR2T11 |
| OR2T12 | OR2T2 | OR2T27 | OR2T3 | OR2T33 |
| OR2T34 | OR2T35 | OR2T4 | OR2T5 | OR2T6 |
| OR2T8 | OR2V2 | OR2W1 | OR2W3 | OR2W5 |
| OR2Y1 | OR2Z1 | OR3A1 | OR3A3 | OR3A4 |
| OR4A13P | OR4A15 | OR4A16 | OR4A47 | OR4A5 |
| OR4B1 | OR4C11 | OR4C12 | OR4C13 | OR4C15 |
| OR4C16 | OR4C3 | OR4C46 | OR4C5_HUMAN | OR4C6 |
| OR4D1 | OR4D10 | OR4D11 | OR4D2 | OR4D5 |
| OR4D6 | OR4D9 | OR4E2 | OR4F15 | OR4F16 |
| OR4F17 | OR4F21 | OR4F29 | OR4F3 | OR4F4 |
| OR4F5 | OR4F6 | OR4K1 | OR4K13 | OR4K14 |
| OR4K15 | OR4K17 | OR4K2 | OR4K5 | OR4L1 |
| OR4M1 | OR4M2 | OR4N2 | OR4N4 | OR4N5 |
| OR4P4 | OR4Q3 | OR4S1 | OR4S2 | OR4X1 |
| OR4X2 | OR51A2 | OR51A4 | OR51A7 | OR51B2 |
| OR51B4 | OR51B5 | OR51B6 | OR51D1 | OR51E1 |
| OR51E2 | OR51F1 | OR51F2 | OR51G1 | OR51G2 |
| OR51H1P | OR51I1 | OR51I2 | OR51J1 | OR51L1 |
| OR51M1 | OR51Q1 | OR51S1 | OR51T1 | OR51V1 |
| OR52A1 | OR52A4 | OR52A5 | OR52B4 | OR52B6 |
| OR52D1 | OR52E2 | OR52E4 | OR52E6 | OR52E8 |
| OR52H1 | OR52I1 | OR52I2 | OR52J3 | OR52K1 |
| OR52K2 | OR52L1 | OR52M1 | OR52N1 | OR52N2 |
| OR52N4 | OR52N5 | OR52R1 | OR52W1 | OR56A1 |
| OR56A3 | OR56A4 | OR56B1 | OR56B4 | OR5A1 |
| OR5A2 | OR5AC2 | OR5AK2 | OR5AN1 | OR5AP2 |
| OR5AR1 | OR5AS1 | OR5AU1 | OR5AX1 | OR5B12 |
| OR5B17 | OR5B2 | OR5B21 | OR5B3 | OR5C1 |
| OR5D13 | OR5D14 | OR5D16 | OR5D18 | OR5D3P |
| OR5E1P | OR5F1 | OR5H1 | OR5H14 | OR5H15 |
| OR5H2 | OR5H6 | OR5I1 | OR5J2 | OR5K1 |
| OR5K2 | OR5K3 | OR5K4 | OR5L1 | OR5L2 |
| OR5M1 | OR5M3 | OR5M8 | OR5M9 | OR5P2 |
| OR5P3 | OR5R1 | OR5T1 | OR5T2 | OR5T3 |
| OR5V1 | OR5W2 | OR6A2 | OR6B1 | OR6B3 |
| OR6C1 | OR6C2 | OR6C3 | OR6C4 | OR6C6 |
| OR6C65 | OR6C68 | OR6C70 | OR6C74 | OR6C75 |
| OR6C76 | OR6F1 | OR6J1_HUMAN | OR6K2 | OR6K3 |
| OR6K6 | OR6M1 | OR6N1 | OR6N2 | OR6P1 |
| OR6Q1 | OR6S1 | OR6T1 | OR6W1P | OR6X1 |
| OR6Y1 | OR7A10 | OR7A17 | OR7A5 | OR7C1 |
| OR7C2 | OR7D2 | OR7D4 | OR7E24 | OR7E5P |
| OR7G1 | OR7G2 | OR7G3 | OR8A1 | OR8B12 |
| OR8B2 | OR8B3 | OR8B4 | OR8B8 | OR8D1 |
| OR8D2 | OR8D4 | OR8H1 | OR8H2 | OR8H3 |
| OR8I2 | OR8J1 | OR8J3 | OR8K1 | OR8K3 |
| OR8K5 | OR8S1 | OR8U1 | OR9A2 | OR9A4 |
| OR9G1 | OR9G4 | OR9I1 | OR9K2 | OR9Q1 |
| OR9Q2 | ORAI1 | ORAI2 | ORAI3 | ORAOV1 |
| ORC1L | ORC2L | ORC3L | ORC4L | ORC5L |
| ORC6L | ORM1 | ORM2 | ORMDL1 | ORMDL2 |
| ORMDL3 | OS9 | OSBP | OSBP2 | OSBPL10 |
| OSBPL10_ENST00000396556 | OSBPL11 | OSBPL1A | OSBPL2 | OSBPL3 |
| OSBPL5 | OSBPL6 | OSBPL7 | OSBPL8 | OSBPL9 |
| OSCAR | OSCP1 | OSGEP | OSGIN1 | OSGIN2 |
| OSM | OSMR | OSR1 | OSR2 | OSTC |
| OSTCL | OSTF1 | OSTM1 | OSTN | OSTalpha |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| OSTbeta | OTC | OTOA | OTOF | OTOF_ENST00000361394 |
| OTOG | OTOP1 | OTOP2 | OTOP3 | OTOR |
| OTOS | OTP | OTUB1 | OTUB2 | OTUD1 |
| OTUD3 | OTUD4 | OTUD5 | OTUD5_ENST00000453548 | OTUD6A |
| OTUD7A | OTUD7B | OTX1 | OTX2 | OVCH1 |
| OVCH2 | OVGP1 | OVOL1 | OVOL2 | OXA1L |
| OXCT1 | OXCT2 | OXER1 | OXGR1 | OXNAD1 |
| OXR1 | OXSM | OXSR1 | OXT | OXTR |
| P117 | P2RX1 | P2RX2 | P2RX3 | P2RX4 |
| P2RX5 | P2RX7 | P2RXL1 | P2RY1 | P2RY10 |
| P2RY11 | P2RY12 | P2RY13 | P2RY14 | P2RY2 |
| P2RY4 | P2RY6 | P2RY8 | P461_HUMAN | P4HA1 |
| P4HA2 | P4HA3 | P4HB | P4HTM | P78389_HUMAN |
| P78561_HUMAN | PA2G4 | PAAF1 | PABPC1 | PABPC1L |
| PABPC1L2A | PABPC1L2B | PABPC3 | PABPC4 | PABPC5 |
| PABPCP2 | PABPN1 | PACRG | PACRGL | PACS1 |
| PACS2 | PACSIN1 | PACSIN2 | PACSIN3 | PADI1 |
| PADI2 | PADI3 | PADI4 | PADI6 | PAEP |
| PAF1 | PAFAH1B1 | PAFAH1B2 | PAFAH1B3 | PAFAH2 |
| PAG1 | PAGE1 | PAGE2 | PAGE2B | PAGE3 |
| PAGE4 | PAGE5 | PAH | PAICS | PAIP1 |
| PAIP2 | PAIP2B | PAK1 | PAK1IP1 | PAK2 |
| PAK3 | PAK4 | PAK6 | PAK7 | PALB2 |
| PALLD | PALM | PALM2 | PALM2-AKAP2 | PALMD |
| PAM | PAMR1 | PAN2 | PAN3 | PANK1 |
| PANK2 | PANK3 | PANK4 | PANX1 | PANX2 |
| PANX3 | PAOX | PAOX_ENST00000357296 | PAP2D | PAPD4 |
| PAPD5 | PAPD5_ENST00000436909 | PAPD7 | PAPLN | PAPOLA |
| PAPOLB | PAPOLG | PAPPA | PAPPA2 | PAPSS1 |
| PAPSS2 | PAQR3 | PAQR4 | PAQR5 | PAQR6 |
| PAQR7 | PAQR8 | PAQR9 | PARD3 | PARD3B |
| PARD6A | PARD6B | PARD6G | PARG | PARK2 |
| PARK7 | PARL | PARP1 | PARP10 | PARP11 |
| PARP12 | PARP14 | PARP15 | PARP16 | PARP2 |
| PARP3 | PARP4 | PARP6 | PARP8 | PARP9 |
| PARS2 | PARVA | PARVB | PARVG | PASD1 |
| PASK | PATE1 | PATE2 | PATZ1 | PAWR |
| PAX1 | PAX2 | PAX3 | PAX4 | PAX5 |
| PAX6 | PAX7 | PAX8 | PAX9 | PAXIP1 |
| PBK | PBLD | PBRM1 | PBX1 | PBX2 |
| PBX3 | PBX4 | PBXIP1 | PC | PCBD1 |
| PCBD2 | PCBP1 | PCBP2 | PCBP3 | PCBP4 |
| PCCA | PCCB | PCDH1 | PCDH10 | PCDH11X |
| PCDH11Y | PCDH12 | PCDH15 | PCDH17 | PCDH18 |
| PCDH19 | PCDH19_NM_020766_1 | PCDH20 | PCDH24 | PCDH7 |
| PCDH8 | PCDH9 | PCDHA1 | PCDHA10 | PCDHA10_ENST00000505235 |
| PCDHA11 | PCDHA13 | PCDHA2 | PCDHA3 | PCDHA4 |
| PCDHA5 | PCDHA6 | PCDHA7 | PCDHA8 | PCDHA9 |
| PCDHAC1 | PCDHAC2 | PCDHB1 | PCDHB10 | PCDHB11 |
| PCDHB12 | PCDHB13 | PCDHB14 | PCDHB15 | PCDHB16 |
| PCDHB18 | PCDHB2 | PCDHB3 | PCDHB4 | PCDHB5 |
| PCDHB6 | PCDHB7 | PCDHB8 | PCDHGA1 | PCDHGA12 |
| PCDHGA12_ENST00000252085 | PCDHGA2 | PCDHGA3 | PCDHGA6 | PCDHGB7 |
| PCDHGC3 | PCDHGC3_ENST00000308177 | PCDHGC4 | PCDHGC5 | PCDHGC5_ENST00000252087 |
| PCF11 | PCGF1 | PCGF2 | PCGF3 | PCGF5 |
| PCGF6 | PCID2 | PCIF1 | PCK1 | PCK2 |
| PCM1 | PCMT1 | PCMTD1 | PCMTD2 | PCNA |
| PCNP | PCNT | PCNX | PCNXL2 | PCNXL3 |
| PCOLCE | PCOLCE2 | PCP2 | PCP4 | PCQAP |
| PCSK1 | PCSK1N | PCSK2 | PCSK4 | PCSK5 |
| PCSK5_ENST00000376767 | PCSK7 | PCSK9 | PCTP | PCYOX1 |
| PCYOX1L | PCYT1A | PCYT1B | PCYT2 | PDAP1 |
| PDC | PDCD1 | PDCD10 | PDCD11 | PDCD1LG2 |
| PDCD2 | PDCD2L | PDCD4 | PDCD5 | PDCD6 |
| PDCD6IP | PDCD7 | PDCD8 | PDCL | PDCL3 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| PDDC1 | PDE10A | PDE11A | PDE12 | PDE1A |
| PDE1B | PDE1C | PDE2A | PDE3A | PDE3B |
| PDE4A | PDE4B | PDE4B_ENST00000423207 | PDE4C | PDE4D |
| PDE4DIP | PDE5A | PDE6A | PDE6B | PDE6C |
| PDE6D | PDE6G | PDE6H | PDE7A | PDE7B |
| PDE8A | PDE8B | PDE9A | PDGFA | PDGFB |
| PDGFC | PDGFD | PDGFRA | PDGFRB | PDGFRL |
| PDHA1 | PDHA2 | PDHB | PDHX | PDIA2 |
| PDIA3 | PDIA4 | PDIA5 | PDIA6 | PDIK1L |
| PDILT | PDK1 | PDK2 | PDK3 | PDK4 |
| PDLIM1 | PDLIM2 | PDLIM3 | PDLIM4 | PDLIM5 |
| PDLIM7 | PDP1 | PDP2 | PDPK1 | PDPN |
| PDPR | PDRG1 | PDS5B | PDSS1 | PDSS2 |
| PDX1 | PDXDC1 | PDXDC2 | PDXK | PDXP |
| PDYN | PDZD11 | PDZD2 | PDZD3 | PDZD4 |
| PDZD7 | PDZD8 | PDZK1 | PDZK1IP1 | PDZRN3 |
| PDZRN4 | PEA15 | PEAR1 | PEBP1 | PEBP4 |
| PECI | PECR | PEF1 | PEG10 | PEG3 |
| PELI1 | PELI2 | PELI3 | PELO | PELP1 |
| PEMT | PENK | PEPD | PER1 | PER2 |
| PER3 | PERP | PES1 | PET112L | PEX1 |
| PEX10 | PEX11A | PEX11B | PEX11G | PEX12 |
| PEX13 | PEX14 | PEX16 | PEX19 | PEX2 |
| PEX26 | PEX3 | PEX5 | PEX5L | PEX6 |
| PEX7 | PF4 | PF4V1 | PFAS | PFDN1 |
| PFDN2 | PFDN4 | PFDN5 | PFDN6 | PFKFB1 |
| PFKFB2 | PFKFB3 | PFKFB4 | PFKL | PFKM |
| PFKP | PFN1 | PFN2 | PFN3 | PFN4 |
| PGA3 | PGA4 | PGA5 | PGAM1 | PGAM1_HUMAN |
| PGAM2 | PGAM4 | PGAM5 | PGAP1 | PGAP3 |
| PGBD1 | PGBD2 | PGBD3 | PGBD4 | PGBD5 |
| PGC | PGCP | PGD | PGF | PGGT1B |
| PGK1 | PGK2 | PGLS | PGLYRP1 | PGLYRP2 |
| PGLYRP3 | PGLYRP4 | PGM1 | PGM2 | PGM2L1 |
| PGM3 | PGM5 | PGP | PGPEP1 | PGR |
| PGRMC1 | PGRMC2 | PGS1 | PHACTR2 | PHACTR3 |
| PHACTR4 | PHAX | PHB | PHC1 | PHC1B |
| PHC2 | PHC3 | PHEX | PHF1 | PHF10 |
| PHF11 | PHF12 | PHF13 | PHF14 | PHF15 |
| PHF16 | PHF17 | PHF19 | PHF2 | PHF20 |
| PHF20L1 | PHF21A | PHF21B | PHF23 | PHF3 |
| PHF5A | PHF6 | PHF7 | PHF8 | PHGDH |
| PHIP | PHKA1 | PHKA2 | PHKB | PHKG1 |
| PHKG2 | PHLDA1 | PHLDA2 | PHLDA3 | PHLDB1 |
| PHLDB2 | PHLDB3 | PHLPP | PHLPP2 | PHOSPHO1 |
| PHOSPHO2 | PHOX2A | PHOX2B | PHPT1 | PHTF1 |
| PHYH | PHYHD1 | PHYHIP | PHYHIPL | PI15 |
| PI16 | PI3 | PI4K2A | PI4K2B | PI4KA |
| PI4KAP2 | PI4KB | PIAS1 | PIAS2 | PIAS3 |
| PIAS4 | PIBF1 | PICALM | PICK1 | PID1 |
| PIF1 | PIGA | PIGB | PIGC | PIGF |
| PIGG | PIGH | PIGK | PIGL | PIGM |
| PIGN | PIGO | PIGP | PIGQ | PIGR |
| PIGS | PIGT | PIGU | PIGV | PIGW |
| PIGX | PIGZ | PIH1D1 | PIH1D2 | PIK3AP1 |
| PIK3C2A | PIK3C2B | PIK3C2G | PIK3C3 | PIK3CA |
| PIK3CB | PIK3CD | PIK3CG | PIK3IP1 | PIK3R1 |
| PIK3R2 | PIK3R3 | PIK3R4 | PIK3R5 | PIKFYVE |
| PILRA | PILRB | PIM1 | PIM2 | PIM3 |
| PIN1 | PIN4 | PINK1 | PINX1 | PION |
| PIP | PIP4K2A | PIP4K2B | PIP4K2C | PIP5K1A |
| PIP5K1B | PIP5K1C | PIP5KL1 | PIPOX | PIR |
| PISD | PITPNA | PITPNB | PITPNC1 | PITPNM1 |
| PITPNM2 | PITPNM3 | PITRM1 | PITX1 | PITX2 |
| PITX3 | PIWIL1 | PIWIL2 | PIWIL3 | PIWIL4 |
| PJA1 | PJA2 | PKD1 | PKD1L1 | PKD1L2 |
| PKD1L2_ENST00000360678 | PKD1L3 | PKD2 | PKD2L1 | PKD2L2 |
| PKDREJ | PKHD1 | PKHD1L1 | PKIA | PKIB |
| PKIG | PKLR | PKM2 | PKMYT1 | PKN1 |
| PKN2 | PKN3 | PKNOX1 | PKNOX2 | PKP1 |
| PKP2 | PKP3 | PKP4 | PLA1A | PLA2G10 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| PLA2G12A | PLA2G12B | PLA2G15 | PLA2G16 | PLA2G1B |
| PLA2G2A | PLA2G2C | PLA2G2D | PLA2G2E | PLA2G2F |
| PLA2G3 | PLA2G4A | PLA2G4C | PLA2G4D | PLA2G4F |
| PLA2G5 | PLA2G6 | PLA2G7 | PLA2R1 | PLAA |
| PLAC1 | PLAC1L | PLAC8 | PLAC8L1 | PLAC9 |
| PLAG1 | PLAGL1 | PLAGL2 | PLAT | PLAU |
| PLAUR | PLB1 | PLBD1 | PLBD2 | PLCB1 |
| PLCB2 | PLCB3 | PLCB4 | PLCD1 | PLCD3 |
| PLCD4 | PLCE1 | PLCG1 | PLCG2 | PLCH1 |
| PLCH2 | PLCL1 | PLCL2 | PLCXD1 | PLCXD2 |
| PLCXD3 | PLCZ1 | PLD1 | PLD2 | PLD3 |
| PLD4 | PLD5 | PLD6 | PLDN | PLEC |
| PLEK | PLEK2 | PLEKHA1 | PLEKHA3 | PLEKHA4 |
| PLEKHA5 | PLEKHA5_ENST00000429027 | PLEKHA6 | PLEKHA7 | PLEKHA8 |
| PLEKHA9 | PLEKHB1 | PLEKHB2 | PLEKHF1 | PLEKHF2 |
| PLEKHG1 | PLEKHG2 | PLEKHG3 | PLEKHG4 | PLEKHG4B |
| PLEKHG4B_ENST00000283426 | PLEKHG5 | PLEKHG6 | PLEKHG7 | PLEKHH1 |
| PLEKHH2 | PLEKHH3 | PLEKHJ1 | PLEKHM1 | PLEKHN1 |
| PLEKHO1 | PLEKHO2 | PLG | PLGLB1 | PLGLB2 |
| PLIN1 | PLIN2 | PLIN3 | PLIN4 | PLIN5 |
| PLK1 | PLK2 | PLK3 | PLK4 | PLLP |
| PLN | PLOD1 | PLOD2 | PLOD3 | PLP1 |
| PLP2 | PLRG1 | PLS1 | PLS3 | PLSCR1 |
| PLSCR2 | PLSCR3 | PLSCR3_ENST00000324822 | PLSCR4 | PLTP |
| PLUNC | PLVAP | PLXDC1 | PLXDC2 | PLXNA1 |
| PLXNA2 | PLXNA3 | PLXNA4 | PLXNB1 | PLXNB2 |
| PLXNB3 | PLXNC1 | PLXND1 | PM20D1 | PM20D2 |
| PMAIP1 | PMCH | PMEPA1 | PMF1 | PMFBP1 |
| PML | PMM1 | PMM2 | PMP2 | PMP22 |
| PMPCA | PMPCB | PMS1 | PMS2 | PMS2L1 |
| PMS2L11 | PMS2L3 | PMS2L4 | PMS2L5 | PMVK |
| PNCK | PNKD | PNKP | PNLDC1 | PNLIP |
| PNLIPRP1 | PNLIPRP2 | PNLIPRP3 | PNMA1 | PNMA2 |
| PNMA3 | PNMA5 | PNMA6A | PNMAL1 | PNMAL2 |
| PNMT | PNN | PNO1 | PNOC | PNP |
| PNPLA1 | PNPLA2 | PNPLA3 | PNPLA4 | PNPLA5 |
| PNPLA6 | PNPLA7 | PNPLA8 | PNPO | PNPT1 |
| PNRC1 | PNRC2 | PODN | PODNL1 | PODXL |
| PODXL2 | POF1B | POFUT1 | POFUT2 | POGK |
| POGZ | POL3S | POLA1 | POLA2 | POLB |
| POLD1 | POLD2 | POLD3 | POLD4 | POLDIP3 |
| POLE | POLE2 | POLE3 | POLE4 | POLG |
| POLG2 | POLH | POLI | POLK | POLL |
| POLM | POLN | POLQ | POLR1A | POLR1B |
| POLR1C | POLR1D | POLR1E | POLR2A | POLR2B |
| POLR2C | POLR2D | POLR2E | POLR2F | POLR2G |
| POLR2H | POLR2I | POLR2J | POLR2J2 | POLR2K |
| POLR2L | POLR3A | POLR3B | POLR3C | POLR3D |
| POLR3E | POLR3F | POLR3G | POLR3GL | POLR3H |
| POLR3K | POLRMT | POM121 | POM121L3 | POMC |
| POMGNT1 | POMP | POMT1 | POMT2 | POMZP3 |
| PON1 | PON2 | PON3 | POP1 | POP4 |
| POP5 | POP7 | POPDC2 | POPDC3 | POR |
| PORCN | POSTN | POT1 | POT14_HUMAN | POTE2_HUMAN |
| POTEA | POTEB | POTED | POTEF | POTEG |
| POU1F1 | POU2AF1 | POU2F1 | POU2F2 | POU2F3 |
| POU3F1 | POU3F2 | POU3F3 | POU3F4 | POU4F1 |
| POU4F2 | POU4F3 | POU5F1 | POU6F1 | POU6F2 |
| PPA1 | PPA2 | PPAN | PPAN-P2RY11 | PPAP2A |
| PPAP2B | PPAP2C | PPAPDC1A | PPAPDC2 | PPAPDC3 |
| PPARA | PPARD | PPARG | PPARGC1A | PPARGC1B |
| PPAT | PPBP | PPCDC | PPCS | PPDPF |
| PPEF1 | PPEF2 | PPFIA1 | PPFIA2 | PPFIA3 |
| PPFIA4 | PPFIBP1 | PPFIBP2 | PPHLN1 | PPIA |
| PPIAL4A | PPIAL4G | PPIA_HUMAN | PPIB | PPIC |
| PPID | PPIE | PPIF | PPIG | PPIH |
| PPIL1 | PPIL2 | PPIL3 | PPIL4 | PPIL5 |
| PPIL6 | PPIP5K1 | PPIP5K2 | PPL | PPM1A |
| PPM1B | PPM1D | PPM1E | PPM1F | PPM1G |
| PPM1H | PPM1J | PPM1K | PPM1L | PPOX |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| PPP1CA | PPP1CB | PPP1CC | PPP1R10 | PPP1R11 |
| PPP1R12A | PPP1R12B | PPP1R12C | PPP1R13B | PPP1R13L |
| PPP1R14A | PPP1R14B | PPP1R14C | PPP1R14D | PPP1R15A |
| PPP1R15B | PPP1R16A | PPP1R16B | PPP1R1A | PPP1R1B |
| PPP1R1C | PPP1R2 | PPP1R2P9 | PPP1R3A | PPP1R3B |
| PPP1R3C | PPP1R3D | PPP1R3E | PPP1R3F | PPP1R3G |
| PPP1R7 | PPP1R8 | PPP1R9A | PPP1R9B | PPP2CA |
| PPP2CB | PPP2R1A | PPP2R1B | PPP2R2A | PPP2R2B |
| PPP2R2C | PPP2R2D | PPP2R3A | PPP2R3B | PPP2R3C |
| PPP2R4 | PPP2R5A | PPP2R5B | PPP2R5C | PPP2R5D |
| PPP2R5E | PPP3CA | PPP3CB | PPP3CC | PPP3R1 |
| PPP3R2 | PPP4C | PPP4R1 | PPP4R1L | PPP4R2 |
| PPP4R4 | PPP5C | PPP6C | PPPDE1 | PPPDE2 |
| PPRC1 | PPT1 | PPT2 | PPTC7 | PPWD1 |
| PPY | PPYR1 | PQBP1 | PQLC1 | PQLC2 |
| PQLC3 | PRAF2 | PRAME | PRAMEF1 | PRAMEF10 |
| PRAMEF12 | PRAMEF13 | PRAMEF14 | PRAMEF16 | PRAMEF17 |
| PRAMEF18 | PRAMEF19 | PRAMEF2 | PRAMEF20 | PRAMEF21 |
| PRAMEF22 | PRAMEF3 | PRAMEF4 | PRAMEF5 | PRAMEF6 |
| PRAMEF7 | PRAMEF8 | PRAMEF9 | PRAMEL | PRAP1 |
| PRB1 | PRB2 | PRB4 | PRC1 | PRCC |
| PRCC_ENST00000353233 | PRCD | PRCP | PRDM1 | PRDM10 |
| PRDM11 | PRDM12 | PRDM13 | PRDM14 | PRDM15 |
| PRDM16 | PRDM2 | PRDM4 | PRDM5 | PRDM7 |
| PRDM8 | PRDM9 | PRDX1 | PRDX2 | PRDX3 |
| PRDX4 | PRDX5 | PRDX6 | PREB | PRELID1 |
| PRELID2 | PRELP | PREP | PREPL | PREX1 |
| PREX2 | PRF1 | PRG-3 | PRG2 | PRG3 |
| PRG4 | PRH2 | PRIC285 | PRICKLE1 | PRICKLE2 |
| PRICKLE3 | PRICKLE4 | PRIM2 | PRIMA1 | PRKAA1 |
| PRKAA2 | PRKAA2_ENST00000371244 | PRKAB1 | PRKAB2 | PRKACA |
| PRKACB | PRKACB_ENST00000370685 | PRKACG | PRKAG1 | PRKAG2 |
| PRKAG3 | PRKAR1A | PRKAR1B | PRKAR2A | PRKAR2B |
| PRKCA | PRKCB | PRKCD | PRKCDBP | PRKCE |
| PRKCG | PRKCH | PRKCI | PRKCQ | PRKCSH |
| PRKCZ | PRKD1 | PRKD1_ENST00000331968 | PRKD2 | PRKD3 |
| PRKDC | PRKG1 | PRKG2 | PRKRA | PRKRIP1 |
| PRKRIR | PRKX | PRKY | PRL | PRLH |
| PRLHR | PRLR | PRM1 | PRM2 | PRMT1 |
| PRMT10 | PRMT2 | PRMT3 | PRMT5 | PRMT6 |
| PRMT7 | PRMT8 | PRND | PRNP | PRO1073 |
| PROC | PROCA1 | PROCR | PRODH | PRODH2 |
| PROK1 | PROK2 | PROKR1 | PROKR2 | PROL1 |
| PROM1 | PROM2 | PROP1 | PROS1 | PROSC |
| PROX1 | PROX2 | PROZ | PRPF18 | PRPF19 |
| PRPF3 | PRPF31 | PRPF38A | PRPF38B | PRPF39 |
| PRPF4 | PRPF40A | PRPF40B | PRPF4B | PRPF4B_ENST00000337659 |
| PRPF6 | PRPF8 | PRPH | PRPH2 | PRPS1 |
| PRPS2 | PRPSAP1 | PRPSAP2 | PRR11 | PRR12 |
| PRR13 | PRR14 | PRR15 | PRR15L | PRR16 |
| PRR18 | PRR19 | PRR20A | PRR21 | PRR22 |
| PRR23B | PRR23C | PRR25 | PRR3 | PRR4 |
| PRR5 | PRR5-ARHGAP8 | PRR5L | PRR5_ENST00000432186 | PRR7 |
| PRR8 | PRRC1 | PRRG1 | PRRG2 | PRRG3 |
| PRRG4 | PRRT1 | PRRT2 | PRRT3 | PRRX1 |
| PRRX2 | PRSS1 | PRSS12 | PRSS16 | PRSS2 |
| PRSS21 | PRSS22 | PRSS23 | PRSS27 | PRSS3 |
| PRSS33 | PRSS35 | PRSS36 | PRSS37 | PRSS38 |
| PRSS42 | PRSS50 | PRSS7 | PRSSL1 | PRTFDC1 |
| PRTG | PRTN3 | PRUNE | PRUNE2 | PRUNE2_ENST00000376718 |
| PRX | PRY | PRY2 | PSAP | PSAPL1 |
| PSAT1 | PSD | PSD2 | PSD3 | PSD4 |
| PSD_ENST00000020673 | PSEN1 | PSEN2 | PSENEN | PSG1 |
| PSG1_ENST00000312439 | PSG2 | PSG3 | PSG4 | PSG5 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| PSG6 | PSG8 | PSG9 | PSIP1 | PSIP1_ENST00000380733 |
| PSKH1 | PSKH2 | PSMA1 | PSMA2 | PSMA3 |
| PSMA4 | PSMA5 | PSMA6 | PSMA7 | PSMA8 |
| PSMB1 | PSMB10 | PSMB2 | PSMB3 | PSMB4 |
| PSMB5 | PSMB6 | PSMB7 | PSMB8 | PSMB9 |
| PSMC1 | PSMC2 | PSMC3 | PSMC3IP | PSMC4 |
| PSMC5 | PSMC6 | PSMD1 | PSMD10 | PSMD11 |
| PSMD12 | PSMD13 | PSMD13_ENST00000431206 | PSMD2 | PSMD3 |
| PSMD4 | PSMD5 | PSMD6 | PSMD7 | PSMD8 |
| PSMD9 | PSME1 | PSME2 | PSME3 | PSME4 |
| PSMF1 | PSMG1 | PSMG2 | PSMG3 | PSORS1C1 |
| PSORS1C2 | PSPC1 | PSPH | PSPN | PSRC1 |
| PSTK | PSTPIP2 | PTAFR | PTAR1 | PTBP1 |
| PTBP2 | PTCD1 | PTCD2 | PTCD3 | PTCH1 |
| PTCH1_ENST00000331920 | PTCH2 | PTCHD1 | PTCHD2 | PTCHD3 |
| PTCRA | PTDSS1 | PTDSS2 | PTEN | PTER |
| PTF1A | PTGDR | PTGDS | PTGER1 | PTGER2 |
| PTGER3 | PTGER4 | PTGES | PTGES2 | PTGES3 |
| PTGFR | PTGFRN | PTGFR_ENST00000370758 | PTGIR | PTGIS |
| PTGR1 | PTGS1 | PTGS2 | PTH | PTH1R |
| PTH2 | PTH2R | PTHLH | PTK2 | PTK2B |
| PTK2B_ENST00000397497 | PTK6 | PTK7 | PTMA | PTMS |
| PTN | PTOV1 | PTP4A1 | PTP4A2 | PTP4A3 |
| PTPDC1 | PTPLA | PTPLAD1 | PTPLAD2 | PTPLB |
| PTPMT1 | PTPN1 | PTPN11 | PTPN12 | PTPN13 |
| PTPN14 | PTPN18 | PTPN2 | PTPN20A | PTPN20B |
| PTPN21 | PTPN22 | PTPN23 | PTPN3 | PTPN4 |
| PTPN5 | PTPN6 | PTPN7 | PTPN9 | PTPRA |
| PTPRB | PTPRB_ENST00000334414 | PTPRC | PTPRCAP | PTPRD |
| PTPRE | PTPRF | PTPRG | PTPRH | PTPRJ |
| PTPRK | PTPRM | PTPRN | PTPRN2 | PTPRO |
| PTPRR | PTPRS | PTPRT | PTPRU | PTPRZ1 |
| PTRF | PTRH1 | PTRH2 | PTS | PTTG1 |
| PTTG1IP | PTX3 | PUM1 | PUM2 | PURA |
| PURB | PURG | PURG_ENST00000475541 | PUS1 | PUS10 |
| PUS3 | PUS7 | PUS7L | PUSL1 | PVALB |
| PVR | PVRIG | PVRL1 | PVRL2 | PVRL3 |
| PVRL4 | PWP1 | PWP2 | PWWP2A | PWWP2B |
| PXDN | PXDNL | PXK | PXMP2 | PXMP4 |
| PXN | PXT1 | PYCARD | PYCR1 | PYCR2 |
| PYCRL | PYDC1 | PYGB | PYGL | PYGM |
| PYGO1 | PYGO2 | PYHIN1 | PYROXD1 | PYROXD2 |
| PYY | PYY3 | PZP | ProSAPiP1 | Q0VFX0_HUMAN |
| Q13034_HUMAN | Q13209_HUMAN | Q15202_HUMAN | Q16370_HUMAN | Q1A5X8_HUMAN |
| Q2M2F3_HUMAN | Q2QD04_HUMAN | Q2VIK4_HUMAN | Q2VIK8_HUMAN | Q2VIL1_HUMAN |
| Q3SX88_HUMAN | Q3ZCN4_HUMAN | Q49A61_HUMAN | Q49AQ9_HUMAN | Q4G0P5_HUMAN |
| Q4GOS1_HUMAN | Q4G129_HUMAN | Q4G197_HUMAN | Q4TT42_HUMAN | Q4VXG5_HUMAN |
| Q4VXZ3_HUMAN | Q5I0X0_HUMAN | Q5JSM7_HUMAN | Q5JUV9_HUMAN | Q5JV89_HUMAN |
| Q5JX50_HUMAN | Q5JXA8_HUMAN | Q5JY96_HUMAN | Q5JYU7_HUMAN | Q5SWJ0_HUMAN |
| Q5T344_HUMAN | Q5T669_HUMAN | Q5T6S7_HUMAN | Q5T740_HUMAN | Q5T7C0_HUMAN |
| Q5T909_HUMAN | Q5TBE2_HUMAN | Q5TFB2_HUMAN | Q5VVH2_HUMAN | Q5VZ27_HUMAN |
| Q5VZ43_HUMAN | Q5W1B9_HUMAN | Q69YG7_HUMAN | Q69YJ1_HUMAN | Q6AI01_HUMAN |
| Q6AI40_HUMAN | Q6GMT2_HUMAN | Q6I955_HUMAN | Q6IPT3_HUMAN | Q6NSH2_HUMAN |
| Q6NUR6_HUMAN | Q6NZ63_HUMAN | Q6P094_HUMAN | Q6P462_HUMAN | Q6PEB8_HUMAN |
| Q6RGF6_HUMAN | Q6TXQ4_HUMAN | Q6UXU0_HUMAN | Q6VEP2_HUMAN | Q6YL47_HUMAN |
| Q6ZMS4_HUMAN | Q6ZNB5_HUMAN | Q6ZNL0_HUMAN | Q6ZNV0_HUMAN | Q6ZQP8_HUMAN |
| Q6ZQU9_HUMAN | Q6ZRG5_HUMAN | Q6ZRP8_HUMAN | Q6ZRU5_HUMAN | Q6ZSP4_HUMAN |
| Q6ZSU1_HUMAN | Q6ZSY1_HUMAN | Q6ZTY5_HUMAN | Q6ZU04_HUMAN | Q6ZU24_HUMAN |
| Q6ZUD9_HUMAN | Q6ZUG5_HUMAN | Q6ZUQ5_HUMAN | Q6ZUR4_HUMAN | Q6ZUS2_HUMAN |
| Q6ZV46_HUMAN | Q6ZV65_HUMAN | Q6ZV72_HUMAN | Q6ZVE3_HUMAN | Q6ZVS6_HUMAN |
| Q6ZW54_HUMAN | Q6ZWB7_HUMAN | Q6ZWC0_HUMAN | Q71RG6_HUMAN | Q75L30_HUMAN |
| Q75MH1_HUMAN | Q75MM1_HUMAN | Q76B61_HUMAN | Q7M4M3_HUMAN | Q7Z2M6_HUMAN |
| Q7Z2Q7_HUMAN | Q7Z2S2_HUMAN | Q7Z3M5_HUMAN | Q7Z4Q0_HUMAN | Q7Z4S1_HUMAN |
| Q7Z5Z2_HUMAN | Q7Z7K7_HUMAN | Q86TT0_HUMAN | Q86TU9_HUMAN | Q86U10_HUMAN |
| Q86U47_HUMAN | Q86U89_HUMAN | Q86V52_HUMAN | Q86V94_HUMAN | Q86VG7_HUMAN |
| Q86X61_HUMAN | Q86XG0_HUMAN | Q86Y87 | Q86YR2_HUMAN | Q86YX8_HUMAN |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| Q8IVE0_HUMAN | Q8IVF9_HUMAN | Q8IVN4_HUMAN | Q8IVR1_HUMAN | Q8IXE5_HUMAN |
| Q8IXE7_HUMAN | Q8IXV1_HUMAN | Q8MH63_HUMAN | Q8N0U1_HUMAN | Q8N0W1_HUMAN |
| Q8N164_HUMAN | Q8N1B8_HUMAN | Q8N1G8_HUMAN | Q8N1I6_HUMAN | Q8N1L4_HUMAN |
| Q8N1R6_HUMAN | Q8N1T0_HUMAN | Q8N1X6_HUMAN | Q8N214_HUMAN | Q8N266_HUMAN |
| Q8N2D2_HUMAN | Q8N2E2_HUMAN | Q8N2W8_HUMAN | Q8N3U1_HUMAN | Q8N4W5_HUMAN |
| Q8N5Q1_HUMAN | Q8N642_HUMAN | Q8N646_HUMAN | Q8N6L5_HUMAN | Q8N6V7_HUMAN |
| Q8N6X1_HUMAN | Q8N6X9_HUMAN | Q8N799_HUMAN | Q8N7D3_HUMAN | Q8N7N0_HUMAN |
| Q8N7N2_HUMAN | Q8N7P5_HUMAN | Q8N7Q6_HUMAN | Q8N7Z9_HUMAN | Q8N800_HUMAN |
| Q8N811_HUMAN | Q8N822_HUMAN | Q8N843_HUMAN | Q8N849_HUMAN | Q8N867_HUMAN |
| Q8N8C5_HUMAN | Q8N8C9_HUMAN | Q8N8F0_HUMAN | Q8N8H9_HUMAN | Q8N8K0_HUMAN |
| Q8N8P5_HUMAN | Q8N8S3_HUMAN | Q8N8S4_HUMAN | Q8N950_HUMAN | Q8N997_HUMAN |
| Q8N9F6_HUMAN | Q8N9G5_HUMAN | Q8N9G9_HUMAN | Q8N9H1_HUMAN | Q8N9I1_HUMAN |
| Q8N9J4_HUMAN | Q8N9K3_HUMAN | Q8N9Z1_HUMAN | Q8N9Z5_HUMAN | Q8NA17_HUMAN |
| Q8NA34_HUMAN | Q8NAG9_HUMAN | Q8NAP4_HUMAN | Q8NAP5_HUMAN | Q8NAQ8_HUMAN |
| Q8NAT4_HUMAN | Q8NAV9_HUMAN | Q8NAZ9_HUMAN | Q8NB20_HUMAN | Q8NB83_HUMAN |
| Q8NBE0_HUMAN | Q8NCA1_HUMAN | Q8NCK2_HUMAN | Q8NEQ2_HUMAN | Q8NFX8_HUMAN |
| Q8NGC8_HUMAN | Q8NGD7_HUMAN | Q8NGE6_HUMAN | Q8NGF2_HUMAN | Q8NGG1_HUMAN |
| Q8NGK8_HUMAN | Q8NGM0_HUMAN | Q8NGM4_HUMAN | Q8NGM6_HUMAN | Q8NGP1_HUMAN |
| Q8NGP5_HUMAN | Q8NGP7_HUMAN | Q8NGQ7_HUMAN | Q8NGY4_HUMAN | Q8NH06_HUMAN |
| Q8NH08_HUMAN | Q8NH11_HUMAN | Q8NH32_HUMAN | Q8NH33_HUMAN | Q8NH46_HUMAN |
| Q8NH47_HUMAN | Q8NH58_HUMAN | Q8NH68_HUMAN | Q8NH71_HUMAN | Q8NH75_HUMAN |
| Q8NH77_HUMAN | Q8NH80_HUMAN | Q8NH82_HUMAN | Q8NH88_HUMAN | Q8NH95_HUMAN |
| Q8NH98_HUMAN | Q8NHA6_HUMAN | Q8NHB0_HUMAN | Q8NHB3_HUMAN | Q8NHB5_HUMAN |
| Q8NHC0_HUMAN | Q8NHC1_HUMAN | Q8NHC2_HUMAN | Q8TAF5_HUMAN | Q8TBR1_HUMAN |
| Q8TCI8_HUMAN | Q8TDK1_HUMAN | Q8TDP9_HUMAN | Q8TE05_HUMAN | Q8WM95_HUMAN |
| Q8WTY6_HUMAN | Q8WYW5_HUMAN | Q8WYX1_HUMAN | Q8WZ27_HUMAN | Q8WZ91 |
| Q96AM0_HUMAN | Q96CK5_HUMAN | Q96DR3_HUMAN | Q96HF5_HUMAN | Q96HZ0_HUMAN |
| Q96IP2_HUMAN | Q96K91_HUMAN | Q96M56_HUMAN | Q96M66_HUMAN | Q96M92_HUMAN |
| Q96MC4_HUMAN | Q96MT0_HUMAN | Q96MZ3_HUMAN | Q96NE0_HUMAN | Q96NP5_HUMAN |
| Q96PS2_HUMAN | Q96PS6_HUMAN | Q96QE0_HUMAN | Q96RF1_HUMAN | Q96RI3_HUMAN |
| Q96RW6_HUMAN | Q96RY6_HUMAN | Q96RY9_HUMAN | Q99543-2 | Q9BRP9_HUMAN |
| Q9BSD4_HUMAN | Q9BSM8_HUMAN | Q9BSY8_HUMAN | Q9BVW6_HUMAN | Q9BVX4_HUMAN |
| Q9BZU6_HUMAN | Q9C0K3_HUMAN | Q9GZQ9_HUMAN | Q9H2C7_HUMAN | Q9H354_HUMAN |
| Q9H4I0_HUMAN | Q9H521_HUMAN | Q9H5Q3_HUMAN | Q9H614_HUMAN | Q9H693_HUMAN |
| Q9H6A9_HUMAN | Q9H6K5_HUMAN | Q9H6S2_HUMAN | Q9H6Z8_HUMAN | Q9H8C5_HUMAN |
| Q9H8D1_HUMAN | Q9H960_HUMAN | Q9HAB5_HUMAN | Q9HAC4_HUMAN | Q9HAD2_HUMAN |
| Q9HAJ0_HUMAN | Q9HAZ8_HUMAN | Q9HBS9_HUMAN | Q9NQ39_HUMAN | Q9NRE4_HUMAN |
| Q9NRE7_HUMAN | Q9NSI3_HUMAN | Q9NSQ0_HUMAN | Q9NT31_HUMAN | Q9NU36_HUMAN |
| Q9NW32_HUMAN | Q9NWP0_HUMAN | Q9NYD3_HUMAN | Q9NYS9_HUMAN | Q9NZ01-2 |
| Q9P0C7_HUMAN | Q9P143_HUMAN | Q9P147_HUMAN | Q9P156_HUMAN | Q9P184_HUMAN |
| Q9P1D0_HUMAN | Q9P1G6_HUMAN | Q9P1L5_HUMAN | Q9P1M5_HUMAN | Q9P2A3_HUMAN |
| Q9UHU1_HUMAN | Q9UHU9_HUMAN | Q9UI72_HUMAN | Q9UJN8_HUMAN | Q9UK71_HUMAN |
| Q9Y6V0-3 | QARS | QDPR | QKI | QPCT |
| QPCTL | QPRT | QRFP | QRFPR | QRICH1 |
| QRICH2 | QRSL1 | QSER1 | QSOX1 | QSOX2 |
| QTRT1 | QTRTD1 | R3HCC1 | R3HDM1 | R3HDM2 |
| R3HDML | RAB10 | RAB11A | RAB11B | RAB11FIP1 |
| RAB11FIP2 | RAB11FIP3 | RAB11FIP4 | RAB11FIP5 | RAB12 |
| RAB13 | RAB14 | RAB15 | RAB17 | RAB18 |
| RAB19 | RAB19B | RAB1A | RAB1B | RAB20 |
| RAB21 | RAB22A | RAB23 | RAB24 | RAB25 |
| RAB26 | RAB27A | RAB27B | RAB28 | RAB2A |
| RAB2B | RAB30 | RAB31 | RAB32 | RAB33A |
| RAB33B | RAB34 | RAB35 | RAB36 | RAB37 |
| RAB38 | RAB39 | RAB39B | RAB3A | RAB3B |
| RAB3C | RAB3D | RAB3GAP1 | RAB3GAP2 | RAB3IL1 |
| RAB3IP | RAB40A | RAB40AL | RAB40B | RAB40C |
| RAB41 | RAB42 | RAB43 | RAB44 | RAB4A |
| RAB4B | RAB5A | RAB5B | RAB5C | RAB6A |
| RAB6B | RAB6C | RAB7A | RAB7L1 | RAB8A |
| RAB8B | RAB9A | RAB9B | RABAC1 | RABEP1 |
| RABEP2 | RABEPK | RABGAP1 | RABGAP1L | RABGEF1 |
| RABGGTB | RABIF | RABL2A | RABL2B | RABL3 |
| RABL4 | RABL5 | RAC1 | RAC1P4 | RAC2 |
| RAC3 | RACGAP1 | RAD1 | RAD17 | RAD18 |
| RAD21 | RAD23A | RAD23B | RAD50 | RAD51 |
| RAD51AP1 | RAD51AP2 | RAD51C | RAD51L1 | RAD51L3 |
| RAD52 | RAD54B | RAD54L | RAD54L2 | RAD9A |
| RAD9B | RADIL | RAE1 | RAET1E | RAET1G |
| RAET1L | RAF1 | RAG1 | RAG1AP1 | RAG2 |
| RAGE | RAI1 | RAI14 | RAI16 | RAI2 |
| RALA | RALB | RALBP1 | RALGAPA1 | RALGAPB |
| RALGDS | RALGPS1 | RALGPS2 | RALY | RAMP1 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| RAMP2 | RAMP3 | RAN | RANBP1 | RANBP10 |
| RANBP17 | RANBP2 | RANBP3 | RANBP3L | RANBP6 |
| RANBP9 | RANGAP1 | RANGRF | RAP1A | RAP1B |
| RAP1GAP | RAP1GAP__ENST00000374761 | RAP1GDS1 | RAP2A | RAP2B |
| RAP2C | RAPGEF1 | RAPGEF2 | RAPGEF3 | RAPGEF4 |
| RAPGEF5 | RAPGEF5__ENST00000344041 | RAPGEF6 | RAPGEFL1 | RAPH1 |
| RAPSN | RARA | RARB | RARG | RARRES1 |
| RARRES2 | RARRES3 | RARS | RARS2 | RASA1 |
| RASA2 | RASA3 | RASA4 | RASAL1 | RASAL2 |
| RASD1 | RASD2 | RASEF | RASGEF1A | RASGEF1B |
| RASGEF1C | RASGRF1 | RASGRF2 | RASGRP1 | RASGRP2 |
| RASGRP3 | RASGRP4 | RASIP1 | RASL10A | RASL10B |
| RASL11A | RASL11B | RASL12 | RASL2_HUMAN | RASSF1 |
| RASSF2 | RASSF3 | RASSF4 | RASSF5 | RASSF5__ENST00000304534 |
| RASSF6 | RASSF7 | RASSF8 | RAVER1 | RAVER2 |
| RAX | RAX2 | RB1 | RB1CC1 | RBAK |
| RBBP4 | RBBP5 | RBBP6 | RBBP7 | RBBP8 |
| RBBP9 | RBCK1 | RBKS | RBL1 | RBL2 |
| RBM10 | RBM12 | RBM12B | RBM14 | RBM15 |
| RBM15B | RBM16 | RBM17 | RBM18 | RBM19 |
| RBM22 | RBM23 | RBM24 | RBM25 | RBM26 |
| RBM27 | RBM28 | RBM3 | RBM34 | RBM34__ENST00000408888 |
| RBM39 | RBM4 | RBM41 | RBM42 | RBM43 |
| RBM45 | RBM46 | RBM47 | RBM4B | RBM5 |
| RBM6 | RBM7 | RBM8A | RBM9 | RBMS1 |
| RBMS2 | RBMS3 | RBMX | RBMX2 | RBMXL2 |
| RBMY1A1 | RBMY1B | RBMY1D | RBMY1E | RBMY1F |
| RBMY1J | RBP1 | RBP2 | RBP3 | RBP4 |
| RBP5 | RBP7 | RBPJ | RBPJL | RBPMS |
| RBPMS2 | RBX1 | RC3H1 | RC3H2 | RCAN1 |
| RCAN2 | RCAN3 | RCBTB1 | RCBTB2 | RCC1 |
| RCC2 | RCCD1 | RCE1 | RCHY1 | RCL1 |
| RCN1 | RCN2 | RCN3 | RCOR1 | RCOR2 |
| RCOR3 | RCSD1 | RCVRN | RD3 | RDBP |
| RDH10 | RDH11 | RDH12 | RDH13 | RDH14 |
| RDH16 | RDH5 | RDH8 | RDM1 | RDX |
| REC8 | RECK | RECQL | RECQL4 | RECQL5 |
| REEP1 | REEP2 | REEP4 | REEP5 | REEP6 |
| REEP6__ENST00000395484 | REG1A | REG1B | REG3A | REG3G |
| REG4 | REL | RELA | RELB | RELL1 |
| RELL2 | RELN | RELT | REM1 | REM2 |
| REN | RENBP | RENBP__ENST00000393700 | REP15 | REPIN1 |
| REPS1 | REPS2 | RER1 | RERE | RERG |
| RERGL | RESP18 | REST | RET | RETN |
| RETNLB | RETSAT | REV1 | REV3L | REXO1 |
| REXO2 | REXO4 | RFC1 | RFC2 | RFC3 |
| RFC4 | RFC5 | RFESD | RFFL | RFK |
| RFNG | RFPL1 | RFPL2 | RFPL3 | RFPL4A |
| RFPL4B | RFT1 | RFTN1 | RFTN2 | RFWD2 |
| RFWD3 | RFX1 | RFX2 | RFX3 | RFX4 |
| RFX5 | RFX6 | RFX7 | RFXANK | RFXAP |
| RG9MTD1 | RG9MTD2 | RG9MTD3 | RGAG1 | RGAG4 |
| RGL1 | RGL2 | RGL3 | RGL3__ENST00000380456 | RGL4 |
| RGMA | RGN | RGPD2 | RGPD5 | RGPD6 |
| RGPD7 | RGR | RGS1 | RGS10 | RGS11 |
| RGS12 | RGS13 | RGS14 | RGS16 | RGS17 |
| RGS18 | RGS19 | RGS20 | RGS21 | RGS21 |
| RGS22 | RGS3 | RGS4 | RGS5 | RGS6 |
| RGS7 | RGS7BP | RGS8 | RGS9 | RGS9BP |
| RGSL1 | RGSL2 | RHAG | RHBDD1 | RHBDD2 |
| RHBDD3 | RHBDF1 | RHBDF2 | RHBDL1 | RHBDL2 |
| RHBDL3 | RHBG | RHCE | RHCG | RHD |
| RHEB | RHEBL1 | RHO | RHOA | RHOB |
| RHOBTB1 | RHOBTB2 | RHOBTB3 | RHOC | RHOD |
| RHOF | RHOG | RHOH | RHOJ | RHOQ |
| RHOT1 | RHOT2 | RHOU | RHOV | RHOXF1 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| RHOXF2 | RHOXF2B | RHPN1 | RHPN2 | RIBC1 |
| RIBC2 | RIC3 | RIC8A | RIC8B | RICTOR |
| RIF1 | RILP | RILPL2 | RIMBP2 | RIMKLA |
| RIMS1 | RIMS2 | RIMS2_ENST00000436393 | RIMS3 | RIMS4 |
| RIN1 | RIN2 | RIN3 | RING1 | RINL |
| RINT1 | RIOK1 | RIOK2 | RIOK3 | RIPK1 |
| RIPK2 | RIPK3 | RIPK4 | RIPPLY1 | RIPPLY2 |
| RIT1 | RIT2 | RL17_HUMAN | RL41_HUMAN | RLBP1 |
| RLBP1L1 | RLF | RLIM | RLN1 | RLN2 |
| RLN3 | RLTPR | RLTPR_ENST00000334583 | RMI1 | RMND1 |
| RMND5A | RMND5B | RNASE1 | RNASE10 | RNASE11 |
| RNASE12 | RNASE13 | RNASE2 | RNASE3 | RNASE4 |
| RNASE6 | RNASE7 | RNASE8 | RNASE9 | RNASEH1 |
| RNASEH2A | RNASEH2B | RNASEH2C | RNASEK | RNASEL |
| RNASEN | RNASET2 | RND1 | RND2 | RND3 |
| RNF10 | RNF103 | RNF11 | RNF111 | RNF112 |
| RNF113A | RNF113B | RNF114 | RNF115 | RNF121 |
| RNF122 | RNF123 | RNF125 | RNF126 | RNF128 |
| RNF13 | RNF130 | RNF133 | RNF134 | RNF135 |
| RNF138 | RNF139 | RNF14 | RNF141 | RNF144A |
| RNF144B | RNF145 | RNF146 | RNF148 | RNF149 |
| RNF150 | RNF151 | RNF152 | RNF157 | RNF160 |
| RNF165 | RNF166 | RNF167 | RNF168 | RNF169 |
| RNF17 | RNF170 | RNF180 | RNF181 | RNF182 |
| RNF183 | RNF185 | RNF186 | RNF187 | RNF19A |
| RNF19B | RNF2 | RNF20 | RNF207 | RNF208 |
| RNF212 | RNF213 | RNF214 | RNF215 | RNF216 |
| RNF217 | RNF219 | RNF220 | RNF222 | RNF24 |
| RNF25 | RNF26 | RNF31 | RNF32 | RNF34 |
| RNF38 | RNF39 | RNF4 | RNF40 | RNF41 |
| RNF43 | RNF44 | RNF5 | RNF6 | RNF7 |
| RNF8 | RNFT1 | RNGTT | RNH1 | RNLS |
| RNMT | RNMTL1 | RNPEP | RNPEPL1 | RNPS1 |
| ROBLD3 | ROBO1 | ROBO1_ENST00000305299 | ROBO2 | ROBO3 |
| ROBO4 | ROCK1 | ROCK2 | ROD1 | ROGDI |
| ROM1 | ROMO1 | ROPN1 | ROPN1B | ROPN1L |
| ROR1 | ROR2 | RORA | RORB | RORC |
| ROS1 | RP1 | RP1-19N1_1 | RP1-21O18_1 | RP1-21O18_1_NEW |
| RP1-241P17_4 | RP1-32I10.10 | RP11-274K13_2 | RP11-45B20_2 | RP11-529I10_4 |
| RP11-551L14.1 | RP11-9816_3 | RP13-218H24_1 | RP13-36C9_1 | RP1L1 |
| RP2 | RP3-364I1_1 | RP3-402G11_5 | RP3-527F8_2 | RP4-545K15_3 |
| RP4-765F13_3 | RP5-113911_4 | RP6-149D17_1 | RP9 | RPA1 |
| RPA2 | RPA2_ENST00000313433 | RPA3 | RPA4 | RPAIN |
| RPAP1 | RPAP2 | RPAP3 | RPE | RPE65 |
| RPF1 | RPF2 | RPGR | RPGRIP1 | RPGRIP1L |
| RPH3A | RPH3AL | RPIA | RPL10 | RPL10A |
| RPL10AP3 | RPL10L | RPL11 | RPL12 | RPL13 |
| RPL13A | RPL13AP25 | RPL14 | RPL14P5 | RPL15 |
| RPL17P39 | RPL18 | RPL18A | RPL19 | RPL21 |
| RPL21P128 | RPL21P20 | RPL21P44 | RPL22 | RPL23 |
| RPL23A | RPL23AP82 | RPL24 | RPL26 | RPL26L1 |
| RPL27 | RPL27A | RPL27AP6 | RPL28 | RPL29 |
| RPL29P12 | RPL3 | RPL30 | RPL31 | RPL32 |
| RPL32P3 | RPL32P36 | RPL34 | RPL35 | RPL35A |
| RPL35P1 | RPL36 | RPL36A | RPL36AL | RPL36P14 |
| RPL37 | RPL37A | RPL38 | RPL39 | RPL39L |
| RPL3L | RPL4 | RPL41 | RPL5 | RPL6 |
| RPL7 | RPL7A | RPL7L1 | RPL8 | RPL9 |
| RPL9P7 | RPLP0 | RPLP1 | RPLP1P3 | RPLP2 |
| RPN1 | RPN2 | RPP14 | RPP21 | RPP25 |
| RPP30 | RPP38 | RPP40 | RPRD1A | RPRD1B |
| RPRM | RPRML | RPS10 | RPS11 | RPS12 |
| RPS13 | RPS14 | RPS15 | RPS15A | RPS15P4 |
| RPS16 | RPS17 | RPS18 | RPS19 | RPS19BP1 |
| RPS2 | RPS20 | RPS20P14 | RPS21 | RPS23 |
| RPS24 | RPS25 | RPS26 | RPS26P11 | RPS26P3 |
| RPS27 | RPS27A | RPS27AP17 | RPS27L | RPS28 |
| RPS29 | RPS2P55 | RPS3 | RPS3A | RPS3AP6 |
| RPS4X | RPS4Y1 | RPS4Y2 | RPS5 | RPS6 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| RPS6KA1 | RPS6KA2 | RPS6KA3 | RPS6KA4 | RPS6KA5 |
| RPS6KA6 | RPS6KB1 | RPS6KB2 | RPS6KC1 | RPS6KL1 |
| RPS6P1 | RPS7 | RPS7P4 | RPS8 | RPS9 |
| RPSA | RPTN | RPTOR | RPUSD1 | RPUSD2 |
| RPUSD3 | RPUSD4 | RQCD1 | RRAD | RRAGA |
| RRAGB | RRAGC | RRAGD | RRAS | RRAS2 |
| RRBP1 | RREB1 | RRH | RRM1 | RRM2 |
| RRM2B | RRN3 | RRP1 | RRP12 | RRP15 |
| RRP1B | RRP7A | RRP8 | RRP9 | RRS1 |
| RS1 | RSAD1 | RSAD2 | RSBN1 | RSBN1L |
| RSC1A1 | RSF1 | RSL1D1 | RSL24D1 | RSPH1 |
| RSPH10B | RSPH10B2 | RSPH3 | RSPH4A | RSPH6A |
| RSPH9 | RSPO1 | RSPO2 | RSPO3 | RSPO4 |
| RSPRY1 | RSRC1 | RSRC2 | RSU1 | RTBDN |
| RTCD1 | RTDR1 | RTEL1 | RTF1 | RTKN |
| RTKN2 | RTN1 | RTN2 | RTN3 | RTN4 |
| RTN4IP1 | RTN4R | RTN4RL2 | RTP1 | RTP2 |
| RTP3 | RTP4 | RTTN | RUFY1 | RUFY2 |
| RUFY3 | RUNDC1 | RUNDC2A | RUNDC2B | RUNDC3B |
| RUNX1 | RUNX1T1 | RUNX1T1_ENST00000265814 | RUNX2 | RUNX3 |
| RUSC1 | RUSC2 | RUVBL1 | RUVBL2 | RWDD1 |
| RWDD2A | RWDD2B | RWDD3 | RWDD4A | RXFP1 |
| RXFP2 | RXFP3 | RXFP4 | RXRA | RXRB |
| RXRG | RYK | RYR1 | RYR2 | RYR3 |
| S100A1 | S100A10 | S100A11 | S100A12 | S100A13 |
| S100A14 | S100A16 | S100A2 | S100A3 | S100A4 |
| S100A5 | S100A6 | S100A7 | S100A7A | S100A7L2 |
| S100A8 | S100A9 | S100B | S100G | S100P |
| S100PBP | S100Z | S1PR1 | S1PR2 | S1PR3 |
| S1PR4 | S1PR5 | SAA1 | SAA2 | SAA3P |
| SAA4 | SAAL1 | SAC3D1 | SACM1L | SACS |
| SAE1 | SAFB | SAFB2 | SAGE1 | SALL1 |
| SALL2 | SALL3 | SALL4 | SAMD10 | SAMD11 |
| SAMD12 | SAMD13 | SAMD14 | SAMD3 | SAMD4A |
| SAMD4B | SAMD5 | SAMD7 | SAMD8 | SAMD8_ENST00000372690 |
| SAMD9 | SAMD9L | SAMHD1 | SAMM50 | SAMSN1 |
| SAP130 | SAP18 | SAP30 | SAP30BP | SAP30L |
| SAPS1 | SAPS2 | SAPS3 | SAR1A | SAR1B |
| SARDH | SARNP | SARS | SARS2 | SART1 |
| SART3 | SASH1 | SASH3 | SASS6 | SAT1 |
| SAT2 | SATB1 | SATB2 | SATL1 | SAV1 |
| SBDS | SBF1 | SBF2 | SBK1 | SBK2 |
| SBNO1 | SBSN | SC4MOL | SC5DL | SC65 |
| SCAF1 | SCAI | SCAMP2 | SCAMP3 | SCAMP4 |
| SCAND1 | SCAND3 | SCAP | SCAPER | SCARA3 |
| SCARA5 | SCARB1 | SCARB2 | SCARF1 | SCARF2 |
| SCCPDH | SCD | SCD5 | SCEL | SCFD1 |
| SCFD2 | SCG2 | SCG3 | SCGB1A1 | SCGB1C1 |
| SCGB1D1 | SCGB1D2 | SCGB1D4 | SCGB2A1 | SCGB2A2 |
| SCGB3A1 | SCGB3A2 | SCGBL | SCGN | SCHIP1 |
| SCLT1 | SCLY | SCMH1 | SCML1 | SCML2 |
| SCML4 | SCN10A | SCN11A | SCN1A | SCN1B |
| SCN2A | SCN2B | SCN3A | SCN3B | SCN4A |
| SCN4B | SCN5A | SCN7A | SCN9A | SCNM1 |
| SCNN1A | SCNN1B | SCNN1D | SCNN1G | SCO1 |
| SCO2 | SCOC | SCP2 | SCPEP1 | SCRG1 |
| SCRIB | SCRN1 | SCRN2 | SCRN3 | SCRT1 |
| SCRT2 | SCTR | SCUBE1 | SCUBE2 | SCUBE3 |
| SCXB | SCYL1 | SCYL2 | SCYL3 | SDAD1 |
| SDC1 | SDC2 | SDC3 | SDC4 | SDCBP |
| SDCBP2 | SDCCAG1 | SDCCAG3 | SDCCAG3L | SDCCAG8 |
| SDF2 | SDF2L1 | SDF4 | SDHA | SDHAF1 |
| SDHAF2 | SDHB | SDHC | SDHD | SDK1 |
| SDPR | SDR16C5 | SDR42E1 | SDR9C7 | SDS |
| SDSL | SEC11B | SEC11C | SEC13 | SEC14L1 |
| SEC14L2 | SEC14L3 | SEC14L4 | SEC16B | SEC22A |
| SEC22C | SEC23A | SEC23B | SEC23IP | SEC24A |
| SEC24B | SEC24C | SEC24D | SEC31A | SEC31B |
| SEC61A1 | SEC61A2 | SEC61B | SEC61G | SEC62 |
| SEC63 | SECISBP2 | SECISBP2L | SECTM1 | SEH1L |
| SEL1L | SEL1L2 | SELE | SELENBP1 | SELI |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| SELL | SELM | SELP | SELPLG | SELV |
| SEMA3A | SEMA3B | SEMA3C | SEMA3D | SEMA3E |
| SEMA3F | SEMA3G | SEMA4A | SEMA4B | SEMA4C |
| SEMA4D | SEMA4F | SEMA4G | SEMA5A | SEMA5B |
| SEMA6A | SEMA6B | SEMA6C | SEMA6D | SEMA7A |
| SEMG1 | SEMG2 | SENP1 | SENP2 | SENP3 |
| SENP5 | SENP6 | SENP7 | SENP8 | 15-Sep |
| SEPHS1 | SEPHS2 | SEPN1 | SEPP1 | SEPSECS |
| 01-Sep | 10-Sep | 11-Sep | 12-Sep | 02-Sep |
| 03-Sep | 04-Sep | 05-Sep | 06-Sep | 08-Sep |
| 09-Sep | SEPX1 | SERAC1 | SERBP1 | SERF1A |
| SERF1B | SERF2 | SERGEF | SERHL | SERHL2 |
| SERINC1 | SERINC2 | SERINC3 | SERINC4 | SERP1 |
| SERP1_ENST00000491660 | SERP2 | SERPINA1 | SERPINA10 | SERPINA11 |
| SERPINA12 | SERPINA13 | SERPINA2 | SERPINA3 | SERPINA4 |
| SERPINA5 | SERPINA6 | SERPINA7 | SERPINA9 | SERPINA9_ENST00000337425 |
| SERPINB1 | SERPINB10 | SERPINB11 | SERPINB12 | SERPINB13 |
| SERPINB2 | SERPINB3 | SERPINB4 | SERPINB5 | SERPINB6 |
| SERPINB7 | SERPINB8 | SERPINB9 | SERPINC1 | SERPIND1 |
| SERPINE1 | SERPINE2 | SERPINF1 | SERPINF2 | SERPING1 |
| SERPINH1 | SERPINI1 | SERPINI2 | SERTAD1 | SERTAD2 |
| SERTAD3 | SERTAD4 | SESN1 | SESN2 | SESN3 |
| SESTD1 | SET | SETBP1 | SETD1A | SETD1B |
| SETD2 | SETD2_ENST00000409792 | SETD3 | SETD4 | SETD5 |
| SETD6 | SETD7 | SETD8 | SETDB1 | SETDB2 |
| SETMAR | SETX | SEZ6 | SEZ6L | SEZ6L2 |
| SF1 | SF3A1 | SF3A2 | SF3A3 | SF3B1 |
| SF3B14 | SF3B2 | SF3B3 | SF3B4 | SF3B5 |
| SF4 | SFI1 | SFMBT1 | SFMBT2 | SFN |
| SFPQ | SFRP1 | SFRP2 | SFRP4 | SFRP5 |
| SFRS1 | SFRS11 | SFRS12 | SFRS12IP1 | SFRS13B |
| SFRS14 | SFRS15 | SFRS16 | SFRS17A | SFRS18 |
| SFRS2 | SFRS2IP | SFRS3 | SFRS4 | SFRS5 |
| SFRS6 | SFRS7 | SFRS8 | SFRS9 | SFT2D1 |
| SFT2D2 | SFT2D3 | SFTA2 | SFTPA1B | SFTPA2 |
| SFTPA2B | SFTPB | SFTPC | SFTPD | SFXN1 |
| SFXN2 | SFXN3 | SFXN4 | SFXN5 | SG223_HUMAN |
| SG269_HUMAN | SGCA | SGCB | SGCE | SGCG |
| SGCZ | SGEF | SGIP1 | SGK1 | SGK2 |
| SGK3 | SGMS1 | SGMS2 | SGOL1 | SGOL2 |
| SGPL1 | SGPP1 | SGPP2 | SGSH | SGSM1 |
| SGSM2 | SGSM3 | SGTA | SGTB | SH2B1 |
| SH2B3 | SH2D1A | SH2D1B | SH2D2A | SH2D3A |
| SH2D3C | SH2D4A | SH2D4B | SH2D5 | SH2D6 |
| SH3BGR | SH3BGRL | SH3BGRL2 | SH3BGRL3 | SH3BP1 |
| SH3BP2 | SH3BP4 | SH3BP5 | SH3BP5L | SH3D19 |
| SH3D20 | SH3GL1 | SH3GL2 | SH3GL3 | SH3GLB1 |
| SH3GLB2 | SH3KBP1 | SH3PXD2A | SH3PXD2B | SH3RF1 |
| SH3RF2 | SH3TC1 | SH3TC2 | SH3YL1 | SHANK1 |
| SHANK2 | SHANK3 | SHARPIN | SHB | SHBG |
| SHC1 | SHC1_ENST00000448116 | SHC2 | SHC3 | SHC4 |
| SHCBP1 | SHD | SHE | SHF | SHFM1 |
| SHH | SHISA2 | SHISA3 | SHISA4 | SHISA5 |
| SHKBP1 | SHMT1 | SHMT2 | SHOC2 | SHOX |
| SHOX2 | SHPK | SHPRH | SHQ1 | SHROOM1 |
| SHROOM2 | SHROOM3 | SHROOM4 | SI | SIAE |
| SIAH1 | SIAH1L | SIAH2 | SIAH3 | SIDT1 |
| SIDT2 | SIGIRR | SIGLEC1 | SIGLEC10 | SIGLEC11 |
| SIGLEC12 | SIGLEC12_ENST00000439889 | SIGLEC14 | SIGLEC15 | SIGLEC5 |
| SIGLEC6 | SIGLEC7 | SIGLEC8 | SIGLEC9 | SIGMAR1 |
| SIK1 | SIK2 | SIK3 | SIKE1 | SIL1 |
| SILV | SIM1 | SIM2 | SIN3A | SIN3B |
| SIP1 | SIPA1 | SIPA1L1 | SIPA1L2 | SIPA1L3 |
| SIRPA | SIRPB1 | SIRPB2 | SIRPD | SIRPG |
| SIRT1 | SIRT2 | SIRT3 | SIRT4 | SIRT5 |
| SIRT6 | SIRT7 | SIT1 | SIVA1 | SIX1 |
| SIX2 | SIX3 | SIX4 | SIX5 | SIX6 |
| SK681 | SKA1 | SKA3 | SKAP1 | SKAP2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| SKI | SKIL | SKIP | SKIV2L | SKIV2L2 |
| SKP1 | SKP2 | SLA | SLA2 | SLAIN1 |
| SLAMF1 | SLAMF6 | SLAMF7 | SLAMF8 | SLAMF9 |
| SLBP | SLC10A1 | SLC10A2 | SLC10A3 | SLC10A4 |
| SLC10A5 | SLC10A6 | SLC10A7 | SLC11A1 | SLC11A2 |
| SLC12A1 | SLC12A2 | SLC12A3 | SLC12A4 | SLC12A5 |
| SLC12A6 | SLC12A7 | SLC12A8 | SLC12A9 | SLC13A1 |
| SLC13A2 | SLC13A3 | SLC13A4 | SLC13A5 | SLC14A1 |
| SLC14A2 | SLC15A1 | SLC15A2 | SLC15A3 | SLC15A4 |
| SLC16A1 | SLC16A10 | SLC16A11 | SLC16A12 | SLC16A13 |
| SLC16A14 | SLC16A2 | SLC16A3 | SLC16A4 | SLC16A5 |
| SLC16A6 | SLC16A7 | SLC16A8 | SLC16A9 | SLC17A1 |
| SLC17A2 | SLC17A3 | SLC17A4 | SLC17A5 | SLC17A6 |
| SLC17A7 | SLC17A8 | SLC17A9 | SLC18A1 | SLC18A2 |
| SLC18A3 | SLC19A1 | SLC19A2 | SLC19A3 | SLC1A1 |
| SLC1A2 | SLC1A3 | SLC1A4 | SLC1A5 | SLC1A6 |
| SLC1A7 | SLC20A1 | SLC20A2 | SLC22A1 | SLC22A10 |
| SLC22A11 | SLC22A12 | SLC22A13 | SLC22A14 | SLC22A15 |
| SLC22A16 | SLC22A17 | SLC22A18 | SLC22A2 | SLC22A20 |
| SLC22A23 | SLC22A25 | SLC22A3 | SLC22A4 | SLC22A5 |
| SLC22A6 | SLC22A7 | SLC22A8 | SLC22A9 | SLC23A1 |
| SLC23A2 | SLC23A3 | SLC24A2 | SLC24A3 | SLC24A4 |
| SLC24A5 | SLC24A6 | SLC25A1 | SLC25A10 | SLC25A11 |
| SLC25A12 | SLC25A13 | SLC25A14 | SLC25A15 | SLC25A16 |
| SLC25A17 | SLC25A18 | SLC25A19 | SLC25A2 | SLC25A20 |
| SLC25A21 | SLC25A22 | SLC25A23 | SLC25A24 | SLC25A25 |
| SLC25A27 | SLC25A28 | SLC25A29 | SLC25A3 | SLC25A30 |
| SLC25A31 | SLC25A32 | SLC25A33 | SLC25A34 | SLC25A35 |
| SLC25A36 | SLC25A37 | SLC25A38 | SLC25A39 | SLC25A4 |
| SLC25A40 | SLC25A42 | SLC25A43 | SLC25A44 | SLC25A45 |
| SLC25A46 | SLC25A5 | SLC25A6 | SLC26A1 | SLC26A10 |
| SLC26A11 | SLC26A2 | SLC26A3 | SLC26A4 | SLC26A5 |
| SLC26A6 | SLC26A7 | SLC26A8 | SLC26A9 | SLC27A1 |
| SLC27A2 | SLC27A3 | SLC27A4 | SLC27A5 | SLC27A6 |
| SLC28A1 | SLC28A2 | SLC28A3 | SLC29A1 | SLC29A2 |
| SLC29A3 | SLC29A4 | SLC2A1 | SLC2A10 | SLC2A11 |
| SLC2A12 | SLC2A13 | SLC2A14 | SLC2A2 | SLC2A3 |
| SLC2A4 | SLC2A4RG | SLC2A5 | SLC2A6 | SLC2A7 |
| SLC2A8 | SLC2A9 | SLC30A1 | SLC30A10 | SLC30A2 |
| SLC30A3 | SLC30A4 | SLC30A5 | SLC30A6 | SLC30A7 |
| SLC30A8 | SLC30A9 | SLC31A1 | SLC31A2 | SLC32A1 |
| SLC33A1 | SLC34A1 | SLC34A2 | SLC34A3 | SLC35A1 |
| SLC35A2 | SLC35A3 | SLC35A4 | SLC35A5 | SLC35B1 |
| SLC35B2 | SLC35B3 | SLC35B4 | SLC35C1 | SLC35C2 |
| SLC35D1 | SLC35D2 | SLC35D3 | SLC35E1 | SLC35E2 |
| SLC35E3 | SLC35E4 | SLC35F1 | SLC35F2 | SLC35F3 |
| SLC35F5 | SLC36A1 | SLC36A2 | SLC36A3 | SLC36A4 |
| SLC37A1 | SLC37A2 | SLC37A3 | SLC37A4 | SLC38A1 |
| SLC38A10 | SLC38A11 | SLC38A2 | SLC38A3 | SLC38A4 |
| SLC38A5 | SLC38A6 | SLC38A7 | SLC38A8 | SLC38A9 |
| SLC39A1 | SLC39A10 | SLC39A11 | SLC39A12 | SLC39A13 |
| SLC39A14 | SLC39A2 | SLC39A3 | SLC39A4 | SLC39A5 |
| SLC39A6 | SLC39A7 | SLC39A8 | SLC39A9 | SLC3A1 |
| SLC3A2 | SLC40A1 | SLC41A1 | SLC41A2 | SLC41A3 |
| SLC43A1 | SLC43A2 | SLC43A3 | SLC44A1 | SLC44A2 |
| SLC44A3 | SLC44A4 | SLC44A5 | SLC45A1 | SLC45A2 |
| SLC45A3 | SLC45A4 | SLC46A2 | SLC46A3 | SLC47A1 |
| SLC47A2 | SLC48A1 | SLC4A1 | SLC4A10 | SLC4A11 |
| SLC4A1AP | SLC4A2 | SLC4A3 | SLC4A4 | SLC4A5 |
| SLC4A7 | SLC4A8 | SLC4A9 | SLC4A9_ENST00000506757 | SLC5A1 |
| SLC5A10 | SLC5A11 | SLC5A12 | SLC5A2 | SLC5A3 |
| SLC5A4 | SLC5A5 | SLC5A6 | SLC5A7 | SLC5A8 |
| SLC5A9 | SLC6A1 | SLC6A11 | SLC6A12 | SLC6A13 |
| SLC6A14 | SLC6A15 | SLC6A16 | SLC6A17 | SLC6A18 |
| SLC6A19 | SLC6A2 | SLC6A20 | SLC6A3 | SLC6A4 |
| SLC6A5 | SLC6A6 | SLC6A7 | SLC6A8 | SLC6A9 |
| SLC7A1 | SLC7A10 | SLC7A11 | SLC7A13 | SLC7A14 |
| SLC7A2 | SLC7A3 | SLC7A4 | SLC7A5 | SLC7A6 |
| SLC7A6OS | SLC7A7 | SLC7A8 | SLC7A9 | SLC8A1 |
| SLC8A2 | SLC8A3 | SLC9A1 | SLC9A10 | SLC9A11 |
| SLC9A2 | SLC9A3 | SLC9A3R1 | SLC9A3R2 | SLC9A4 |
| SLC9A5 | SLC9A6 | SLC9A7 | SLC9A8 | SLC9A9 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| SLCO1A2 | SLCO1B1 | SLCO1B3 | SLCO1C1 | SLCO2A1 |
| SLCO2B1 | SLCO3A1 | SLCO4A1 | SLCO4C1 | SLCO5A1 |
| SLCO6A1 | SLFN11 | SLFN12 | SLFN13 | SLFN14 |
| SLFN5 | SLFNL1 | SLIT1 | SLIT2 | SLITS |
| SLITRK1 | SLITRK2 | SLITRK3 | SLITRK4 | SLITRK5 |
| SLITRK6 | SLK | SLMAP | SLMO1 | SLMO2 |
| SLN | SLPI | SLTM | SLU7 | SLURP1 |
| SMAD1 | SMAD2 | SMAD3 | SMAD4 | SMAD5 |
| SMAD5OS | SMAD6 | SMAD7 | SMAD9 | SMAP1 |
| SMAP2 | SMARCA1 | SMARCA2 | SMARCA4 | SMARCA5 |
| SMARCAD1 | SMARCAL1 | SMARCB1 | SMARCC1 | SMARCC2 |
| SMARCD1 | SMARCD2 | SMARCD3 | SMARCE1 | SMC1A |
| SMC1B | SMC2 | SMC2L1 | SMC3 | SMC4 |
| SMC5 | SMC6 | SMCHD1 | SMCP | SMCR7 |
| SMCR7L | SMCR8 | SMEK1 | SMEK1_ENST00000417249 | SMEK2 |
| SMG1 | SMG5 | SMG6 | SMG7 | SMN1 |
| SMN2 | SMNDC1 | SMO | SMOC1 | SMOC2 |
| SMOX | SMPD1 | SMPD2 | SMPD3 | SMPD4 |
| SMPDL3A | SMPDL3B | SMPX | SMR3A | SMR3B |
| SMS | SMTN | SMTNL2 | SMU1 | SMUG1 |
| SMURF1 | SMURF2 | SMYD1 | SMYD2 | SMYD3 |
| SMYD4 | SMYD5 | SNAI1 | SNAI2 | SNAI3 |
| SNAP23 | SNAP25 | SNAP29 | SNAP47 | SNAPC1 |
| SNAPC2 | SNAPC3 | SNAPC4 | SNAPC5 | SNAPIN |
| SNCA | SNCAIP | SNCB | SNCG | SND1 |
| SNED1 | SNF8 | SNIP1 | SNN | SNPH |
| SNRK | SNRNP200 | SNRNP25 | SNRNP27 | SNRNP35 |
| SNRNP48 | SNRNP70 | SNRPA | SNRPA1 | SNRPB |
| SNRPB2 | SNRPC | SNRPD1 | SNRPD2 | SNRPD3 |
| SNRPE | SNRPEL1 | SNRPF | SNRPG | SNRPN |
| SNTA1 | SNTB1 | SNTB2 | SNTG1 | SNTG2 |
| SNTN | SNUPN | SNURF | SNW1 | SNX1 |
| SNX10 | SNX11 | SNX12 | SNX13 | SNX14 |
| SNX15 | SNX16 | SNX17 | SNX18 | SNX19 |
| SNX2 | SNX20 | SNX21 | SNX22 | SNX24 |
| SNX25 | SNX27 | SNX3 | SNX30 | SNX31 |
| SNX32 | SNX33 | SNX4 | SNX5 | SNX6 |
| SNX7 | SNX8 | SNX9 | SOAT1 | SOAT2 |
| SOBP | SOCS1 | SOCS2 | SOCS3 | SOCS4 |
| SOCS5 | SOCS6 | SOCS7 | SOD1 | SOD2 |
| SODS | SOHLH1 | SOHLH2 | SOLH | SON |
| SORBS1 | SORBS2 | SORBS3 | SORCS1 | SORCS2 |
| SORCS3 | SORD | SORL1 | SORT1 | SOS1 |
| SOS2 | SOST | SOSTDC1 | SOX1 | SOX10 |
| SOX11 | SOX12 | SOX13 | SOX14 | SOX15 |
| SOX17 | SOX18 | SOX2 | SOX21 | SOX3 |
| SOX30 | SOX4 | SOX5 | SOX6 | SOX7 |
| SOX8 | SOX9 | SP1 | SP100 | SP110 |
| SP140 | SP140L | SP2 | SP3 | SP4 |
| SP5 | SP6 | SP8 | SP17 | SPACA1 |
| SPACA3 | SPACA4 | SPACA5 | SPACA5B | SPAG1 |
| SPAG11A | SPAG11B | SPAG16 | SPAG17 | SPAG4 |
| SPAG5 | SPAG6 | SPAG7 | SPAG8 | SPAG9 |
| SPAM1 | SPANX-N1 | SPANXA1 | SPANXA2 | SPANXB1 |
| SPANXC | SPANXD | SPANXN1 | SPANXN2 | SPANXN3 |
| SPANXN4 | SPANXN5 | SPARC | SPARCL1 | SPAST |
| SPATA1 | SPATA12 | SPATA13 | SPATA16 | SPATA17 |
| SPATA18 | SPATA19 | SPATA2 | SPATA20 | SPATA21 |
| SPATA22 | SPATA2L | SPATA4 | SPATA5 | SPATA5L1 |
| SPATA6 | SPATA7 | SPATA8 | SPATA9 | SPATC1 |
| SPATS1 | SPATS2 | SPC25 | SPCS1 | SPCS2 |
| SPDEF | SPDYA | SPDYC | SPDYE1 | SPDYE2 |
| SPEF1 | SPEF2 | SPEF2_ENST00000356031 | SPEG | SPEM1 |
| SPEM1_ENST00000323383 | SPEN | SPERT | SPESP1 | SPFH1 |
| SPG11 | SPG20 | SPG21 | SPG7 | SPHAR |
| SPHK1 | SPHK2 | SPHKAP | SPI1 | SPIB |
| SPIC | SPIN1 | SPIN2A | SPIN2B | SPIN3 |
| SPIN4 | SPINK1 | SPINK2 | SPINK4 | SPINK5 |
| SPINK5L2 | SPINK5L3 | SPINK6 | SPINK7 | SPINK9 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| SPINLW1 | SPINLW1_ENST00000336443 | SPINT1 | SPINT2 | SPINT4 |
| SPIRE1 | SPIRE2 | SPN | SPNS1 | SPNS2 |
| SPNS3 | SPO11 | SPOCD1 | SPOCK1 | SPOCK2 |
| SPOCK3 | SPON2 | SPOP | SPOPL | SPP1 |
| SPP2 | SPPL2A | SPR | SPRED1 | SPRED2 |
| SPRED3 | SPRN | SPRR1A | SPRR1B | SPRR2A |
| SPRR2B | SPRR2D | SPRR2E | SPRR2F | SPRR2G |
| SPRR3 | SPRR4 | SPRY1 | SPRY2 | SPRY3 |
| SPRY4 | SPRYD3 | SPRYD4 | SPRYD5 | SPRYD5_ENST00000327733 |
| SPSB1 | SPSB2 | SPSB3 | SPSB4 | SPTA1 |
| SPTAN1 | SPTB | SPTBN1 | SPTBN2 | SPTBN4 |
| SPTBN5 | SPTLC1 | SPTLC2 | SPTLC3 | SPTY2D1 |
| SPZ1 | SQLE | SQRDL | SQSTM1 | SR140_HUMAN |
| SRA1 | SRBD1 | SRC | SRCAP | SRCRB4D |
| SRD5A1 | SRD5A3 | SREBF1 | SREBF2 | SRF |
| SRFBP1 | SRGAP1 | SRGAP2P1 | SRGAP3 | SRGN |
| SRI | SRL | SRM | SRMS | SRP14 |
| SRP19 | SRP54 | SRP68 | SRP72 | SRP9 |
| SRP9L1 | SRPK1 | SRPK2 | SRPK3 | SRPK3_ENST00000489426 |
| SRPR | SRPRB | SRPX | SRPX2 | SRR |
| SRRD | SRRM1 | SRRM2 | SRRT | SRXN1 |
| SRY | SS18 | SS18L1 | SS18L2 | SSB |
| SSBP1 | SSBP2 | SSBP3 | SSBP4 | SSFA2 |
| SSH1 | SSH2 | SSH3 | SSNA1 | SSPN |
| SSR1 | SSR2 | SSR3 | SSR4 | SSRP1 |
| SSSCA1 | SST | SSTR1 | SSTR2 | SSTR3 |
| SSTR4 | SSTR5 | SSU72 | SSX1 | SSX2 |
| SSX2IP | SSX3 | SSX4 | SSX4B | SSX5 |
| SSX6 | SSX7 | SSX9 | ST13 | ST14 |
| ST18 | ST20 | ST3GAL1 | ST3GAL2 | ST3GAL3 |
| ST3GAL4 | ST3GAL5 | ST3GAL6 | ST5 | ST6GAL1 |
| ST6GAL2 | ST6GALNAC1 | ST6GALNAC2 | ST6GALNAC3 | ST6GALNAC4 |
| ST6GALNAC5 | ST6GALNAC6 | ST7 | ST7L | ST8SIA1 |
| ST8SIA2 | ST8SIA3 | ST8SIA4 | ST8SIA5 | ST8SIA6 |
| STAB1 | STAB2 | STAC | STAC2 | STAC3 |
| STAG1 | STAG2 | STAG3 | STAG3L1 | STAG3L3 |
| STAG3L4 | STAM | STAM2 | STAMBP | STAMBPL1 |
| STAP1 | STAP2 | STAR | STARD10 | STARD13 |
| STARD3 | STARD3NL | STARD4 | STARD5 | STARD6 |
| STARD7 | STARD8 | STARD8_ENST00000252336 | STARD9 | STAT1 |
| STAT2 | STAT3 | STAT4 | STAT5A | STAT5B |
| STAT6 | STATH | STAU1 | STAU2 | STBD1 |
| STC1 | STC2 | STEAP1 | STEAP2 | STEAP3 |
| STEAP4 | STIL | STIM1 | STIM2 | STIP1 |
| STK10 | STK11 | STK11IP | STK16 | STK17A |
| STK17B | STK19 | STK24 | STK25 | STK3 |
| STK31 | STK32A | STK32B | STK32C | STK33 |
| STK35 | STK36 | STK38 | STK38L | STK39 |
| STK4 | STK40 | STMN1 | STMN2 | STMN3 |
| STMN4 | STOM | STOML1 | STOML2 | STOML3 |
| STON1 | STON1-GTF2A1L | STON2 | STOX1 | STOX2 |
| STRA13 | STRA6 | STRA8 | STRADA | STRADB |
| STRAP | STRBP | STRC | STRN | STRN3 |
| STRN4 | STS | STT3A | STT3B | STUB1 |
| STX10 | STX11 | STX12 | STX16 | STX17 |
| STX18 | STX19 | STX1A | STX1B | STX2 |
| STX3 | STX4 | STX5 | STX6 | STX7 |
| STX8 | STXBP1 | STXBP2 | STXBP3 | STXBP4 |
| STXBP5 | STXBP5L | STXBP6 | STYK1 | STYX |
| STYXL1 | SUB1 | SUCLA2 | SUCLG1 | SUCLG2 |
| SUCNR1 | SUDS3 | SUFU | SUGT1 | SULF1 |
| SULF2 | SULT1A1 | SULT1A2 | SULT1A3 | SULT1A4 |
| SULT1B1 | SULT1C2 | SULT1C3 | SULT1C4 | SULT1E1 |
| SULT2A1 | SULT2B1 | SULT4A1 | SULT6B1 | SUMF1 |
| SUMF2 | SUMO1 | SUMO1P1 | SUMO2 | SUMO3 |
| SUMO4 | SUN1 | SUN2 | SUN3 | SUN5 |
| SUOX | SUPT16H | SUPT3H | SUPT4H1 | SUPT5H |
| SUPT6H | SUPT7L | SUPV3L1 | SURF1 | SURF2 |
| SURF4 | SURF5 | SURF6 | SUSD1 | SUSD2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| SUSD3 | SUSD4 | SUSD5 | SUV39H1 | SUV39H2 |
| SUV420H1 | SUV420H2 | SUZ12 | SUZ12P | SV2A |
| SV2B | SV2C | SVEP1 | SVIL | SVIP |
| SVOPL | SWAP70 | SYAP1 | SYCE1 | SYCE2 |
| SYCN | SYCP1 | SYCP2 | SYCP2L | SYCP3 |
| SYDE1 | SYDE2 | SYF2 | SYK | SYMPK |
| SYN1 | SYN2 | SYN3 | SYNC | SYNCRIP |
| SYNE1 | SYNE1_ENST00000265368 | SYNE2 | SYNGAP1 | SYNGAP1_ENST00000293748 |
| SYNGR1 | SYNGR2 | SYNGR3 | SYNGR4 | SYNJ1 |
| SYNJ2 | SYNJ2BP | SYNM | SYNPO | SYNPO2 |
| SYNPO2L | SYNRG | SYP | SYPL1 | SYPL2 |
| SYP_ENST00000263233 | SYS1 | SYT1 | SYT10 | SYT11 |
| SYT12 | SYT13 | SYT14 | SYT14L | SYT15 |
| SYT15_ENST00000374328 | SYT16 | SYT17 | SYT2 | SYT3 |
| SYT4 | SYT5 | SYT6 | SYT7 | SYT8 |
| SYT9 | SYTL1 | SYTL2 | SYTL3 | SYTL4 |
| SYTL5 | SYVN1 | SgK069 | SgK085 | SgK110 |
| SgK223 | SgK269 | SgK424 | SgK493 | SgK494 |
| SgK495 | T | T183B_HUMAN | TAAR1 | TAAR2 |
| TAAR5 | TAAR6 | TAAR8 | TAB1 | TAB2 |
| TAB3 | TAC1 | TAC3 | TAC4 | TACC1 |
| TACC2 | TACC3 | TACO1 | TACR1 | TACR2 |
| TACR3 | TACSTD2 | TADA1 | TADA2A | TADA2B |
| TADA3L | TAF1 | TAF10 | TAF11 | TAP12 |
| TAP13 | TAF15 | TAF1A | TAF1B | TAF1C |
| TAF1D | TAF1L | TAF2 | TAF3 | TAF4 |
| TAF4B | TAF5 | TAF5L | TAF6 | TAF6L |
| TAF7 | TAF7L | TAF8 | TAF9 | TAF9B |
| TAGAP | TAGLN | TAGLN2 | TAGLN3 | TAL1 |
| TAL2 | TALDO1 | TANC1 | TANK | TAOK1 |
| TAOK2 | TAOK3 | TAP1 | TAP2 | TAP2_ENST00000458336 |
| TAPBP | TAPBPL | TAPT1 | TARBP1 | TARBP2 |
| TARDBP | TARS | TARS2 | TARSL2 | TAS1R1 |
| TAS1R2 | TAS1R3 | TAS2R1 | TAS2R10 | TAS2R13 |
| TAS2R14 | TAS2R16 | TAS2R19 | TAS2R20 | TAS2R3 |
| TAS2R38 | TAS2R4 | TAS2R41 | TAS2R42 | TAS2R5 |
| TAS2R50 | TAS2R60 | TAS2R7 | TAS2R8 | TAS2R9 |
| TASP1 | TAT | TATDN1 | TATDN2 | TATDN3 |
| TAX1BP1 | TAX1BP3 | TAZ | TBC1D1 | TBC1D10A |
| TBC1D10C | TBC1D12 | TBC1D13 | TBC1D14 | TBC1D15 |
| TBC1D16 | TBC1D17 | TBC1D19 | TBC1D2 | TBC1D20 |
| TBC1D21 | TBC1D22A | TBC1D22B | TBC1D23 | TBC1D24 |
| TBC1D25 | TBC1D26 | TBC1D28 | TBC1D29 | TBC1D2B |
| TBC1D3 | TBC1D30 | TBC1D3B | TBC1D3C | TBC1D3E |
| TBC1D3F | TBC1D3G | TBC1D3H | TBC1D3P2 | TBC1D4 |
| TBC1D5 | TBC1D7 | TBC1D8B | TBC1D9B | TBCA |
| TBCB | TBCC | TBCCD1 | TBCD | TBCE |
| TBCEL | TBCK | TBK1 | TBKBP1 | TBL1X |
| TBL1XR1 | TBL1Y | TBL2 | TBL3 | TBP |
| TBPL1 | TBPL2 | TBR1 | TBRG1 | TBRG4 |
| TBX1 | TBX10 | TBX15 | TBX18 | TBX19 |
| TBX2 | TBX20 | TBX21 | TBX22 | TBX3 |
| TBX4 | TBX5 | TBX6 | TBXA2R | TEXAS1 |
| TC2N | TCAP | TCEA1 | TCEA2 | TCEAL1 |
| TCEAL2 | TCEAL3 | TCEAL4 | TCEAL5 | TCEAL6 |
| TCEAL7 | TCEAL8 | TCEANC | TCEB1 | TCEB2 |
| TCEB3 | TCEB3B | TCEB3C | TCERG1 | TCERG1L |
| TCF12 | TCF15 | TCF19 | TCF20 | TCF21 |
| TCF23 | TCF25 | TCF3 | TCF4 | TCF7 |
| TCF7L1 | TCF7L2 | TCFL5 | TCHH | TCHHL1 |
| TCHP | TCIRG1 | TCL1A | TCL1B | TCL6 |
| TCN1 | TCN2 | TCOF1 | TCP1 | TCP10 |
| TCP10L | TCP11 | TCP11L1 | TCP11L2 | TCTA |
| TCTE1 | TCTE3 | TCTEX1D1 | TCTEX1D2 | TCTEX1D4 |
| TCTN1 | TCTN2 | TCTN3 | TDG | TDGF1 |
| TDH | TDO2 | TDP1 | TDRD1 | TDRD10 |
| TDRD3 | TDRD5 | TDRD6 | TDRD7 | TDRD9 |
| TDRKH | TEAD1 | TEAD2 | TEAD4 | TEC |
| TECPR1 | TECPR2 | TECR | TECRL | TECTA |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| TECTB | TEDDM1 | TEF | TEK | TEKT1 |
| TEKT2 | TEKT3 | TEKT4 | TEKT5 | TELO2 |
| TENC1 | TEP1 | TEPP | TERF1 | TERF2 |
| TERF2IP | TERT | TES | TESC | TESK1 |
| TESK2 | TET1 | TET2 | TEX10 | TEX101 |
| TEX11 | TEX12 | TEX13A | TEX13B | TEX14 |
| TEX15 | TEX19 | TEX2 | TEX261 | TEX264 |
| TEX28 | TEX9 | TF | TFAM | TFAP2A |
| TFAP2B | TFAP2C | TFAP2D | TFAP2E | TFAP4 |
| TFB1M | TFB2M | TFCP2 | TFCP2L1 | TFDP1 |
| TFDP2 | TFDP3 | TFE3 | TFEB | TFEC |
| TFF1 | TFF2 | TFF3 | TFG | TFIP11 |
| TFPI | TFPI2 | TFPT | TFR2 | TFRC |
| TFSM1_HUMAN | TG | TGDS | TGFA | TGFB1 |
| TGFB1I1 | TGFB2 | TGFB3 | TGFBI | TGFBR1 |
| TGFBR2 | TGFBR3 | TGFBRAP1 | TGIF1 | TGIF2 |
| TGIF2LX | TGIF2LY | TGM1 | TGM2 | TGM3 |
| TGM4 | TGM5 | TGM6 | TGM7 | TGOLN2 |
| TGS1 | TH | TH1L | THADA | THAP1 |
| THAP10 | THAP11 | THAP2 | THAP3 | THAP4 |
| THAP5 | THAP6 | THAP7 | THAP8 | THAP9 |
| THBD | THBS1 | THBS2 | THBS3 | THBS4 |
| THEG | THEM4 | THEM5 | THEMIS | THG1L |
| THNSL1 | THNSL2 | THOC1 | THOC2 | THOC3 |
| THOC4 | THOC5 | THOC6 | THOC7 | THOP1 |
| THPO | THRA | THRAP3 | THRB | THRSP |
| THSD1 | THSD4 | THSD7A | THSD7B | THTPA |
| THUMPD1 | THUMPD2 | THUMPD3 | THY1 | THYN1 |
| TIA1 | TIAF1 | TIAL1 | TIAM1 | TIAM2 |
| TICAM1 | TICAM2 | TIE1 | TIF1 | TIFA |
| TIFAB | TIGD1 | TIGD2 | TIGD3 | TIGD4 |
| TIGD5 | TIGD6 | TIGD7 | TIGIT | TIMD4 |
| TIMELESS | TIMM10 | TIMM13 | TIMM17A | TIMM17B |
| TIMM22 | TIMM23 | TIMM44 | TIMM50 | TIMM8A |
| TIMM8B | TIMM9 | TIMP1 | TIMP2 | TIMP3 |
| TIMP4 | TINAG | TINAGL1 | TINF2 | TIPARP |
| TIPIN | TIPRL | TIRAP | TJAP1 | TJP1 |
| TJP2 | TJP3 | TK1 | TK2 | TKT |
| TKTL1 | TKTL2 | TLCD1 | TLCD2 | TLE1 |
| TLE3 | TLE4 | TLE6 | TLK1 | TLK2 |
| TLL1 | TLL2 | TLN1 | TLN2 | TLR1 |
| TLR10 | TLR2 | TLR3 | TLR4 | TLR5 |
| TLR6 | TLR7 | TLR8 | TLR9 | TLX1 |
| TLX2 | TLX3 | TM2D1 | TM2D2 | TM2D3 |
| TM4SF1 | TM4SF18 | TM4SF19 | TM4SF2 | TM4SF20 |
| TM4SF5 | TM6SF1 | TM6SF2 | TM7SF2 | TM7SF3 |
| TM7SF4 | TM9SF1 | TM9SF2 | TM9SF3 | TM9SF4 |
| TMBIM1 | TMBIM4 | TMBIM6 | TMC1 | TMC2 |
| TMC3 | TMC4 | TMC5 | TMC6 | TMC7 |
| TMC8 | TMCC1 | TMCC2 | TMCC3 | TMCO1 |
| TMCO2 | TMCO3 | TMCO4 | TMCO5A | TMCO6 |
| TMCO7 | TMED1 | TMED10 | TMED2 | TMED3 |
| TMED4 | TMED5 | TMED6 | TMED7 | TMED8 |
| TMED9 | TMEFF1 | TMEFF2 | TMEM100 | TMEM101 |
| TMEM102 | TMEM104 | TMEM105 | TMEM106A | TMEM106B |
| TMEM106C | TMEM107 | TMEM108 | TMEM109 | TMEM11 |
| TMEM110 | TMEM111 | TMEM115 | TMEM116 | TMEM117 |
| TMEM119 | TMEM120B | TMEM121 | TMEM123 | TMEM125 |
| TMEM126A | TMEM126B | TMEM127 | TMEM128 | TMEM129 |
| TMEM130 | TMEM131 | TMEM132A | TMEM132B | TMEM132C |
| TMEM132D | TMEM132E | TMEM133 | TMEM134 | TMEM135 |
| TMEM136 | TMEM138 | TMEM139 | TMEM140 | TMEM141 |
| TMEM143 | TMEM144 | TMEM145 | TMEM146 | TMEM147 |
| TMEM149 | TMEM14A | TMEM14B | TMEM14C | TMEM150A |
| TMEM150B | TMEM151A | TMEM154 | TMEM155 | TMEM156 |
| TMEM159 | TMEM160 | TMEM161A | TMEM161B | TMEM163 |
| TMEM164 | TMEM165 | TMEM167A | TMEM167B | TMEM168 |
| TMEM169 | TMEM17 | TMEM170A | TMEM170B | TMEM171 |
| TMEM173 | TMEM174 | TMEM175 | TMEM176A | TMEM176B |
| TMEM177 | TMEM178 | TMEM179 | TMEM179B | TMEM18 |
| TMEM180 | TMEM181 | TMEM182 | TMEM183A | TMEM184A |
| TMEM184B | TMEM184C | TMEM185A | TMEM185B | TMEM186 |
| TMEM187 | TMEM189 | TMEM189-UBE2V1 | TMEM19 | TMEM190 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| TMEM192 | TMEM194A | TMEM195 | TMEM196 | TMEM198 |
| TMEM199 | TMEM2 | TMEM20 | TMEM200A | TMEM200B |
| TMEM201 | TMEM202 | TMEM203 | TMEM204 | TMEM205 |
| TMEM206 | TMEM207 | TMEM209 | TMEM211 | TMEM214 |
| TMEM215 | TMEM217 | TMEM218 | TMEM219 | TMEM22 |
| TMEM220 | TMEM222 | TMEM225 | TMEM229B | TMEM25 |
| TMEM26 | TMEM27 | TMEM30A | TMEM30B | TMEM31 |
| TMEM33 | TMEM35 | TMEM37 | TMEM38A | TMEM38B |
| TMEM39A | TMEM39B | TMEM40 | TMEM41A | TMEM41B |
| TMEM42 | TMEM43 | TMEM44 | TMEM45A | TMEM45B |
| TMEM47 | TMEM48 | TMEM49 | TMEM5 | TMEM50A |
| TMEM50B | TMEM51 | TMEM52 | TMEM53 | TMEM54 |
| TMEM55A | TMEM55B | TMEM56 | TMEM57 | TMEM59 |
| TMEM59L | TMEM60 | TMEM61 | TMEM62 | TMEM63A |
| TMEM63B | TMEM64 | TMEM65 | TMEM66 | TMEM67 |
| TMEM68 | TMEM69 | TMEM70 | TMEM71 | TMEM72 |
| TMEM74 | TMEM78 | TMEM79 | TMEM80 | TMEM81 |
| TMEM82 | TMEM85 | TMEM86A | TMEM86B | TMEM87A |
| TMEM87B | TMEM88 | TMEM89 | TMEM8A | TMEM8B |
| TMEM8C | TMEM9 | TMEM90A | TMEM90B | TMEM91 |
| TMEM92 | TMEM93 | TMEM95 | TMEM97 | TMEM98 |
| TMEM99 | TMEM9B | TMF1 | TMIE | TMIGD1 |
| TMIGD2 | TMLHE | TMOD1 | TMOD2 | TMOD3 |
| TMOD4 | TMPO | TMPO_ENST00000266732 | TMPPE | TMPRSS11A |
| TMPRSS11B | TMPRSS11D | TMPRSS11E | TMPRSS11E2 | TMPRSS11F |
| TMPRSS13 | TMPRSS2 | TMPRSS2_ENST00000332149 | TMPRSS3 | TMPRSS4 |
| TMPRSS6 | TMPRSS7 | TMPRSS9 | TMSB10 | TMSB15A |
| TMSB15B | TMSB4X | TMSB4Y | TMSL2 | TMSL3 |
| TMTC1 | TMTC2 | TMTC3 | TMTC4 | TMUB1 |
| TMUB2 | TMX1 | TMX2 | TMX3 | TMX4 |
| TNAP | TNC | TNF | TNFAIP1 | TNFAIP2 |
| TNFAIP3 | TNFAIP6 | TNFAIP8L1 | TNFAIP8L2 | TNFAIP8L3 |
| TNFRSF10A | TNFRSF10B | TNFRSF10C | TNFRSF10D | TNFRSF11A |
| TNFRSF11B | TNFRSF12A | TNFRSF13B | TNFRSF13C | TNFRSF14 |
| TNFRSF17 | TNFRSF18 | TNFRSF19 | TNFRSF1A | TNFRSF1B |
| TNFRSF21 | TNFRSF25 | TNFRSF4 | TNFRSF6B | TNFRSF8 |
| TNFRSF9 | TNFRSF10 | TNFSF11 | TNFSF12 | TNFSF12-TNFSF13 |
| TNFSF13 | TNFSF13B | TNFSF14 | TNFSF15 | TNFSF18 |
| TNFSF4 | TNFSF8 | TNFSF9 | TNIK | TNIP1 |
| TNIP2 | TNIP3 | TNK1 | TNK2 | TNK2_ENST00000381916 |
| TNKS | TNKS1BP1 | TNKS2 | TNMD | TNN |
| TNNC1 | TNNC2 | TNNI1 | TNNI2 | TNNI3 |
| TNNI3K | TNNT1 | TNNT2 | TNNT3 | TNP1 |
| TNPO1 | TNPO2 | TNPO3 | TNR | TNRC18 |
| TNRC6A | TNRC6B | TNS1 | TNS3 | TNS4 |
| TNXB | TNXB_ENST00000375247 | TOB1 | TOB2 | TOB2P1 |
| TOE1 | TOLLIP | TOM1 | TOM1L1 | TOM1L2 |
| TOMM20 | TOMM20L | TOMM22 | TOMM34 | TOMM40 |
| TOMM40L | TOMM5 | TOMM7 | TOMM70A | TOP1 |
| TOP1MT | TOP2A | TOP2B | TOP3A | TOP3B |
| TOP3B_ENST00000357179 | TOPBP1 | TOPORS | TOR1A | TOR1AIP1 |
| TOR1AIP2 | TOR1B | TOR2A | TOR3A | TOX |
| TOX2 | TOX3 | TOX4 | TP53 | TP53AIP1 |
| TP53BP1 | TP53BP2 | TP53I11 | TP53I13 | TP53I3 |
| TP53INP1 | TP53INP2 | TP53RK | TP53TG1 | TP53TG5 |
| TP63 | TP73 | TPBG | TPCN1 | TPCN2 |
| TPD52 | TPD52L1 | TPD52L2 | TPD52L3 | TPH1 |
| TPH2 | TPI1 | TPK1 | TPM1 | TPM2 |
| TPM3 | TPM4 | TPM4_ENST00000344824 | TPMT | TPO |
| TPP1 | TPP2 | TPPP | TPPP2 | TPPP3 |
| TPR | TPRA1 | TPRG1 | TPRG1L | TPRKB |
| TPRX1 | TPRXL | TPSAB1 | TPSD1 | TPSG1 |
| TPST1 | TPST2 | TPT1 | TPTE | TPTE2 |
| TPX2 | TRA2A | TRA2B | TRABD | TRAD |
| TRADD | TRAF1 | TRAF2 | TRAF3 | TRAF3IP1 |
| TRAF3IP2 | TRAF3IP3 | TRAF4 | TRAF5 | TRAF6 |
| TRAF7 | TRAFD1 | TRAIP | TRAK1 | TRAK2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| TRAM1 | TRAM1L1 | TRAM2 | TRANK1 | TRAP1 |
| TRAPPC1 | TRAPPC10 | TRAPPC2 | TRAPPC2L | TRAPPC3 |
| TRAPPC4 | TRAPPC5 | TRAPPC6A | TRAPPC6B | TRAPPC9 |
| TRAT1 | TRDMT1 | TRDN | TREM1 | TREM2 |
| TREML1 | TREML2 | TREML4 | TRERF1 | TREX1 |
| TREX2 | TRH | TRHDE | TRHR | TRIAP1 |
| TRIB1 | TRIB2 | TRIB3 | TRIM10 | TRIM11 |
| TRIM13 | TRIM14 | TRIM15 | TRIM16 | TRIM16L |
| TRIM17 | TRIM2 | TRIM21 | TRIM22 | TRIM23 |
| TRIM24 | TRIM25 | TRIM26 | TRIM27 | TRIM28 |
| TRIM29 | TRIM3 | TRIM31 | TRIM32 | TRIM33 |
| TRIM34 | TRIM35 | TRIM36 | TRIM37 | TRIM38 |
| TRIM39 | TRIM4 | TRIM40 | TRIM41 | TRIM42 |
| TRIM43 | TRIM44 | TRIM45 | TRIM46 | TRIM47 |
| TRIM48 | TRIM49 | TRIM5 | TRIM50 | TRIM52 |
| TRIM54 | TRIM55 | TRIM56 | TRIM58 | TRIM59 |
| TRIM6 | TRIM6-TRIM34 | TRIM60 | TRIM61 | TRIM62 |
| TRIM63 | TRIM64C | TRIM65 | TRIM66 | TRIM67 |
| TRIM68 | TRIM69 | TRIM7 | TRIM71 | TRIM72 |
| TRIM73 | TRIM74 | TRIM8 | TRIM9 | TRIML1 |
| TRIML2 | TRIO | TRIOBP | TRIOBP_ENST00000344404 | TRIP10 |
| TRIP11 | TRIP12 | TRIP13 | TRIP4 | TRIP6 |
| TRIT1 | TRMT1 | TRMT11 | TRMT112 | TRMT12 |
| TRMT2A | TRMT2B | TRMT5 | TRMT6 | TRMT61A |
| TRMT61B | TRMU | TRNAU1AP | TRNP1 | TRNT1 |
| TRO | TROAP | TROVE2 | TRPA1 | TRPC1 |
| TRPC3 | TRPC4 | TRPC4AP | TRPC5 | TRPC6 |
| TRPM1 | TRPM2 | TRPM3 | TRPM4 | TRPM5 |
| TRPM6 | TRPM7 | TRPM8 | TRPS1 | TRPT1 |
| TRPV2 | TRPV3 | TRPV4 | TRPV5 | TRPV6 |
| TRRAP | TRUB1 | TRUB2 | TRYX3 | TSC1 |
| TSC2 | TSC22D1 | TSC22D2 | TSC22D3 | TSC22D4 |
| TSC2_ENST00000219476 | TSEN15 | TSEN2 | TSEN34 | TSEN54 |
| TSFM | TSG101 | TSGA10 | TSGA10IP | TSGA13 |
| TSGA14 | TSHB | TSHR | TSHZ1 | TSHZ2 |
| TSHZ3 | TSKS | TSKU | TSLP | TSN |
| TSNARE1 | TSNAX | TSNAXIP1 | TSPAN1 | TSPAN11 |
| TSPAN12 | TSPAN13 | TSPAN14 | TSPAN15 | TSPAN16 |
| TSPAN17 | TSPAN18 | TSPAN2 | TSPAN3 | TSPAN31 |
| TSPAN32 | TSPAN33 | TSPAN4 | TSPAN5 | TSPAN6 |
| TSPAN7 | TSPAN8 | TSPAN9 | TSPO | TSPO2 |
| TSPY2 | TSPY3 | TSPYL1 | TSPYL2 | TSPYL5 |
| TSPYL6 | TSR1 | TSR2 | TSSC1 | TSSC4 |
| TSSK1B | TSSK2 | TSSK3 | TSSK4 | TSSK6 |
| TST | TSTA3 | TSTD2 | TTBK1 | TTBK2 |
| TTC1 | TTC12 | TTC13 | TTC14 | TTC15 |
| TTC16 | TTC17 | TTC18 | TTC19 | TTC21A |
| TTC21B | TTC22 | TTC23 | TTC26 | TTC27 |
| TTC29 | TTC3 | TTC30A | TTC31 | TTC32 |
| TTC33 | TTC35 | TTC36 | TTC37 | TTC38 |
| TTC39A | TTC39B | TTC39C | TTC3L | TTC4 |
| TTC5 | TTC6 | TTC7A | TTC7B | TTC8 |
| TTC9B | TTC9C | TTF1 | TTF2 | TTK |
| TTL | TTLL1 | TTLL10 | TTLL11 | TTLL12 |
| TTLL13 | TTLL2 | TTLL3 | TTLL4 | TTLL5 |
| TTLL6 | TTLL6_ENST00000393382 | TTLL7 | TTLL9 | TTN |
| TTN_ENST00000356127 | TTN_ENST00000360870 | TTPA | TTPAL | TTR |
| TTRAP | TTYH1 | TTYH2 | TTYH3 | TUB |
| TUBA1A | TUBA1B | TUBA1C | TUBA3C | TUBA3D |
| TUBA3E | TUBA4A | TUBA4A_ENST00000392088 | TUBA8 | TUBAL3 |
| TUBB | TUBB1 | TUBB2A | TUBB2B | TUBB2C |
| TUBB3 | TUBB4 | TUBB4Q | TUBB6 | TUBB8 |
| TUBD1 | TUBE1 | TUBG1 | TUBG2 | TUBGCP2 |
| TUBGCP3 | TUBGCP4 | TUBGCP5 | TUBGCP6 | TUFM |
| TUFT1 | TULP1 | TULP2 | TULP3 | TULP4 |
| TUSC1 | TUSC2 | TUSC3 | TUSC4 | TUSC5 |
| TUT1 | TWF1 | TWF2 | TWIST1 | TWISTNB |
| TWSG1 | TXK | TXLNA | TXLNB | TXN |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| TXN2 | TXNDC11 | TXNDC12 | TXNDC15 | TXNDC16 |
| TXNDC17 | TXNDC2 | TXNDC3 | TXNDC5 | TXNDC6 |
| TXNDC8 | TXNDC9 | TXNIP | TXNL1 | TXNL2 |
| TXNL4A | TXNL4B | TXNRD1 | TXNRD2 | TXNRD3IT1 |
| TYK2 | TYMP | TYMS | TYR | TYRO3 |
| TYROBP | TYRP1 | TYSND1 | TYW1 | TYW3 |
| U258_HUMAN | U2AF1 | U2AF1L4 | U2AF2 | U2D3L_HUMAN |
| U464_HUMAN | U66061_1 | U66061_1_ENST00000390396 | UACA | UAP1 |
| UAP1L1 | UBA1 | UBA2 | UBA3 | UBA5 |
| UBA52 | UBA6 | UBA7 | UBAC1 | UBAC2 |
| UBAP1 | UBAP2 | UBAP2L | UBASH3A | UBASH3B |
| UBB | UBC | UBD | UBE2A | UBE2B |
| UBE2C | UBE2CBP | UBE2D1 | UBE2D2 | UBE2D3 |
| UBE2D4 | UBE2E1 | UBE2E2 | UBE2E3 | UBE2F |
| UBE2G1 | UBE2G2 | UBE2H | UBE2I | UBE2J1 |
| UBE2J2 | UBE2K | UBE2L3 | UBE2L6 | UBE2M |
| UBE2N | UBE2NL | UBE2O | UBE2Q1 | UBE2Q2 |
| UBE2R2 | UBE2S | UBE2T | UBE2U | UBE2V1 |
| UBE2V2 | UBE3A | UBE3B | UBE3C | UBE4A |
| UBE4B | UBFD1 | UBIAD1 | UBL3 | UBL4A |
| UBL4B | UBL5 | UBL7 | UBLCP1 | UBN1 |
| UBN2 | UBOX5 | UBP1 | UBQLN1 | UBQLN2 |
| UBQLN3 | UBQLN4 | UBQLNL | UBR1 | UBR2 |
| UBR3 | UBR3_ENST00000272793 | UBR4 | UBR5 | UBR7 |
| UBTD1 | UBTD2 | UBTF | UBXN1 | UBXN10 |
| UBXN11 | UBXN2A | UBXN2B | UBXN4 | UBXN6 |
| UBXN7 | UBXN8 | UCHL1 | UCHL3 | UCHL5 |
| UCK1 | UCK2 | UCKL1 | UCMA | UCN |
| UCN2 | UCN3 | UCP1 | UCP2 | UCP3 |
| UEVLD | UFC1 | UFD1L | UFM1 | UFSP1 |
| UFSP2 | UGCG | UGDH | UGGT1 | UGGT2 |
| UGP2 | UGT1A1 | UGT1A10 | UGT1A3 | UGT1A4 |
| UGT1A5 | UGT1A6 | UGT1A7 | UGT1A8 | UGT1A9 |
| UGT2A1 | UGT2A3 | UGT2B11 | UGT2B15 | UGT2B17 |
| UGT2B28 | UGT2B4 | UGT2B7 | UGT3A1 | UGT3A2 |
| UGT8 | UHMK1 | UHRF1 | UHRF1BP1 | UHRF1BP1L |
| UHRF2 | UIMC1 | ULBP1 | ULBP2 | ULBP3 |
| ULK1 | ULK2 | ULK3 | ULK4 | UMOD |
| UMODL1 | UMPS | UNC119 | UNC119B | UNC13B |
| UNC13D | UNC45A | UNC45B | UNC50 | UNC5A |
| UNC5B | UNC5C | UNC5CL | UNC5D | UNC80 |
| UNC93A | UNC93B6 | UNCX | UNG | UNG_ENST00000242576 |
| UNK | UNKL | UNQ1887 | UNQ3045 | UNQ9391 |
| UPB1 | UPF1 | UPF2 | UPF3A | UPF3B |
| UPK1A | UPK1B | UPK2 | UPK3A | UPK3B |
| UPP1 | UPP2 | UPRT | UQCC | UQCR11 |
| UQCRB | UQCRC1 | UQCRC2 | UQCRFS1 | UQCRH |
| UQCRQ | URB2 | URGCP | URM1 | UROC1 |
| UROD | UROS | URP2 | USF1 | USF2 |
| USH1C | USH1G | USH2A | USHBP1 | USMG5 |
| USMG5P1 | USO1 | USP1 | USP10 | USP11 |
| USP12 | USP13 | USP14 | USP15 | USP16 |
| USP17L2 | USP18 | USP19 | USP2 | USP20 |
| USP21 | USP22 | USP24 | USP25 | USP26 |
| USP27X | USP28 | USP29 | USP3 | USP30 |
| USP31 | USP32 | USP33 | USP34 | USP35 |
| USP35_ENST00000263311 | USP36 | USP37 | USP38 | USP39 |
| USP4 | USP41 | USP42 | USP43 | USP44 |
| USP45 | USP46 | USP47 | USP48 | USP49 |
| USP5 | USP50 | USP51 | USP53 | USP54 |
| USP54_ENST00000408019 | USP6 | USP6NL | USP7 | USP8 |
| USP9X | USP9Y | USPL1 | UST | UTF1 |
| UTP11L | UTP14A | UTP14C | UTP15 | UTP18 |
| UTP20 | UTP23 | UTP3 | UTP6 | UTRN |
| UTS2 | UTS2D | UTS2R | UTY | UVRAG |
| UXT | VAC14 | VAMP1 | VAMP2 | VAMP3 |
| VAMP4 | VAMP5 | VAMP7 | VAMP8 | VANGL1 |
| VANGL2 | VAPA | VAPB | VARS | VARS2 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| VASH1 | VASH2 | VASN | VASP | VAT1 |
| VAT1L | VAV1 | VAV2 | VAV3 | VAX1 |
| VAX2 | VBP1 | VCAM1 | VCAN | VCL |
| VCP | VCPIP1 | VCX | VCX2 | VCX3A |
| VCY | VCY1B | VDAC1 | VDAC2 | VDAC3 |
| VDAC4 | VDR | VEGFA | VEGFB | VEGFC |
| VENTX | VEPH1 | VEZF1 | VGF | VGLL1 |
| VGLL2 | VGLL3 | VGLL4 | VHL | VHLL |
| VIL1 | VILL | VIM | VIP | VIPAR |
| VIPR1 | VIPR2 | VIT | VKORC1 | VKORC1L1 |
| VLDLR | VMA21 | VMAC | VMO1 | VN1R1 |
| VN1R2 | VN1R4 | VN2R1P | VNN1 | VNN2 |
| VNN3 | VPRBP | VPREB1 | VPREB3 | VPS11 |
| VPS13A | VPS13B | VPS13C | VPS13D | VPS16 |
| VPS18 | VPS24 | VPS25 | VPS26A | VPS26B |
| VPS28 | VPS29 | VPS33A | VPS33B | VPS35 |
| VPS36 | VPS37A | VPS37B | VPS37C | VPS37D |
| VPS39 | VPS41 | VPS45 | VPS4B | VPS52 |
| VPS53 | VPS54 | VPS72 | VPS8 | VRK1 |
| VRK2 | VRK3 | VSIG1 | VSIG2 | VSIG4 |
| VSIG7 | VSIG8 | VSNL1 | VSTM1 | VSTM2B |
| VSTM2L | VSX1 | VSX2 | VTA1 | VTCN1 |
| VTI1A | VTI1B | VTN | VWA1 | VWA2 |
| VWA3A | VWA3B | VWA5A | VWC2 | VWCE |
| VWDE | VWF | WAG | WAPAL | WARS |
| WARS2 | WAS | WASF1 | WASF2 | WASF3 |
| WASF4 | WASL | WBP1 | WBP11 | WBP2 |
| WBP2NL | WBP4 | WBP5 | WBSCR16 | WBSCR17 |
| WBSCR22 | WBSCR27 | WBSCR28 | WDFY1 | WDFY2 |
| WDFY3 | WDFY4 | WDHD1 | WDR11 | WDR12 |
| WDR13 | WDR16 | WDR17 | WDR18 | WDR19 |
| WDR20 | WDR23 | WDR24 | WDR25 | WDR26 |
| WDR27 | WDR27_ENST00000333572 | WDR3 | WDR31 | WDR33 |
| WDR34 | WDR35 | WDR36 | WDR37 | WDR38 |
| WDR4 | WDR41 | WDR43 | WDR44 | WDR44_ENST00000435384 |
| WDR45 | WDR45L | WDR46 | WDR47 | WDR48 |
| WDR49 | WDR5 | WDR51A | WDR51B | WDR52 |
| WDR52_ENST00000393845 | WDR53 | WDR54 | WDR55 | WDR57 |
| WDR59 | WDR5B | WDR6 | WDR60 | WDR61 |
| WDR62 | WDR63 | WDR64 | WDR65 | WDR66 |
| WDR67 | WDR69 | WDR7 | WDR70 | WDR72 |
| WDR73 | WDR75 | WDR76 | WDR77 | WDR78 |
| WDR8 | WDR81 | WDR82 | WDR82_ENST00000296490 | WDR83 |
| WDR85 | WDR88 | WDR89 | WDR90 | WDR91 |
| WDR92 | WDR93 | WDSUB1 | WDTC1 | WDYHV1 |
| WEE1 | WEE2 | WFDC1 | WFDC10A | WFDC10B |
| WFDC11 | WFDC12 | WFDC13 | WFDC2 | WFDC3 |
| WFDC5 | WFDC6 | WFDC8 | WFDC9 | WFIKKN1 |
| WFIKKN2 | WFS1 | WHAMM_ENST00000234505 | WHSC1 | WHSC1L1 |
| WHSC2 | WIF1 | WIPF1 | WIPF2 | WIPF3 |
| WIPI1 | WIPI2 | WISP1 | WISP2 | WISP3 |
| WIT1 | WIZ | WLS | WNK1 | WNK2 |
| WNK3 | WNK4 | WNT1 | WNT10A | WNT10B |
| WNT11 | WNT16 | WNT2 | WNT2B | WNT3 |
| WNT3A | WNT4 | WNT5A | WNT5B | WNT6 |
| WNT7A | WNT7B | WNT8A | WNT8B | WNT9A |
| WNT9B | WRAP53 | WRB | WRN | WRNIP1 |
| WSB1 | WSB2 | WSCD1 | WSCD2 | WT1 |
| WTAP | WTIP | WWC1 | WWC2 | WWC3 |
| WWOX | WWP1 | WWP2 | WWTR1 | XAB1 |
| XAB2 | XAF1 | XAGE1C | XAGE1D | XAGE2 |
| XAGE3 | XAGE5 | XBP1 | XCL1 | XCL2 |
| XCR1 | XDH | XG | XIAP | XIRP1 |
| XIRP2 | XIRP2_ENST00000409728 | XK | XKR3 | XKR4 |
| XKR5 | XKR6 | XKR7 | XKR8 | XKR9 |
| XKRX | XPA | XPC | XPNPEP1 | XPNPEP2 |
| XPNPEP3 | XPO1 | XPO4 | XPO5 | XPO6 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
| --- | --- | --- | --- | --- |
| XPO7 | XPOT | XPR1 | XRCC1 | XRCC2 |
| XRCC3 | XRCC4 | XRCC5 | XRCC6 | XRCC6BP1 |
| XRN1 | XRN2 | XRRA1 | XXyac-YX155B6_1 | XYLB |
| XYLT1 | XYLT2 | YAF2 | YAP1 | YARS |
| YARS2 | YBX1 | YBX2 | YDJC | YEATS2 |
| YEATS4 | YES1 | YIF1A | YIF1B | YIPF1 |
| YIPF2 | YIPF3 | YIPF4 | YIPF5 | YIPF6 |
| YJEFN3 | YKT6 | YLPM1 | YME1L1 | YOD1 |
| YPEL1 | YPEL2 | YPEL3 | YPEL4 | YPEL5 |
| YRDC | YSK4 | YSK4_ ENST00000375845 | YTHDC1 | YTHDC2 |
| YTHDF1 | YTHDF2 | YV009_HUMAN | YWHAB | YWHAE |
| YWHAG | YWHAH | YWHAQ | YWHAZ | YY1 |
| YY1AP1 | YY2 | ZACN | ZADH1 | ZADH2 |
| ZAK | ZAN | ZAP70 | ZAR1 | ZAR1L |
| ZBBX | ZBBX_ ENST00000455345 | ZBED1 | ZBED2 | ZBED3 |
| ZBED4 | ZBP1 | ZBTB1 | ZBTB10 | ZBTB11 |
| ZBTB12 | ZBTB16 | ZBTB17 | ZBTB2 | ZBTB20 |
| ZBTB22 | ZBTB24 | ZBTB25 | ZBTB26 | ZBTB3 |
| ZBTB32 | ZBTB33 | ZBTB34 | ZBTB37 | ZBTB38 |
| ZBTB39 | ZBTB4 | ZBTB40 | ZBTB41 | ZBTB43 |
| ZBTB44 | ZBTB45 | ZBTB46 | ZBTB48 | ZBTB49 |
| ZBTB5 | ZBTB6 | ZBTB7A | ZBTB7B | ZBTB7C |
| ZBTB8A | ZBTB8B_ ENST00000291374 | ZBTB8OS | ZBTB9 | ZC3H10 |
| ZC3H11A | ZC3H12A | ZC3H12B | ZC3H12B_ ENST00000338957 | ZC3H12C |
| ZC3H13 | ZC3H14 | ZC3H15 | ZC3H18 | ZC3H3 |
| ZC3H4 | ZC3H6 | ZC3H7A | ZC3H7B | ZC3H8 |
| ZC3HAV1 | ZC3HAV1L | ZC3HC1 | ZC4H2 | ZCCHC10 |
| ZCCHC11 | ZCCHC12 | ZCCHC13 | ZCCHC14 | ZCCHC16 |
| ZCCHC17 | ZCCHC24 | ZCCHC3 | ZCCHC4 | ZCCHC5 |
| ZCCHC6 | ZCCHC7 | ZCCHC8 | ZCCHC9 | ZCRB1 |
| ZCWPW1 | ZCWPW2 | ZDHHC1 | ZDHHC11 | ZDHHC11_ ENST00000424784 |
| ZDHHC12 | ZDHHC13 | ZDHHC14 | ZDHHC15 | ZDHHC16 |
| ZDHHC18 | ZDHHC19 | ZDHHC21 | ZDHHC23 | ZDHHC24 |
| ZDHHC3 | ZDHHC4 | ZDHHC5 | ZDHHC6 | ZDHHC7 |
| ZDHHC8 | ZDHHC9 | ZEB1 | ZEB2 | ZER1 |
| ZFAND1 | ZFAND2A | ZFAND2B | ZFAND3 | ZFAND5 |
| ZFAND6 | ZFAT | ZFC3H1 | ZFHX3 | ZFHX4 |
| ZFP1 | ZFP106 | ZFP112 | ZFP14 | ZFP161 |
| ZFP2 | ZFP28 | ZFP3 | ZFP30 | ZFP36 |
| ZFP36L1 | ZFP36L2 | ZFP37 | ZFP41 | ZFP42 |
| ZFP57 | ZFP64 | ZFP64_ ENST00000361387 | ZFP82 | ZFP90 |
| ZFP91 | ZFP91-CNTF | ZFP92 | ZFPL1 | ZFPM1 |
| ZFPM2 | ZFR | ZFR2 | ZFX | ZFY |
| ZFYVE1 | ZFYVE16 | ZFYVE19 | ZFYVE20 | ZFYVE21 |
| ZFYVE26 | ZFYVE27 | ZFYVE28 | ZFYVE9 | ZG16B |
| ZGPAT | ZHX1 | ZHX2 | ZHX3 | ZIC1 |
| ZIC2 | ZIC3 | ZIC4 | ZIC5 | ZIK1 |
| ZIM2 | ZIM3 | ZKSCAN1 | ZKSCAN2 | ZKSCAN3 |
| ZKSCAN4 | ZKSCAN5 | ZMAT1 | ZMAT2 | ZMAT3 |
| ZMAT4 | ZMAT5 | ZMIZ1 | ZMIZ2 | ZMPSTE24 |
| ZMYM1 | ZMYM2 | ZMYM3 | ZMYM4 | ZMYM5 |
| ZMYM6 | ZMYND10 | ZMYND11 | ZMYND12 | ZMYND15 |
| ZMYND17 | ZMYND19 | ZMYND8 | ZNF10 | ZNF100 |
| ZNF101 | ZNF107 | ZNF10_ ENST00000228289 | ZNF114 | ZNF117 |
| ZNF12 | ZNF121 | ZNF123 | ZNF124 | ZNF131 |
| ZNF132 | ZNF133 | ZNF134 | ZNF135 | ZNF136 |
| ZNF138 | ZNF14 | ZNF140 | ZNF141 | ZNF142 |
| ZNF143 | ZNF146 | ZNF148 | ZNF154 | ZNF155 |
| ZNF157 | ZNF16 | ZNF160 | ZNF165 | ZNF167 |
| ZNF169 | ZNF17 | ZNF174 | ZNF175 | ZNF177 |
| ZNF18 | ZNF180 | ZNF181 | ZNF182 | ZNF184 |
| ZNF185 | ZNF189 | ZNF19 | ZNF192 | ZNF193 |
| ZNF195 | ZNF197 | ZNF198 | ZNF2 | ZNF20 |
| ZNF200 | ZNF202 | ZNF205 | ZNF207 | ZNF211 |
| ZNF212 | ZNF213 | ZNF214 | ZNF215 | ZNF217 |
| ZNF219 | ZNF22 | ZNF221 | ZNF222 | ZNF223 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ZNF224 | ZNF227 | ZNF229 | ZNF23 | ZNF230 |
| ZNF232 | ZNF233 | ZNF235 | ZNF236 | ZNF238 |
| ZNF239 | ZNF24 | ZNF248 | ZNF25 | ZNF251 |
| ZNF253 | ZNF254 | ZNF256 | ZNF257 | ZNF257_ENST00000435820 |
| ZNF259 | ZNF26 | ZNF260 | ZNF263 | ZNF264 |
| ZNF266 | ZNF267 | ZNF271 | ZNF273 | ZNF274 |
| ZNF275 | ZNF276 | ZNF277 | ZNF278 | ZNF28 |
| ZNF280A | ZNF280B | ZNF280C | ZNF280D | ZNF281 |
| ZNF282 | ZNF283 | ZNF285A | ZNF286A | ZNF287 |
| ZNF292 | ZNF295 | ZNF296 | ZNF3 | ZNF30 |
| ZNF300 | ZNF304 | ZNF311 | ZNF317 | ZNF318 |
| ZNF319 | ZNF32 | ZNF320 | ZNF321 | ZNF322A |
| ZNF322B | ZNF323 | ZNF324 | ZNF324B | ZNF326 |
| ZNF329 | ZNF330 | ZNF331 | ZNF333 | ZNF334 |
| ZNF335 | ZNF337 | ZNF33A | ZNF33B | ZNF34 |
| ZNF341 | ZNF343 | ZNF345 | ZNF346 | ZNF347 |
| ZNF35 | ZNF350 | ZNF354A | ZNF354B | ZNF354C |
| ZNF358 | ZNF362 | ZNF365 | ZNF366 | ZNF367 |
| ZNF37A | ZNF382 | ZNF383 | ZNF384 | ZNF385 |
| ZNF385A | ZNF385B | ZNF385C | ZNF385D | ZNF391 |
| ZNF394 | ZNF395 | ZNF396 | ZNF397 | ZNF397OS |
| ZNF398 | ZNF407 | ZNF408 | ZNF41 | ZNF410 |
| ZNF414 | ZNF414_ENST00000393927 | ZNF415 | ZNF416 | ZNF417 |
| ZNF418 | ZNF419 | ZNF420 | ZNF423 | ZNF425 |
| ZNF426 | ZNF428 | ZNF429 | ZNF43 | ZNF430 |
| ZNF431 | ZNF432 | ZNF432_ENST00000354939 | ZNF434 | ZNF436 |
| ZNF438 | ZNF439 | ZNF440 | ZNF441 | ZNF442 |
| ZNF443 | ZNF444 | ZNF445 | ZNF446 | ZNF449 |
| ZNF45 | ZNF451 | ZNF454 | ZNF460 | ZNF462 |
| ZNF467 | ZNF468 | ZNF470 | ZNF471 | ZNF473 |
| ZNF474 | ZNF479 | ZNF48 | ZNF480 | ZNF483 |
| ZNF484 | ZNF485 | ZNF486 | ZNF488 | ZNF490 |
| ZNF491 | ZNF492 | ZNF492_ENST00000456783 | ZNF493 | ZNF496 |
| ZNF497 | ZNF498 | ZNF500 | ZNF501 | ZNF502 |
| ZNF503 | ZNF506 | ZNF507 | ZNF510 | ZNF511 |
| ZNF512 | ZNF512B | ZNF513 | ZNF514 | ZNF516 |
| ZNF517 | ZNF518B | ZNF519 | ZNF521 | ZNF524 |
| ZNF526 | ZNF527 | ZNF528 | ZNF529 | ZNF530 |
| ZNF532 | ZNF534 | ZNF536 | ZNF540 | ZNF541 |
| ZNF543 | ZNF544 | ZNF546 | ZNF547 | ZNF548 |
| ZNF549 | ZNF550 | ZNF551 | ZNF552 | ZNF554 |
| ZNF555 | ZNF556 | ZNF557 | ZNF558 | ZNF559 |
| ZNF560 | ZNF561 | ZNF562 | ZNF563 | ZNF564 |
| ZNF565 | ZNF566 | ZNF567 | ZNF568 | ZNF569 |
| ZNF57 | ZNF570 | ZNF571 | ZNF572 | ZNF573 |
| ZNF574 | ZNF575 | ZNF576 | ZNF577 | ZNF579 |
| ZNF580 | ZNF581 | ZNF582 | ZNF583 | ZNF584 |
| ZNF585A | ZNF585B | ZNF586 | ZNF587 | ZNF589 |
| ZNF592 | ZNF593 | ZNF594 | ZNF596 | ZNF597 |
| ZNF599 | ZNF600 | ZNF605 | ZNF606 | ZNF607 |
| ZNF608 | ZNF609 | ZNF610 | ZNF611 | ZNF613 |
| ZNF614 | ZNF615 | ZNF616 | ZNF618 | ZNF619 |
| ZNF620 | ZNF621 | ZNF622 | ZNF623 | ZNF624 |
| ZNF625 | ZNF626 | ZNF627 | ZNF628 | ZNF628_ENST00000391718 |
| ZNF630 | ZNF638 | ZNF639 | ZNF641 | ZNF642 |
| ZNF643 | ZNF644 | ZNF645 | ZNF646 | ZNF648 |
| ZNF649 | ZNF652 | ZNF653 | ZNF654 | ZNF655 |
| ZNF658 | ZNF658B | ZNF660 | ZNF662 | ZNF664 |
| ZNF665 | ZNF667 | ZNF668 | ZNF669 | ZNF67 |
| ZNF670 | ZNF671 | ZNF672 | ZNF673 | ZNF674 |
| ZNF675 | ZNF676 | ZNF677 | ZNF678 | ZNF680 |
| ZNF682 | ZNF684 | ZNF687 | ZNF688 | ZNF689 |
| ZNF69 | ZNF691 | ZNF692 | ZNF696 | ZNF697_ENST00000271263 |
| ZNF699 | ZNF7 | ZNF70 | ZNF700 | ZNF701 |
| ZNF703 | ZNF704 | ZNF705A | ZNF705D | ZNF706 |
| ZNF707 | ZNF708 | ZNF709 | ZNF71 | ZNF710 |
| ZNF711 | ZNF713 | ZNF714 | ZNF738 | ZNF74 |

TABLE 3-continued

List of genes which contain cancer-related somatic mutations. The list was adapted from Sanger Center's COSMIC database(Bamford et al, 2004; Forbes et al., 2008; Forbes et al.; Forbes et al.; Friedberg; Pleasance et al.). The gene names are uniquely assigned by HUGO Gene Nomenclature Committee (http://www.genenames.org/index.html, accessed Jan. 31, 2011).

| HGNC Gene Name | HGNC Gene Name | HGNC Gene Name | HGNC Gene Name | HGNC Gene Name |
|---|---|---|---|---|
| ZNF746 | ZNF747 | ZNF750 | ZNF75A | ZNF75D |
| ZNF76 | ZNF761 | ZNF763 | ZNF764 | ZNF765 |
| ZNF765_ENST00000396408 | ZNF767 | ZNF768 | ZNF77 | ZNF770 |
| ZNF772 | ZNF773 | ZNF774 | ZNF775 | ZNF776 |
| ZNF777 | ZNF780A | ZNF781 | ZNF782 | ZNF784 |
| ZNF785 | ZNF786 | ZNF787 | ZNF788 | ZNF789 |
| ZNF79 | ZNF790 | ZNF791 | ZNF793 | ZNF799 |
| ZNF8 | ZNF80 | ZNF800 | ZNF804A | ZNF804B |
| ZNF81 | ZNF816A | ZNF821 | ZNF826 | ZNF827 |
| ZNF828 | ZNF829 | ZNF83 | ZNF830 | ZNF831 |
| ZNF833 | ZNF834 | ZNF835 | ZNF836 | ZNF837 |
| ZNF839 | ZNF84 | ZNF841_ENST00000359973 | ZNF843 | ZNF846 |
| ZNF85 | ZNF862 | ZNF879 | ZNF90 | ZNF90_ENST00000418063 |
| ZNF91 | ZNF91_ENST00000300619 | ZNF92 | ZNF93 | ZNFX1 |
| ZNHIT1 | ZNHIT2 | ZNHIT3 | ZNHIT6 | ZNRD1 |
| ZNRF1 | ZNRF2 | ZNRF3 | ZNRF4 | ZP1 |
| ZP2 | ZP3 | ZP4 | ZPBP | ZPBP2 |
| ZPLD1 | ZRANB1 | ZRANB2 | ZRANB3 | ZRSR2 |
| ZSCAN1 | ZSCAN10 | ZSCAN16 | ZSCAN18 | ZSCAN2 |
| ZSCAN20 | ZSCAN21 | ZSCAN22 | ZSCAN23 | ZSCAN29 |
| ZSCAN4 | ZSCAN5A | ZSWIM1 | ZSWIM2 | ZSWIM3 |
| ZSWIM4 | ZSWIM5 | ZSWIM7 | ZUFSP | ZW10 |
| ZWILCH | ZWINT | ZXDA | ZXDB | ZXDC |
| ZYG11B | ZYX | ZZEF1 | ZZZ3 | dJ341D10_1 |
| hCG_1642425 | hCG_1644301 | hCG_17324 | hCG_1757335 | hCG_1793639 |
| hCG_2000329 | hCG_2015269 | hCG_2023776 | hCG_2026038 | hCG_38941 |
| mir-223 | mir-424 | | | |

TABLE 4

Exemplary transposable elements in GBM microvesicles

| Name | GenBank Accession No. |
|---|---|
| Homo sapiens transposon-derived Buster1 transposase-like protein gene (LOC58486) | [NM_021211] |
| Human endogenous retrovirus H protease/integrase-derived ORF1, ORF2, and putative envelope protein mRNA, complete cds | [U88896] |
| Human endogenous retrovirus type C oncovirus sequence | [M74509] |
| Human endogenous retroviral H protease/integrase-derived ORF1 mRNA, complete cds, and putative envelope protein mRNA, partial cds. | [U88898] |
| Homo sapiens Cas-Br-M (murine) ecotropic retroviral transforming sequence (CBL) | [NM_005188] |
| Homo sapiens endogenous retroviral sequence K, 6 (ERVK6) | [NM_001007236] |
| Homo sapiens endogenous retroviral family W, env(C7), member 1 (syncytin) (ERVWE1) | [NM_014590] |
| Homo sapiens Cas-Br-M (murine) ecotropic retroviral transforming sequence b (CBLB) | [NM_170662] |
| Homo sapiens mRNA containing human endogenous retrovirus H and human endogenous retrovirus E sequences | [AF026246] |
| Homo sapiens cDNA FLJ11804 fis, clone HEMBA1006272, moderately similar to RETROVIRUS-RELATED PROTEASE (EC 3.4.23.-). | [AK021866] |
| Human DNA/endogenous retroviral long terminal repeat (LTR) junction mRNA, clone lambda-LTR22 | [M32220] |
| ALU8_HUMAN (P39195) Alu subfamily SX sequence contamination warning entry, partial (7%) | [THC2390306] |
| AA436686 zv59a12.s1 Soares_testis_NHT Homo sapiens cDNA clone IMAGE:757918 3' similar to contains Alu repetitive element | [AA436686] |
| ALU6_HUMAN (P39193) Alu subfamily SP sequence contamination warning entry, partial (19%) | [THC2314369] |
| ALU1_HUMAN (P39188) Alu subfamily J sequence contamination warning entry, partial (8%) | [THC2320431] |
| BF476310 naa21a07.x1 NCI_CGAP_Pr28 Homo sapiens cDNA clone IMAGE:3255444 3' similar to contains Alu repetitive element;contains element MIR MIR repetitive element | [BF476310] |
| ALU4_HUMAN (P39191) Alu subfamily SB2 sequence contamination warning entry, partial (4%) | [THC2284657] |
| LIN1_NYCCO (P08548) LINE-1 reverse transcriptase homolog, partial (5%) | [THC2379144] |
| od56h08.s1 NCI_CGAP_GCB1 Homo sapiens cDNA clone IMAGE:1371999 3' similar to gb:M19503 LINE-1 REVERSE TRANSCRIPTASE HOMOLOG (HUMAN) | [AA827885] |
| B28096 line-1 protein ORF2 - human (Homo sapiens), partial (4%) | [THC2281068] |
| Homo sapiens LINE-1 type transposase domain containing 1 (L1TD1) | [NM_019079] |
| Q6D545 (Q6D545) Transposase transposon tn1721 (Fragment), partial (12%) | [THC2407148] |

TABLE 4-continued

Exemplary transposable elements in GBM microvesicles

| Name | GenBank Accession No. |
|---|---|
| Human clone 279131 defective mariner transposon Hsmar2 mRNA sequence | [U92025] |
| Homo sapiens retrotransposon gag domain containing 4 (RGAG4) | [NM_001024455] |
| Homo sapiens transposon-derived Buster3 transposase-like (LOC63920) | [NM_022090] |
| Homo sapiens retrotransposon gag domain containing 1 (RGAG1) | [NM_020769] |
| Human EST clone 251800 mariner transposon Hsmar1 sequence | [U80770] |
| Homo sapiens SET domain and mariner transposase fusion gene (SETMAR) | [NM_006515] |
| Homo sapiens tigger transposable element derived 5 (TIGD5) | [NM_032862] |
| Homo sapiens tigger transposable element derived 1 (TIGD1) | [NM_145702] |
| Homo sapiens pogo transposable element with KRAB domain (POGK) | [NM_017542] |
| Homo sapiens pogo transposable element with ZNF domain (POGZ), transcript variant 1 | [NM_015100] |
| Homo sapiens tigger transposable element derived 6 (TIGD6) | [NM_030953] |
| Homo sapiens piggyBac transposable element derived 4 (PGBD4) | [NM_152595] |

TABLE 5

Human transposable elements.
The list is adapted from Repbase-GIRI.
http://www.girinst.org/, accessed Jan. 31, 2011.

| Type of Transposon | ID |
|---|---|
| CR1 | CR1_HS |
| CR1 | L3 |
| DNA transposon | LOOPER |
| DNA transposon | MER105 |
| DNA transposon | MER116 |
| DNA transposon | MER28 |
| DNA transposon | MER45B |
| DNA transposon | MER45R |
| DNA transposon | MER53 |
| DNA transposon | MER63A |
| DNA transposon | MER63B |
| DNA transposon | MER69C |
| DNA transposon | MER75 |
| DNA transposon | MER75B |
| DNA transposon | MER85 |
| DNA transposon | MER91A |
| DNA transposon | MER91C |
| DNA transposon | MER99 |
| DNA transposon | ZAPHOD |
| Endogenous Retrovirus | HERV1_LTR |
| Endogenous Retrovirus | HERV151 |
| Endogenous Retrovirus | HERV18 |
| Endogenous Retrovirus | HERV23 |
| Endogenous Retrovirus | HERV30I |
| Endogenous Retrovirus | HERV38I |
| Endogenous Retrovirus | HERV39 |
| Endogenous Retrovirus | HERV4_LTR |
| Endogenous Retrovirus | HERV46I |
| Endogenous Retrovirus | HERV52I |
| Endogenous Retrovirus | HERV57I |
| Endogenous Retrovirus | HERVFH19I |
| Endogenous Retrovirus | HERVG25 |
| Endogenous Retrovirus | HERVH48I |
| Endogenous Retrovirus | HERVL_40 |
| Endogenous Retrovirus | HERVP71A_I |
| Endogenous Retrovirus | HUERS-P2 |
| Endogenous Retrovirus | HUERS-P3B |
| Endogenous Retrovirus | MER31 |

TABLE 5-continued

Human transposable elements.
The list is adapted from Repbase-GIRI.
http://www.girinst.org/, accessed Jan. 31, 2011.

| Type of Transposon | ID |
|---|---|
| Endogenous Retrovirus | MER31_I |
| Endogenous Retrovirus | MER34B_I |
| Endogenous Retrovirus | MER41F |
| Endogenous Retrovirus | MER41I |
| Endogenous Retrovirus | MER4BI |
| Endogenous Retrovirus | MER57A_I |
| Endogenous Retrovirus | MER57I |
| Endogenous Retrovirus | MER61A |
| Endogenous Retrovirus | MER84I |
| Endogenous Retrovirus | PRIMA4_I |
| Endogenous Retrovirus | PRIMA41 |
| Endogenous Retrovirus | PRIMAX_I |
| ERV1 | HARLEQUIN |
| ERV1 | HERV17 |
| ERV1 | HERV19I |
| ERV1 | HERV3 |
| ERV1 | HERV35I |
| ERV1 | HERV4_I |
| ERV1 | HERV49I |
| ERV1 | HERV9 |
| ERV1 | HERVE |
| ERV1 | HERVI |
| ERV1 | HERVIP10F |
| ERV1 | HERVIP10FH |
| ERV1 | LOR1I |
| ERV1 | LTR06 |
| ERV1 | LTR1 |
| ERV1 | LTR10B |
| ERV1 | LTR10B2 |
| ERV1 | LTR10C |
| ERV1 | LTR10D |
| ERV1 | LTR10F |
| ERV1 | LTR12B |
| ERV1 | LTR12C |
| ERV1 | LTR12D |
| ERV1 | LTR12E |
| ERV1 | LTR15 |
| ERV1 | LTR17 |
| ERV1 | LTR1B |
| ERV1 | LTR1B1 |
| ERV1 | LTR1C |
| ERV1 | LTR1C2 |
| ERV1 | LTR1D |
| ERV1 | LTR1E |
| ERV1 | LTR1F |
| ERV1 | LTR2 |
| ERV1 | LTR21A |
| ERV1 | LTR21B |
| ERV1 | LTR21C |
| ERV1 | LTR23 |
| ERV1 | LTR24 |
| ERV1 | LTR24B |
| ERV1 | LTR24C |
| ERV1 | LTR25 |
| ERV1 | LTR26 |
| ERV1 | LTR26E |
| ERV1 | LTR27 |
| ERV1 | LTR2752 |
| ERV1 | LTR27B |
| ERV1 | LTR27C |
| ERV1 | LTR27D |
| ERV1 | LTR27E |
| ERV1 | LTR28 |
| ERV1 | LTR28B |
| ERV1 | LTR28C |
| ERV1 | LTR29 |
| ERV1 | LTR2B |
| ERV1 | LTR2C |
| ERV1 | LTR30 |
| ERV1 | LTR31 |
| ERV1 | LTR34 |
| ERV1 | LTR35 |
| ERV1 | LTR35B |

TABLE 5-continued

Human transposable elements.
The list is adapted from Repbase-GIRI.
http://www.girinst.org/, accessed
Jan. 31, 2011.

| Type of Transposon | ID |
| --- | --- |
| ERV1 | LTR36 |
| ERV1 | LTR37A |
| ERV1 | LTR37B |
| ERV1 | LTR38 |
| ERV1 | LTR38A1 |
| ERV1 | LTR38B |
| ERV1 | LTR38C |
| ERV1 | LTR39 |
| ERV1 | LTR4 |
| ERV1 | LTR43 |
| ERV1 | LTR43B |
| ERV1 | LTR44 |
| ERV1 | LTR45 |
| ERV1 | LTR45B |
| ERV1 | LTR45C |
| ERV1 | LTR46 |
| ERV1 | LTR48 |
| ERV1 | LTR48B |
| ERV1 | LTR49 |
| ERV1 | LTR51 |
| ERV1 | LTR56 |
| ERV1 | LTR58 |
| ERV1 | LTR59 |
| ERV1 | LTR60 |
| ERV1 | LTR60B |
| ERV1 | LTR61 |
| ERV1 | LTR64 |
| ERV1 | LTR65 |
| ERV1 | LTR6A |
| ERV1 | LTR6B |
| ERV1 | LTR70 |
| ERV1 | LTR71A |
| ERV1 | LTR71B |
| ERV1 | LTR72 |
| ERV1 | LTR72B |
| ERV1 | LTR73 |
| ERV1 | LTR76 |
| ERV1 | LTR77 |
| ERV1 | LTR78B |
| ERV1 | LTR8 |
| ERV1 | LTR81AB |
| ERV1 | LTR8A |
| ERV1 | LTR8B |
| ERV1 | LTR9 |
| ERV1 | LTR9A1 |
| ERV1 | LTR9B |
| ERV1 | LTR9C |
| ERV1 | LTR9D |
| ERV1 | MER101 |
| ERV1 | MER101B |
| ERV1 | MER110 |
| ERV1 | MER110A |
| ERV1 | MER110I |
| ERV1 | MER21I |
| ERV1 | MER31B |
| ERV1 | MER34 |
| ERV1 | MER34B |
| ERV1 | MER34C |
| ERV1 | MER34C2 |
| ERV1 | MER39 |
| ERV1 | MER39B |
| ERV1 | MER41A |
| ERV1 | MER41B |
| ERV1 | MER41C |
| ERV1 | MER41D |
| ERV1 | MER41G |
| ERV1 | MER48 |
| ERV1 | MER49 |
| ERV1 | MER4A |
| ERV1 | MER4A1 |
| ERV1 | MER4B |
| ERV1 | MER4C |
| ERV1 | MER4CL34 |
| ERV1 | MER4D |
| ERV1 | MER4D1 |
| ERV1 | MER4E |
| ERV1 | MER4E1 |
| ERV1 | MER50 |
| ERV1 | MER50B |
| ERV1 | MER50I |
| ERV1 | MER51A |
| ERV1 | MER51B |
| ERV1 | MER51C |
| ERV1 | MER51D |
| ERV1 | MER51E |
| ERV1 | MER52A |
| ERV1 | MER52AI |
| ERV1 | MER52C |
| ERV1 | MER52D |
| ERV1 | MER57A1 |
| ERV1 | MER57B2 |
| ERV1 | MER57F |
| ERV1 | MER61B |
| ERV1 | MER61C |
| ERV1 | MER65B |
| ERV1 | MER65C |
| ERV1 | MER65D |
| ERV1 | MER66_I |
| ERV1 | MER66A |
| ERV1 | MER66B |
| ERV1 | MER66C |
| ERV1 | MER66D |
| ERV1 | MER67A |
| ERV1 | MER67B |
| ERV1 | MER67C |
| ERV1 | MER67D |
| ERV1 | MER72 |
| ERV1 | MER72B |
| ERV1 | MER83 |
| ERV1 | MER83AI |
| ERV1 | MER83B |
| ERV1 | MER83BI |
| ERV1 | MER83C |
| ERV1 | MER84 |
| ERV1 | MER87 |
| ERV1 | MER87B |
| ERV1 | MER89 |
| ERV1 | MER89I |
| ERV1 | MER90 |
| ERV1 | MER92A |
| ERV1 | MER92B |
| ERV1 | PABL_A |
| ERV1 | PABL_AI |
| ERV1 | PABL_B |
| ERV1 | PABL_BI |
| ERV1 | PRIMA4_LTR |
| ERV1 | PrimLTR79 |
| ERV2 | HERVK11DI |
| ERV2 | HERVK11I |
| ERV2 | HERVK13I |
| ERV2 | HERVK3I |
| ERV2 | HERVK9I |
| ERV2 | LTR13 |
| ERV2 | LTR13A |
| ERV2 | LTR14 |
| ERV2 | LTR14A |
| ERV2 | LTR14B |
| ERV2 | LTR14C |
| ERV2 | LTR22A |
| ERV2 | LTR22B |
| ERV2 | LTR22B1 |
| ERV2 | LTR22B2 |
| ERV2 | LTR22C2 |
| ERV2 | LTR22E |
| ERV2 | LTR3 |
| ERV2 | LTR3B |

TABLE 5-continued

Human transposable elements.
The list is adapted from Repbase-GIRI.
http://www.girinst.org/, accessed
Jan. 31, 2011.

| Type of Transposon | ID |
|---|---|
| ERV2 | LTR5 |
| ERV2 | LTR5B |
| ERV2 | MER11A |
| ERV2 | MER11C |
| ERV2 | MER11D |
| ERV2 | MER9 |
| ERV2 | MER9B |
| ERV2 | RLTR10B |
| ERV2 | RLTR10C |
| ERV3 | ERV3-16A3_1 |
| ERV3 | ERV3-16A3_LTR |
| ERV3 | ERVL |
| ERV3 | HERV16 |
| ERV3 | HERVL |
| ERV3 | HERVL74 |
| ERV3 | LTR16 |
| ERV3 | LTR16A1 |
| ERV3 | LTR16A2 |
| ERV3 | LTR16C |
| ERV3 | LTR16D |
| ERV3 | LTR16E |
| ERV3 | LTR18A |
| ERV3 | LTR18B |
| ERV3 | LTR18C |
| ERV3 | LTR19A |
| ERV3 | LTR19B |
| ERV3 | LTR19C |
| ERV3 | LTR32 |
| ERV3 | LTR40A |
| ERV3 | LTR40B |
| ERV3 | LTR40C |
| ERV3 | LTR41 |
| ERV3 | LTR41B |
| ERV3 | LTR41C |
| ERV3 | LTR42 |
| ERV3 | LTR47A |
| ERV3 | LTR47A2 |
| ERV3 | LTR47B |
| ERV3 | LTR47B2 |
| ERV3 | LTR50 |
| ERV3 | LTR52 |
| ERV3 | LTR53 |
| ERV3 | LTR53B |
| ERV3 | LTR55 |
| ERV3 | LTR57 |
| ERV3 | LTR62 |
| ERV3 | LTR66 |
| ERV3 | LTR69 |
| ERV3 | LTR75 |
| ERV3 | LTR75B |
| ERV3 | LTR77B |
| ERV3 | LTR7A |
| ERV3 | LTR7B |
| ERV3 | LTR7C |
| ERV3 | MER21 |
| ERV3 | MER21A |
| ERV3 | MER54_EC |
| ERV3 | MER54A |
| ERV3 | MER54B |
| ERV3 | MER68B |
| ERV3 | MER68C |
| ERV3 | MER70A |
| ERV3 | MER70B |
| ERV3 | MER70C |
| ERV3 | MER73 |
| ERV3 | MER74B |
| ERV3 | MER74C |
| ERV3 | MER76 |
| ERV3 | MER77 |
| ERV3 | MER88 |
| ERV3 | MLT1G |
| ERV3 | MLT1G1 |
| ERV3 | MLT1G2 |
| ERV3 | MLT1G3 |
| ERV3 | MLT1H |
| ERV3 | MLT1H1 |
| ERV3 | MLT1H2 |
| ERV3 | MLT1I |
| ERV3 | MLT1K |
| ERV3 | MLT1L |
| ERV3 | MLT1N2 |
| ERV3 | MLT2A1 |
| ERV3 | MLT2A2 |
| ERV3 | MLT2C2 |
| ERV3 | MLT2D |
| ERV3 | MSTB |
| ERV3 | MSTD |
| ERV3 | RMER10B |
| ERV3 | THE1A |
| ERV3 | THE1C |
| ERV3 | THE1D |
| hAT | CHARLIE10 |
| hAT | CHARLIE2A |
| hAT | CHARLIE2B |
| hAT | CHARLIE3 |
| hAT | CHARLIE5 |
| hAT | CHARLIE6 |
| hAT | CHARLIE7 |
| hAT | CHARLIE8 |
| hAT | CHARLIE9 |
| hAT | CHESHIRE |
| hAT | CHESHIRE_A |
| hAT | CHESHIRE_B |
| hAT | FORDPREFECT |
| hAT | FORDPREFECT_A |
| hAT | MER103B |
| hAT | MER103C |
| hAT | MER106 |
| hAT | MER106B |
| hAT | MER107 |
| hAT | MER112 |
| hAT | MER113 |
| hAT | MER113B |
| hAT | MER117 |
| hAT | MER119 |
| hAT | MER1A |
| hAT | MER1B |
| hAT | MER20 |
| hAT | MER20B |
| hAT | MER30B |
| hAT | MER33 |
| hAT | MER45 |
| hAT | MER45C |
| hAT | MER5B |
| hAT | MER63D |
| hAT | MER80B |
| hAT | MER81 |
| hAT | MER94 |
| hAT | MER94B |
| hAT | MER96 |
| hAT | MER96B |
| hAT | MER97A |
| hAT | MER97B |
| hAT | MER97C |
| L1 | HAL1B |
| L1 | IN25 |
| L1 | L1 |
| L1 | L1HS |
| L1 | L1M1B_5 |
| L1 | L1M2_5 |
| L1 | L1M2A_5 |
| L1 | L1M2A1_5 |
| L1 | L1M2B_5 |
| L1 | L1M2C_5 |
| L1 | L1M3B_5 |
| L1 | L1M3C_5 |

TABLE 5-continued

Human transposable elements.
The list is adapted from Repbase-GIRI.
http://www.girinst.org/, accessed
Jan. 31, 2011.

| Type of Transposon | ID |
| --- | --- |
| L1 | L1M4B |
| L1 | L1M6B_5end |
| L1 | L1MA1 |
| L1 | L1MA2 |
| L1 | L1MA3 |
| L1 | L1MA4 |
| L1 | L1MA4A |
| L1 | L1MA5 |
| L1 | L1MA5A |
| L1 | L1MA6 |
| L1 | L1MA7 |
| L1 | L1MA8 |
| L1 | L1MA9 |
| L1 | L1MB1 |
| L1 | L1MB2 |
| L1 | L1MB3 |
| L1 | L1MB3_5 |
| L1 | L1MB4 |
| L1 | L1MB5 |
| L1 | L1MB8 |
| L1 | L1MC1 |
| L1 | L1MC2 |
| L1 | L1MC4 |
| L1 | L1MCA_5 |
| L1 | L1MCB_5 |
| L1 | L1MCC_5 |
| L1 | L1MD1 |
| L1 | L1MD2 |
| L1 | L1MD3 |
| L1 | L1MDB_5 |
| L1 | L1ME_ORF2 |
| L1 | L1ME1 |
| L1 | L1ME2 |
| L1 | L1ME3 |
| L1 | L1ME3A |
| L1 | L1ME4A |
| L1 | L1MEA_5 |
| L1 | L1MEB_5 |
| L1 | L1MED_5 |
| L1 | L1MEE_5 |
| L1 | L1PA10 |
| L1 | L1PA11 |
| L1 | L1PA12 |
| L1 | L1PA12_5 |
| L1 | L1PA13 |
| L1 | L1PA13_5 |
| L1 | L1PA14 |
| L1 | L1PA14_5 |
| L1 | L1PA15 |
| L1 | L1PA16 |
| L1 | L1PA16_5 |
| L1 | L1PA17_5 |
| L1 | L1PA2 |
| L1 | L1PA3 |
| L1 | L1PA4 |
| L1 | L1PA5 |
| L1 | L1PA6 |
| L1 | L1PA7 |
| L1 | L1PA7_5 |
| L1 | L1PA8 |
| L1 | L1PB1 |
| L1 | L1PB2 |
| L1 | L1PB2c |
| L1 | L1PB3 |
| L1 | L1PB4 |
| L1 | L1PBA_5 |
| L1 | L1PBA1_5 |
| L1 | L1PBB_5 |
| L1 | L1PREC1 |
| L1 | L1PREC2 |
| LTR Retrotransposon | HARLEQUINLTR |
| LTR Retrotransposon | HERV-K14CI |
| LTR Retrotransposon | HERV-K14I |
| LTR Retrotransposon | HUERS-P3 |
| LTR Retrotransposon | LORI |
| LTR Retrotransposon | LTR11 |
| LTR Retrotransposon | MER4I |
| LTR Retrotransposon | MER511 |
| LTR Retrotransposon | MER52B |
| LTR Retrotransposon | MER61D |
| LTR Retrotransposon | MER61E |
| LTR Retrotransposon | MER61F |
| LTR Retrotransposon | MER61I |
| LTR Retrotransposon | MER95 |
| LTR Retrotransposon | PTR5 |
| LTR Retrotransposon | THE1_I |
| Mariner/Tc1 | GOLEM_A |
| Mariner/Tc1 | GOLEM_C |
| Mariner/Tc1 | HSMAR1 |
| Mariner/Tc1 | HSMAR2 |
| Mariner/Tc1 | HSTC2 |
| Mariner/Tc1 | KANGA2_A |
| Mariner/Tc1 | MADE1 |
| Mariner/Tc1 | MARINER1_EC |
| Mariner/Tc1 | MARNA |
| Mariner/Tc1 | MER44A |
| Mariner/Tc1 | MER44B |
| Mariner/Tc1 | MER44C |
| Mariner/Tc1 | MER6B |
| Mariner/Tc1 | MER8 |
| Mariner/Tc1 | TIGGER1 |
| Mariner/Tc1 | TIGGER2 |
| Mariner/Tc1 | TIGGER5 |
| Mariner/Tc1 | TIGGER6B |
| Mariner/Tc1 | TIGGER7 |
| Mariner/Tc1 | TIGGER8 |
| Mariner/Tc1 | TIGGER9 |
| Mariner/Tc1 | ZOMBI_A |
| Merlin | Merlin1_HS |
| SINE | SVA |
| SINE1/7SL | AluYa5 |
| SINE1/7SL | AluYb8 |
| SINE1/7SL | AluYb9 |
| SINE1/7SL | AluYk13 |
| SINE3/5S | AninSINE1_HS |
| Transposable Element | MER54 |
| Transposable Element | TARE |

TABLE 6

Satellite correlated genes. Adapted from
Ting et al.(Tinget al., 2011)

| Gene Names |
| --- |
| A2ML1 |
| ABCA9 |
| ACADSB |
| ACBD7 |
| ADAMTSL3 |
| ALG11 |
| ANGEL2 |
| ANKRD20A1 |
| AP1S3 |
| APOL4 |
| APOL6 |
| ATP10B |
| BNC1 |
| C11ORF72 |
| C11ORF74 |
| C12ORF5 |
| C13ORF29 |
| C15ORF2 |

TABLE 6-continued

Satellite correlated genes. Adapted from Ting et al.(Tinget al., 2011)

| Gene Names |
|---|
| C15ORF28 |
| C17ORF77 |
| C1ORF130 |
| C1ORF69 |
| C1ORF84 |
| C21ORF82 |
| C3ORF20 |
| C6ORF170 |
| C7ORF44 |
| C7ORF46 |
| C8ORF12 |
| C9ORF68 |
| CAGE1 |
| CCBP2 |
| CCDC122 |
| CCDC52 |
| CD3EAP |
| CDON |
| CENPM |
| CES3 |
| CES7 |
| CHRM5 |
| CLCC1 |
| COX18 |
| CPM |
| CPSF2 |
| CYP46A1 |
| DBF4B |
| DCHS2 |
| DDO |
| DHRS4L2 |
| DKFZP434L187 |
| DKFZP779L1853 |
| DNAH5 |
| DNAH8 |
| DSG3 |
| DUSP19 |
| DZIP3 |
| EEF2K |
| F2RL3 |
| FAM111B |
| FAM122C |
| FAM22G |
| FAM75A2 |
| FAM83D |
| FAT3 |
| FBXO15 |
| FBXW10 |
| FCF1 |
| FER |
| FGF5 |
| FLJ11292 |
| FLJ41649 |
| FLJ43763 |
| FUT1 |
| GALNT13 |
| GBP4 |
| GK5 |
| GLIPR1L2 |
| GPR110 |
| GPR157 |
| GTPBP10 |
| GTSE1 |
| GUSBP1 |
| HERC4 |
| HESRG |
| HIF3A |
| HMGA2 |
| HRH4 |
| HUNK |
| HYDIN |
| IL12RB1 |
| IPO9 |
| KCTD18 |
| KIAA1245 |
| KIAA1257 |
| KIAA1328 |
| KIR3DX1 |
| LEPREI |
| LOC147804 |
| LOC349196 |
| LOC440313 |
| LOC441242 |
| LOC441426 |
| LOC642980 |
| LOC643406 |
| LOC649305 |
| LOC91948 |
| LRRC2 |
| LTV1 |
| LYRM2 |
| LYRM7 |
| MCFD2 |
| MED18 |
| MORC4 |
| MSH5 |
| MTBP |
| MX2 |
| MYH1 |
| MYO3B |
| MYOM3 |
| NBPF1 |
| NEB |
| NHEDC1 |
| NIPSNAP3B |
| NME7 |
| NMNAT1 |
| NUP43 |
| ODF2L |
| OR11I1 |
| OR11H12 |
| OR4F16 |
| OR4K15 |
| OR7D2 |
| OR7E156P |
| ORC6L |
| PCBD2 |
| PDDC1 |
| PGPEP1 |
| PHACTR4 |
| PHTF1 |
| PLA2G2D |
| PLEKHA5 |
| PRKRIR |
| PRND |
| PXMP4 |
| QTRTD1 |
| RASGRP3 |
| REXO1L1 |
| RGR |
| RNF125 |
| SIGLEC10 |
| SIGLEC8 |
| SIRPB1 |
| SLC13A2 |
| SLC14A2 |
| SLCI6A12 |
| SLCI9A3 |
| SLC1A6 |
| SLC27A1 |
| SLC31A1 |
| SMU1 |
| SP100 |
| STRC |
| STX17 |
| TAOK1 |
| TCL6 |
| TEX9 |
| TGFB2 |
| TIGD1 |

TABLE 6-continued

Satellite correlated genes. Adapted from Ting et al.(Tinget al., 2011)

Gene Names

TNFRSF19
TRIM43
TRPM3
TTN
ULBP1
USPL1
UTP14C
WDR17
WDR31
XKR9
XRCC2
ZFYVE20
ZMYM1
ZMYND17
ZNF100
ZNF192
ZNF208
ZNF273
ZNF320
ZNF331
ZNF37A
ZNF383
ZNF431
ZNF445
ZNF471
ZNF480
ZNF490
ZNF492
ZNF493
ZNF528
ZNF562
ZNF621
ZNF623
ZNF667
ZNF670
ZNF7
ZNF720
ZNF804B
BC029464
BC082237
BC050580
BC039319
AK096834
BC042893
BC043508
HBET1
NR_003246
LOC643079
BC040190
AK095450
BC036442
DKFZP761G18121
AK092337
KIAA0379
FLJ44076
AX748237
AX747345
AX747165
CR627148
UNQ2963
DKFZP667M2411
AK125319
AK125996
AK026805
AK129982
CR592614
AK095077
BC035989
CR623134
AK026100
RP1-140A9.6
AX747405
NR_002828
NR_003130
BIRC4BP
AK054836
AX747417
AY314745
NR_001318
AX747586
AK125128
AK055694
BC035084
WUGSC:H_DJ0855D2
1.2
CR596262
AX746734
AK024378
BC037952
BC041998
BC008050
NR_003133
AX748369
BC043541
AK131347
FLJ00140
CR620525
AX748243
AX747639
AX746484
CR605783
AK097143
BC052952
AK124179
FLJ16008
BC073807
BC015784
CR592225
BC031280
DKFZP686F19123
AX747440
AK096469
AK124893
AX747721
AK123584
NR_003263
DKFZP762C213
BC094791
CR627394
AK124673
NR_002910
FRABIN
BC069727
BC037884
BX648696
CR627383
BC034569
AX747308
AK123585
BC011779
DKFZP686I1615
BC070093
BX537874
AX748226
CR598144
BC040189
AL832479
NR_002939
AL833449
BC047600
KIAA1031
AK095766
AL832786
BC035181
NR_002220
DQ596646
NM_001001704
AL832797
AK129672
AK123838

TABLE 6-continued

Satellite correlated genes. Adapted from Ting et al.(Tinget al., 2011)

Gene Names

AX746771
C20ORF38
AX746989
LOC285382
MGC102966
AK124194
FLJ45337
AK126334
AK057596
NR_003128
AK096077
DERP7
AK098126
BC033330
BC029555
LOC129881
AK097527
BX648961
AK096499
AK097777
AK091028
FLJ37953
PTPN1L
AK096196
AK056351
AX746750
LOC440053
BC068605
UNQ9369
PFDN6L
AK125042
AK125489
BC013681
AK056866
AX747590
AX746620
FLJ00310
NM_001042703
AK094618
AX748002
BC041646
AJ617629
AL833139
AK097428
AK056105
MGC13098
AK127557
KIAA1456
BC069809
LOC441108
NM_001039909
AK096291
BX537710
BC041449
NR_002836
CR598129
BC035112
CR613732
DQ597733
AX747172
AK128266
TCAM-1
BC050344
BC047380
AL832439
BC042121
BC041426
C15ORF20
AK125310
DKFZP434P055
KIAA0010
COX18HS
BC038578
AY314748
AK023134

TABLE 6-continued

Satellite correlated genes. Adapted from Ting et al.(Tinget al., 2011)

Gene Names

AK131313
BC041865
AX746851
LOC606495
AK127238
LOC441282
BOZF1
AK026825
AK128305
AL713649
DQ573949
AK091996
CR606964
HSKRP1
AX747556
NR_003266
CR749689
BC049371
AX747988
FLJ35848
WHDC1L1
AK126491
AK024841
AX746688
FLJ37357
FLJ44955
BC040631
CR627135
DKFZP451M2119
CR627206
AK127460
BC019672
IIERV-IIIIILA1_
FUSION
AK057632
FLJ00264
NY-REN-7
AK125288
AF086203
LOC94431
BC043415
AK098333
BC042588
AX747864
AY314747
AK128216
BC044257
AX747062
BX649144
AL137270
PP8961
AK056558
AK094845
AX747742
AK095981
CTRP6
NR_002821
AX746880
AK125817
AK056417
AK026469
AK090984
AK131520
AL833246
AK125832
BC041455
AF380582
AX747658
AX721193
BC047626
FLJ44060
KIAA0982
AK093513
BC038431
BX161428

TABLE 6-continued

Satellite correlated genes. Adapted from Ting et al.(Tinget al., 2011)

Gene Names

DKFZP686O248
AK096335
BX640887
BC009626
AY338954
BC036412
NM_001001681
AK056892
DQ573361
BC041466
NR_002210
FLJ33706
KIAA1767
MBL1P1
BC071776
AK127888
NR_002943
AX747340
LOC401252
AX746585
AK091594
AK096412
FLJ34047
AX747756
BC090058
CR611653
AL137733
BX537706
NR_001565
MGC4836
MGC29891
AK098240
AX748249
C1ORF140
AK055868
BC122562
BC041363
BC047625
BC021741
AK056524
BX647358
AK023515
AK125311
AK123891
LOC339809
AK128523
AK094859
PJCG6
AX748371
UNQ3037
AK054880
AK094224
AL833510
KENAE1
BC012110
BC052779
AK097893
BC105727
AK091527
WBSCR23
BC043378
AK056246
LOC401898
AK023856
UNQ1849
BC048997
FLJ36492
KIAA2023
AK054869
CR749689
BC029555
AK024378
NR_002821
DKFZP686F19123

TABLE 7

Categories of repeated DNA.

| Class | Size of repeat | Major chromosomal location(s) |
|---|---|---|
| 'Megasatellite' DNA (blocks of hundreds of kb in some cases) | several kb | Various locations on selected chromosomes |
| RS447 | 4.7 kb | ~50-70 copies on 4p15 plus several copies on distal 8p |
| untitled | 2.5 kb | ~400 copies on 4q31 and 19q13 |
| untitled | 3.0 kb | ~50 copies on the X chromosome |
| Satellite DNA (blocks often from 100 kb to several Mb in length) | 5-171 bp | Especially at centromeres |
| α (alphoid DNA) | 171 bp | Centromeric heterochromatin of all chromosomes |
| β (Sau3 A family) | 68 bp | Centromeric heterochromatin of 1, 9, 13, 14, 15, 21, 22 and Y |
| Satellite 1 (AT-rich) | 25-48 bp | Centromeric heterochromatin of most chromosomes and other heterochromatic regions |
| Satellites 2 and 3 | 5 bp | Most, possibly all, chromosomes |
| Minisatellite DNA (blocks often within the 0.1-20 kb range) | 6-64 bp | At or close to telomeres of all chromosomes |
| telomeric family | 6 bp | All telomeres |
| hypervariable family | 9-64 bp | All chromosomes, often near telomeres |
| Microsatellite DNA (blocks often less than 150 bp) | 1-4 bp | Dispersed throughout all chromosomes |

TABLE 8

Repeated DNA elements.
The list is adapted from Repbase-GIRI.
http://www.girinst.org/,
accessed January 31, 2011.

Name of Repeat (AC)n
(AG)n
(AT)n
(C)n
(CAA)n
(CAAA)n
(CAAAA)n
(CAAAAA)n
(CCA)n
(CCCCA)n
(CCCCAA)n
(CCCCCA)n
(CCCGAA)n
(CCCTAA)n
(CCCTCA)n
(CCTA)n
(CG)n
(CGAA)n
(CGGA)n
(CTA)n
(CTCCA)n
(GAA)n
(GAAA)n
(GAAAA)n
(GAAAAA)n
(GACA)n
(GAGACA)n
(GCA)n
(GCC)n
(GCCA)n
(GCCC)n
(GCCCA)n
(GCCCC)n
(GCCCCA)n
(GCCCCC)n
(GCGCA)n
(GCTCA)n

TABLE 8-continued

Repeated DNA elements.
The list is adapted from Repbase-GIRI.
http://www.girinst.org/,
accessed January 31, 2011.

Name of Repeat (GGA)n
(GGAA)n
(GGAGA)n
(GGAGAA)n
(GGCA)n
(GGCCC)n
(GGGA)n
(GGGAGA)n
(GGGGA)n
(GGGGGA)n
(TAA)n
(TAAA)n
(TAAAA)n
(TAAAAA)n
(TACA)n
(TACAA)n
(TAGA)n
(TAGAA)n
(TATACA)n
(TCA)n
(TCAA)n
(TCACCA)n
(TCCA)n
(TCCCA)n
(TCTAA)n
(TGAA)n
(TGGAA)n
(TGGCCC)n
(TTAA)n
(TTAAA)n
ACRO1
ALR
ALR_
ALR1
ALR2
ALRa TABLE 8-continued Repeated DNA elements.
The list is adapted from Repbase-GIRI.
http://www.girinst.org/,
accessed January 31, 2011.

Name of Repeat

ALRa_

ALRb

BSR

BSRa

\>BSRb

\>BSRd

\>BSRf

\>CER

\>D20S16

\>GGAAT

\>GSAT

\>GSATII

\>GSATX

\>HSAT4

\>HSAT5

\>HSAT6

\>HSATI

\>HSATII

\>LSAU

\>MSR1

\>REP522

\>SAR

\>SATR1

\>SATR2

\>SN5

\>SUBTEL_sat

\>SUBTEL2_sat

\>SVA2

\>TAR1

TABLE 9

Examples of non-coding RNAs in nature.

| Non-coding RNA | Abbreviation | Example of function | Reference |
|---|---|---|---|
| Transfer RNA | tRNA | Translation | (Aitken et al., 2010) |
| Ribosomal RNA | rRNA | Translation | (Aitken et al., 2010) |
| Signal recognition particle RNA | 7SL RNA or SRP RNA | Translocation of proteins across the Endoplasmatic Reticulum | (Gribaldo and Brochier-Armanet, 2006) |
| Small nuclear RNA | snRNA | Splicing | (Valadkhan, 2010) |
| Small nucleolar RNA | snoRNA | Guides chemical modifications of other RNAs (like methylation and pseudouridylation). | (Kiss, 2002) |
| Short Interspersed repetitive elements | SINE | The most common SINE is the Alu element (~10% of the genome). Alu is upregulated in response to stress and binds RNA polymerase II to suppress transcription. | (Mariner et al., 2008) |
| microRNA | miRNA | Post-transcriptional gene silencing | (Bartel, 2009) |
| Small interfering RNA | siRNA | Post-transcriptional gene silencing | (Elbashir et al., 2001) |
| Piwi-interacting RNA | piRNA | Transcriptional gene silencing, defense against retrotransposons | (Taft et al., 2010) |
| Ribonuclease P | RNase P | Ribozyme involved in tRNA maturation | (Guerrier-Takada et al., 1983) |
| Ribonuclease MRP | RNase MRP | Ribozyme involved in rRNA maturation as well as mitochondrial DNA replication | (Li et al., 2002) |
| Y RNA | Y RNA | RNA processing, DNA replication | (Lerner et al., 1981) |
| Telomerase RNA | | Telomere synthesis | (Feng et al., 1995) |
| Antisense RNA | aRNA | Transcriptional attenuation/mRNA degradation/mRNA stabilisation/ translation block | (Katayama et al., 2005) |

TABLE 9-continued

Examples of non-coding RNAs in nature.

| Non-coding RNA | Abbreviation | Example of function | Reference |
|---|---|---|---|
| Long ncRNA, large intervening ncRNA (>200 nt) | Long ncRNA, lincRNA | regulation of gene transcription, post-transcriptional regulation, epigenetic regulation | (Kapranov et al., 2007) |

REFERENCES

Aitken, C. E., A. Petrov, and J. D. Puglisi. 2010. Single ribosome dynamics and the mechanism of translation. *Annu Rev Biophys*. 39:491-513.

Alessi, D. R., L. R. Pearce, and J. M. Garcia-Martinez. 2009. New insights into mTOR signaling: mTORC2 and beyond. *Sci Signal*. 2:pe27.

Asch, H. L., E. Eliacin, T. G. Fanning, J. L. Connolly, G. Bratthauer, and B. B. Asch. 1996. Comparative expression of the LINE-1 p40 protein in human breast carcinomas and normal breast tissues. *Oncol Res*. 8:239-47.

Bartel, D. P. 2009. MicroRNAs: target recognition and regulatory functions. *Cell*. 136:215-33.

Bergsmedh, A., A. Szeles, M. Henriksson, A. Bratt, M. J. Folkman, A. L. Spetz, and L.

Holmgren. 2001. Horizontal transfer of oncogenes by uptake of apoptotic bodies. *Proc Nati Acad Sci USA*. 98:6407-11.

Cheng, G. Z., S. Park, S. Shu, L. He, W. Kong, W. Zhang, Z. Yuan, L. H. Wang, and J. Q. Cheng. 2008. Advances of AKT pathway in human oncogenesis and as a target for anti-cancer drug discovery. *Curr Cancer Drug Targets*. 8:2-6.

Cotton, R. G., N. R. Rodrigues, and R. D. Campbell. 1988. Reactivity of cytosine and thymine in single-base-pair mismatches with hydroxylamine and osmium tetroxide and its application to the study of mutations. *Proc Natl Acad Sci USA*. 85:4397-401.

Cowell, J. K., and K. C. Lo. 2009. Application of oligonucleotides arrays for coincident comparative genomic hybridization, ploidy status and loss of heterozygosity studies in human cancers. *Methods Mol Biol*. 556:47-65.

Cristofanilli, M., and J. Mendelsohn. 2006. Circulating tumor cells in breast cancer: Advanced tools for "tailored" therapy? *Proc Natl Acad Sci USA*. 103:17073-4.

Day, J. R., M. Jost, M. A. Reynolds, J. Groskopf, and H. Rittenhouse. 2011. PCA3: from basic molecular science to the clinical lab. *Cancer Lett*. 301:1-6.

Dinger, M. E., K. C. Pang, T. R. Mercer, and J. S. Mattick. 2008. Differentiating protein-coding and noncoding RNA: challenges and ambiguities. *PLoS Comput Biol*. 4:e1000176.

Dowling, R. J., I. Topisirovic, T. Alain, M. Bidinosti, B. D. Fonseca, E. Petroulakis, X. Wang, O. Larsson, A. Selvaraj, Y. Liu, S. C. Kozma, G. Thomas, and N. Sonenberg. mTORC1-mediated cell proliferation, but not cell growth, controlled by the 4E-BPs. *Science*. 328:1172-6.

Elbashir, S. M., W. Lendeckel, and T. Tuschl. 2001. RNA interference is mediated by 21- and 22-nucleotide RNAs. *Genes Dev*. 15:188-200.

Ender, C., A. Krek, M. R. Friedlander, M. Beitzinger, L. Weinmann, W. Chen, S. Pfeffer, N. Rajewsky, and G. Meister. 2008. A human snoRNA with microRNA-like functions. *Mol Cell*. 32:519-28.

Feng, J., W. D. Funk, S. S. Wang, S. L. Weinrich, A. A. Avilion, C. P. Chiu, R. R. Adams, E. Chang, R. C. Allsopp, J. Yu, and et al. 1995. The RNA component of human telomerase. *Science*. 269:1236-41.

Golan, M., A. Hizi, J. H. Resau, N. Yaal-Hahoshen, H. Reichman, I. Keydar, and I. Tsarfaty. 2008. Human endogenous retrovirus (HERV-K) reverse transcriptase as a breast cancer prognostic marker. *Neoplasia*. 10:521-33.

Goodier, J. L., and H. H. Kazazian, Jr. 2008. Retrotransposons revisited: the restraint and rehabilitation of parasites. *Cell*. 135:23-35.

Gribaldo, S., and C. Brochier-Armanet. 2006. The origin and evolution of Archaea: a state of the art. *Philos Trans R Soc Lond B Biol Sci*. 361:1007-22.

Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. *Proc Natl Acad Sci USA*. 87:1874-8.

Guerrier-Takada, C., K. Gardiner, T. Marsh, N. Pace, and S. Altman. 1983. The RNA moiety of ribonuclease P is the catalytic subunit of the enzyme. *Cell*. 35:849-57.

Gupta, R. A., N. Shah, K. C. Wang, J. Kim, H. M. Horlings, D. J. Wong, M. C. Tsai, T. Hung, P. Argani, J. L. Rinn, Y. Wang, P. Brzoska, B. Kong, R. Li, R. B. West, M. J. van de Vijver, S. Sukumar, and H. Y. Chang. 2010. Long non-coding RNA HOTAIR reprograms chromatin state to promote cancer metastasis. *Nature*. 464:1071-6.

Hahn, P. J. 1993. Molecular biology of double-minute chromosomes. *Bioessays*. 15:477-84.

Halicka, H. D., E. Bedner, and Z. Darzynkiewicz. 2000. Segregation of RNA and separate packaging of DNA and RNA in apoptotic bodies during apoptosis. *Exp Cell Res*. 260:248-56.

Hanahan, D., and R. A. Weinberg. 2000. The hallmarks of cancer. *Cell*. 100:57-70.

Hildebrandt, M. A., H. Yang, M. C. Hung, J. G. Izzo, M. Huang, J. Lin, J. A. Ajani, and X. Wu. 2009. Genetic variations in the PI3K/PTEN/AKT/mTOR pathway are associated with clinical outcomes in esophageal cancer patients treated with chemoradiotherapy. *J Clin Oncol*. 27:857-71.

Jarrous, N., and R. Reiner. 2007. Human RNase P: a tRNA-processing enzyme and transcription factor. *Nucleic Acids Res*. 35:3519-24.

Jemal, A., R. Siegel, E. Ward, Y. Hao, J. Xu, T. Murray, and M. J. Thun. 2008. Cancer statistics, 2008. *CA Cancer J Clin*. 58:71-96.

Ji, P., S. Diederichs, W. Wang, S. Boing, R. Metzger, P. M. Schneider, N. Tidow, B. Brandt, H. Buerger, E. Bulk, M. Thomas, W. E. Berdel, H. Serve, and C. Muller-Tidow. 2003. MALAT-1, a novel noncoding RNA, and thymosin beta4 predict metastasis and survival in early-stage non-small cell lung cancer. *Oncogene*. 22:8031-41.

Kapranov, P., J. Cheng, S. Dike, D. A. Nix, R. Duttagupta, A. T. Willingham, P. F. Stadler, J. Hertel, J. Hackermuller, I. L. Hofacker, I. Bell, E. Cheung, J. Drenkow, E. Dumais, S. Patel, G. Helt, M. Ganesh, S. Ghosh, A. Piccolboni, V. Sementchenko, H. Tammana, and T. R. Gingeras. 2007. RNA maps reveal new RNA classes and a possible function for pervasive transcription. *Science*. 316:1484-8.

Katayama, S., Y. Tomaru, T. Kasukawa, K. Waki, M. Nakanishi, M. Nakamura, H. Nishida, C. C. Yap, M. Suzuki, H. Suzuki, P. Carninci, Y. Hayashizaki, C. Wells, M. Frith, T. Ravasi, K. C. Pang, J. Hallinan, J. Mattick, D. A. Hume, L. Lipovich, S. Batalov, P. G. Engstrom, Y. Mizuno, M. A. Faghihi, A. Sandelin, A. M. Chalk, S. Mottagui-Tabar, Z. Liang, B. Lenhard, and C. Wahlestedt. 2005. Antisense transcription in the mammalian transcriptome. *Science.* 309:1564-6.

Kiss, T. 2002. Small nucleolar RNAs: an abundant group of noncoding RNAs with diverse cellular functions. *Cell.* 109:145-8.

Klemke, R. L., S. Cai, A. L. Giannini, P. J. Gallagher, P. de Lanerolle, and D. A. Cheresh. 1997. Regulation of cell motility by mitogen-activated protein kinase. *J Cell Biol.* 137:481-92.

Kwoh, D. Y., G. R. Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. *Proc Natl Acad Sci USA.* 86:1173-7.

Lakkaraju, A., and E. Rodriguez-Boulan. 2008. Itinerant exosomes: emerging roles in cell and tissue polarity. *Trends Cell Biol.* 18:199-209.

Lerner, M. R., J. A. Boyle, J. A. Hardin, and J. A. Steitz. 1981. Two novel classes of small ribonucleoproteins detected by antibodies associated with lupus erythematosus. *Science.* 211:400-2.

Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. *Nat Med.* 14:579-84.

Li, X., D. N. Frank, N. Pace, J. M. Zengel, and L. Lindahl. 2002. Phylogenetic analysis of the structure of RNase MRP RNA in yeasts. *RNA.* 8:740-51.

Lipson, D., T. Raz, A. Kieu, D. R. Jones, E. Giladi, E. Thayer, J. F. Thompson, S. Letovsky, P. Milos, and M. Causey. 2009. Quantification of the yeast transcriptome by single-molecule sequencing. *Nat Biotechnol.* 27:652-8.

Lower, R., J. Lower, and R. Kurth. 1996. The viruses in all of us: characteristics and biological significance of human endogenous retrovirus sequences. *Proc Natl Acad Sci USA.* 93:5177-84.

Mariner, P. D., R. D. Walters, C. A. Espinoza, L. F. Drullinger, S. D. Wagner, J. F. Kugel, and J. A. Goodrich. 2008. Human Alu RNA is a modular transacting repressor of mRNA transcription during heat shock. *Mol Cell.* 29:499-509.

Mattick, J. S. 2004. RNA regulation: a new genetics? *Nat Rev Genet.* 5:316-23.

Maxam, A. M., and W. Gilbert. 1977. A new method for sequencing DNA. *Proc Natl Acad Sci USA.* 74:560-4.

Miele, E. A., D. R. Mills, and F. R. Kramer. 1983. Autocatalytic replication of a recombinant RNA. *J Mol Biol.* 171:281-95.

Miranda, K. C., D. T. Bond, M. McKee, J. Skog, T. G. Paunescu, N. Da Silva, D. Brown, and L. M. Russo. 2010. Nucleic acids within urinary exosomes/microvesicles are potential biomarkers for renal disease. *Kidney Int.* 78:191-9.

Myers, R. M., Z. Larin, and T. Maniatis. 1985. Detection of single base substitutions by ribonuclease cleavage at mismatches in RNA:DNA duplexes. *Science.* 230:1242-6.

Ng, K., D. Pullirsch, M. Leeb, and A. Wutz. 2007. Xist and the order of silencing. *EMBO Rep.* 8:34-9.

Nilsson, J., J. Skog, A. Nordstrand, V. Baranov, L. Mincheva-Nilsson, X. O. Breakefield, and A. Widmark. 2009. Prostate cancer-derived urine exosomes: a novel approach to biomarkers for prostate cancer. *Br J Cancer.* 100:1603-7.

Orita, M., H. Iwahana, H. Kanazawa, K. Hayashi, and T. Sekiya. 1989. Detection of polymorphisms of human DNA by gel electrophoresis as single-strand conformation polymorphisms. *Proc Natl Acad Sci USA.* 86:2766-70.

Orozco, A. F., and D. E. Lewis. 2010. Flow cytometric analysis of circulating microparticles in plasma. *Cytometry A.* 77:502-14.

Pelloski, C. E., K. V. Ballman, A. F. Furth, L. Zhang, E. Lin, E. P. Sulman, K. Bhat, J. M. McDonald, W. K. Yung, H. Colman, S. Y. Woo, A. B. Heimberger, D. Suki, M. D. Prados, S. M. Chang, F. G. Barker, 2nd, J. C. Buckner, C. D. James, and K. Aldape. 2007. Epidermal growth factor receptor variant III status defines clinically distinct subtypes of glioblastoma. *J Clin Oncol.* 25:2288-94.

Rinn, J. L., M. Kertesz, J. K. Wang, S. L. Squazzo, X. Xu, S. A. Brugmann, L. H. Goodnough, J. A. Helms, P. J. Farnham, E. Segal, and H. Y. Chang. 2007. Functional demarcation of active and silent chromatin domains in human HOX loci by noncoding RNAs. *Cell.* 129:1311-23.

Sanger, F., S. Nicklen, and A. R. Coulson. 1977. DNA sequencing with chain-terminating inhibitors. *Proc Natl Acad Sci USA.* 74:5463-7.

Sarbassov, D. D., S. M. Ali, S. Sengupta, J. H. Sheen, P. P. Hsu, A. F. Bagley, A. L. Markhard, and D. M. Sabatini. 2006. Prolonged rapamycin treatment inhibits mTORC2 assembly and Akt/PKB. *Mol Cell.* 22:159-68.

Simons, M., and G. Raposo. 2009. Exosomes—vesicular carriers for intercellular communication. *Curr Opin Cell Biol.* 21:575-81.

Sliva, K., and B. S. Schnierle. Selective gene silencing by viral delivery of short hairpin RNA. *Virol J.* 7:248.

Srikantan, V., Z. Zou, G. Petrovics, L. Xu, M. Augustus, L. Davis, J. R. Livezey, T. Connell, I. A. Sesterhenn, K. Yoshino, G. S. Buzard, F. K. Mostofi, D. G. McLeod, J. W. Moul, and S. Srivastava. 2000. PCGEM1, a prostate-specific gene, is overexpressed in prostate cancer. *Proc Natl Acad Sci USA.* 97:12216-21.

Steemers, F. J., W. Chang, G. Lee, D. L. Barker, R. Shen, and K. L. Gunderson. 2006. Whole-genome genotyping with the single-base extension assay. *Nat Methods.* 3:31-3.

Storey, J. D., and R. Tibshirani. 2003. Statistical methods for identifying differentially expressed genes in DNA microarrays. *Methods Mol Biol.* 224:149-57.

Taft, R. J., K. C. Pang, T. R. Mercer, M. Dinger, and J. S. Mattick. 2010. Non-coding RNAs: regulators of disease. *J Pathol.* 220:126-39.

Tez, S., A. Koktener, G. Guler, and P. Ozisik. 2008. Atypical teratoid/rhabdoid tumors: imaging findings of two cases and review of the literature. *Turk Neurosurg.* 18:30-4.

Ting, D. T., D. Lipson, S. Paul, B. W. Brannigan, S. Akhavanfard, E. J. Coffman, G. Contino, V. Deshpande, A. J. Iafrate, S. Letovsky, M. N. Rivera, N. Bardeesy, S. Maheswaran, and D. A. Haber. 2011. Aberrant overexpression of satellite repeats in pancreatic and other epithelial cancers. *Science.* 331:593-6.

Valadkhan, S. 2010. Role of the snRNAs in spliceosomal active site. *RNA Biol.* 7:345-53.

Velculescu, V. E., L. Zhang, B. Vogelstein, and K. W. Kinzler. 1995. Serial analysis of gene expression. *Science.* 270:484-7.

Voisset, C., R. A. Weiss, and D. J. Griffiths. 2008. Human RNA "rumor" viruses: the search for novel human retroviruses in chronic disease. *Microbiol Mol Biol Rev.* 72:157-96, table of contents.

We claim:

1. A method for identifying the presence of a retrotransposon element in a microvesicle from a subject comprising the steps of:
   a. isolating microvesicles derived from a tumor cell from the subject;
   b. treating the isolated microvesicles with a combination of DNAse and Exonuclease III;
   c. extracting at least one nucleic acid from the treated microvesicles; and
   d. detecting the presence of the retrotransposon element in the extracted nucleic acid.

2. The method of claim 1, wherein the retrotransposon element is LINE, SINE or HERV, or a fragment thereof.

3. The method of claim 2, wherein the retrotransposon element is Line1 (L1), ALU, HERV-H, HERV-K, HERV-K6, HERV-W or HERV-C, or a fragment thereof.

4. A method for determining the expression level of a retrotransposon element in a microvesicle from a subject comprising the steps of:
   a. isolating microvesicles derived from a tumor cell from the subject;
   b. treating the isolated microvesicles with a combination of DNAse and Exonuclease III;
   c. extracting at least one nucleic acid from the treated microvesicles; and
   d. determining the expression level of the retrotransposon element biomarker in the extracted nucleic acid.

5. The method of claim 4, wherein the retrotransposon element is LINE, SINE or HERV, or a fragment thereof.

6. The method of claim 5, wherein the retrotransposon element is Line1 (L1), ALU, HERV-H, HERV-K, HERV-K6, HERV-W or HERV-C, or a fragment thereof.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
tctacccgga cgaagatgac                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
agctcgttct caagcagcat                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tcaagaggcg aacacacaac                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
taactacctt gggggccttt                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
cctaccctct caacgacagc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
ctctgacctt ttgccaggag                                                 20

<210> SEQ ID NO 7
<211> LENGTH: 19
<212> TYPE: DNA
<213> ORGANISM: Artificial Sequence

```
<220> FEATURE:
<223> OTHER INFORMATION: Synthetic Primer

<400> SEQUENCE: 7
caacccttgc cgcatccac                                                    19

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer

<400> SEQUENCE: 8
agtcgcgtcc ttgctcgg                                                     18

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9 atcctgggggg ttctatttgg                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
ctccaggttg cctctcactc                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
ctctgctcct cctgttcgac                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
acgaccaaat ccgttgactc                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
caaaactccc gtgctgatca                                                   20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
ggctggagtg cagtggctat                                               20

<210> SEQ ID NO 15
<211> LENGTH: 15
<212> TYPE: DNA
<213> ORGANISM: Artificial Sequence
<220> FEATURE:
<223> OTHER INFORMATION: Synthetic Probe

<400> SEQUENCE: 15
tgggatcgcg cctgt                                                    15

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer

<400> SEQUENCE: 16
tatgtcctca ttgccctcaa ca                                            22

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer

<400> SEQUENCE: 17
ctgatgatct gcaggttttc ca                                            22

<210> SEQ ID NO 18
<211> LENGTH: 18
<212> TYPE: DNA
<213> ORGANISM: Artificial Sequence
<220> FEATURE:
<223> OTHER INFORMATION: Synthetic Probe

<400> SEQUENCE: 18
aaggaattcg ctccactg                                                 18

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
ctctgctcct cctgttcgac                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 20
acgaccaaat ccgttgactc                                                 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
taagggcagc cagagagaaa                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
gcctggtggt gacaaaatct                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
ggagagaagc tgtcctgtgg                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic Primer

<400> SEQUENCE: 24
tgactggact tgcacgtagg                                                 20

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
catgtgggtt agcctggtct                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
ttcccacatt gcgtcattta                                                 20
```